United States Patent
Zhang et al.

(10) Patent No.: US 11,021,445 B2
(45) Date of Patent: Jun. 1, 2021

(54) CARBOXYLIC ACID DERIVATIVE AS AT₂R RECEPTOR ANTAGONIST

(71) Applicant: SHANDONG DANHONG PHARMACEUTICAL CO., LTD., Heze (CN)

(72) Inventors: Yang Zhang, Shanghai (CN); Wentao Wu, Shanghai (CN); Zhixiang Li, Shanghai (CN); Mingxing Teng, Shanghai (CN); Guangwen Yang, Shanghai (CN); Jie Li, Shanghai (CN); Jian Li, Shanghai (CN); Shuhui Chen, Shanghai (CN)

(*) Notice: Subject to any disclaimer, the term of this patent is extended or adjusted under 35 U.S.C. 154(b) by 0 days.

(21) Appl. No.: 16/700,978

(22) Filed: Dec. 2, 2019

(65) Prior Publication Data
US 2020/0102275 A1 Apr. 2, 2020

Related U.S. Application Data

(63) Continuation of application No. PCT/CN2018/090432, filed on Jun. 8, 2018.

(30) Foreign Application Priority Data

Jun. 9, 2017 (CN) .......................... 201710434262.2

(51) Int. Cl.
C07D 217/26 (2006.01)
C07D 401/12 (2006.01)
C07D 405/12 (2006.01)
C07D 409/12 (2006.01)
C07D 417/12 (2006.01)

(52) U.S. Cl.
CPC ......... C07D 217/26 (2013.01); C07D 401/12 (2013.01); C07D 405/12 (2013.01); C07D 409/12 (2013.01); C07D 417/12 (2013.01)

(58) Field of Classification Search
CPC .. C07D 217/26; C07D 401/12; C07D 405/12; C07D 409/12; C07D 417/12
See application file for complete search history.

(56) References Cited

U.S. PATENT DOCUMENTS

| | | | |
|---|---|---|---|
| 8,614,227 B2 | 12/2013 | McCarthy et al. | |
| 8,927,575 B2 | 1/2015 | McCarthy et al. | |
| 9,095,587 B2 | 8/2015 | McCarthy et al. | |
| 2004/0167197 A1 | 8/2004 | Rudolph et al. | |
| 2012/0022101 A1 | 1/2012 | Boyle et al. | |
| 2012/0136006 A1 | 5/2012 | Colburn et al. | |
| 2013/0131103 A1 | 5/2013 | McCarthy et al. | |
| 2016/0145213 A1 | 5/2016 | McCarthy et al. | |

FOREIGN PATENT DOCUMENTS

| | | |
|---|---|---|
| CN | 102821765 A | 12/2012 |
| CN | 103003244 A | 3/2013 |
| CN | 106478502 A | 3/2017 |
| JP | 2012500267 A | 1/2012 |
| JP | 2013517300 A | 5/2013 |
| JP | 2016525093 A | 8/2016 |
| NO | 2017036318 A1 | 3/2017 |
| WO | 2011088504 A1 | 7/2011 |
| WO | WO2017/036318 | * 3/2017 |

OTHER PUBLICATIONS

First Office Action of European Application No. 18813230.2 From EPO, dated Aug. 25, 2020.
Office Action From Korean Patent Office 10-2020-7000587, dated Mar. 12, 2020.
Office Action From Australian Patent Office 2018279669, dated Apr. 1, 2020.
EPO Search Report 18813230.2, dated Mar. 6, 2020.
Internatinal Search Report of PCT/CN2018/090432, dated Sep. 12, 2018.
Written Opinion of PCT/CN2018/090432, dated Sep. 12, 2018.
Expert Opin. Investig. Drugs. 2014, 23, 1-12.
Expert. Opin. Ther. Targets. 2015, 19, 25-35.
Pain. Medicine. 2013, 14, 1557-1568.
Pain. Medicine. 2013, 14, 692-705.
Lancet. 2014, 383, 1637-1647.
First Office Action of Japanese Application No. 2019-567596, dated Jan. 5, 2021.

* cited by examiner

*Primary Examiner* — Timothy R Rozof
(74) *Attorney, Agent, or Firm* — W&K IP

(57) ABSTRACT

The present invention relates to a compound shown in formula (II) or a pharmaceutically acceptable salt thereof and an application of the same in preparing a drug for treating a disease related to angiotensin II receptor type 2 (AT₂R).(II)

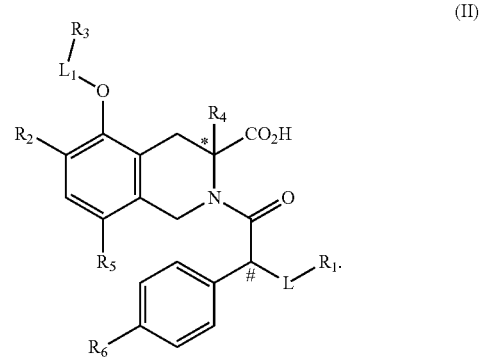

20 Claims, No Drawings

CARBOXYLIC ACID DERIVATIVE AS AT₂R RECEPTOR ANTAGONIST

CROSS-REFERENCE TO RELATED APPLICATIONS

This application is a continuation application of International Patent Application No. PCT/CN2018/090432 with an international filing date of Jun. 8, 2018, designating the United States, now pending, and further claims priority benefits to Chinese Patent Application No. 201710434262.2, filed on Jun. 9, 2017. The contents of all of the aforementioned applications are incorporated herein by reference.

TECHNICAL FIELD

The present disclosure relates to a compound of a formula (II) or a pharmaceutically acceptable salt thereof, and use of the same in the manufacture of a medicament for treating a disease associated with angiotensin II receptor 2 ($AT_2R$).

BACKGROUND

Angiotensin II (Ang II) is an octapeptide substance produced by the hydrolysis of angiotensin I under the action of angiotensin converting enzyme, and has the functions of regulating blood pressure, body fluid balance and pain perception. Angiotensin receptors are G-protein coupled receptors that use angiotensin as a ligand and are an important component of the renin-angiotensin system. AngII activates angiotensin II receptor 1 ($AT_1R$) and angiotensin II receptor 2 ($AT_2R$). Wherein, $AT_2R$ is related to the pain mechanism in the nervous system, mainly expressed in dorsal root ganglia and trigeminal ganglion. Damaged nerves and painful neuromas have higher $AT_2R$ expression than normal nerves. The second messenger pathway activated by the G-protein coupled receptors after $AT_2R$ activation sensitizes ion channels in neurons. Sensitization causes ion channel activation to excite neurons. $AT_2R$ antagonists have been proven to be useful for relieving pains in animal experiments (Pain. Medicine. 2013, 14, 1557-1568; Pain. Medicine. 2013, 14, 692-705) and clinical trials (Lancet. 2014, 383, 1637-1647). A related review report can be found in Expert Opin. Investig. Drugs. 2014, 23, 1-12; Expert. Opin. Ther. Targets. 2015, 19, 25-35, etc.

WO 2011088504 discloses a compound EMA-401.

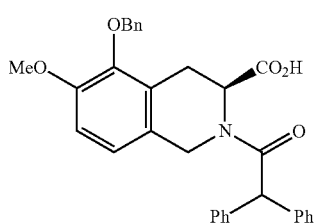

EMA-401

SUMMARY

The present disclosure provides a compound of a formula (I) and a pharmaceutically acceptable salt thereof,

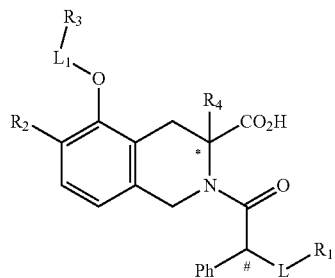

(I)

wherein,

L is selected from —O—, —S—, —N(R)—, —N(R)C(=O)— and —C(=O)O—;

$L_1$ is selected from a single bond, —$CH_2$— and —$CH_2CH_2$—;

$R_1$ is selected from the group consisting of $C_{1-6}$ alkyl, $C_{1-6}$ heteroalkyl, $C_{3-7}$ cycloalkyl, 3-7 membered heterocycloalkyl, 6-10 membered aryl and 5-6 membered heteroaryl, wherein each is optionally substituted by one, two or three R groups;

$R_2$ is selected from H, halogen, OH, $NH_2$ and CN; or selected from the group consisting of $C_{1-6}$ alkyl and $C_{1-6}$ heteroalkyl, wherein each is optionally substituted by one, two or three R groups;

$R_3$ is selected from the group consisting of phenyl, 5-6 membered heteroaryl and 5-6 membered heterocycloalkyl, wherein each is optionally substituted by one, two or three R groups;

$R_4$ is selected from H, or selected from $C_{1-3}$ alkyl optionally substituted by one, two or three R groups;

R is selected from H, halogen, OH, $NH_2$, CN, or selected from the group consisting of $C_{1-3}$ alkyl optionally substituted by one, two or three R' groups and $C_{1-3}$ heteroalkyl optionally substituted by one, two or three R' groups;

R' is selected from F, Cl, Br, I, OH, CN and $NH_2$;

a carbon atom with "*" is a chiral carbon atom, and is present in a single enantiomer form of (R) or (S) or in a form rich in one enantiomer;

a carbon atom with "#" is a chiral carbon atom, and is present in a single enantiomer form of (R) or (S) or in a form rich in one enantiomer;

the "hetero" of the 4-6 membered heterocycloalkyl, 5-6 membered heteroaryl, $C_{1-6}$ heteroalkyl and $C_{1-3}$ heteroalkyl is independently selected from —C(=O)NH—, —NH—, N, —O—, —S—, —C(=O)O— and —C(=O)—; and in any one of the above cases, the number of heteroatoms or heteroatom groups is independently selected from 1, 2 or 3.

In some embodiments of the present disclosure, the carbon atom with "*" or "#" is a chiral carbon atom, and is present in a single enantiomer form of (R) or (S) or in a form rich in one enantiomer. "Being rich in one enantiomer" refers to the content of one of the enantiomers <100%, and ≥60%, preferably ≥70%, more preferably ≥80%, more preferably ≥90%, more preferably ≥95%, more preferably ≥96%, more preferably ≥97%, more preferably ≥98%, more preferably ≥99%, more preferably ≥99.5%, more preferably ≥99.6%, more preferably ≥99.7%, more preferably ≥99.8%, and more preferably ≥99.9%.

In some embodiments of the present disclosure, the above R is selected from the group consisting of H, halogen, OH, $NH_2$, and CN; or selected from the group consisting $C_{1-3}$ alkyl optionally substituted by one, two or three R' groups and C$_{1-3}$ alkoxy optionally substituted by one, two or three R' groups.

In some embodiments of the present disclosure, the above R is selected from H, F, Cl, Br, I, OH, NH$_2$, CN, Me, Et, CF$_3$ and

In some embodiments of the present disclosure, the above L is selected from —O—, —S—, —NH—, —N(CH$_3$)—, —NHC(=O)—, —N(CH$_3$)C(=O)— and —C(=O)O—.

In some embodiments of the present disclosure, the above R$_1$ is selected from the group consisting of C$_{1-4}$ alkyl, C$_{3-7}$ cycloalkyl, 3-7 membered heterocycloalkyl, 6-10 membered aryl and 5-6 membered heteroaryl, wherein each is optionally substituted by one, two or three R groups.

In some embodiments of the present disclosure, the above R$_1$ is selected from the group consisting of C$_{1-4}$ alkyl, C$_{4-6}$ cycloalkyl, oxetanyl, tetrahydrofuranyl, tetrahydropyranyl, phenyl, naphthyl, thienyl, pyrazolyl, imidazolyl, oxazolyl, thiazolyl, morpholinyl, piperazinyl, piperidinyl, pyridyl, pyrazinyl and pyrimidinyl, wherein each is optionally substituted by one, two or three R groups.

In some embodiments of the present disclosure, the above R$_1$ is selected from the group consisting of Me, Et,

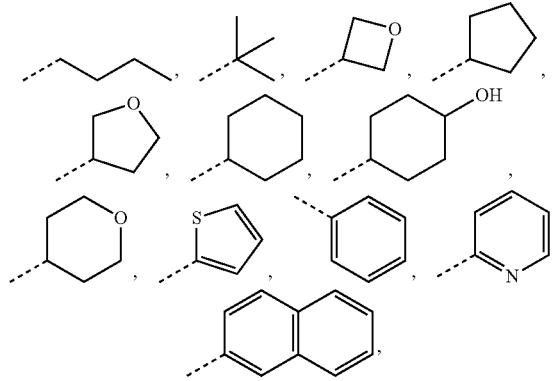

wherein each is optionally substituted by one, two or three R groups.

In some embodiments of the present disclosure, the above R$_1$ is selected from the group consisting of

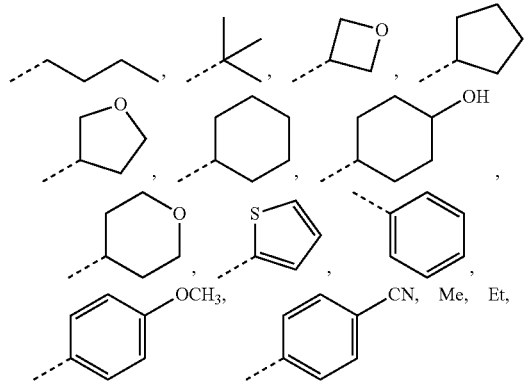

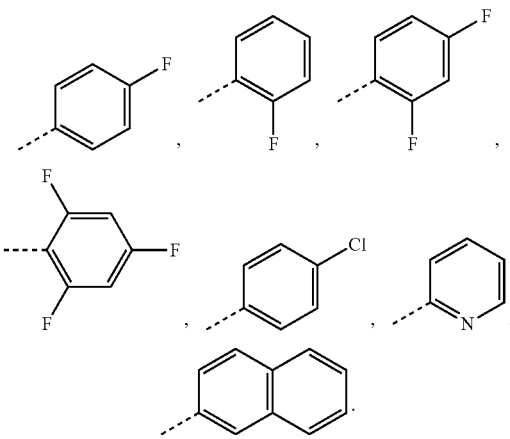

In some embodiments of the present disclosure, the above structural unit

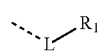

is selected from

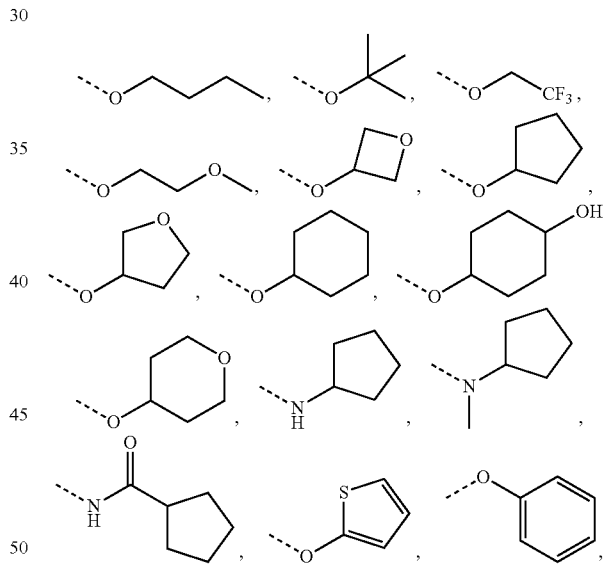

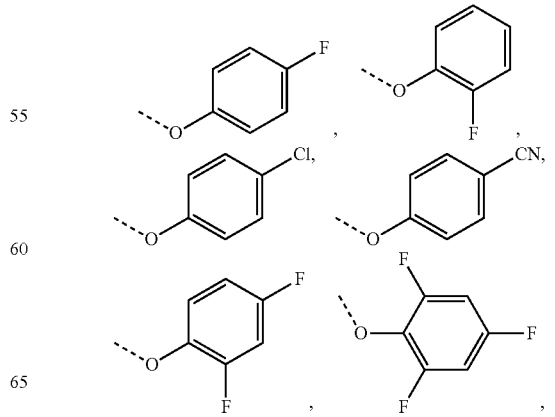

-continued

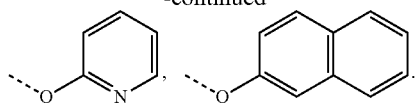

In some embodiments of the present disclosure, the above R$_2$ is selected from H, halogen, OH, NH$_2$ and CN, or selected from the group consisting of C$_{1-3}$ alkyl, C$_{1-3}$ alkoxyl, C$_{1-3}$ alkylthio and C$_{1-3}$ alkylamino, wherein each is optionally substituted by one, two or three R groups.

In some embodiments of the present disclosure, the above R$_2$ is selected from H, F, Cl, Br, I, OH, NH$_2$, CN, Me and

In some embodiments of the present disclosure, the above R$_3$ is selected from the group consisting of phenyl, pyridyl, pyrimidinyl, pyrazinyl, thienyl, thiazolyl, isothiazolyl, oxazolyl, isoxazolyl, tetrahydropyranyl, piperidinyl and morpholinyl, wherein each is optionally substituted by one, two or three R groups.

In some embodiments of the present disclosure, the above R$_3$ is selected from

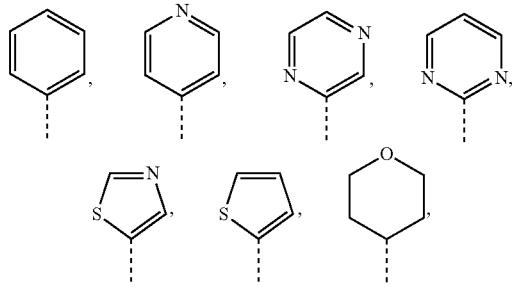

wherein each is optionally substituted by one, two or three R groups.

In some embodiments of the present disclosure, the above R$_3$ is selected from

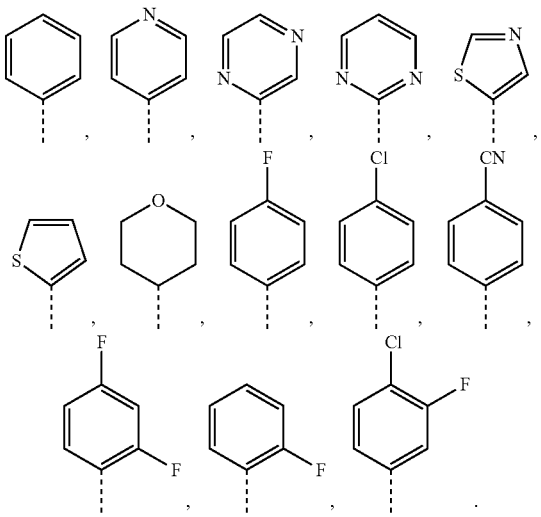

In some embodiments of the present disclosure, the above structural unit

is selected from

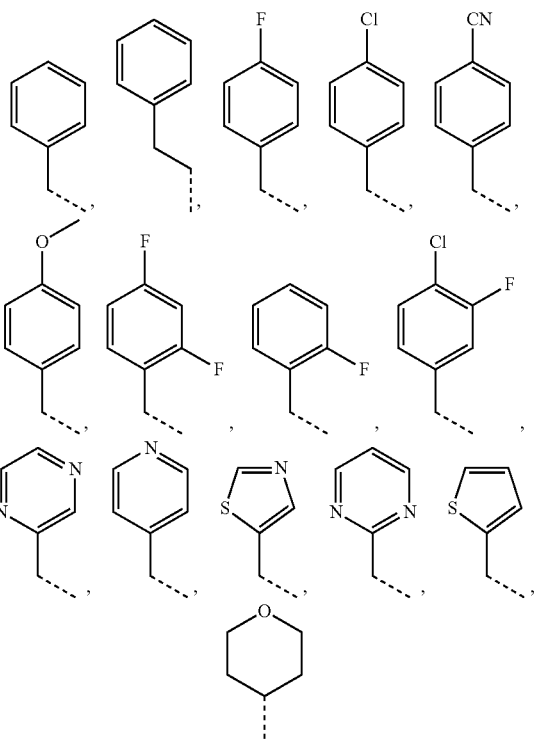

In some embodiments of the present disclosure, the above R$_4$ is selected from H and Me.

In some embodiments of the present disclosure, the above R is selected from H, halogen, OH, NH$_2$, CN, or selected from the group consisting of C$_{1-3}$ alkyl optionally substituted by one, two or three R' groups and C$_{1-3}$ alkoxyl optionally substituted by one, two or three R' groups, and other variables are as defined above.

In some embodiments of the present disclosure, the above R is selected from the group consisting of H, F, Cl, Br, I, OH, NH$_2$, CN, Me, Et, CF$_3$, and

and other variables are as defined above.

In some embodiments of the present disclosure, the above L is selected from the group consisting of —O—, —S—, —NH—, —N(CH$_3$)—, —NHC(=O)—, —N(CH$_3$)C(=O)—, and —C(=O)O—, and other variables are as defined above.

In some embodiments of the disclosure, the above R$_1$ is selected from C$_{1-4}$ alkyl, C$_{3-7}$ cycloalkyl, 3-7 membered heterocycloalkyl, 6-10 membered aryl, and 5-6 membered heteroaryl, wherein each is optionally substituted by one, two or three R groups, and other variables are as defined above.

In some embodiments of the disclosure, the above $R_1$ is selected from the group consisting of $C_{1-4}$ alkyl, $C_{4-6}$ cycloalkyl, oxetanyl, tetrahydrofuranyl, tetrahydropyranyl, phenyl, naphthyl, thienyl, pyrazolyl, imidazolyl, oxazolyl, thiazolyl, morpholinyl, piperazinyl, piperidinyl, pyridyl, pyrazinyl and pyrimidinyl, wherein each is optionally substituted by one, two or three R groups, and other variables are as defined above.

In some embodiments of the present disclosure, the above $R_1$ is selected from the group consisting of Me, Et,

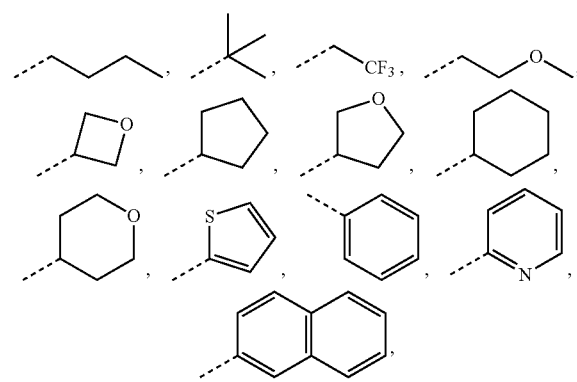

wherein each is optionally substituted by one, two or three R groups, and other variables are as defined above.

In some embodiments of the present disclosure, the above $R_1$ is selected from the group consisting of

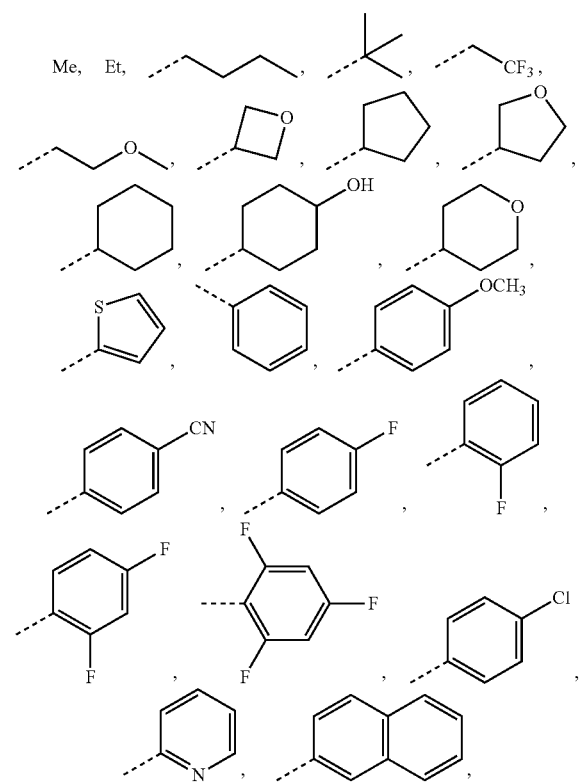

and other variables are as defined above.

In some embodiments of the present disclosure, the above structural unit

is selected from

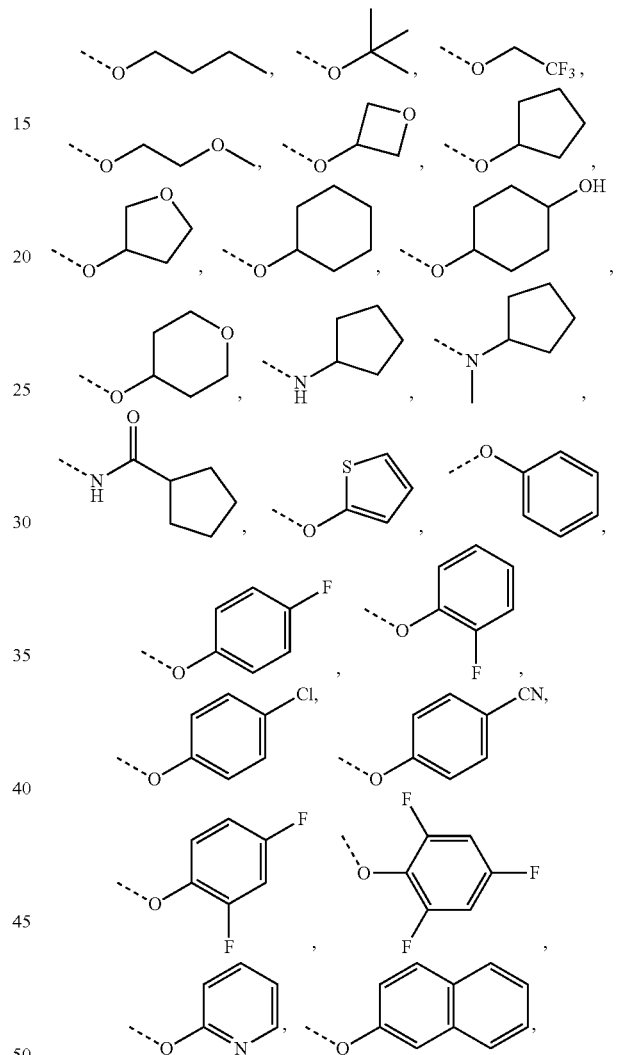

and other variables are as defined above.

In some embodiments of the present disclosure, the above $R_2$ is selected from H, halogen, OH, $NH_2$ and CN, or selected from the group consisting of $C_{1-3}$ alkyl, $C_{1-3}$ alkoxyl, $C_{1-3}$ alkylthio and $C_{1-3}$ alkylamino, wherein each is optionally substituted by one, two or three R groups, and other variables are as defined above.

In some embodiments of the present disclosure, the above $R_2$ is selected from H, F, Cl, Br, I, OH, $NH_2$, CN, Me, and

and other variables are as defined above.

In some embodiments of the present disclosure, the above R₃ is selected from the group consisting of phenyl, pyridyl, pyrimidinyl, pyrazinyl, thienyl, thiazolyl, isothiazolyl, oxazolyl, isoxazolyl, tetrahydropyranyl, piperidinyl and morpholinyl, wherein each is optionally substituted by one, two or three R groups, and other variables are as defined above.

In some embodiments of the present disclosure, the above R₃ is selected from

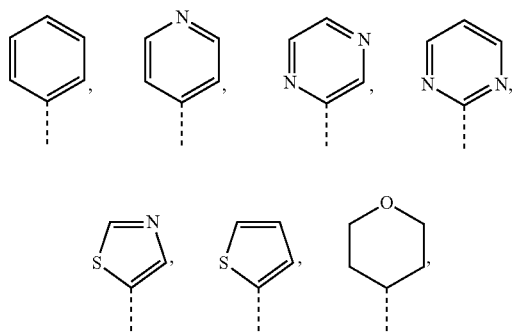

wherein each is optionally substituted by one, two or three R groups, and other variables are as defined above.

In some embodiments of the present disclosure, the above R₃ is selected from

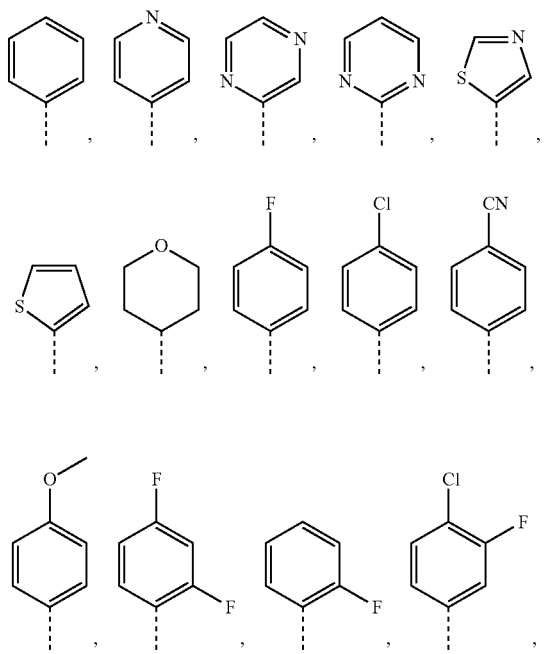

and other variables are as defined above.

In some embodiments of the present disclosure, the above structural unit

is selected from

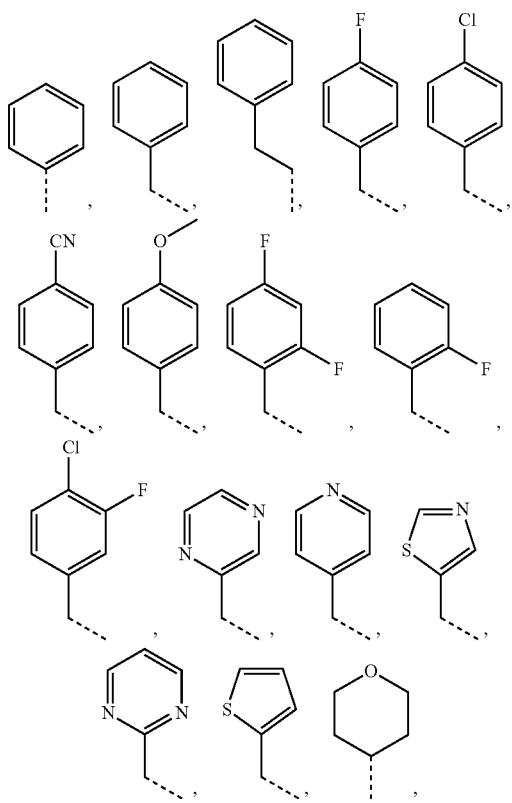

and other variables are as defined above.

In some embodiments of the present disclosure, the above R₄ is selected from H and Me, and other variables are as defined above.

In some embodiments of the disclosure, the above compound and the pharmaceutically acceptable salts thereof are selected from the group consisting of

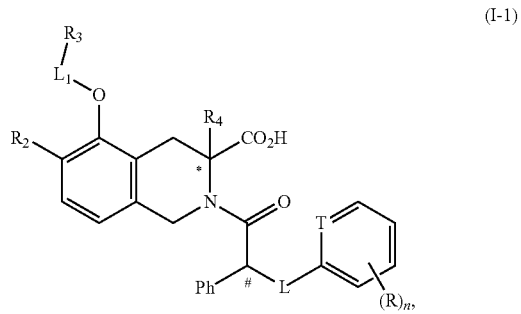

(I-1)

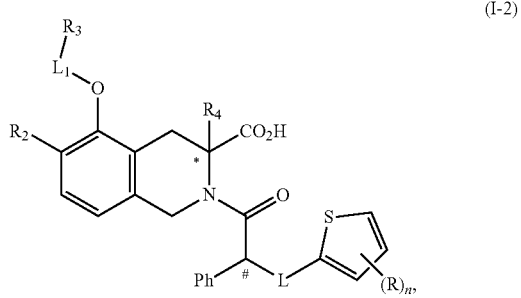

(I-2)

-continued (I-3)
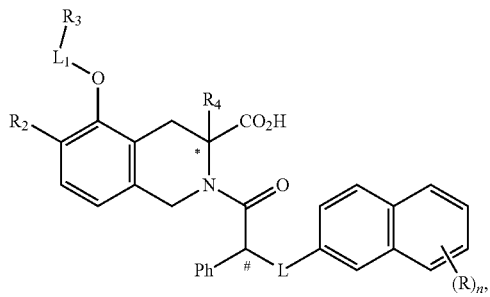

(I-4)
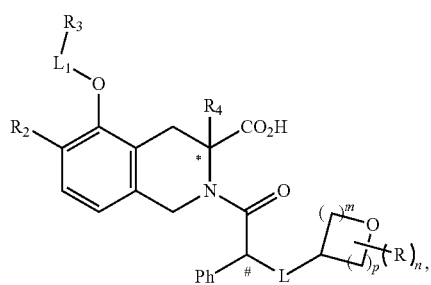

wherein
R, $R_2$, $R_3$, $R_4$, $L_1$ and L are as defined above;
T is selected from N or CH;
D is selected from $CH_2$ or O;
m and p are each independently selected from 0, 1, 2 or 3, and m and p are not simultaneously selected from 0 or 3;
n is selected from 0, 1, 2 or 3;
and n is not selected from 3 when m is selected from 0, and D is selected from O.

The present disclosure provides a compound of a formula (II) and a pharmaceutically acceptable salt thereof, (II)

wherein,
L is selected from —O—, —S—, —N(R)—, —N(R)C(=O)— and —C(=O)O—;
$L_1$ is selected from the group consisting of a single bond, —$CH_2$— and —$CH_2CH_2$—;
$R_1$ is selected from the group consisting of $C_{1-6}$ alkyl, $C_{1-6}$ heteroalkyl, $C_{3-7}$ cycloalkyl, 3-7 membered heterocycloalkyl, 6-10 membered aryl and 5-6 membered heteroaryl, wherein each is optionally substituted by one, two or three R groups;
$R_2$ is selected from H, halogen, OH, $NH_2$ and CN, or selected from the group consisting of $C_{1-6}$ alkyl and $C_{1-6}$ heteroalkyl, wherein each is optionally substituted by one, two or three R groups;

$R_3$ is selected from the group consisting of phenyl, 5-6 membered heteroaryl and 5-6 membered heterocycloalkyl, wherein each is optionally substituted by one, two or three R groups;
$R_4$ is selected from H, or selected from $C_{1-3}$ alkyl optionally substituted by one, two or three R groups;
$R_5$ is selected from H, F, C, Br, I and OH;
$R_6$ is selected from H, F, Cl, Br, I and OH;
R is selected from H, halogen, OH, $NH_2$, CN, or selected from the group consisting of $C_{1-3}$ alkyl optionally substituted by one, two or three R' groups and $C_{1-3}$ heteroalkyl optionally substituted by one, two or three R' groups;
R' is selected from F, Cl, Br, I, OH, CN and $NH_2$;
a carbon atom with "*" is a chiral carbon atom, and is present in a single enantiomer form of (R) or (S) or in a form rich in one enantiomer;
a carbon atom with "#" is a chiral carbon atom, and is present in a single enantiomer form of (R) or (S) or in a form rich in one enantiomer;
the "hetero" of the 3-7 membered heterocycloalkyl, 5-6 membered heteroaryl, $C_{1-6}$ heteroalkyl, $C_{1-3}$ heteroalkyl and 5-6 membered heterocycloalkyl is independently selected from —C(=O)NH—, —NH—, N, —O—, —S—, —C(=O)O— and —C(=O)—;
in any one of the above cases, the number of heteroatoms or heteroatom groups is independently selected from 1, 2 or 3.

In some embodiments of the present disclosure, the carbon atom with "*" or "#" is a chiral carbon atom, and is present in a single enantiomer form of (R) or (S) or in a form rich in one enantiomer. "Being rich in one enantiomer" refers to the content of one of the enantiomers <100%, and ≥260%, preferably ≥70%, more preferably ≥80%, more preferably ≥90%, more preferably ≥95%, more preferably ≥96%, more preferably ≥97%, more preferably ≥98%, more preferably ≥99%, more preferably ≥99.5%, more preferably ≥99.6%, more preferably ≥99.7%, more preferably ≥99.8%, and more preferably ≥99.9%.

In some embodiments of the present disclosure, the above R is selected from the group consisting of H, halogen, OH, $NH_2$, and CN; or selected from the group consisting $C_{1-3}$ alkyl optionally substituted by one, two or three R' groups and $C_{1-3}$ alkoxy optionally substituted by one, two or three R' groups. Other variables are as defined by the present disclosure.

In some embodiments of the present disclosure, the above R is selected from H, F, Cl, Br, I, OH, $NH_2$, CN, Me, Et, $CF_3$ and

Other variables are as defined by the present disclosure.

In some embodiments of the present disclosure, the above L is selected from —O—, —S—, —NH—, —N($CH_3$)—, —NHC(=O)—, —N($CH_3$)C(=O)— and —C(=O)O—. Other variables are as defined by the present disclosure.

In some embodiments of the present disclosure, the above $R_1$ is selected from the group consisting of $C_{1-4}$ alkyl, $C_{3-7}$ cycloalkyl. 3-7 membered heterocycloalkyl, 6-10 membered aryl and 5-6 membered heteroaryl, wherein each is optionally substituted by one, two or three R groups. Other variables are as defined by the present disclosure.

In some embodiments of the present disclosure, the above $R_1$ is selected from the group consisting of $C_{1-4}$ alkyl, cyclobutyl, cyclopentyl, cyclohexyl, bicyclo[3.1.0]hexyl, oxetanyl, tetrahydrofuranyl, tetrahydropyranyl, phenyl, naphthyl, thienyl, pyrazolyl, imidazolyl, oxazolyl, thiazolyl, morpholinyl, piperazinyl, piperidinyl, pyridyl, pyrazinyl and pyrimidinyl, wherein each is optionally substituted by one, two or three R groups. Other variables are as defined by the present disclosure.

In some embodiments of the present disclosure, the above $R_1$ is selected from the group consisting of Me, Et,

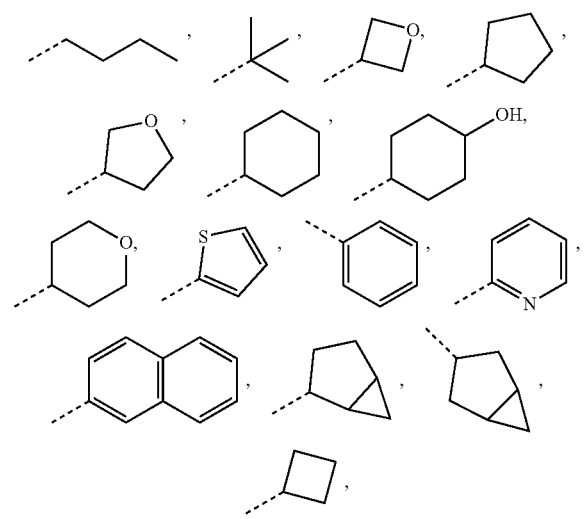

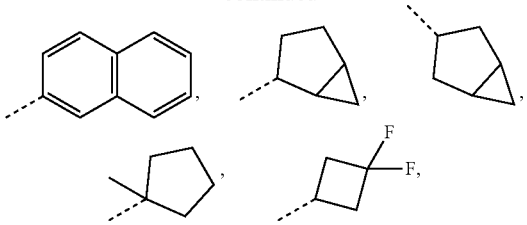

wherein each is optionally substituted by one, two or three R groups. Other variables are as defined by the present disclosure.

In some embodiments of the present disclosure, the above $R_1$ is selected from the group consisting of Me, Et,

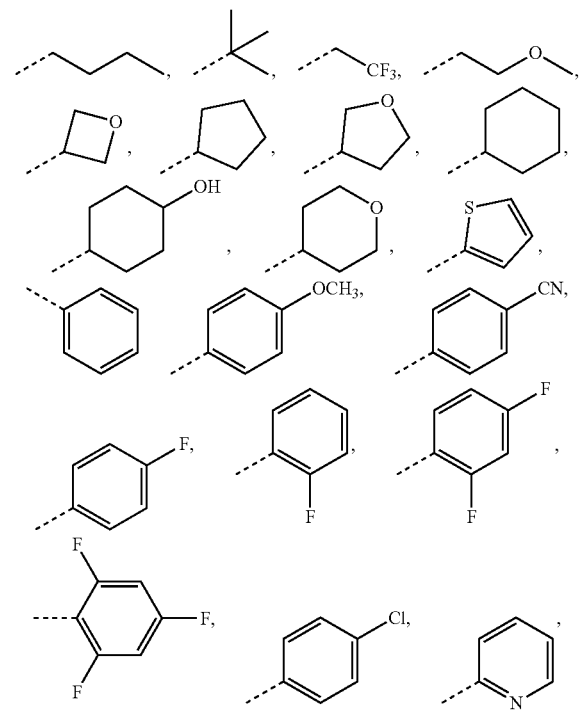

and other variables are as defined by the present disclosure.

In some embodiments of the present disclosure, the above structural unit

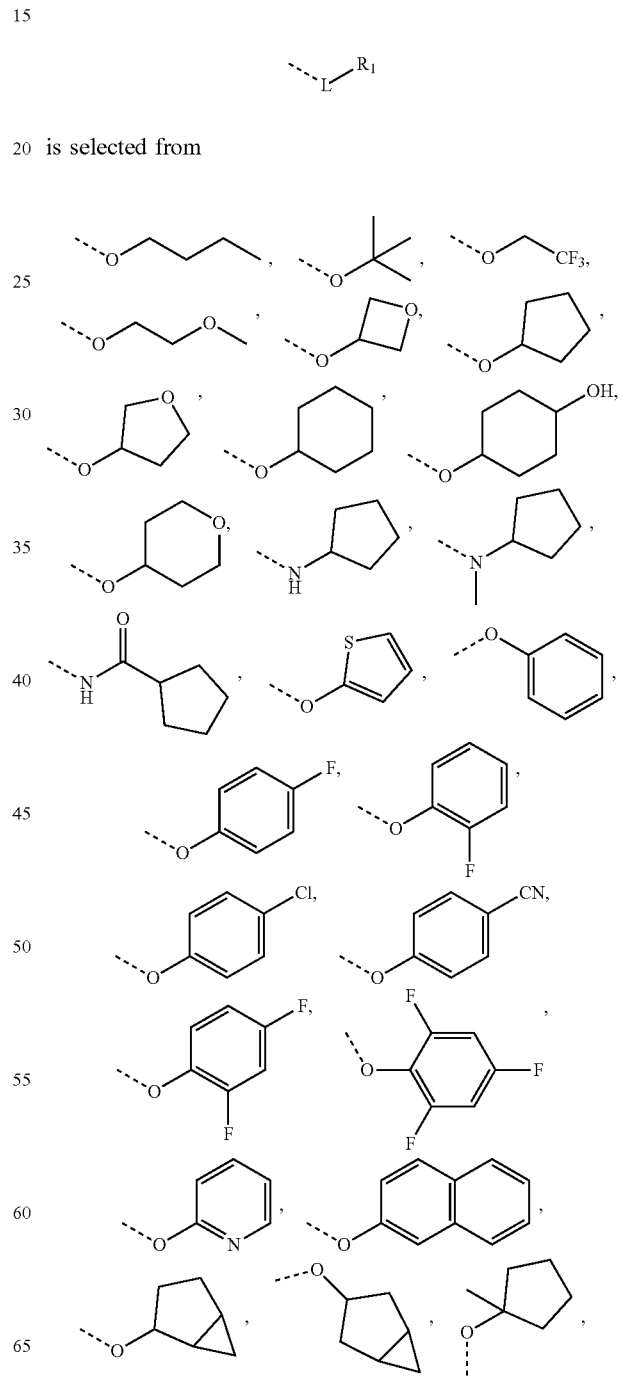

is selected from

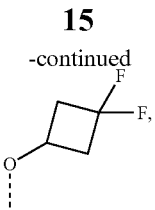

and other variables are as defined by the present disclosure.

In some embodiments of the present disclosure, the above $R_2$ is selected from H, halogen, OH, $NH_2$ and CN; or selected from the group consisting of $C_{1-3}$ alkyl, $C_{1-3}$ alkoxyl, $C_{1-3}$ alkylthio and $C_{1-3}$ alkylamino, wherein each is optionally substituted by one, two or three R groups. Other variables are as defined by the present disclosure.

In some embodiments of the present disclosure, the above $R_2$ is selected from H, F, Cl, Br, I, OH, $NH_2$, CN, Me, and

and other variables are as defined by the present disclosure.

In some embodiments of the present disclosure, the above $R_3$ is selected from the group consisting of phenyl, pyridyl, pyrimidinyl, pyrazinyl, thienyl, thiazolyl, isothiazolyl, oxazolyl, isoxazolyl, tetrahydropyranyl, piperidinyl and morpholinyl, wherein each is optionally substituted by one, two or three R groups. Other variables are as defined by the present disclosure.

In some embodiments of the present disclosure, the above $R_3$ is selected from

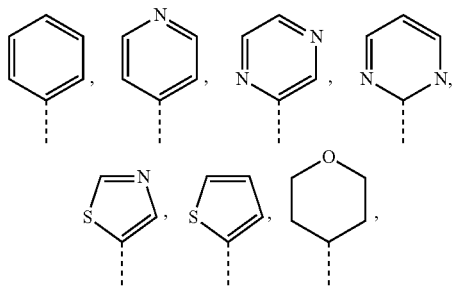

wherein each is optionally substituted by one, two or three R groups. Other variables are as defined by the present disclosure.

In some embodiments of the present disclosure, the above $R_3$ is selected from

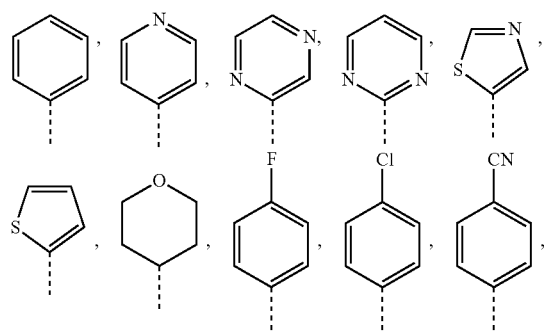

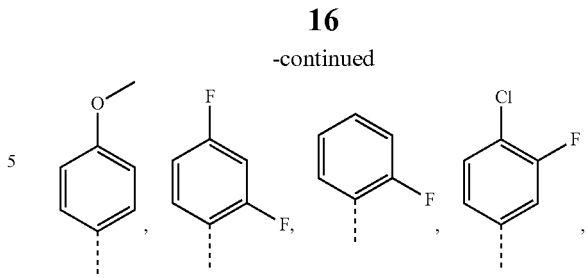

and other variables are as defined by the present disclosure.

In some embodiments of the present disclosure, the above structural unit

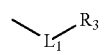

is selected from

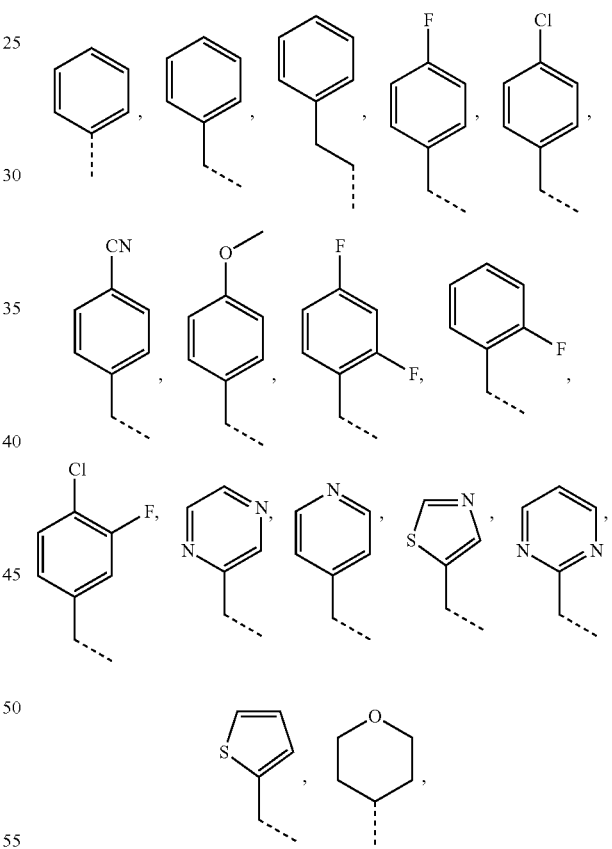

and other variables are as defined by the present disclosure.

In some embodiments of the present disclosure, the above $R_4$ is selected from H and Me.

In some embodiments of the present disclosure, the above $R_4$ is selected from H and Me, and other variables are as defined by the present disclosure.

In some embodiments of the disclosure, the above compound and the pharmaceutically acceptable salt thereof are selected from the group consisting of

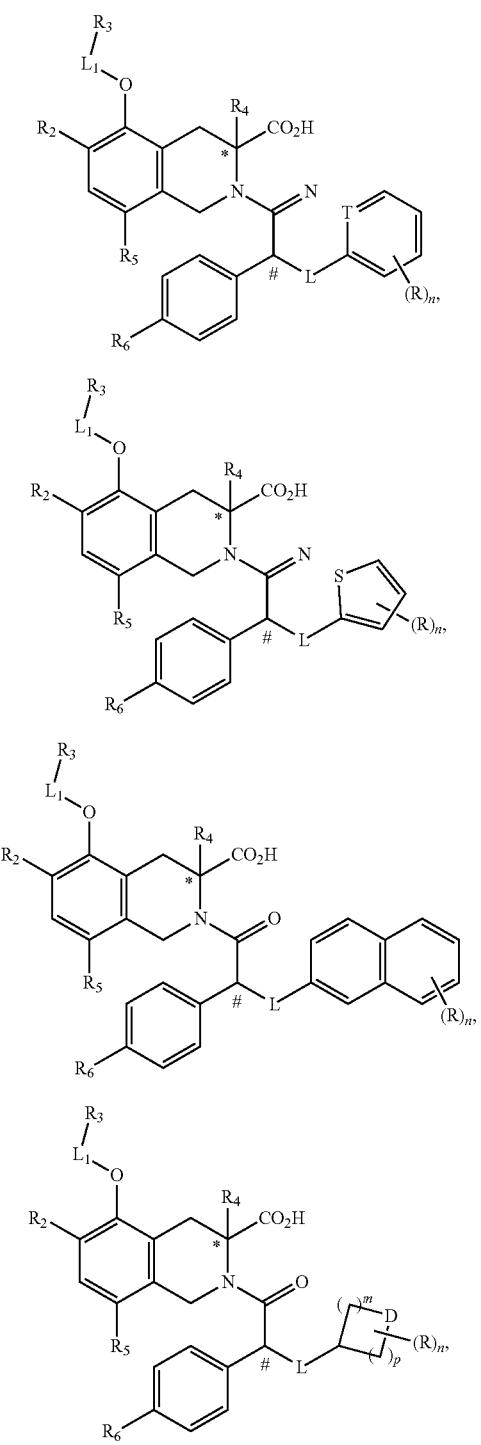

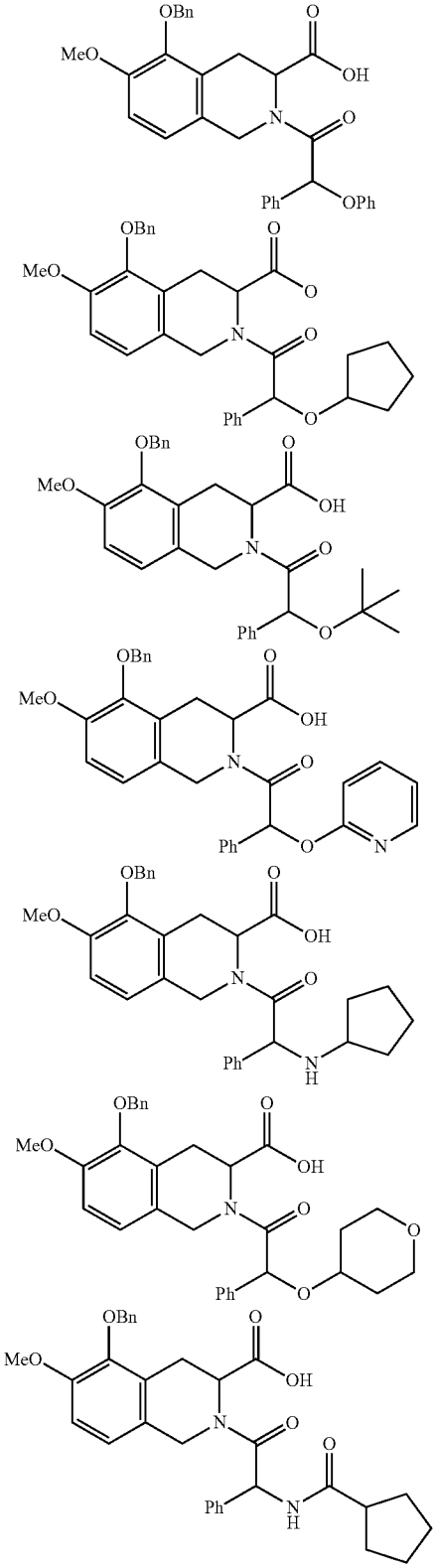

Some embodiments of the present disclosure are arbitrarily combined by the above variables.

The present disclosure provides a compound of the following formula selected from the group consisting of wherein,
R, $R_2$, $R_3$, $R_4$, $R_5$, $R_6$, $L_1$ and L are as defined above;
T is selected from N or CH;
D is selected from $CH_2$ or O;
m and p are each independently selected from 0, 1, 2 or 3, and m and p are not simultaneously selected from 0 or 3;
n is selected from 0, 1, 2 or 3;
and n is not selected from 3 when m is selected from 0, and D is selected from O.

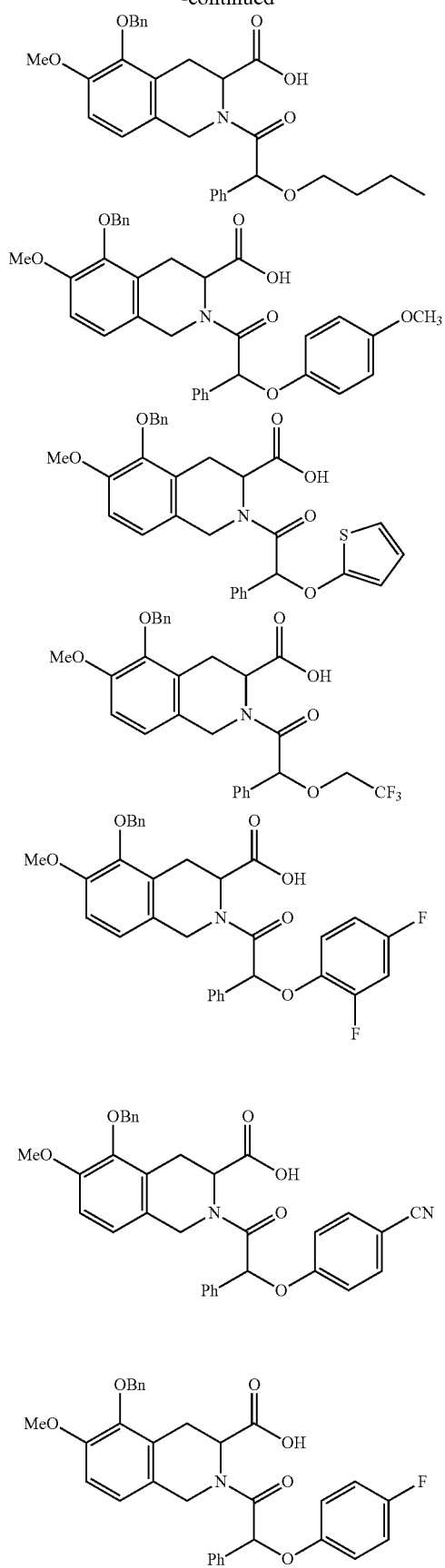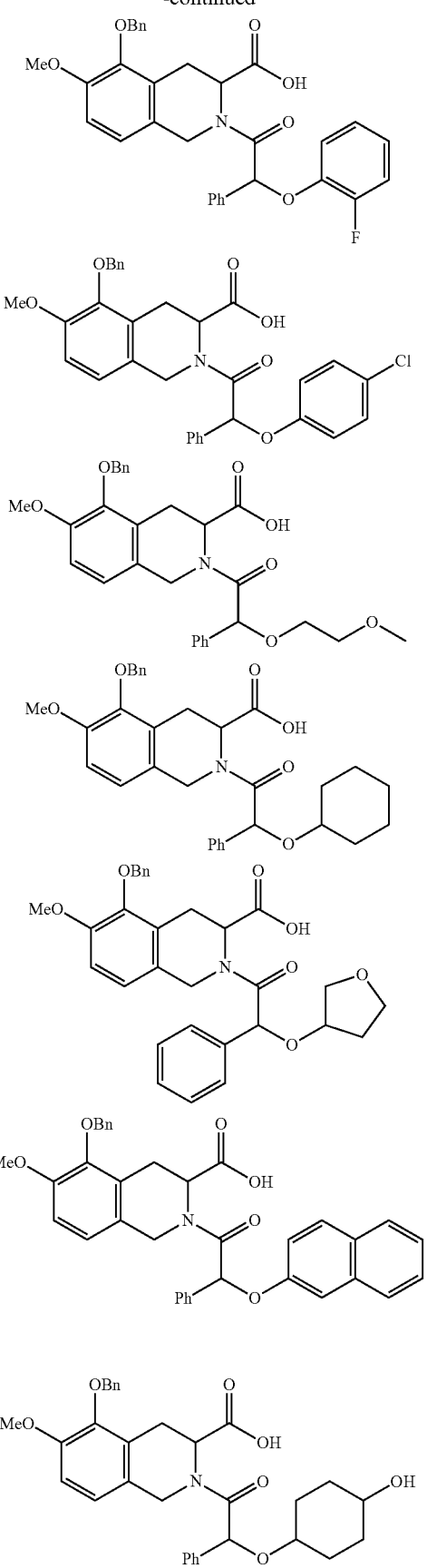

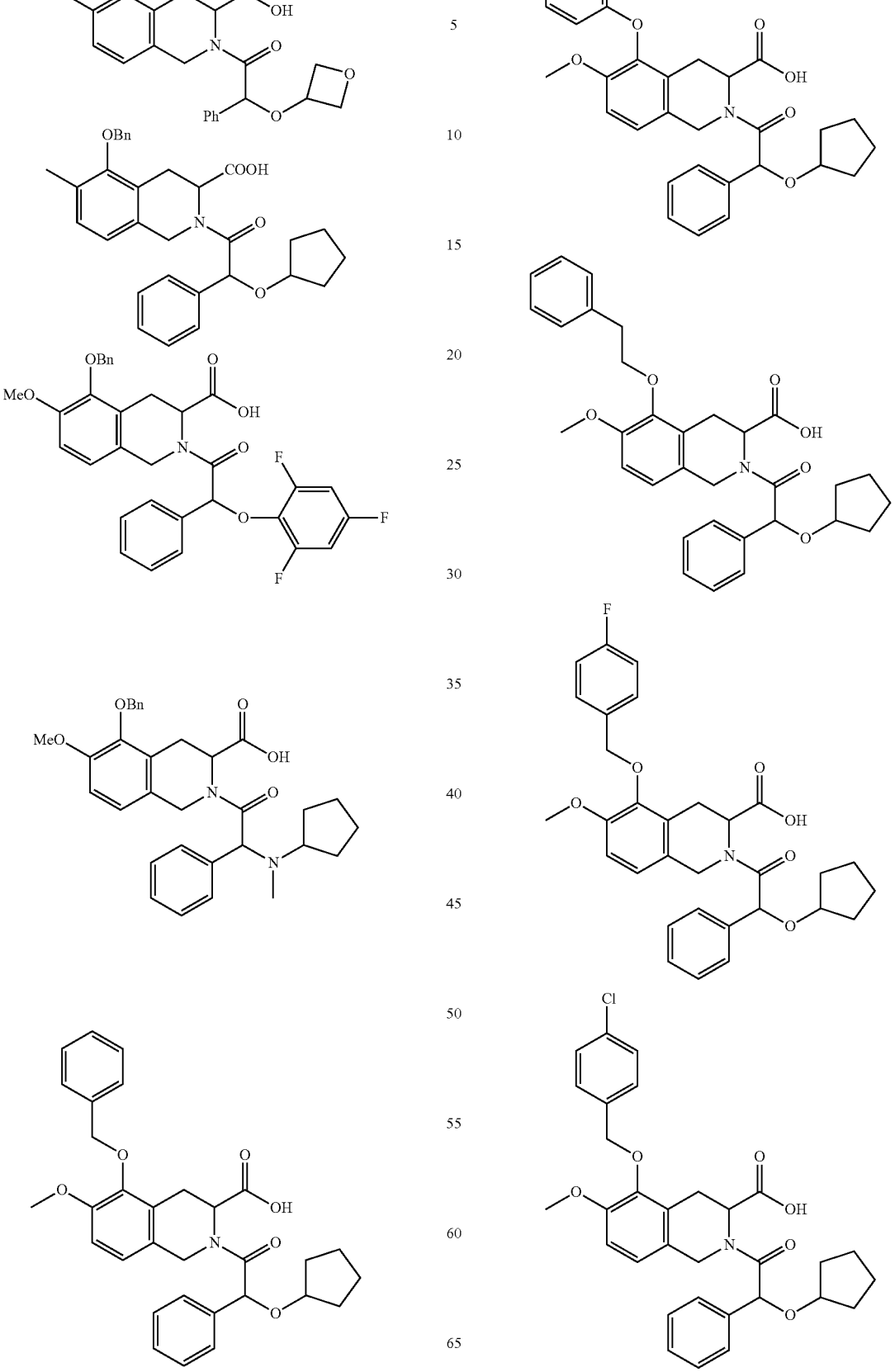

-continued
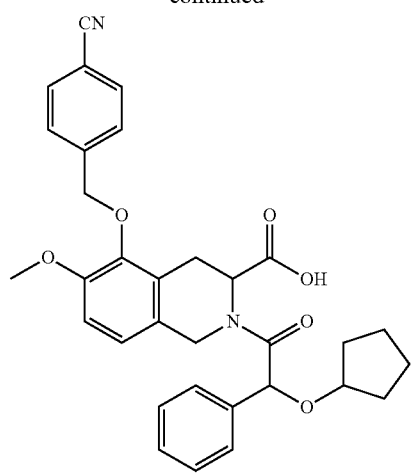
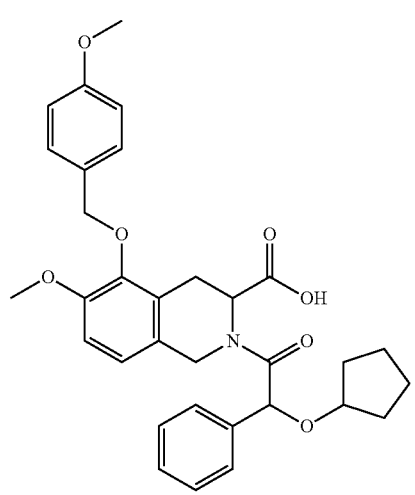
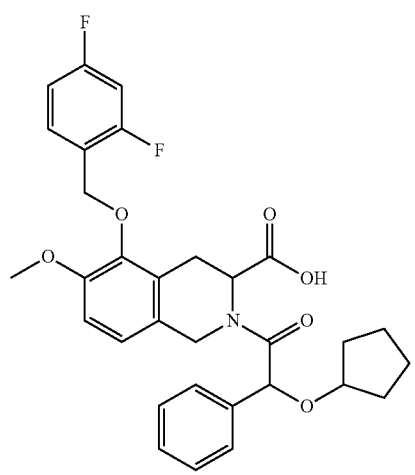
-continued
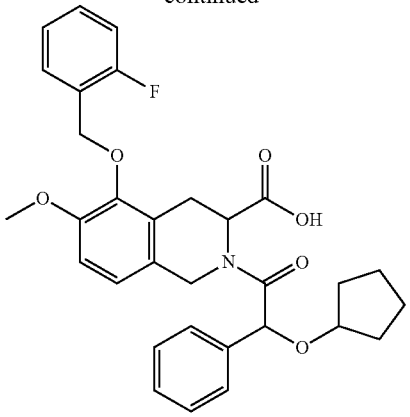
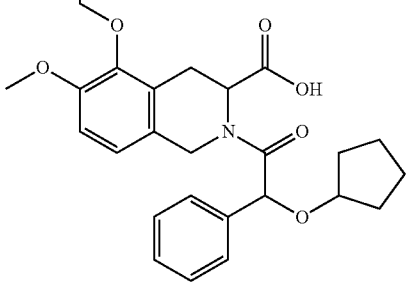
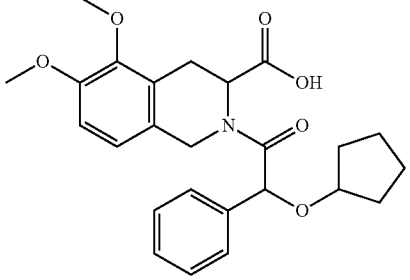
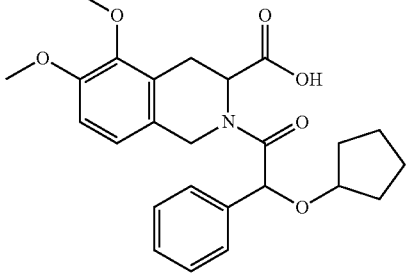

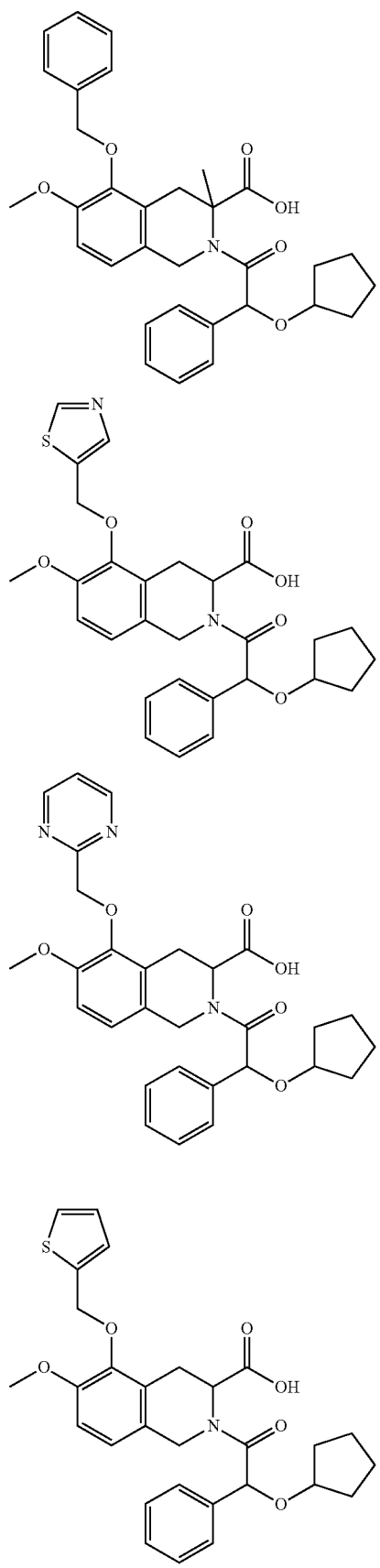
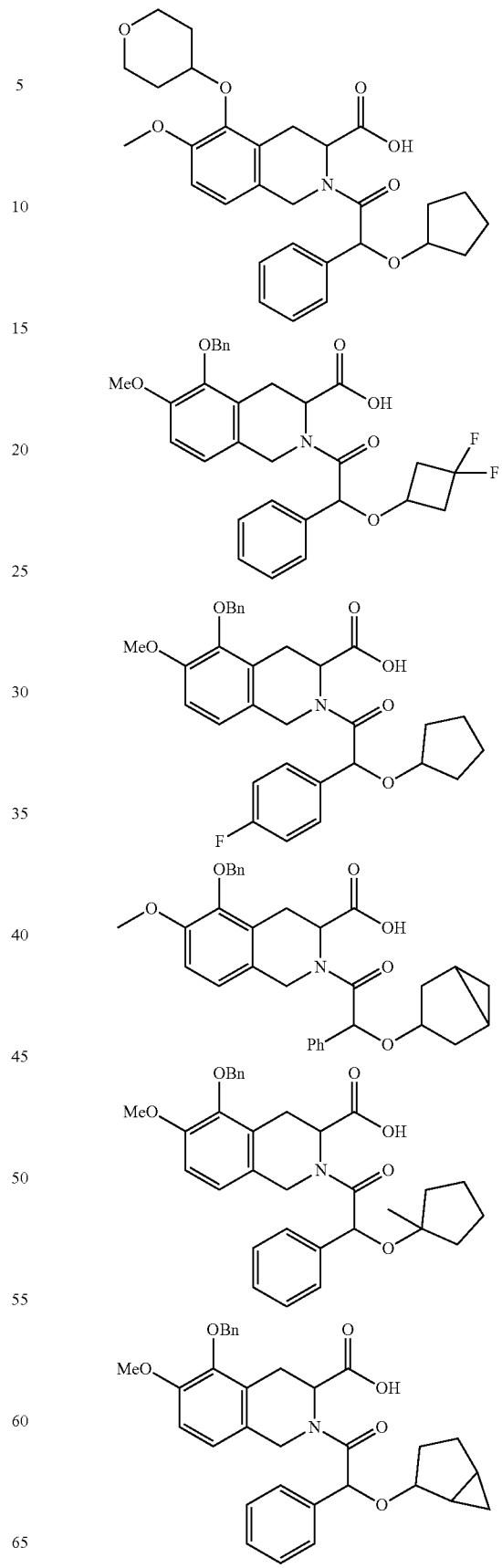

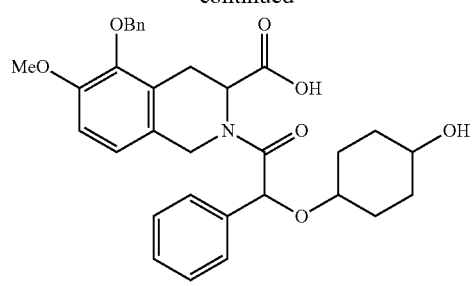
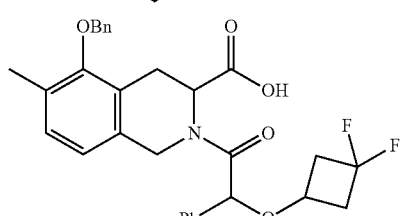
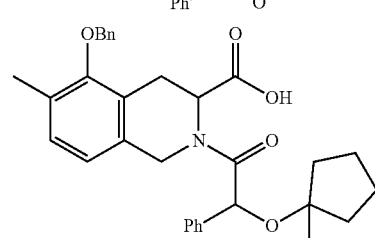
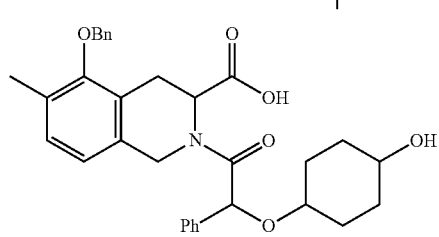
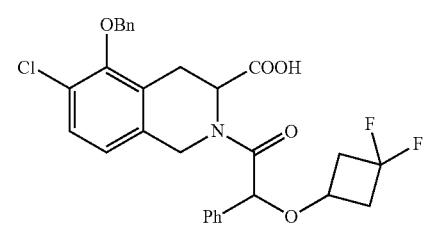
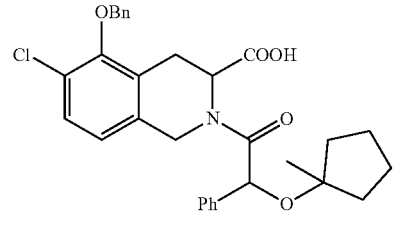
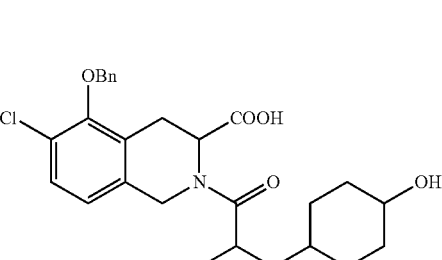
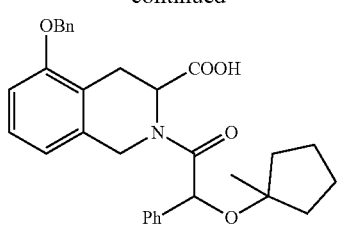
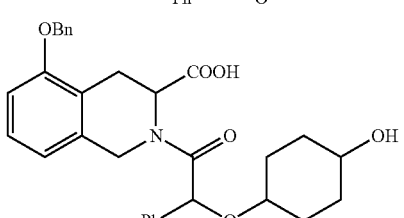
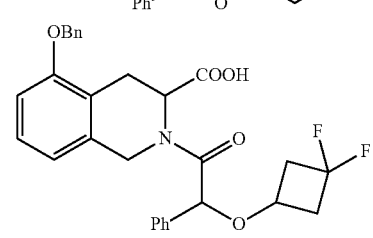
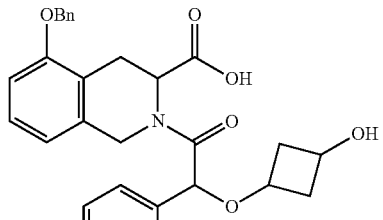
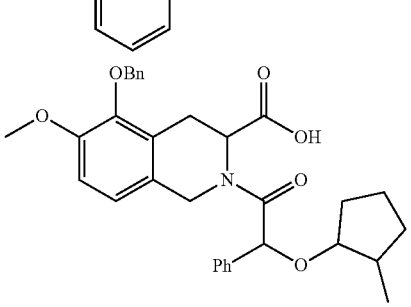
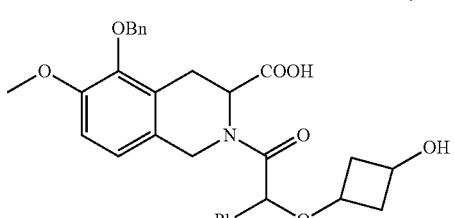
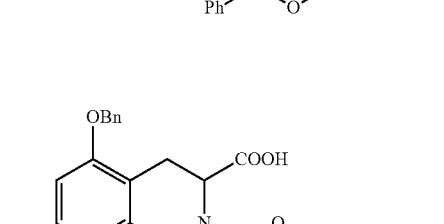

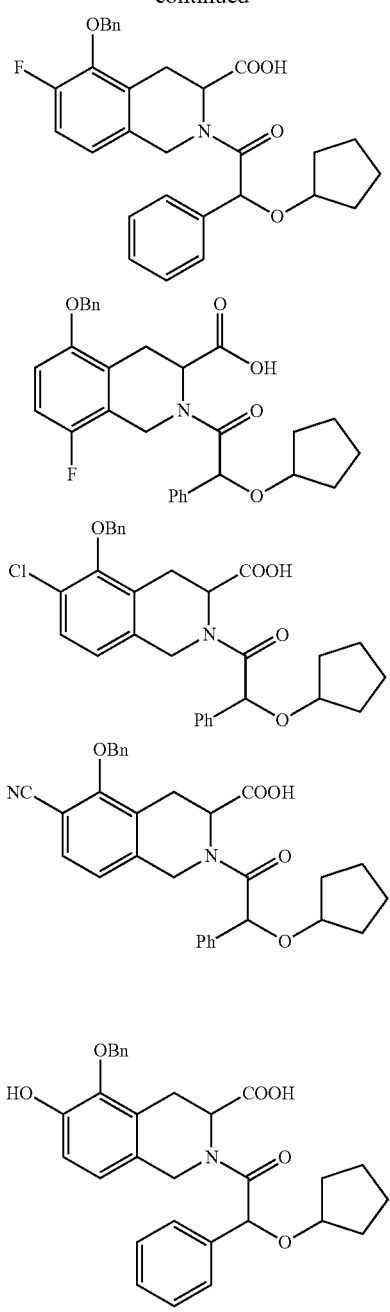
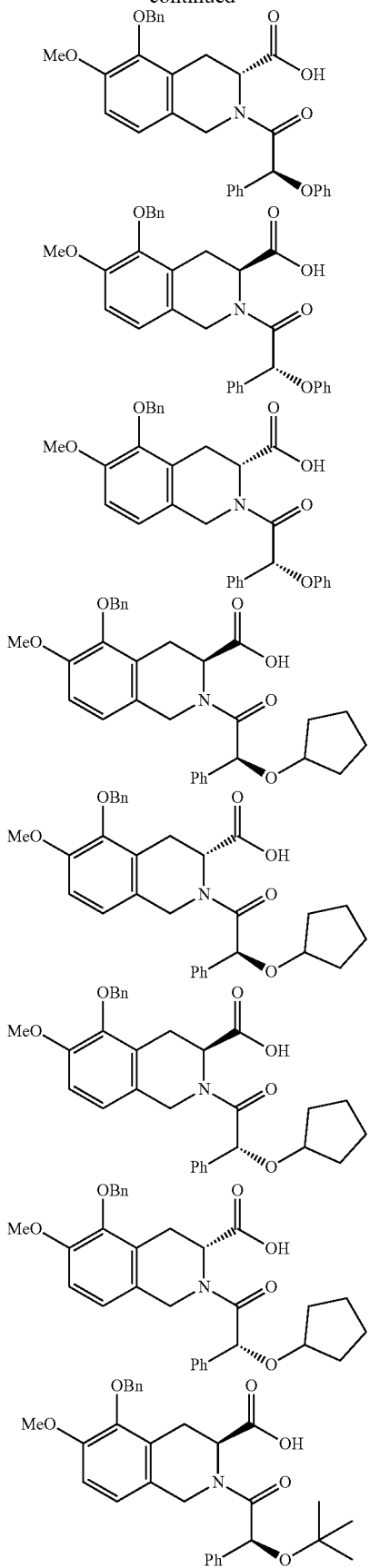
In some embodiments of the disclosure, the above compound is selected from the group consisting of
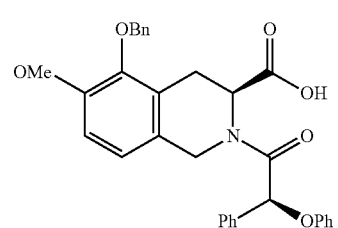

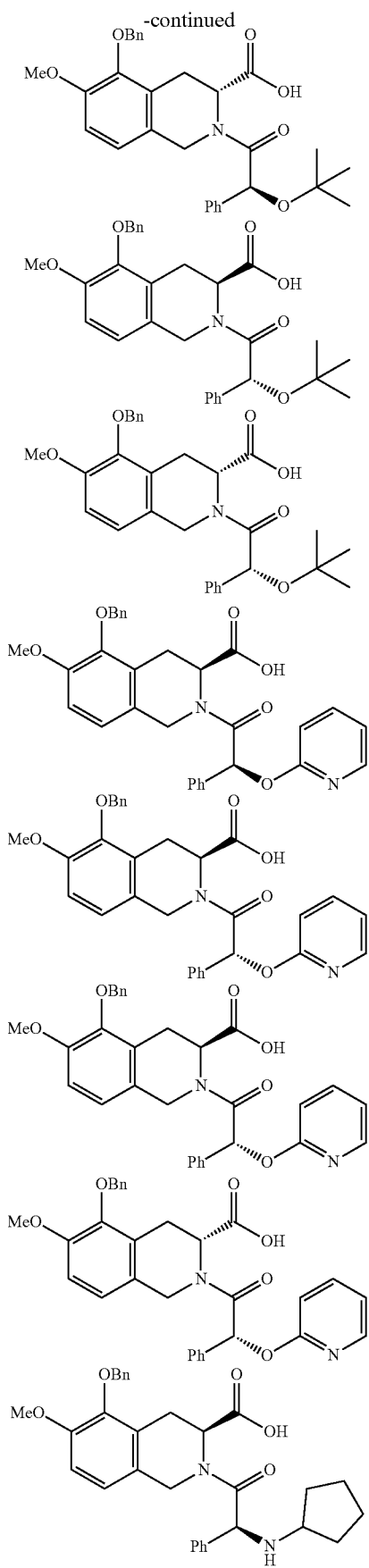
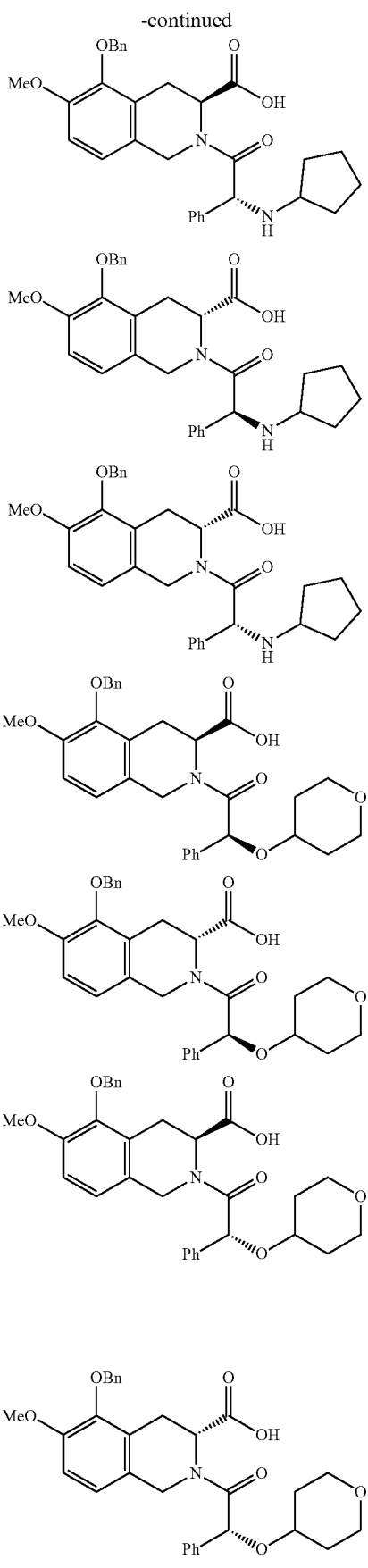

33
-continued
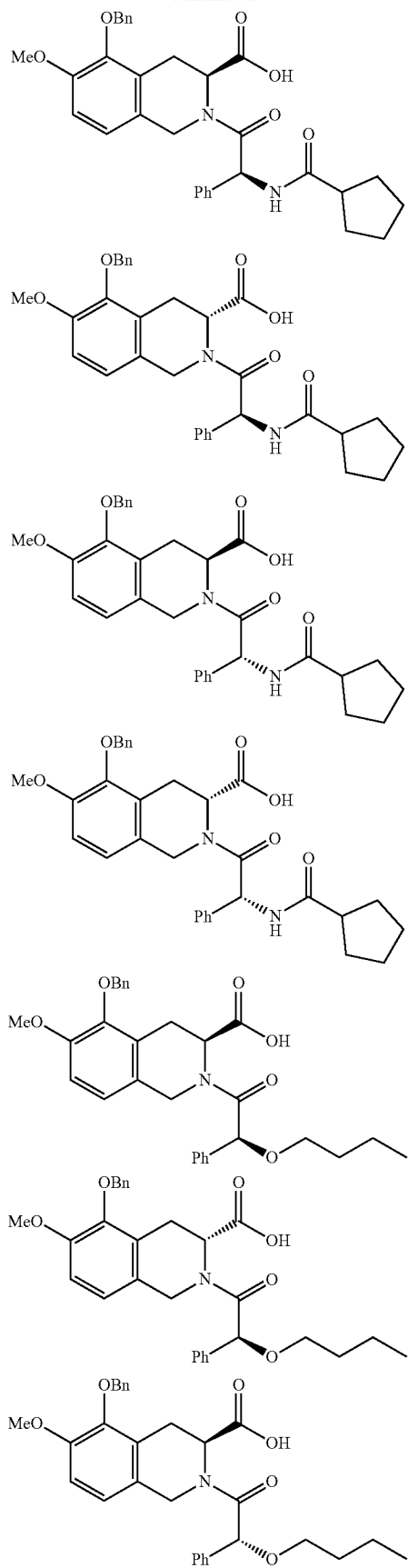
34
-continued
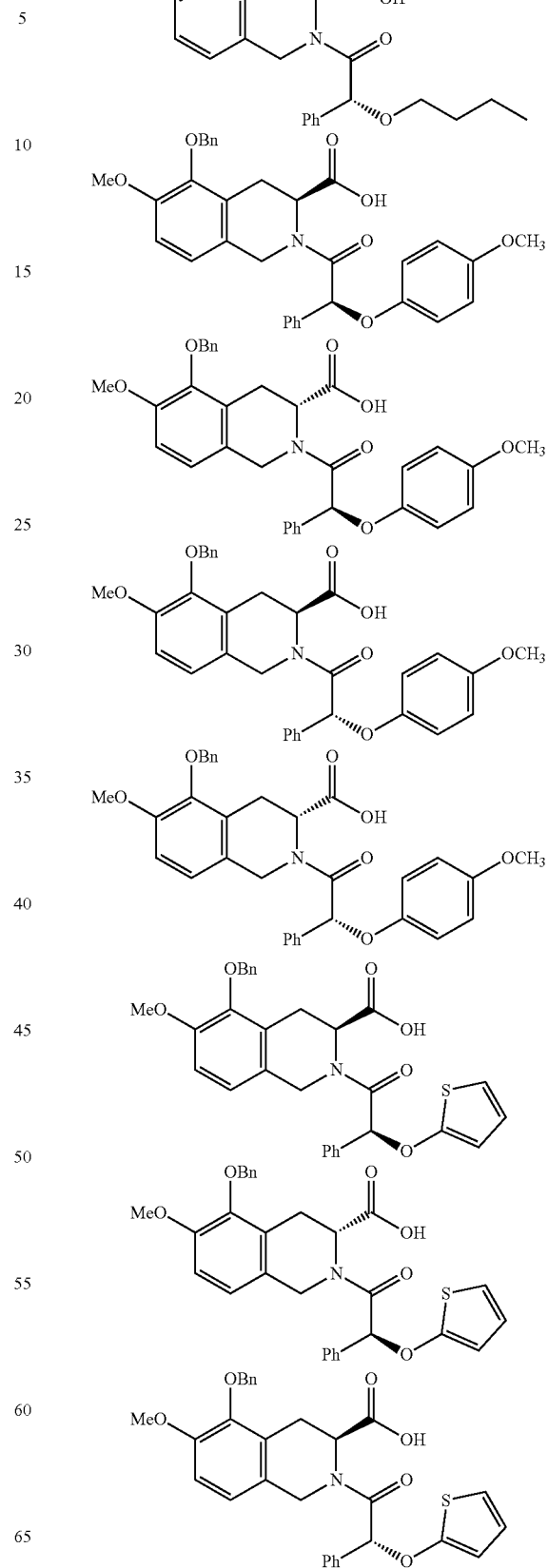

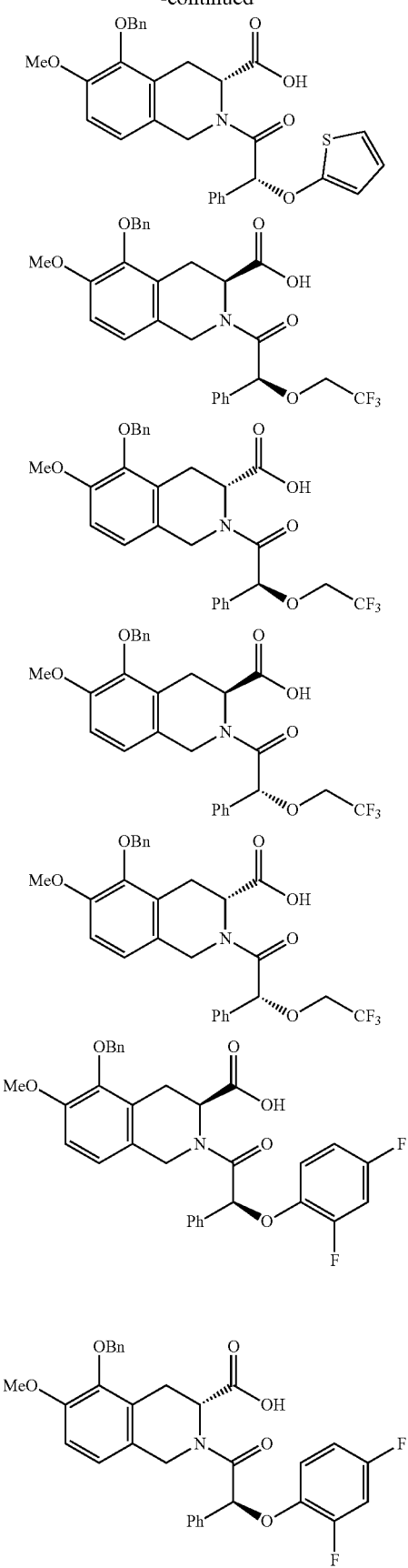
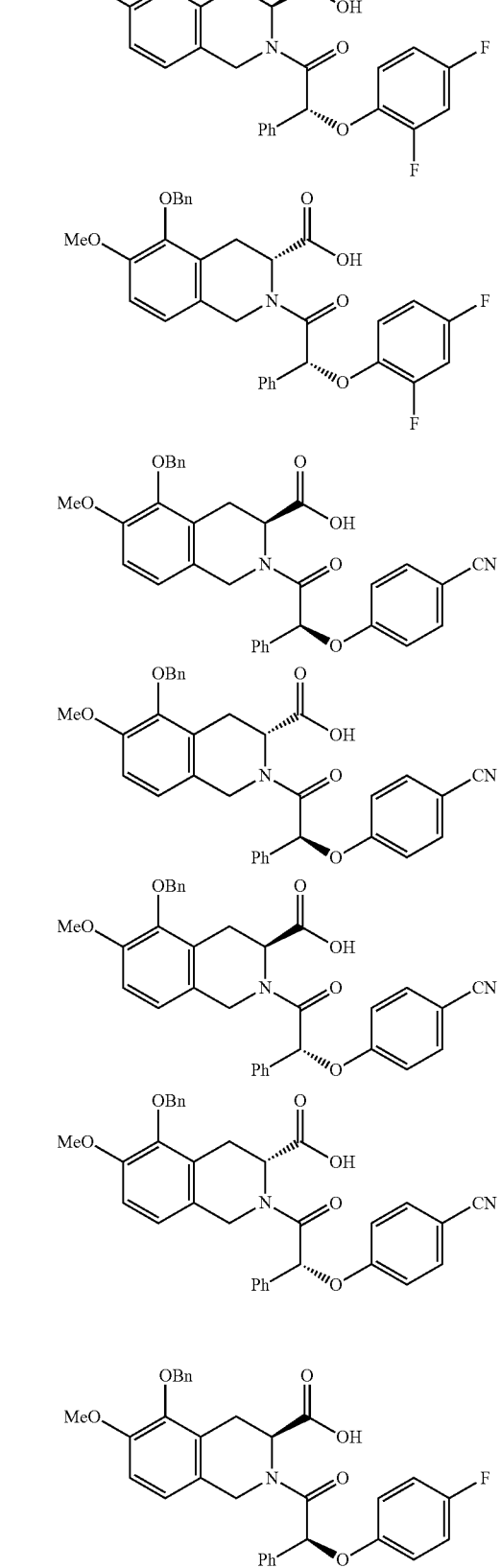

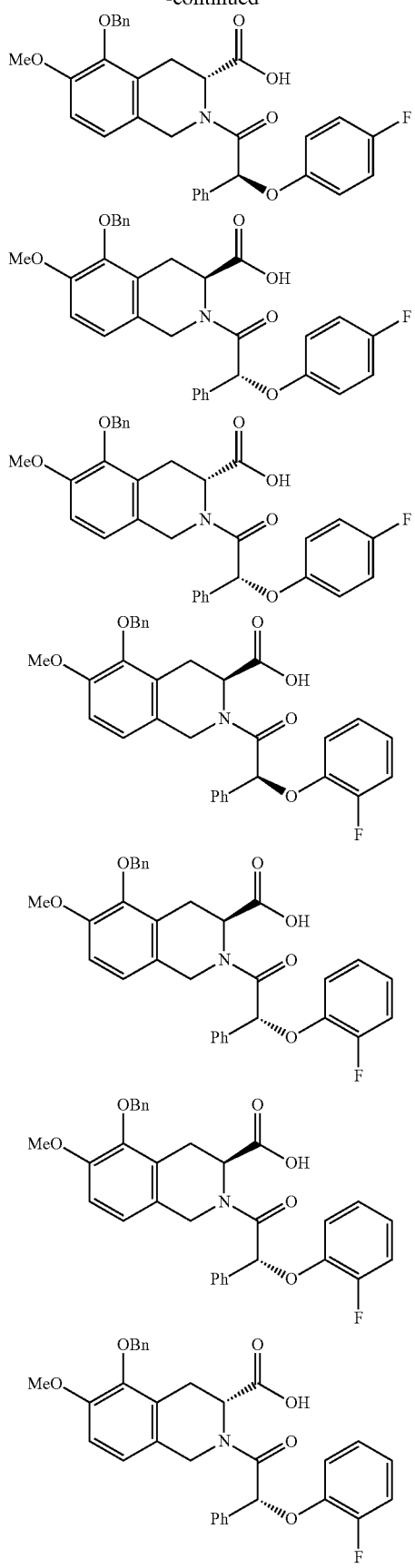
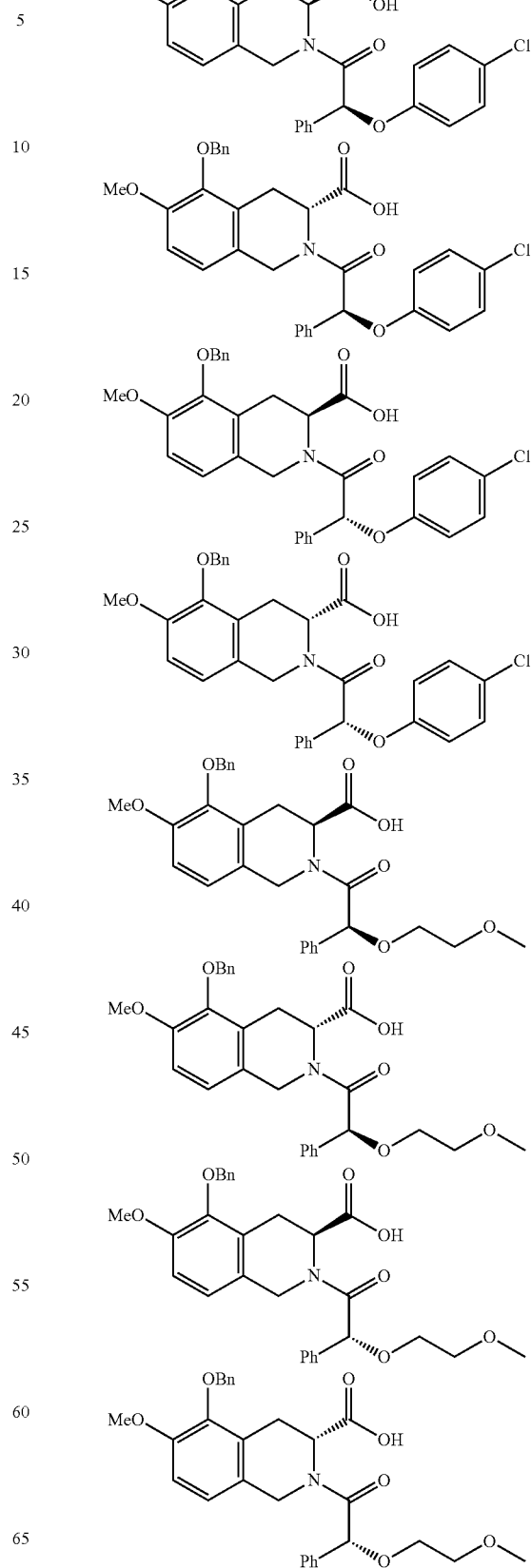

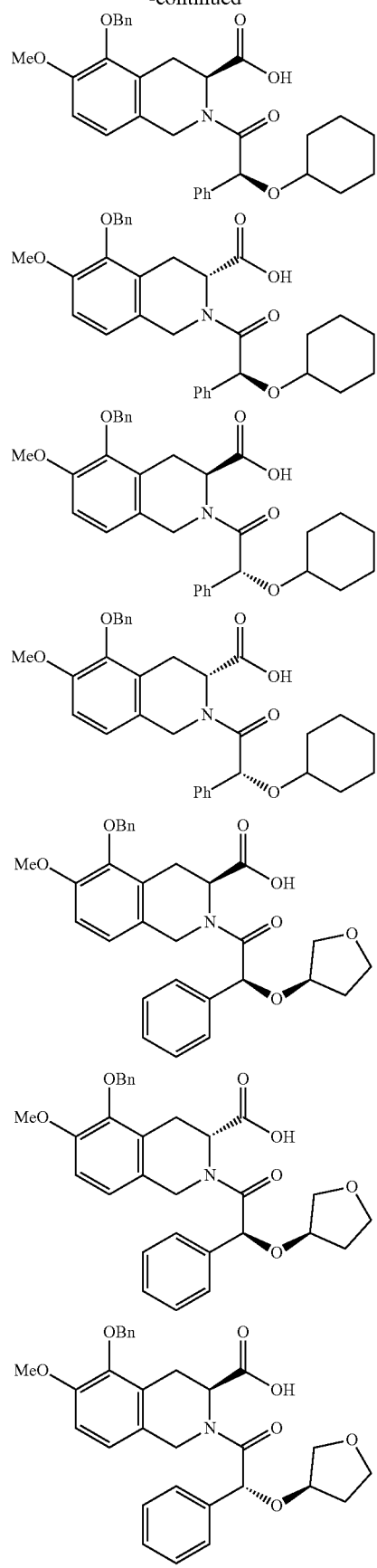
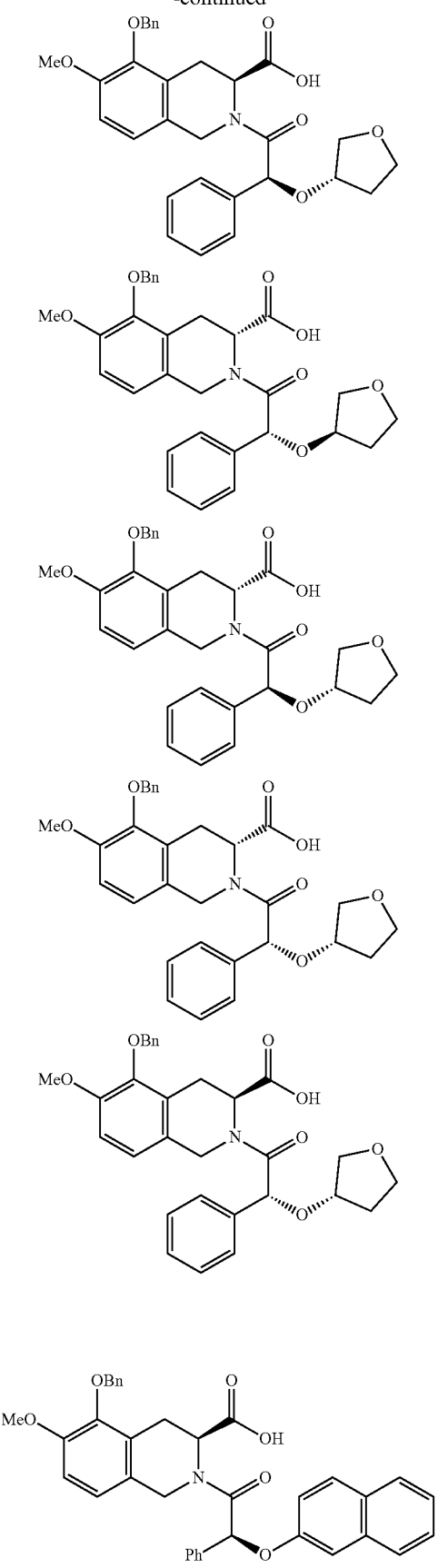

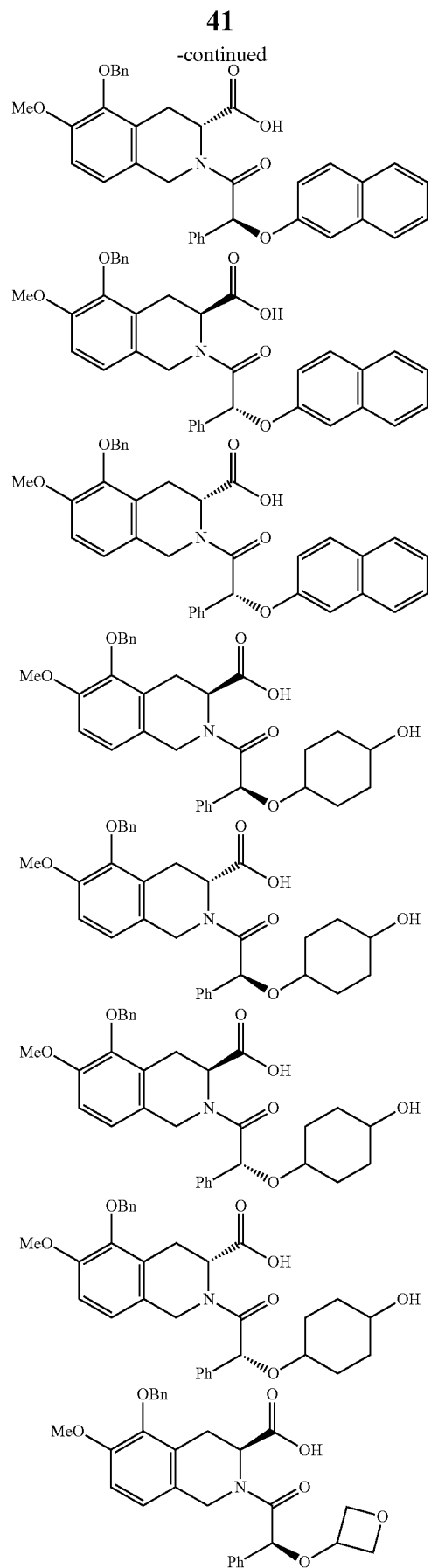
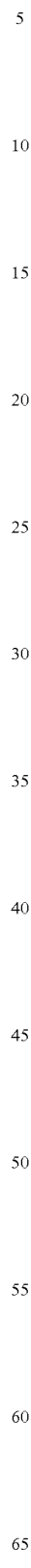
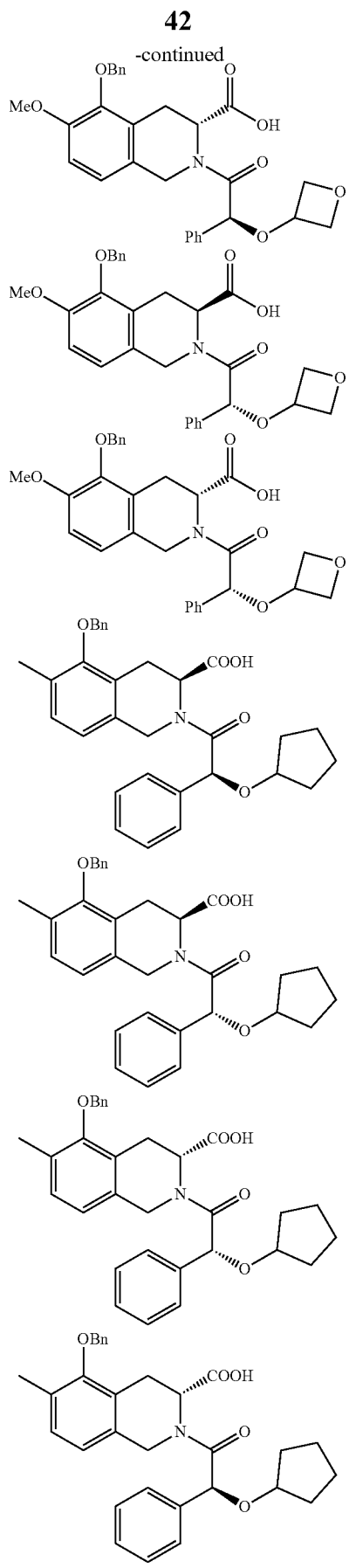

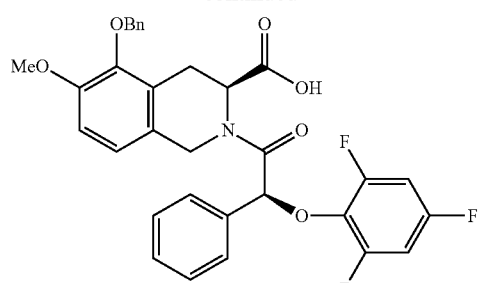
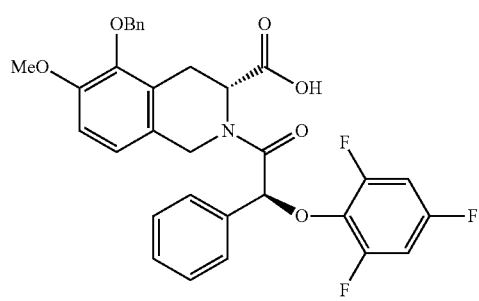
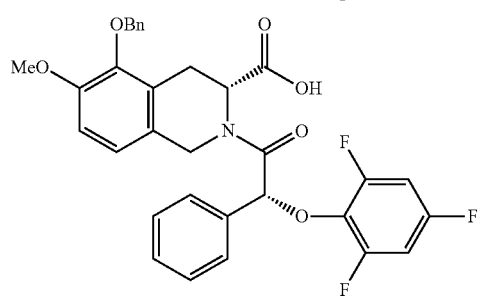
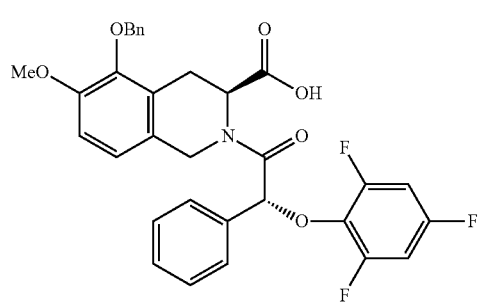
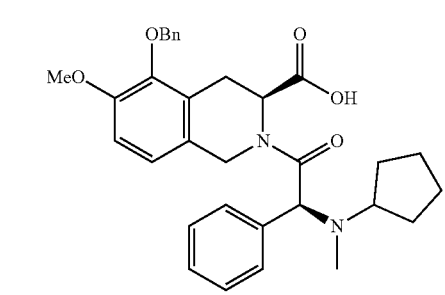
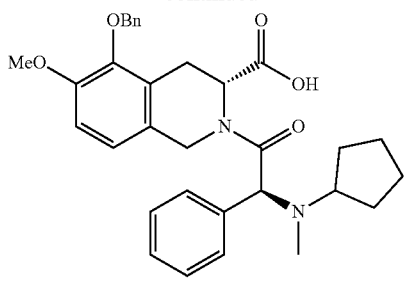
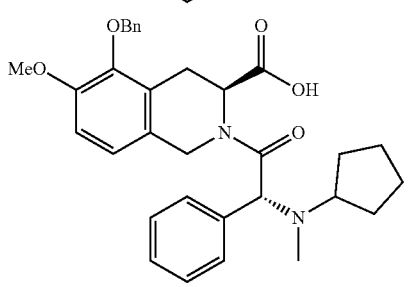
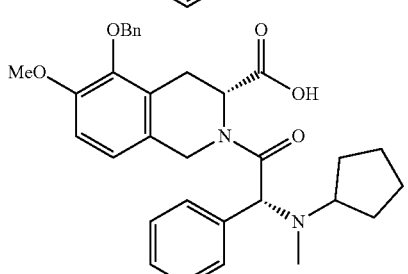
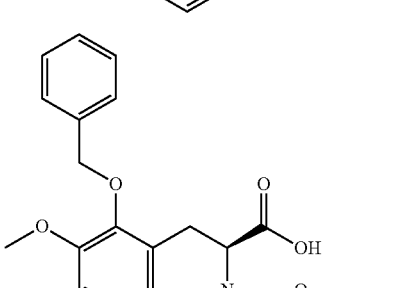
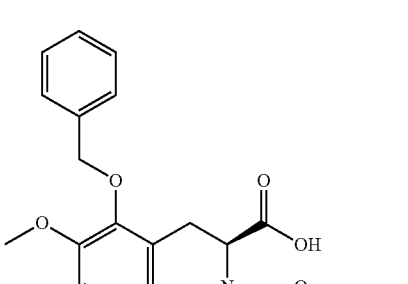

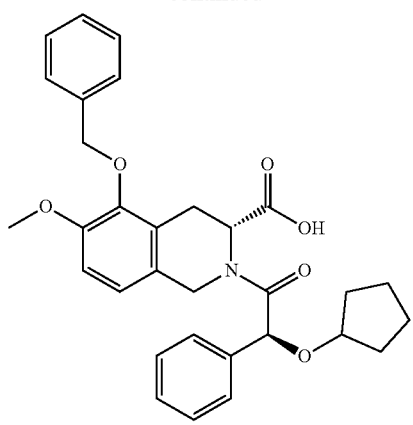
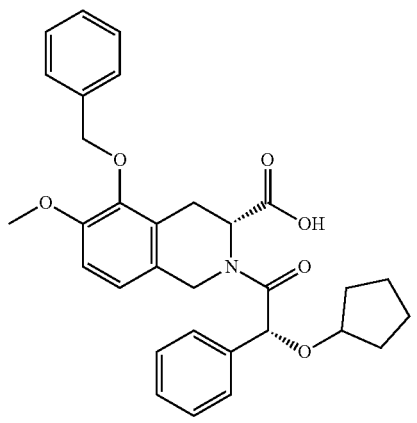
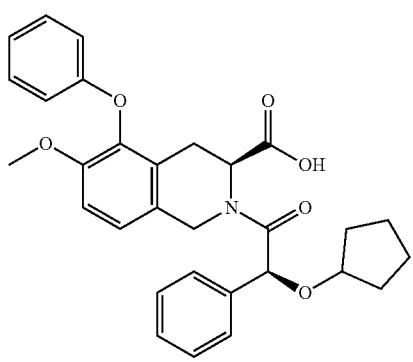
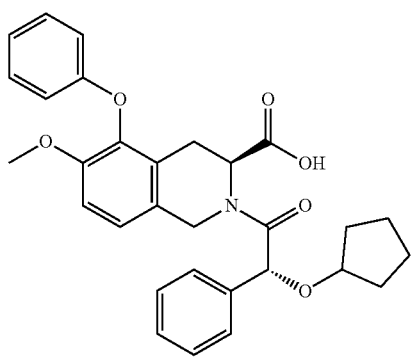
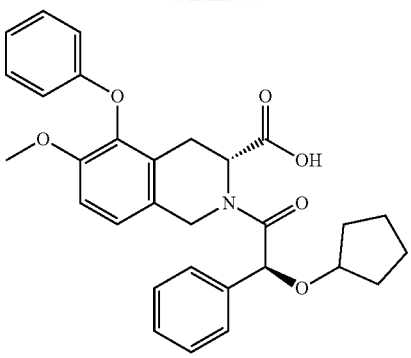
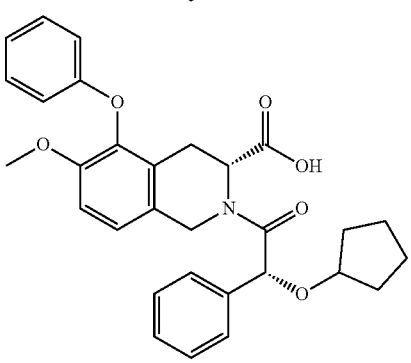
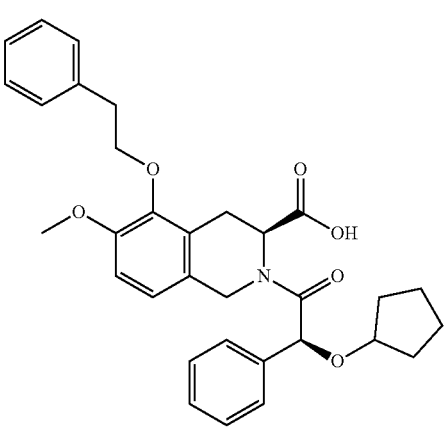
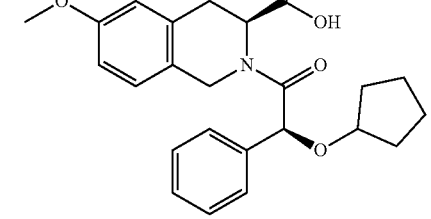

47
-continued
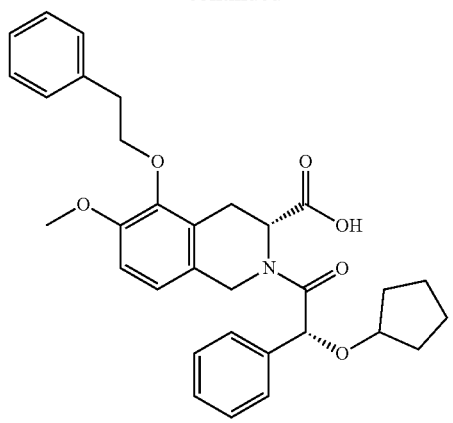
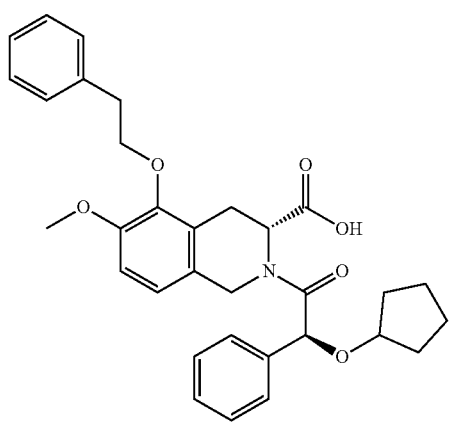
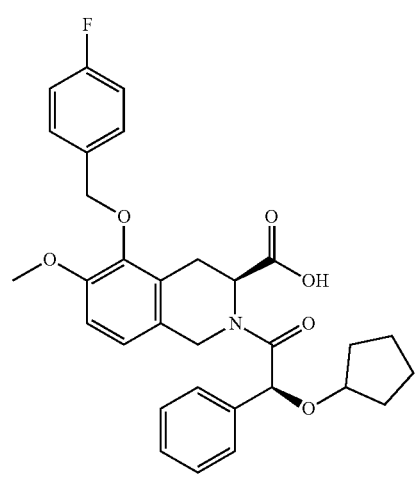
48
-continued
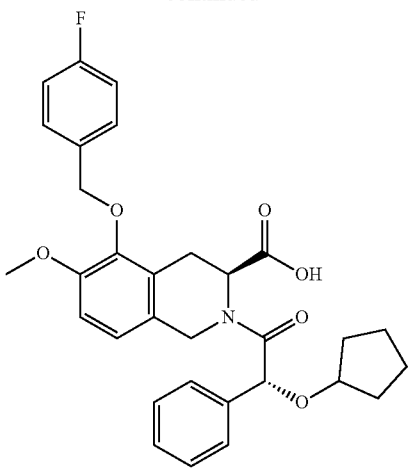
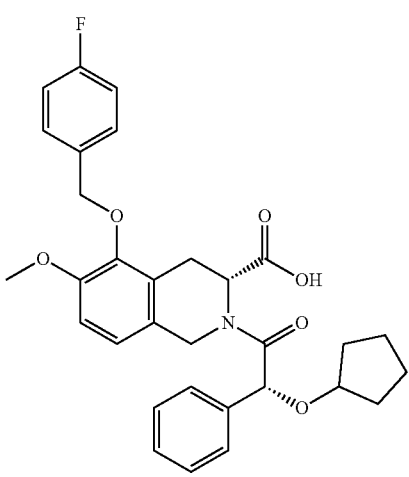
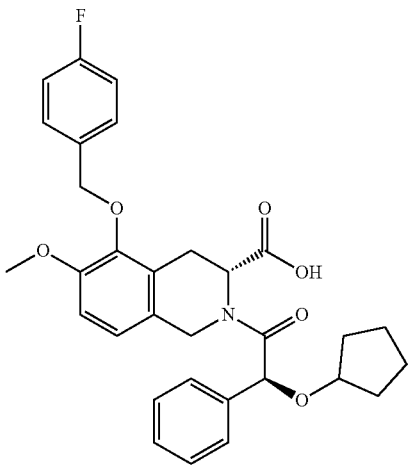

49
-continued
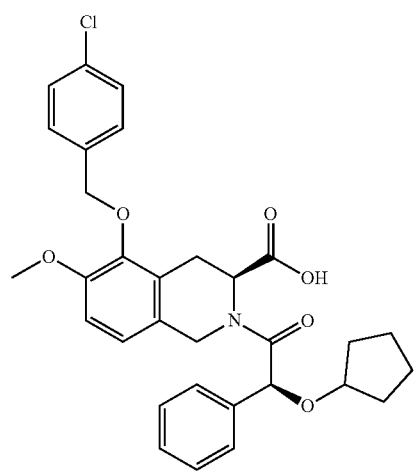
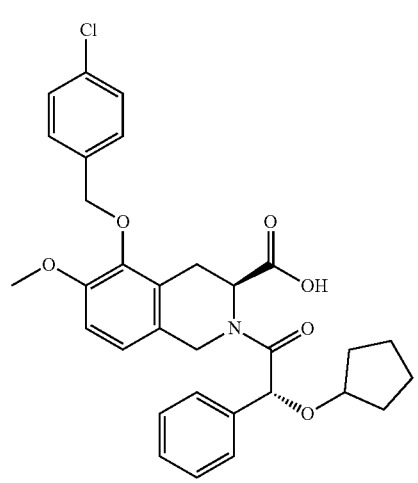
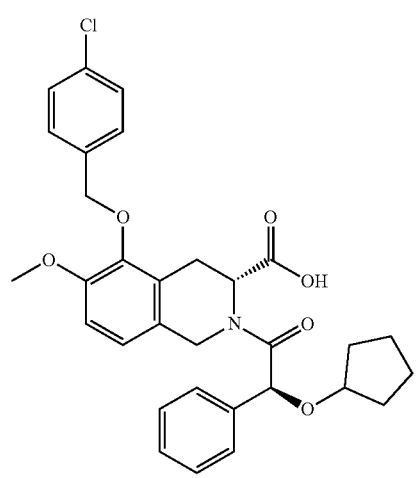
50
-continued
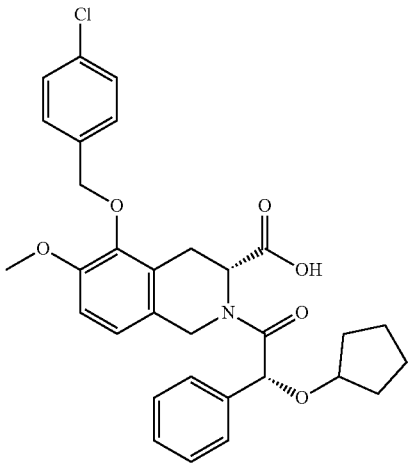
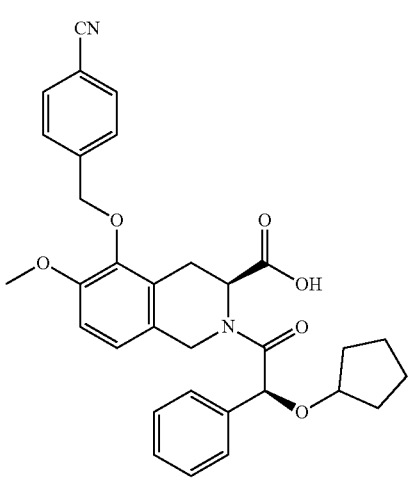
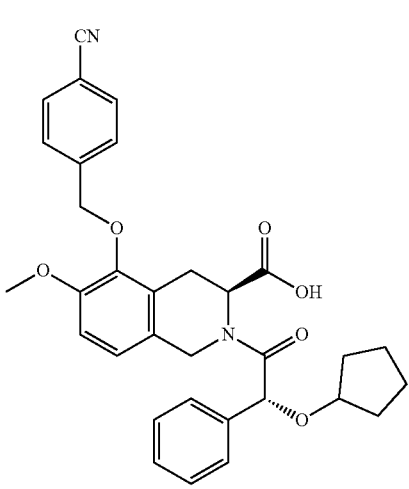

51
-continued
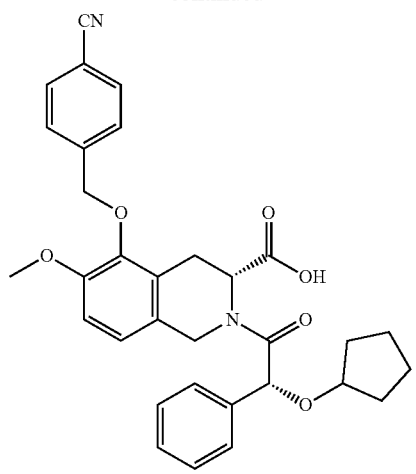
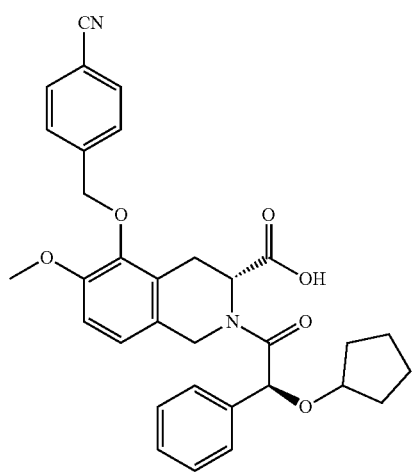
52
-continued
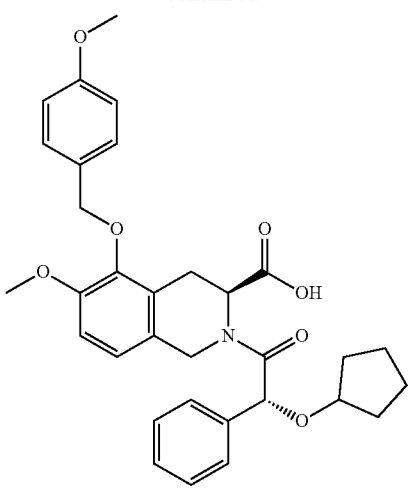
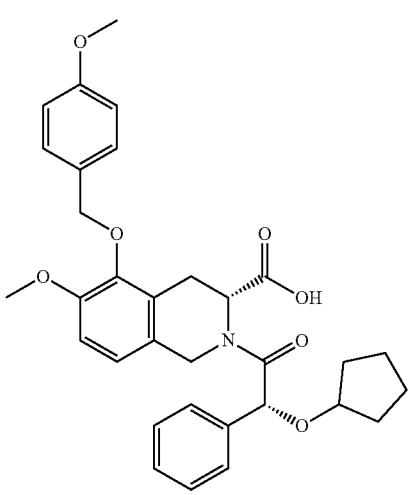

53
-continued
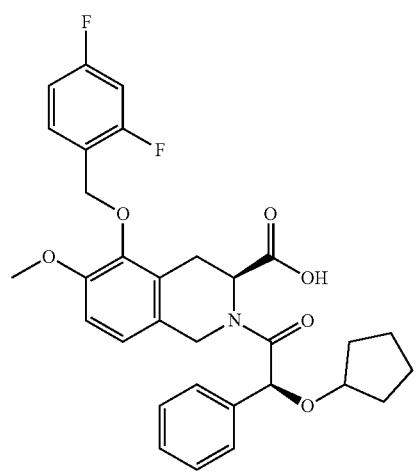
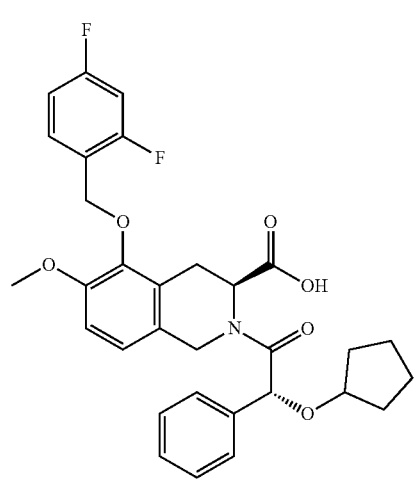
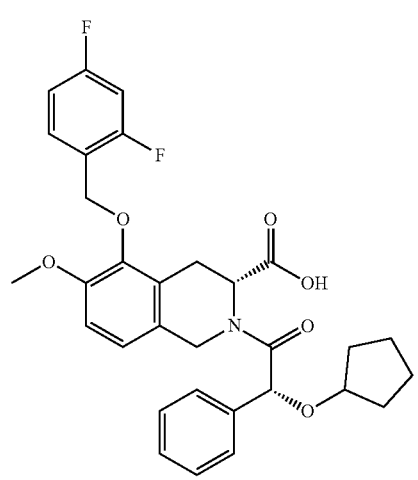
54
-continued
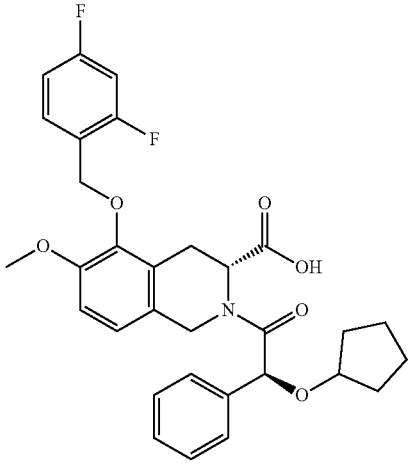
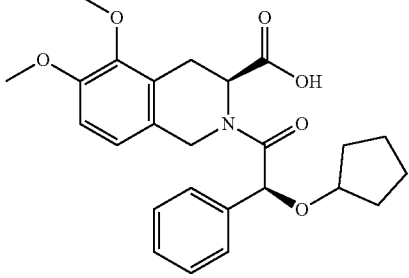
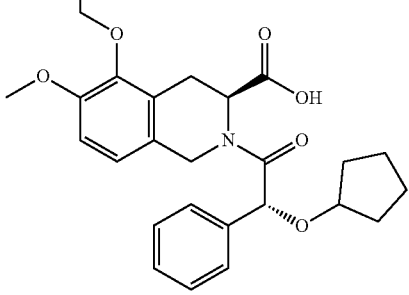
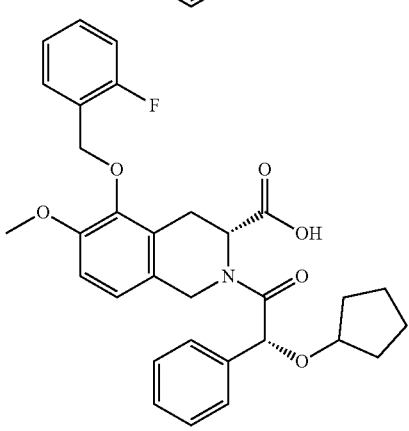

55
-continued
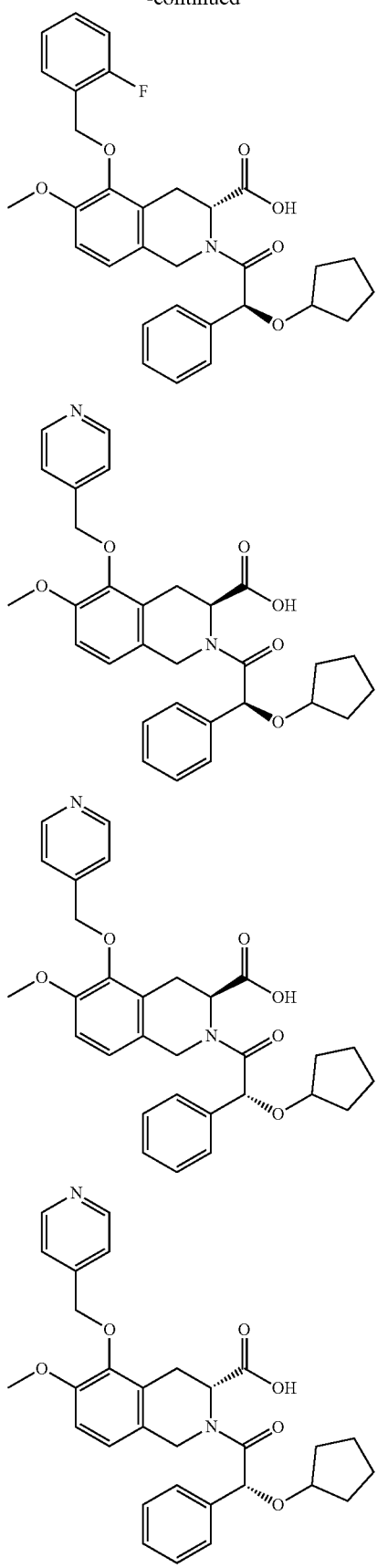
56
-continued
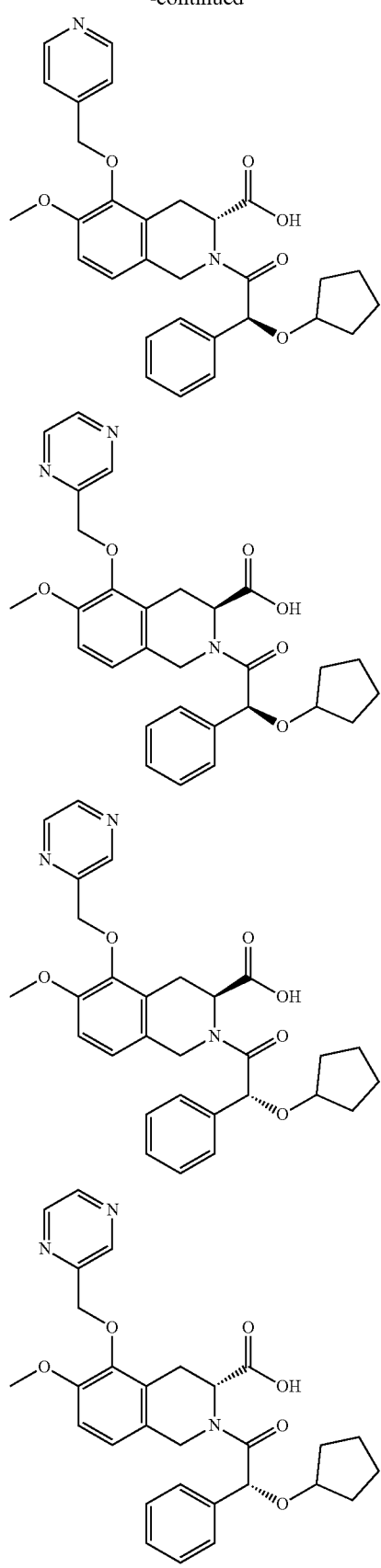

57
-continued
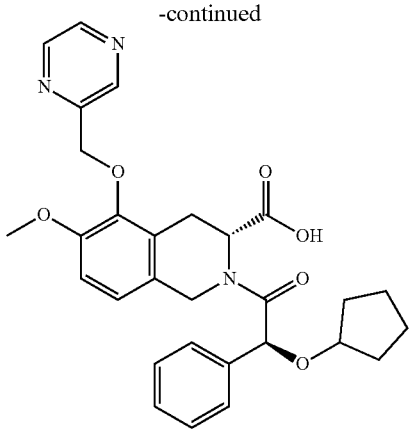
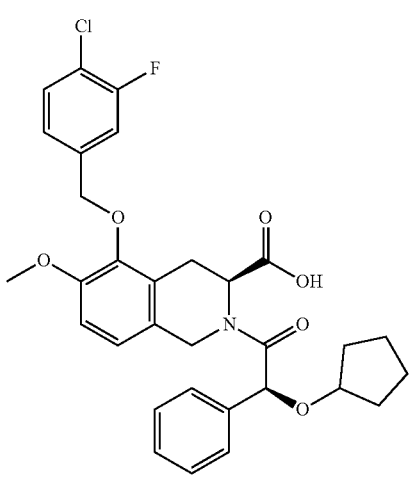
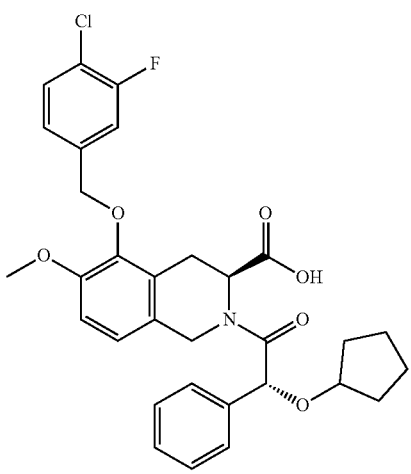
58
-continued
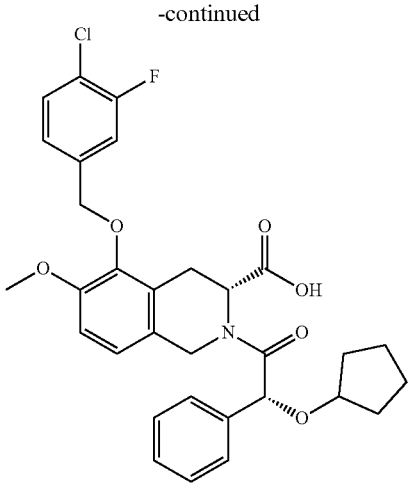
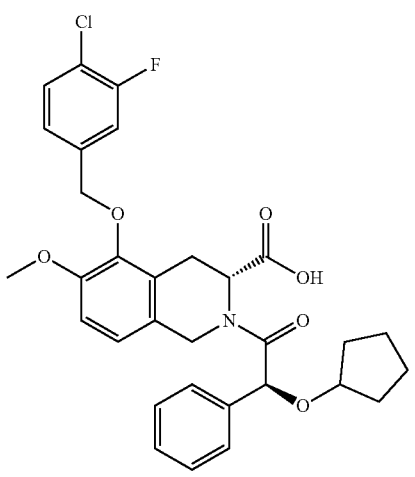
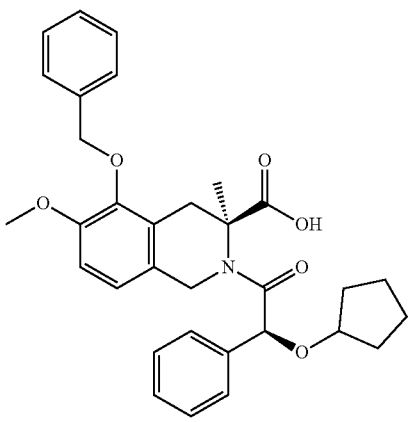

59
-continued
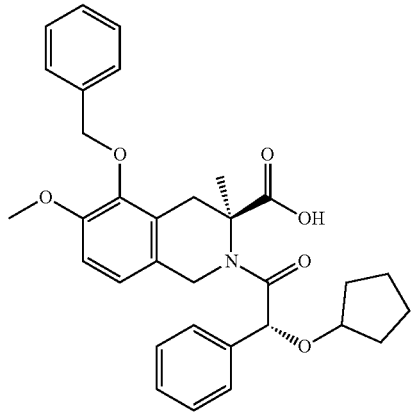
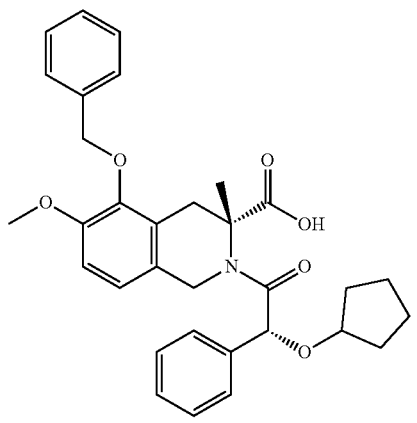
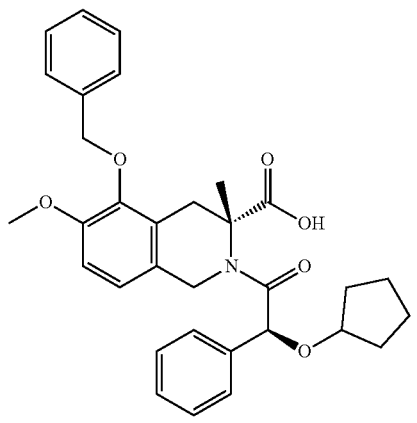
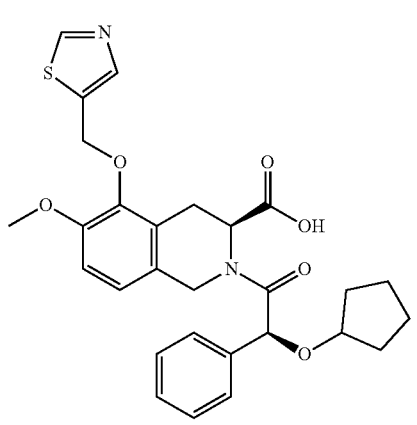
60
-continued
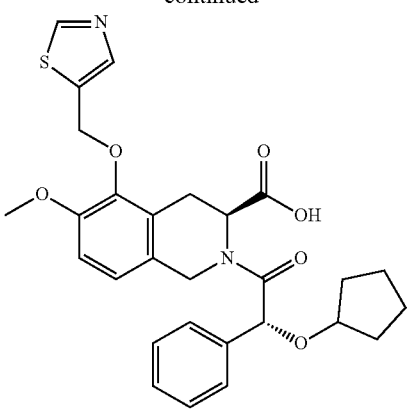
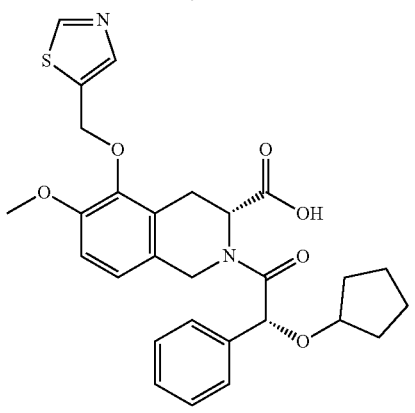
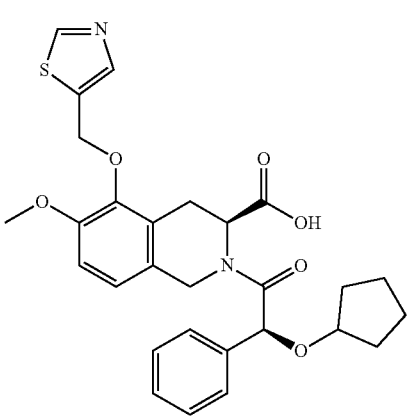

-continued
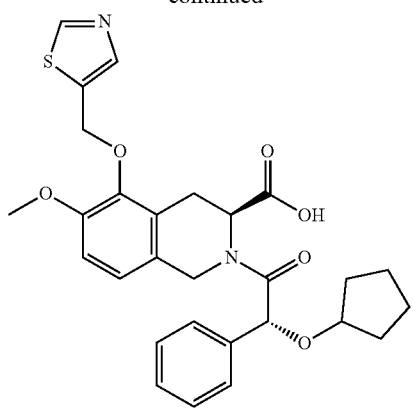
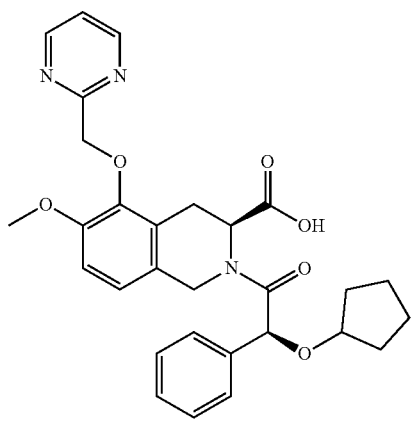
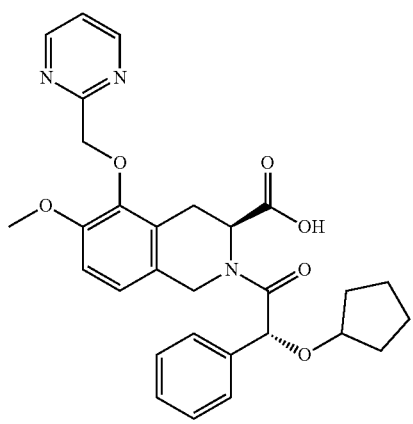
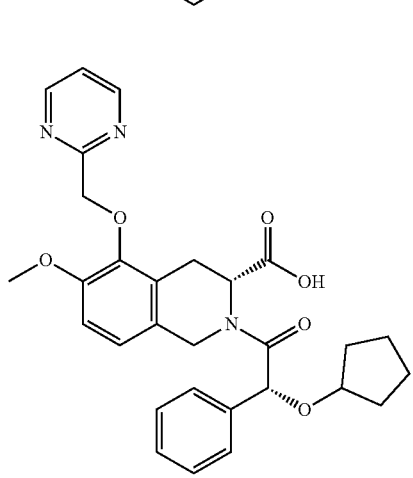
-continued
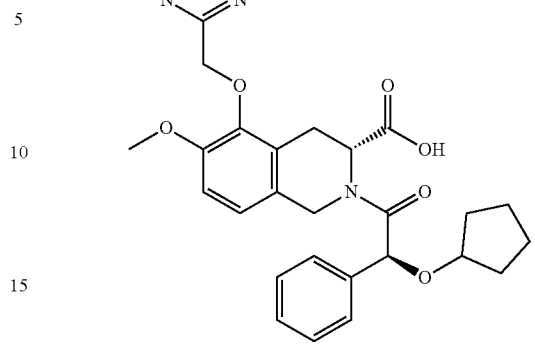
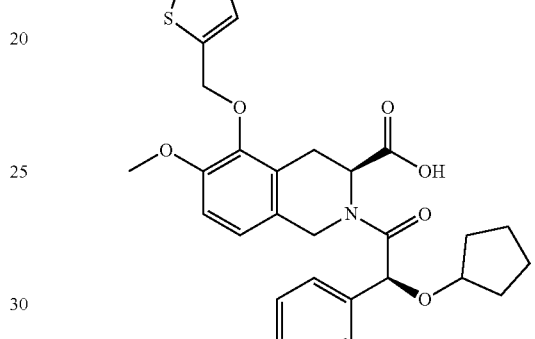
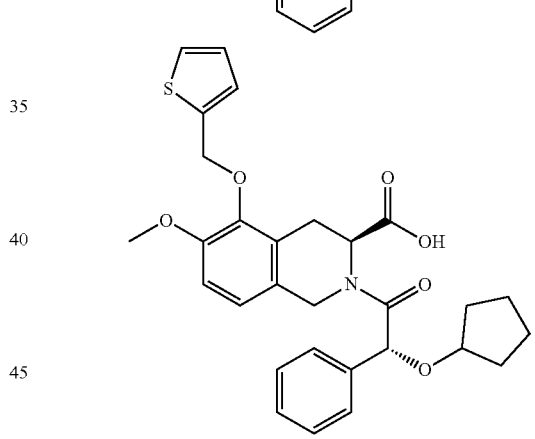
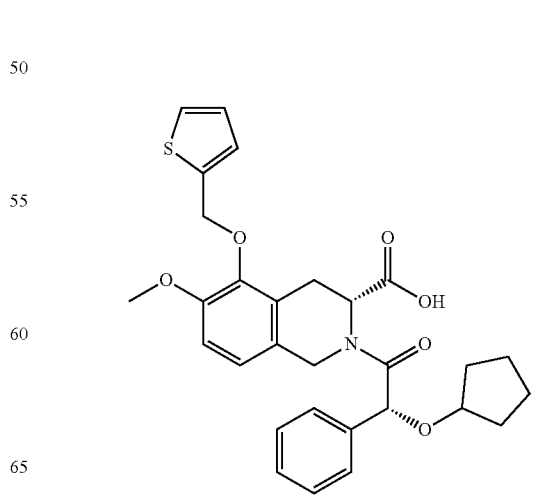

63
-continued
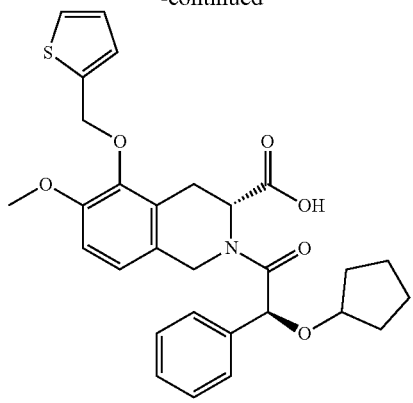
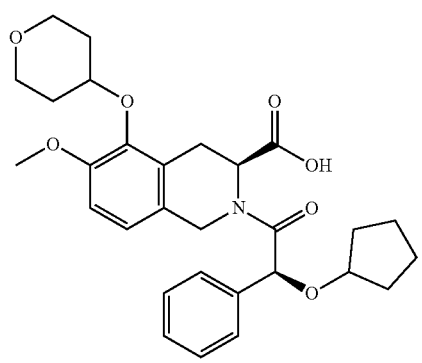
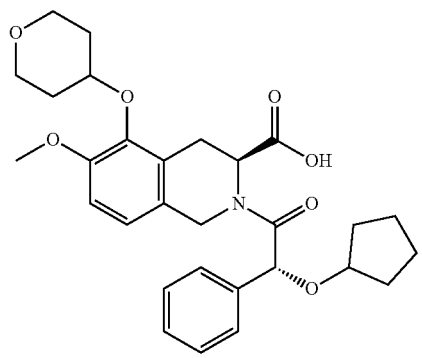
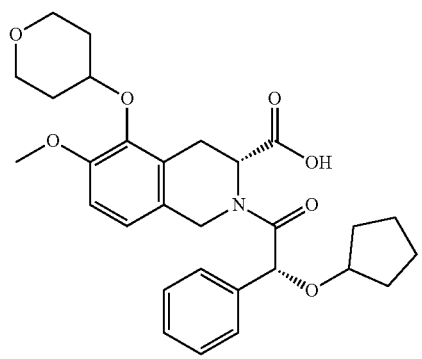
64
-continued
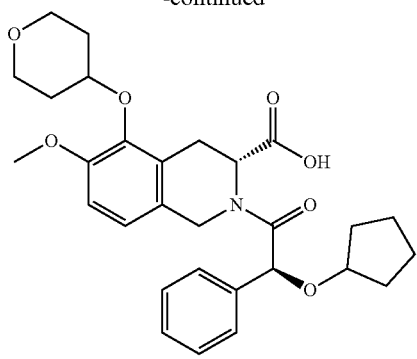
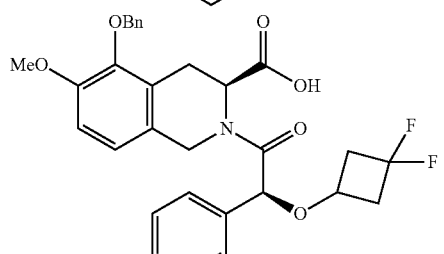
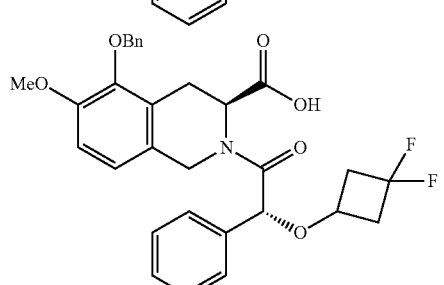
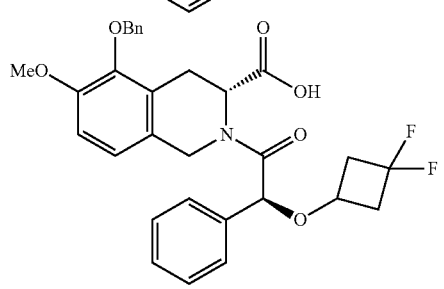
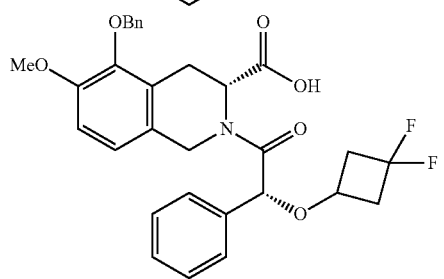
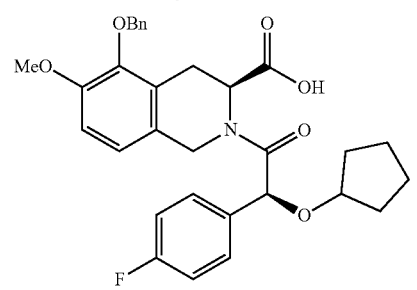

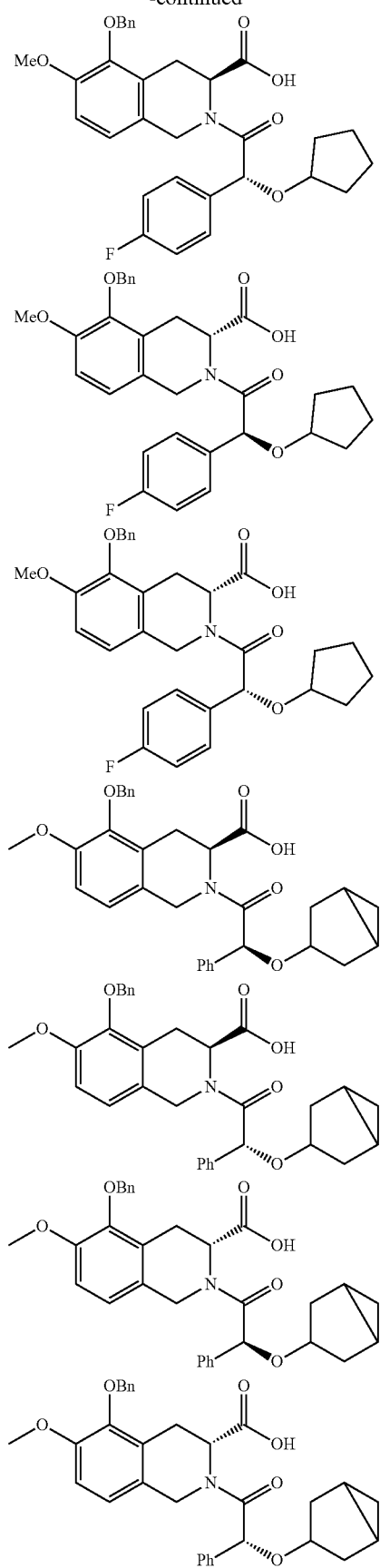
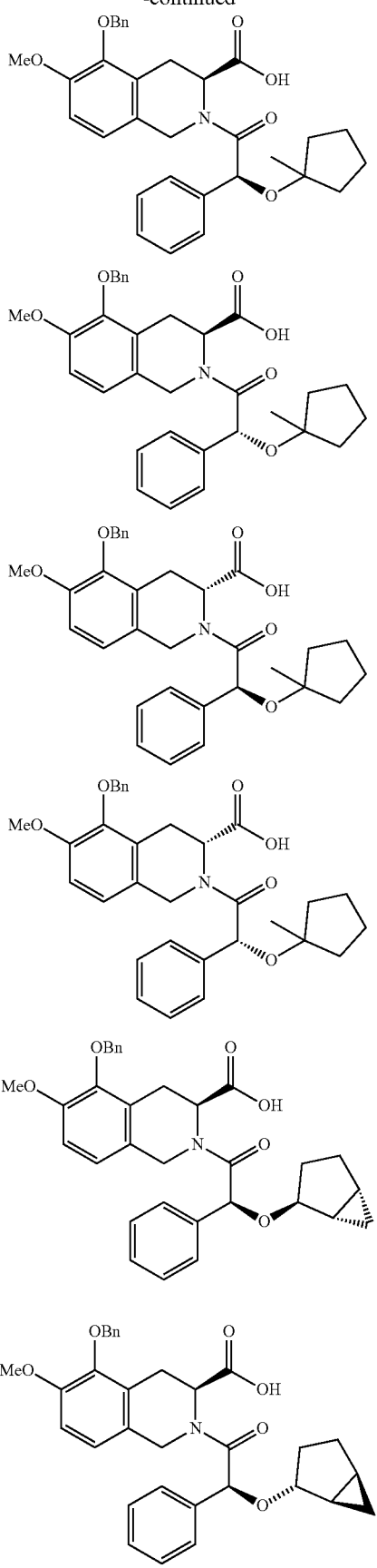

67
-continued
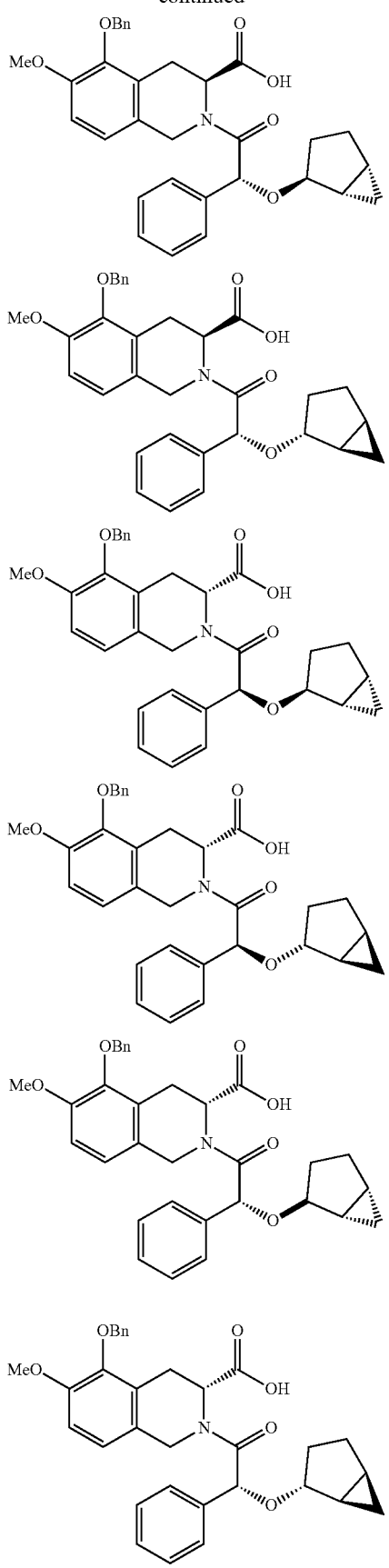
68
-continued
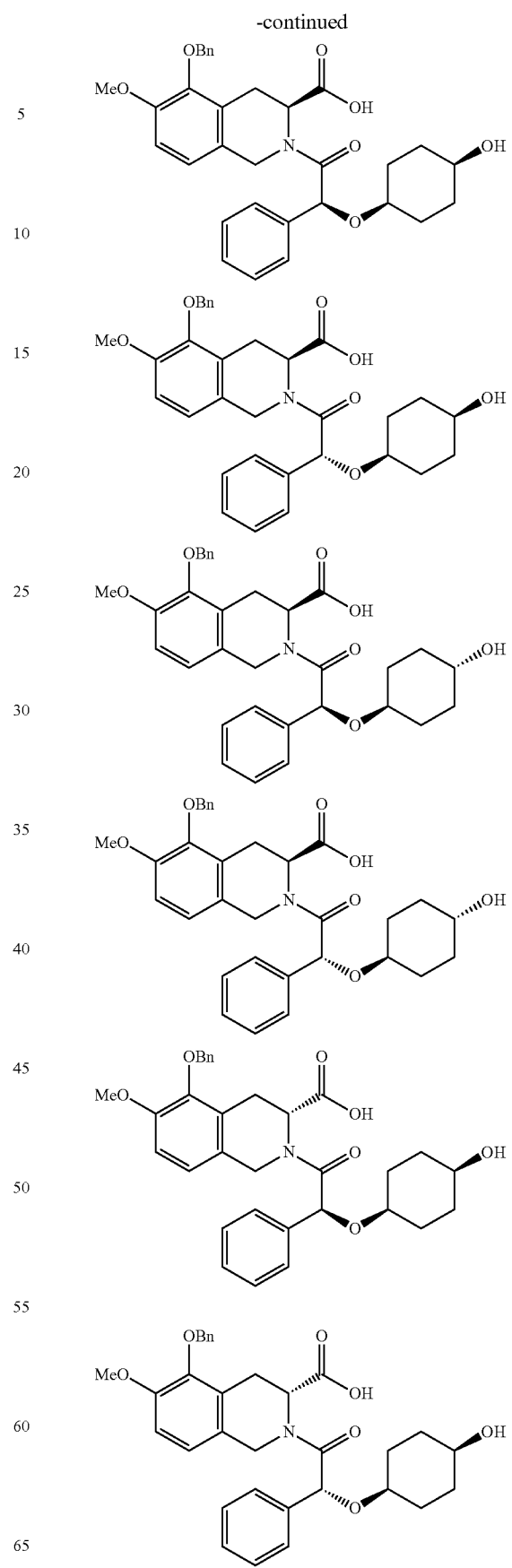

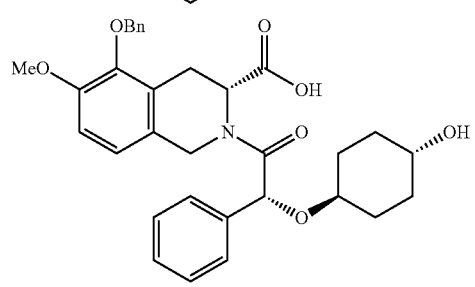
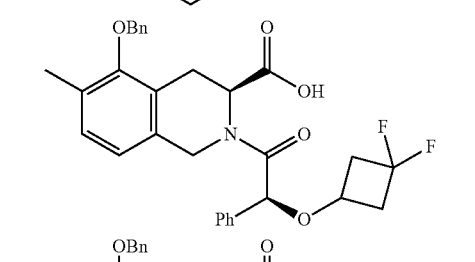
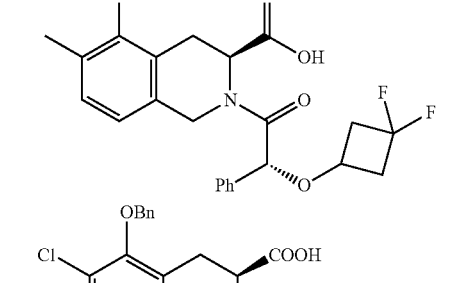
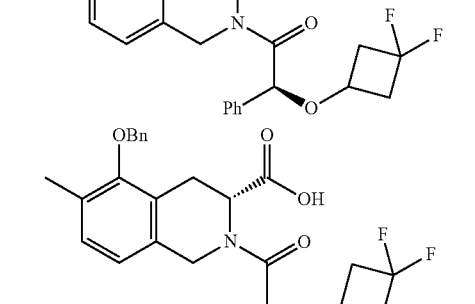
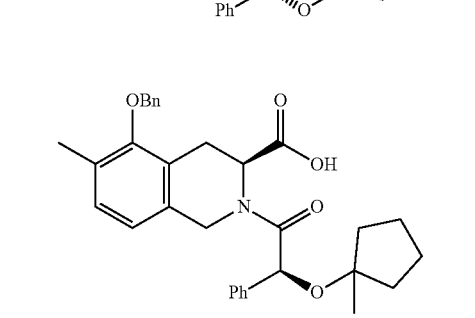
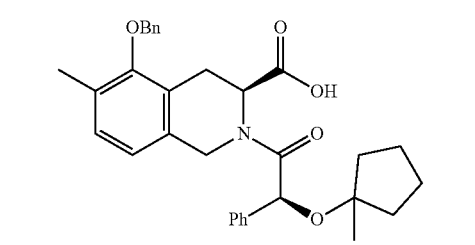
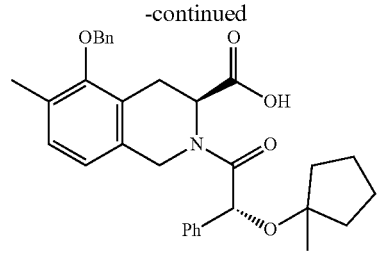
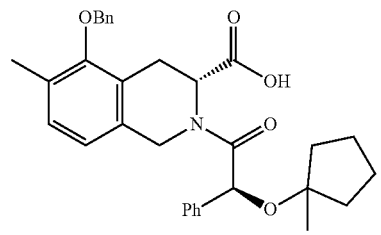
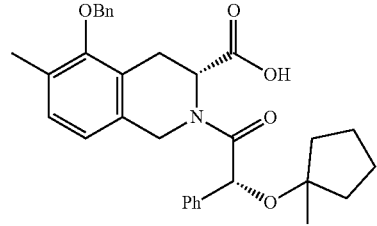
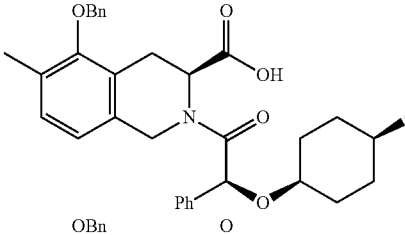
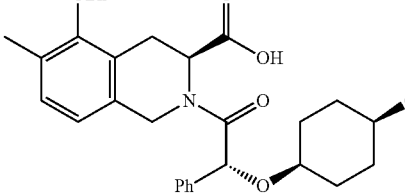
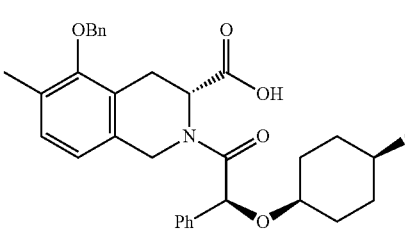
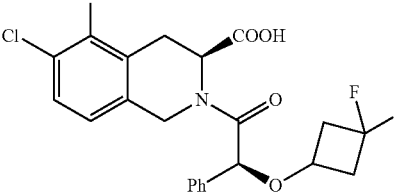

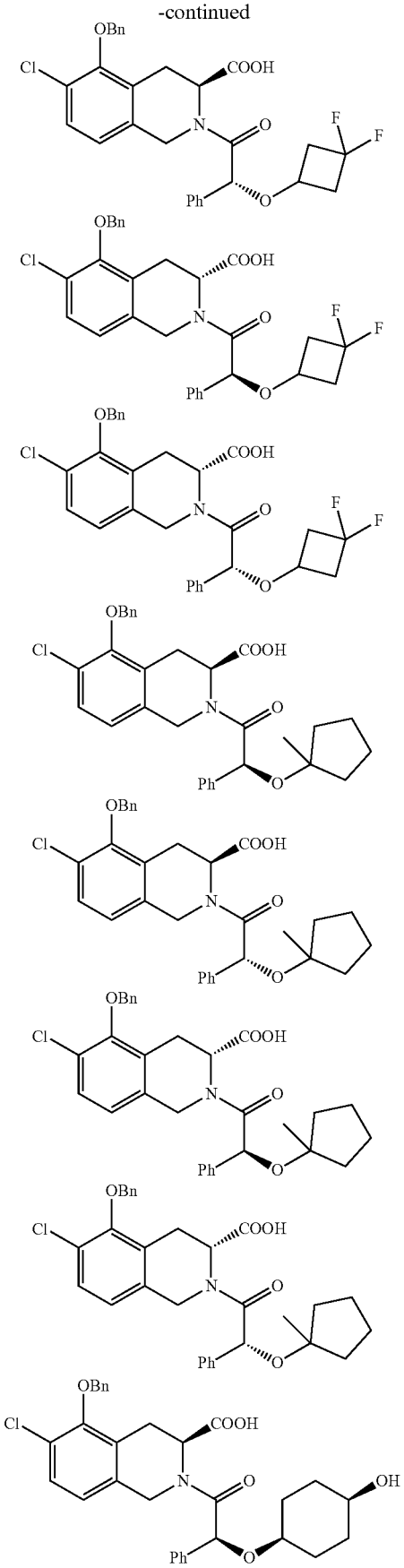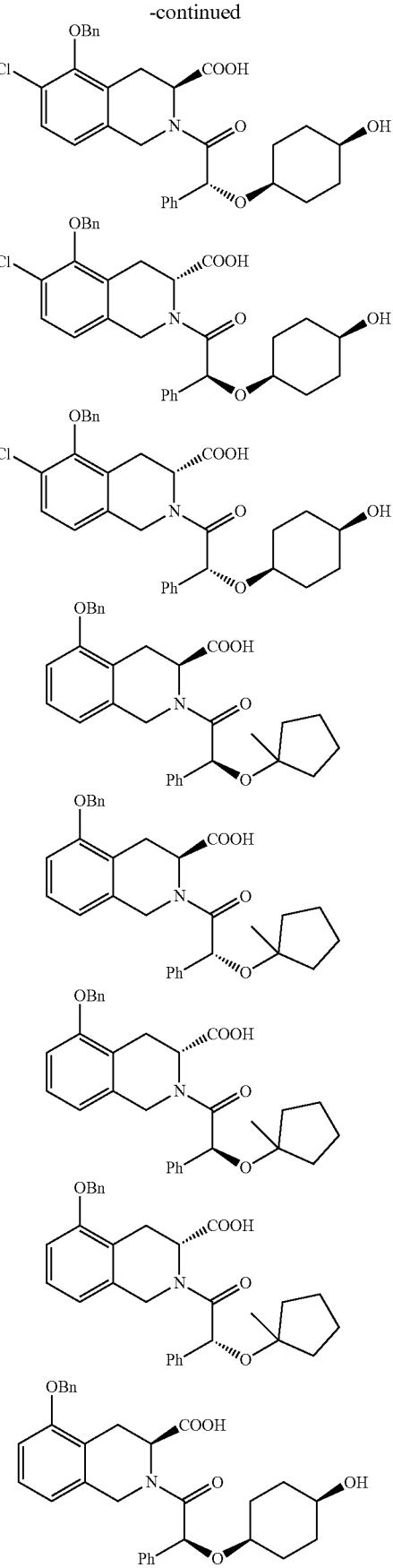

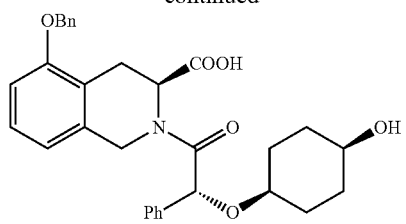
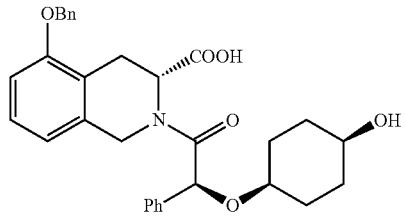
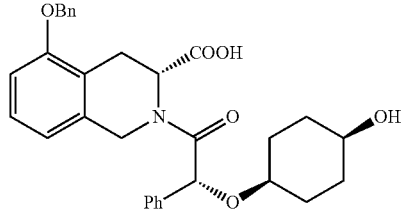
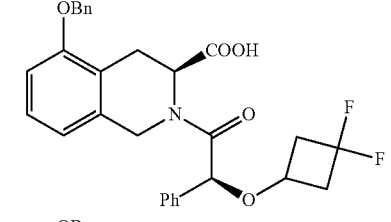
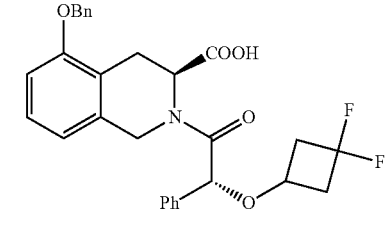
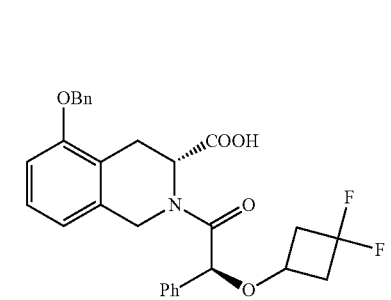
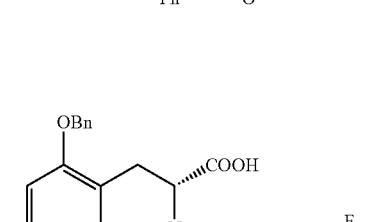
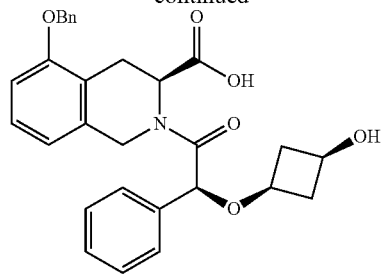
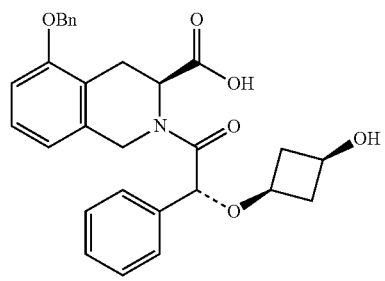
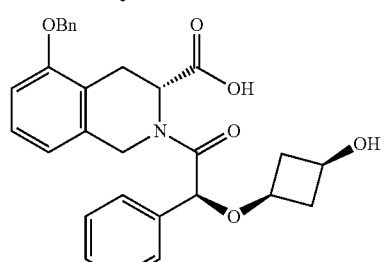
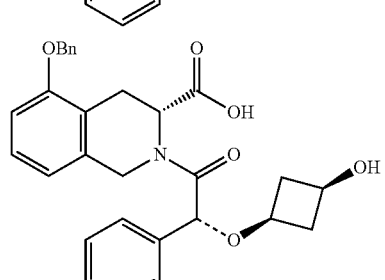
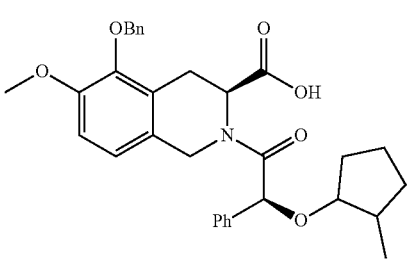
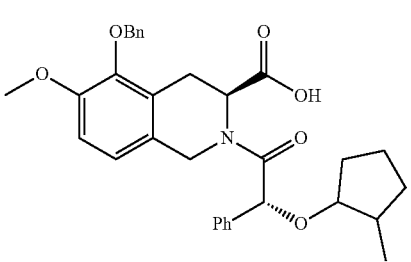

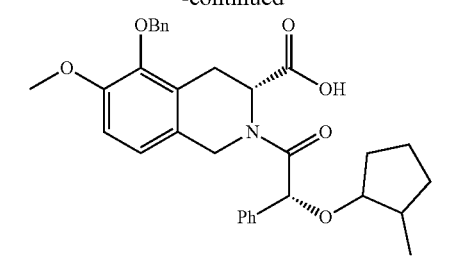
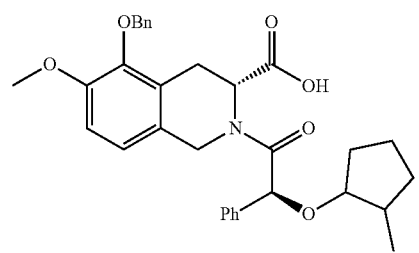
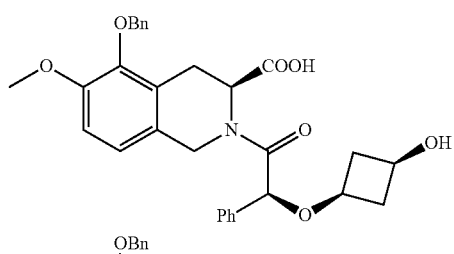
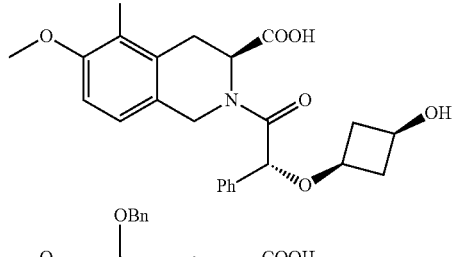
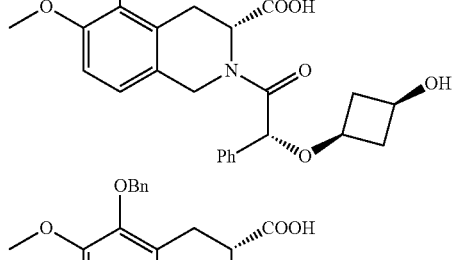
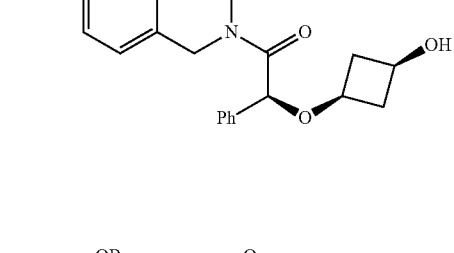
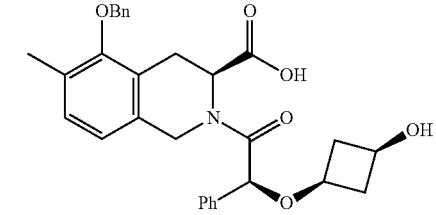
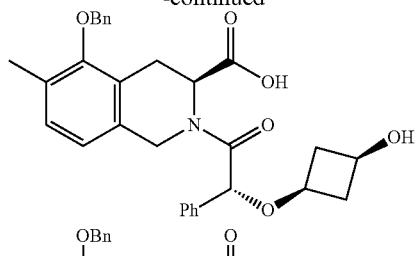
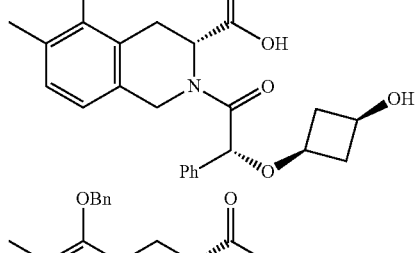
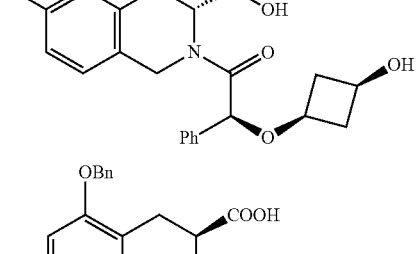
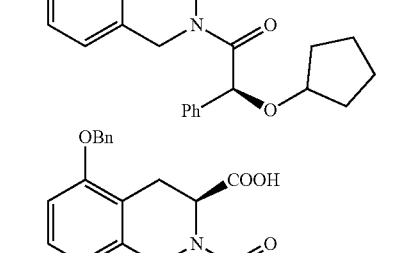
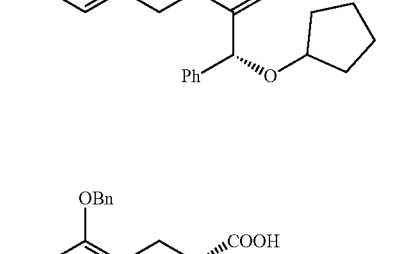
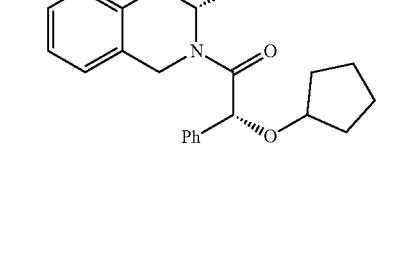
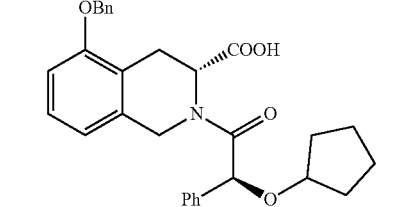

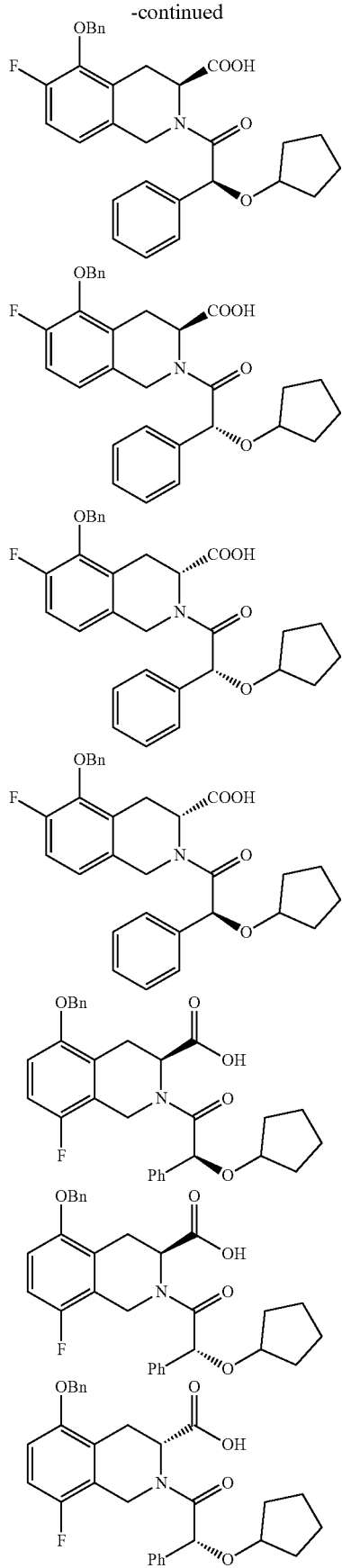
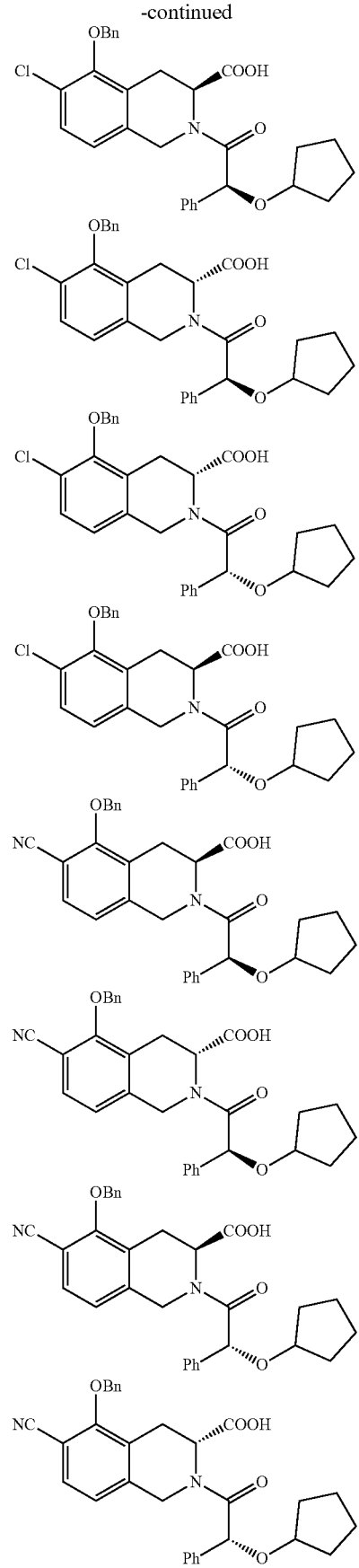

-continued

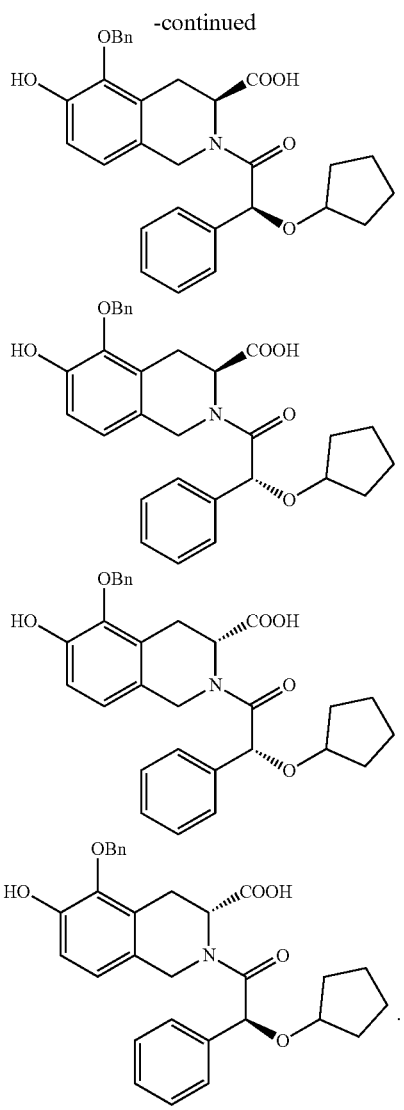

The present disclosure also provides use of the above compound or the pharmaceutically acceptable salt thereof in the manufacture of a medicament for treating a disease associated with an AT$_2$R receptor.

The disclosure also provides use of the compound or the pharmaceutically acceptable salt thereof in the manufacture of a medicament for the treatment of chronic pain.

Definition and Description

Unless otherwise stated, the following terms and phrases as used herein are intended to have the following meanings. A particular term or phrase should not be considered undefined or unclear without a particular definition, but should be understood in the ordinary sense. When a trade name appears herein, it is intended to refer to its corresponding commodity or its active ingredient. The term "pharmaceutically acceptable" as used herein is intended to mean that those compounds, materials, compositions and/or dosage forms are within the scope of sound medical judgment and are suitable for use in contact with human and animal tissues. Without excessive toxicity, irritation, allergic reactions or other problems or complications, it is commensurate with a reasonable benefit/risk ratio.

The term "pharmaceutically acceptable salt" refers to a salt of a compound of the present disclosure, prepared from a compound having a particular substituent found in the present disclosure and a relatively non-toxic acid or base. When a relatively acidic functional group is contained in the compound of the present disclosure, a base addition salt can be obtained by contacting a neutral form of such a compound with a sufficient amount of a base in a pure solution or a suitable inert solvent. Pharmaceutically acceptable base addition salts include sodium, potassium, calcium, ammonium, organic ammonia or magnesium salts or similar salts. When a relatively basic functional group is contained in the compound of the present disclosure, an acid addition salt can be obtained by contacting a neutral form of such a compound with a sufficient amount of an acid in a pure solution or a suitable inert solvent. Examples of pharmaceutically acceptable acid addition salts include inorganic acid salts, wherein inorganic acid includes, for example, hydrochloric acid, hydrobromic acid, nitric acid, carbonic acid, hydrogen carbonate, phosphoric acid, monohydrogen phosphate, dihydrogen phosphate, sulfuric acid, hydrogen sulfate, hydroiodic acid, and phosphorous acid; organic acid salts, wherein organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid; salts of amino acids (such as arginine, etc.), and salts of organic acids such as glucuronic acid (see Berge et al., "Pharmaceutical Salts", Journal of Pharmaceutical Science 66: 1-19 (1977)). Certain specific compounds of the present disclosure contain both basic and acidic functional groups and thus can be converted to any one base or acid addition salt.

Preferably, the salt is contacted with a base or an acid in a conventional manner, and the parent compound is separated, thereby regenerating the neutral form of the compound. The parent form of the compound differs from the form of its various salts in certain physical properties, such as differences in solubility in polar solvents.

As used herein, a "pharmaceutically acceptable salt" is a derivative of a compound of the present disclosure, wherein the parent compound is modified by salt formation with an acid or with a base. Examples of pharmaceutically acceptable salts include, but are not limited to, inorganic or organic acid salts of bases such as amines, alkali metal or organic salts of acid groups such as carboxylic acids. Pharmaceutically acceptable salts include the conventional non-toxic salts or quaternary ammonium salts of the parent compound, for example salts formed from non-toxic inorganic or organic acids. Conventional non-toxic salts include, but are not limited to, those derived from inorganic acids and organic acids selected from the group consisting of 2-acetoxybenzoic acid, 2-hydroxyethanesulfonic acid, acetic acid, ascorbic acid, benzenesulfonic acid, benzoic acid, hydrogen carbonate, carbonic acid, citric acid, edetic acid, ethanedisulfonic acid, ethanesulfonic acid, fumaric acid, glucoheptose, gluconic acid, glutamic acid, glycolic acid, hydrobromic acid, hydrochloric acid, hydroiodide, hydroxyl, hydroxynaphthalene, isethionic acid, lactic acid, lactose, dodecylsulfonic acid, maleic acid, malic acid, mandelic acid, methanesulfonic acid, nitric acid, oxalic acid, pamoic acid, pantothenic acid, phenylacetic acid, phosphoric acid, polygalacturonic acid, propionic acid, salicylic acid, stearic acid, folinic acid, succinic acid, sulfamic acid, p-aminobenzenesulfonic acid, sulfuric acid, tannin, tartaric acid and p-toluenesulfonic acid.

The pharmaceutically acceptable salts of the present disclosure can be synthesized from the parent compound containing an acid group or a basic group by conventional chemical methods. In general, such salts are prepared by reacting these compounds via a free acid or base form with a stoichiometric amount of the appropriate base or acid in water or an organic solvent or a mixture of the two. Generally, a nonaqueous medium such as ether, ethyl acetate, ethanol, isopropanol or acetonitrile is preferred.

Certain compounds of the present disclosure may have asymmetric carbon atoms (optical centers) or double bonds. Racemates, diastereomers, geometric isomers and individual isomers are included within the scope of the present disclosure.

Unless otherwise stated, the wedge and dashed bonds (  ) are used to represent the absolute configuration of a stereocenter, the wavy line  is used to represent a wedge or dashed bond or (  or  ), and   are used to represent the relative configuration of the stereocenter. When the compounds described herein contain olefinic double bonds or other centers of geometric asymmetry, they include the E and Z geometric isomers unless otherwise specified. Likewise, all tautomeric forms are included within the scope of the present disclosure.

The compounds of the disclosure may exist in specific geometric or stereoisomeric forms. The present disclosure contemplates all such compounds, including the cis and trans isomers, the (−)- and (+)-enantiomers, the (R)- and (S)-enantiomers, and the diastereoisomer, a (D)-isomer, a (L)-isomer, and a racemic mixture thereof, and other mixtures such as the mixtures enriched in enantiomer and diastereoisomer, all of which are within the scope of the present disclosure. Additional asymmetric carbon atoms may be present in the substituents such as alkyl groups. All such isomers as well as mixtures thereof are included within the scope of the present disclosure.

The optically active (R)- and (S)-isomers as well as the D and L isomers can be prepared by chiral synthesis or chiral reagents or other conventional techniques. If an enantiomer of a certain compound of the present disclosure is desired, it can be prepared by asymmetric synthesis or by derivatization with a chiral auxiliary, wherein the resulting mixture of diastereomers is separated and the auxiliary group is cleaved to provide the desired pure enantiomer. Alternatively, when a molecule contains a basic functional group (e.g., an amino group) or an acidic functional group (e.g., a carboxyl group), a diastereomeric salt is formed with a suitable optically active acid or base, and then the diastereomers are resolved by conventional methods well known in the art, and the pure enantiomer is recovered. Furthermore, the separation of enantiomers and diastereomers is generally accomplished by the use of chromatography using a chiral stationary phase optionally combined with chemical derivatization (eg, formation of carbamate from an amine).

The compounds of the present disclosure may contain unnatural proportions of atomic isotopes on one or more of the atoms that make up the compound. For example, a compound can be labeled with a radioisotope such as tritium ($^3$H), iodine-125 ($^{125}$I) or C-14 ($^{14}$C). Alterations of all isotopes of the compounds of the present disclosure, whether radioactive or not, are included within the scope of the present disclosure.

"Optional" or "optionally" means that the subsequently described event or condition may, but does not necessarily, occur, and that the description includes instances in which the event or condition occurs and instances in which the event or condition does not occur.

The term "substituted" means that any one or more hydrogen atoms on a particular atom are replaced by a substituent, and may include variants of heavy hydrogen and hydrogen, as long as the valence of the particular atom is normal and the substituted compound is stable. When the substituent is a keto group (ie, =O), it means that two hydrogen atoms are substituted. Ketone substitution does not occur on the aryl group. The term "optionally substituted" means that it may or may not be substituted, and unless otherwise specified, the type and number of substituents may be arbitrary as long as it is chemically achievable.

When any variable (eg, R) occurs one or more times in the composition or structure of a compound, its definition in each case is independent. Thus, for example, if a group is substituted by 0-2 R groups, the group may optionally be substituted at most by two R groups, and R has an independent option in each case. Furthermore, combinations of substituents and/or variants thereof are permissible only if such combinations result in stable compounds.

When the number of one linking group is 0, such as —(CRR)$_0$—, it indicates that the linking group is a single bond.

When one of the variables is selected from a single bond, it means that the two groups to which it is attached are directly linked. For example, when L represents a single bond in A-L-Z, the structure is actually A-Z.

When a substituent is vacant, it means that the substituent is absent. For example, when X is vacant in A-X, the structure is actually A. When a substituent can be attached to one or more atoms on a ring, the substituent can be bonded to any atom on the ring. For example, the structural unit

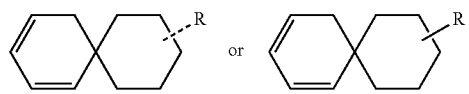

indicates that the substituent R can replace at any position in the cyclohexyl or cyclohexadiene. When the substituents listed do not indicate which atom is attached to the substituted group, such a substituent may be bonded through any atom thereof. For example, as a substituent, pyridyl can be attached to the substituted group through any carbon atom in the pyridine ring. When the listed linking group does not indicate its attachment direction, its attachment direction is arbitrary. For example, the linking group L in

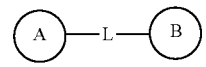

is -M-W—, and at this time -M-W— can connect a ring A and a ring B to form

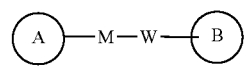

according to the direction the same as the reading direction of from left to right, or -M-W— can connect the ring A and the ring B to form

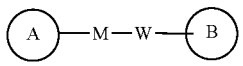

according to the direction opposite to the reading direction of from left to right. The combination of the linking groups, substituents and/or variants thereof is permitted only if such combination produces a stable compound.

Unless otherwise specified, a "ring" means substituted or unsubstituted cycloalkyl, heterocycloalkyl, cycloalkenyl, heterocycloalkenyl, cycloalkynyl, heterocycloalkynyl, aryl or heteroaryl. The so-called rings include single rings, linking rings, spiral rings, fused rings or bridged rings. The number of atoms on the ring is usually defined as the number of members of the ring. For example, a "5-7 membered ring" means 5 to 7 atoms are arranged in a circle. Unless otherwise specified, the ring optionally contains 1 to 3 heteroatoms. Thus, the "5-7 membered ring" includes, for example, phenyl, pyridine, and piperidinyl; on the other hand, the term "5-7 membered heterocycloalkyl ring" includes pyridyl and piperidinyl, but does not include phenyl. The term "ring" also includes a ring system containing at least one ring, wherein each "ring" independently conforms to the above definition.

Unless otherwise specified, the term "heterocycle" or "heterocyclyl" means a stable monocyclic, bicyclic or tricyclic ring containing a heteroatom or a heteroatom group, and it may be saturated, partially unsaturated or unsaturated (aromatic), and it comprises a carbon atom and 1, 2, 3 or 4 heteroatoms in the ring, independently selected from N, O and S, wherein any of the above heterocycles may be fused to a phenyl ring to form a bicyclic ring. The nitrogen and sulfur heteroatoms can be optionally oxidized (i.e., NO and S(O)p, p is 1 or 2). The nitrogen atom can be substituted or unsubstituted (i.e., N or NR, wherein R is H or other substituents as already defined herein). The heterocyclic ring can be attached to the side groups of any heteroatom or carbon atom to form a stable structure. If the resulting compound is stable, the heterocycles described herein can undergo substitutions at the carbon or nitrogen sites. The nitrogen atom in the heterocycle is optionally quaternized. A preferred embodiment is that when the total number of S and O atoms in the heterocycle exceeds 1, these heteroatoms are not adjacent to each other. Another preferred embodiment is that the total number of S and O atoms in the heterocycle does not exceed one. The term "aromatic heterocyclic group" or "heteroaryl" as used herein means a stable 5, 6, or 7 membered monocyclic or bicyclic or aromatic ring of a 7, 8, 9 or 10 membered bicyclic heterocyclic group, and it contains carbon atoms and 1, 2, 3 or 4 heteroatoms in the ring, independently selected from N, O and S. The nitrogen atom can be substituted or unsubstituted (i.e., N or NR, wherein R is H or other substituents as already defined herein). The nitrogen and sulfur heteroatoms can be optionally oxidized (i.e., NO and S(O)p, p is 1 or 2). It is worth noting that the total number of S and O atoms on the aromatic heterocycle does not exceed one. Bridged rings are also included in the definition of heterocycles. A bridged ring is formed when one or more atoms (ie, C, O, N, or S) join two non-adjacent carbon or nitrogen atoms. Preferred bridged rings include, but are not limited to, one carbon atom, two carbon atoms, one nitrogen atom, two nitrogen atoms, and one carbon-nitrogen group. It is worth noting that a bridge always converts a single ring into a tricyclic ring. In the bridged ring, a substituent on the ring can also be present on the bridge.

Examples of heterocyclic compounds include, but are not limited to, acridinyl, azocinyl, benzimidazolyl, benzofuranyl, benzomercaptofuranyl, benzomercaptophenyl, benzoxazolyl, benzoxazolinyl, benzothiazolyl, benzotriazolyl, benzotetrazolyl, benzisoxazolyl, benzisothiazolyl, benzimidazolinyl, carbazolyl, 4aH-carbazolyl, carbolinyl, chromanyl, chromene, cinnolinyl decahydroquinolinyl, 2H,6H-1,5, 2-dithiazinyl, dihydrofuro[2,3-b]tetrahydrofuranyl, furyl, furazanyl, imidazolidinyl, imidazolinyl, imidazolyl, 1H-indazolyl, indolenyl, indolinyl, indolizinyl, indolyl, 3H-indolyl, isobenzofuranyl, isoindolyl, isoindolinyl, isoquinolyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3, 4-oxadiazolyl, oxazolidinyl, oxazolyl, hydroxyindolyl, pyrimidinyl, phenanthridinyl, phenanthrolinyl, phenazine, phenothiazine, benzoxanthinyl, phenooxazinyl, phthalazinyl, piperazinyl, piperidinyl, piperidinone, 4-piperidinone, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridyl, pyrrolidinyl, pyrrolinyl, 2H-pyrrolyl, pyrrolyl, quinazolinyl, quinolyl, 4H-quinolizinyl, quinoxalinyl, quinuclidinyl, tetrahydrofuranyl, tetrahydroisoquinolyl, tetrahydroquinolyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, isothiazolyl thiophenyl, thienooxazolyl, thienothiazolyl, thienoimidazolyl, thienyl, triazinyl, 1,2,3-triazolyl, 1,2,4-triazolyl, 1,2,5-triazolyl, 1,3,4-triazolyl and xanthenyl. Fused and spiro compounds are also included.

Unless otherwise specified, the term "alkyl" is used to denote a straight or branched saturated hydrocarbon group, which may be monosubstituted (eg, —CH$_2$F) or polysubstituted (eg, —CF$_3$), and may be monovalent (eg, methyl), divalent (such as methylene) or polyvalent (such as methine). Examples of the alkyl group include methyl (Me), ethyl (Et), propyl (e.g., n-propyl and isopropyl), butyl (e.g., n-butyl, isobutyl, s-butyl, t-butyl), pentyl (eg, n-pentyl, isopentyl, neopentyl) and the like.

In some embodiments, the term "heteroalkyl" refers to, by itself or in conjunction with another term, a stable straight or branched hydrocarbon group or combination thereof, having a certain number of carbon atoms and at least one heteroatom. In a typical embodiment, the heteroatoms are selected from the group consisting of B, O, N, and S, wherein the nitrogen and sulfur atoms are optionally oxidized, and the nitrogen heteroatoms are optionally quaternized. A heteroatom or heteroatom group can be located at any internal position of a heteroalkyl group, including the position where the alkyl group is attached to the rest of the molecule, but the terms "alkoxy", "alkylamino" and "alkylthio" (or thioalkoxy) are conventional expressions and refer to those alkyl groups which are attached to the remaining parts of the molecule through an oxygen atom, an amino group or a sulfur atom, respectively. Examples include, but are not limited to, —CH$_2$—CH$_2$—O—CH$_3$, —CH$_2$—CH$_2$—NH—CH$_3$, —CH$_2$—CH$_2$N(CH$_3$)—CH$_3$, —CH$_2$S—CH$_2$CH$_3$, —CH$_2$—CH$_2$, —S(O)—CH$_3$, and —CH$_2$—CH$_2$—S(O)$_2$—CH$_3$. At most two heteroatoms can be continuous, such as —CH$_2$—NH—OCH$_3$.

Unless otherwise specified, a cycloalkyl group includes any stable cyclic or polycyclic hydrocarbon group, wherein any carbon atom is saturated, and may be monosubstituted or polysubstituted, and may be monovalent, divalent or multivalent. Examples of such cycloalkyl groups include, but are not limited to, cyclopropyl, norbornyl, [2.2.2]bicyclooctane, [4.4.0]bicyclodecane.

Unless otherwise specified, the term "halo" or "halogen" refers to, by itself or as a part of another substituent, a fluorine, chlorine, bromine or iodine atom. Further, the term "haloalkyl" is intended to include both monohaloalkyl and polyhaloalkyl. For example, the term "halo($C_1$-$C_4$)alkyl" is intended to include, but is not limited to, trifluoromethyl, 2,2,2-trifluoroethyl, 4-chlorobutyl, 3-bromopropyl. Unless otherwise specified, examples of haloalkyl include, but are not limited to, trifluoromethyl, trichloromethyl, pentafluoroethyl and pentachloroethyl.

"Alkoxyl" represents the above alkyl group having a specified number of carbon atoms attached through an oxygen bridge, and unless otherwise specified, $C_{1-6}$ alkoxyl includes $C_1$ alkoxyl, $C_2$ alkoxyl, $C_3$ alkoxyl, $C_4$ alkoxyl, $C_5$ alkoxyl and $C_6$ alkoxyl. Examples of alkoxyl include, but are not limited to, methoxy, ethoxy, n-propoxy, isopropoxy, n-butoxy, sec-butoxy, tert-butoxy, n-pentyloxy and S-pentyloxy.

Unless otherwise specified, the term "aryl" denotes a polyunsaturated aromatic hydrocarbon substituent which may be monosubstituted or polysubstituted, may be monovalent, divalent or polyvalent, and may be monocyclic or polycyclic (for example, 1 to 3 rings, wherein at least one ring is aromatic), they are fused together or covalently linked. The term "heteroaryl" refers to an aryl (or ring) containing one to four heteroatoms. In an illustrative example, the heteroatoms are selected from the group consisting of B, N, O, and S, wherein the nitrogen and sulfur atoms are optionally oxidized, and the nitrogen atom is optionally quaternized. A heteroaryl can be attached to the remaining part of the molecule through a heteroatom. Non-limiting examples of aryl or heteroaryl include phenyl, naphthyl, biphenyl, pyrrolyl, pyrazolyl, imidazolyl, pyrazinyl, oxazolyl, phenyl-oxazolyl, isoxazolyl, thiazolyl, furyl, thienyl, pyridyl, pyrimidinyl, benzothiazolyl, purinyl, benzimidazolyl, indolyl, isoquinolyl, quinoxalinyl, quinolyl, 1-naphthyl, 2-naphthyl, 4-biphenylyl, I-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidinyl, 4-pyrimidinyl, 5-benzothiazolyl, purinyl, 2-benzimidazolyl, 5-indyl, 1-isoquinolinyl, 5-isoquinolinyl, 2-quinoxalinyl, 5-quinoxalinyl, 3-quinolyl and 6-quinolyl. The substituents of any of the above aryl and heteroaryl ring systems are selected from the group of acceptable substituents described below.

Unless otherwise specified, aryl, when used in conjunction with other terms (e.g., aryloxy, arylthio, and aralkyl), include aryl and heteroaryl rings as defined above. Thus, the term "aralkyl" is intended to include those atomic groups (eg, benzyl, phenethyl, and pyridylmethyl) to which an aryl group is attached to an alkyl group, and alkyls of which the carbon atom (eg, methylene) has been substituted by such as an oxygen atom, for example, phenoxymethyl, 2-pyridyloxymethyl 3-(1-naphthyloxy)propyl.

The compounds of the present disclosure can be prepared by a variety of synthetic methods well known to those skilled in the art, including the specific embodiments set forth below, embodiments formed through combinations thereof with other chemical synthetic methods, and those equivalent alternatives well known to those skilled in the art, and preferred embodiments include, but are not limited to, embodiments of the disclosure.

The solvent used in the present disclosure is commercially available. The present disclosure employs the following abbreviations: Bn represents benzyl; aq represents water, HATU represents O-(7-azabenzotriazol-1-yl)-N,N,N',N'-tetramethyl urea hexafluorophosphate; EDC stands for N-(3-dimethylaminopropyl)-N'-ethylcarbodiimide hydrochloride; m-CPBA stands for 3-chloroperoxybenzoic acid; eq stands for equivalent weight, and equal weight; CDI stands for carbonyl diimidazole; DCM stands for dichloromethane; PE stands for petroleum ether; DIAD stands for diisopropyl azodicarboxylate; DMF stands for N,N-dimethylformamide; DMSO stands for dimethyl sulfoxide; EtOAc represents ethyl acetate; EtOH represents ethanol; MeOH represents methanol; CBz represents benzyloxycarbonyl which is an amine protecting group; BOC represents t-butylcarbonyl which is an amine protecting group; HOAc represents acetic acid; $NaCNBH_3$ represents sodium cyanoborohydride; r.t. represents room temperature; O/N stands for overnight; THF stands for tetrahydrofuran; $Boc_2O$ stands for di-tert-butyl-dicarbonate; TFA stands for trifluoroacetic acid; DIPEA stands for diisopropylethylamine; $SOCl_2$ stands for thionyl chloride; $CS_2$ stands for carbon disulfide; TsOH stands for p-toluenesulfonic acid; NFSI stands for N-fluoro-N-(phenylsulfonyl)benzenesulfonamide; NCS stands for 1-chloro-pyrrolidine-2,5-dione; n-$Bu_4$NF stands for tetrabutylammonium fluoride; iPrOH stands for 2-propanol; mp stands for melting point; LDA stands for lithium diisopropylamide; EDCI stands for carbodiimide; HOBt stands for 1-hydroxybenzotriazole; Pd(dppf)$Cl_2$ stands for [1,1'-bis(diphenylphosphino)ferrocene]palladium dichloride.

Compounds are named by hand or by ChemDraw® software, and commercial compounds are based on supplier catalog names.

Technical Effect

In this patent, a series of compounds of the formula (I) are synthesized by a simple preparation method to obtain a novel class of selective inhibitors of angiotensin II type 2 receptor ($AT_2R$) for the treatment of chronic pain. The compounds of the present disclosure all exhibit better biological activity in vitro and exhibit excellent pharmacokinetic properties in a variety of genera.

DETAILED DESCRIPTION

The disclosure is described in detail below by the examples, but is not intended to limit the disclosure. The present disclosure has been described in detail herein, the specific embodiments of the present disclosure are disclosed herein, and various modifications and changes may be made to the embodiments of the present disclosure without departing from the sprit and scope of the present disclosure, which is obvious for those skilled in the art.

Reference Example 1: Synthesis of Intermediate A1

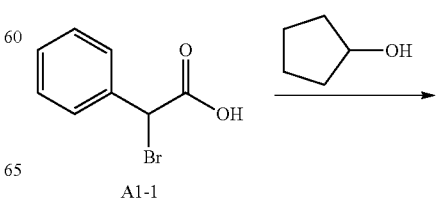

A1-1

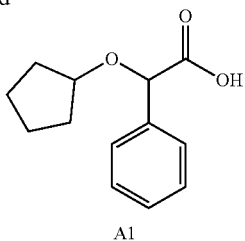

A1

Step 1: Preparation of Compound A1

Under a nitrogen atmosphere, NaH (466.0 mg, 11.7 mmol, purity: 60%) was suspended in anhydrous tetrahydrofuran (2.5 mL), and an anhydrous tetrahydrofuran (2.5 mL) solution of cyclopentanol (301.0 mg, 3.5 mmol, 316.9 uL) was slowly added dropwise. After stirring was performed at 15° C. for 30 minutes, an anhydrous tetrahydrofuran (2.5 mL) solution of A1-1 (500.0 mg, 2.3 mmol) was added. After the addition was completed, the reaction solution was further stirred at 15° C. for 1.5 hours. The reaction solution was slowly poured into water (15 mL). After quenching the reaction, methyl tert-butyl ether (20 mL) was used for washing. The aqueous phase was adjusted to pH of about 3 with 2N hydrochloric acid and extracted with methyl tert-butyl ether (20 mL×3). The mixed organic phase was washed with saturated salt water (20 mL), dried with anhydrous sodium sulfate, filtered and concentrated in vacuum to obtain a crude product. The crude product was separated and purified by a silica gel chromatography column (an eluent: 50-100% ethyl acetate/petroleum ether) to obtain the product A1. $^1$H NMR (400 MHz, CHLOROFORM-d): δ 7.46-7.43 (m, 2H), 7.40-7.36 (m, 3H), 4.94 (s, 1H), 4.07-4.05 (m, 1H), 1.83-1.67 (m, 6H), 1.66-1.46 (m, 2H).

The following compounds were synthesized in a similar manner to compound A1:

| Reference Example | Compound Serial Number | Structural Formula | Spectrogram |
|---|---|---|---|
| 2 | A2 | (tetrahydropyran-4-yloxy phenylacetic acid structure) | $^1$H NMR (400 MHz, CHLOROFORM-d): δ 7.48-7.46 (m, 2H), 7.39-7.37 (m, 3H), 5.06 (s, 1H), 3.99-3.91 (m, 2H), 3.60-3.53 (m, 1H), 3.43-3.39 (m, 2H), 1.93-1.85 (m, 1H), 1.80-1.73 (m, 1H), 1.69-1.54 (m, 2H). MS m/z: 258.9 [M + Na]$^+$. |
| 3 | A3 | (butoxy phenylacetic acid structure) | $^1$H NMR (400 MHz, CHLOROFORM-d): δ 7.47-7.39 (m, 5H), 4.89 (s, 1H), 3.60-3.49 (m, 2H), 1.68-1.64 (m, 2H), 1.43-1.40 (m, 2H) 0.95-0.92 (t, 7.6 Hz, 3H). |
| 4 | A4 | (2,2,2-trifluoroethoxy phenylacetic acid structure) | $^1$H NMR (400 MHz, CHLOROFORM-d): δ 7.48-7.42 (m, 5H), 5.11 (s, 1 H), 3.98-3.85 (m, 2H). |
| 5 | A5 | (4-cyanophenoxy phenylacetic acid structure) | $^1$H NMR(400 MHz, CHLOROFORM-d): δ 7.61-7.58 (m, 4H), 7.45-7.44 (m, 3H), 7.04-7.02 (m, 2H), 5.71 (s, 1H). |

-continued

| Reference Example | Compound Serial Number | Structural Formula | Spectrogram |
|---|---|---|---|
| 6 | A6 | | ¹H NMR (400 MHz, CHLOROFORM-d): δ 7.47-7.45 (m, 2H), 7.38-7.31 (m, 3H), 4.89 (s, 1 H), 3.78-3.60 (m, 4H), 3.42 (s, 3H). |
| 7 | A7 | | ¹H NMR (400 MHz, CHLOROFORM-d): δ 7.47-7.39 (m, 5H), 4.96 (s, 1 H), 4.31-4.24 (m, 1H), 4.07-3.74 (m, 4H), 2.06-1.97 (m, 3H). |
| 8 | A8 | | ¹H NMR (400 MHz, CHLOROFORM-d): δ 7.48-7.37 (m, 5H), 4.88 (s, 1H), 4.83-4.75 (m, 2H), 4.71-4.65 (m, 1H), 4.63-4.57 (m, 2H). |
| 9 | A9 | | 1H NMR (400 MHz, CHLOROFORM-d): δ 7.54-7.52 (m, 2H), 7.40-7.39 (m, 3H), 6.67-6.61 (m, 2H), 5.71 (s, 1H). |
| 10 | A10 | | ¹H NMR (400 MHz, CHLOROFORM-d): δ 7.51-7.40 (m, 5H), 5.05-4.97 (m, 1H), 3.89-3.62 (m, 1H), 3.62-3.43 (m, 1H), 2.00-1.28 (m, 8H). |
| 11 | A11 | | 1H NMR (400 MHz, CHLOROFORM-d): δ 7.79-7.78 (m, 2H), 7.66-7.64 (m, 3H), 7.44-7.41 (m, 5H), 7.29-7.27 (m, 1H), 7.15-7.14 (d, J = 4.0 Hz, 1H), 5.82 (s, 1H). |
| 30 | A25 | | 1H NMR (400 MHz, CHLOROFORM-d): δ 7.45-7.41 (m, 5H), 4.88 (s, 1H), 4.10-4.03 (m, 1H), 2.96-2.55 (m, 4H). |

-continued

| Reference Example | Compound Serial Number | Structural Formula | Spectrogram |
|---|---|---|---|
| 31 | A26 | 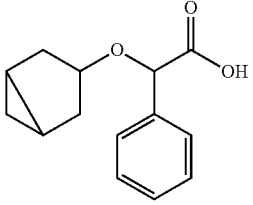 [SMILES: O=C(O)C(OC1CC2CC(C2)C1)c1ccccc1] | 1H NMR (400 MHz, CHLOROFORM-d): δ 7.62-7.29 (m, 5H), 4.89 (s, 1H), 4.12-4.02 (m, 1H), 2.10-1.98 (m, 3H), 1.94-1.83 (m, 1H), 1.29-1.27 (m, 2H), 0.55-0.47 (m, 2H). |
| 32 | A27 | 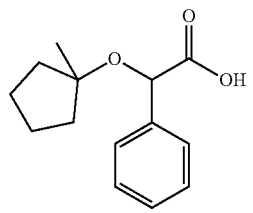 [SMILES: CC1(OC(C(=O)O)c2ccccc2)CCCC1] | 1H NMR (400 MHz, CHLOROFORM-d): δ 7.51-7.49 (m, 2H), 7.41-7.33 (m, 3H), 5.05 (s, 1H), 2.03-1.77 (m, 3H), 1.73-1.48 (m, 5H), 1.34 (s, 3H). |
| 33 | A28 | 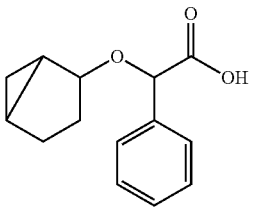 | 1H NMR (400 MHz, CHLOROFORM-d): δ 7.51-7.30 (m, 5H), 5.05-4.95 (m, 1H), 4.07-3.95 (m, 1H), 2.01-1.86 (m, 1H), 1.82-1.59 (m, 2H), 1.56-1.35 (m, 2H), 1.31-1.20 (m, 1H), 0.56-0.35 (m, 1H), 0.08-0.12 (m, 1H). |
| 34 | A29 | 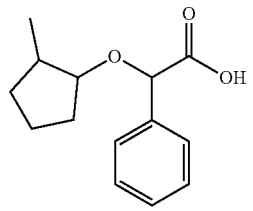 [SMILES: CC1CCCC1OC(C(=O)O)c1ccccc1] | 1H NMR (400 MHz, CHLOROFORM-d): δ 7.50-7.32 (m, 5H), 5.00-4.88 (m, 1H), 3.65-3.47 (m, 1H), 2.16-2.00 (m, 1H), 1.94-1.57 (m, 6H), 1.09-0.96 (m, 3H). |
| 35 | cis-A10 | 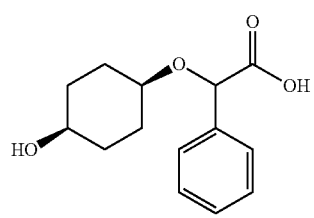 | $^1$H NMR (400 MHz, CHLOROFORM-d): δ 7.40-7.27 (m, 5H), 5.00-4.90 (m, 1H), 3.75-3.65 (m, 1H), 3.60-3.35 (m, 1H), 2.11-0.77 (m, 8H). |
| 36 | trans-A10 | 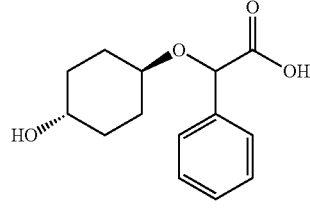 | $^1$H NMR (400 MHz, CHLOROFORM-d): δ 7.46-7.34 (m, 5H), 5.02 (s, 1H), 3.74-3.65 (m, 1H), 3.52-3.42 (m, 1H), 2.19-1.89 (m, 4H), 1.55-1.20 (m, 4H). |
| 37 | A30 | 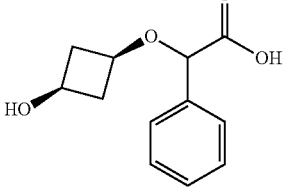 | $^1$H NMR (400 MHz, CHLOROFORM-d): δ 7.49-7.33 (m, 5H), 4.85 (s, 1H), 3.93-3.86 (m, 1H), 3.73-3.60 (m, 1H), 2.80-2.55 (m, 2H), 2.09-1.92 (m, 2H). |

Reference Example 12: Intermediate S-A12

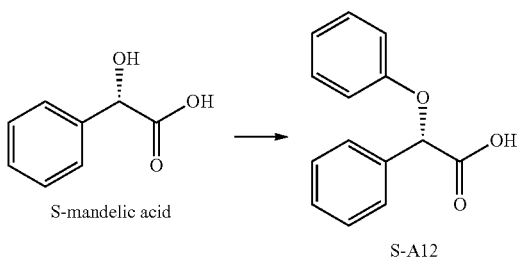 [SMILES: O=C(O)[C@@H](O)c1ccccc1 ; O=C(O)[C@@H](Oc1ccccc1)c1ccccc1]

S-mandelic acid → S-A12

Step 1: Preparation of Compound S-A12

The compound S-mandelic acid (4.6 g, 30.0 mmol) was dissolved in butyronitrile (62.0 mL), followed by the addition of iodobenzene (6.1 g, 30.0 mmol, 3.3 mL) and cesium carbonate (19.6 g, 60.0 mmol), then cuprous iodide (285.7 mg, 1.50 mmol) was added under a nitrogen atmosphere, and the mixture was heated to 75-80° C., and the mixture was subjected to a reaction under stirring for 15 hours. After cooling to room temperature, the reaction solution was concentrated in vacuum to remove the organic solvent. The residue was dissolved in 200 mL of water and washed with ethyl acetate (150 mL×2). The aqueous phase was adjusted to pH of 4 to 5 with a 1N aqueous citric acid solution, and then extracted with ethyl acetate (200 mL×3). The mixed organic phase was washed with saturated brine (200 mL), dried with anhydrous sodium sulfate, filtered and concentrated in vacuum to obtain a crude product. The crude product was separated and purified by column chromatography (an eluent: ethyl acetate/petroleum ether. 0-50%) and then the obtained product was recrystallized with 20 ml of petroleum ether/ethyl acetate (v:v=6:1) to obtain the product S-A12 (41.1% ee). $^1$H NMR (400 MHz, CHLOROFORM-d): δ 7.60-7.58 (m, 2H), 7.46-7.37 (m, 3H), 7.33-7.27 (m, 2H), 7.06-6.92 (m, 3H), 5.68 (s, 1H).

The following compounds were synthesized in a similar manner to the compound S-A12:

| Reference Example | Compound Serial Number | Structural Formula | Spectrogram |
|---|---|---|---|
| 13 | S-A13 | (structure) | $^1$H NMR (400 MHz, CHLOROFORM-d): δ 8.20-8.06 (m, 1H), 7.72-7.57 (m, 3H), 7.48-7.34 (m, 3H), 7.00-6.85 (m, 2H), 6.24 (s, 1H). MS m/z: 229.9 [M + 1]$^+$. SFC: column: Chiralpak AD-3 (150 mm * 4.6 mm, 3 μm); mobile phase: [0.05% DEA EtOH]; B%: 5%-40% 5.5 min, 40% 3 min, 5% 1.5 min; Rt = 4.008 min; 93.2% ee. |
| 14 | S-A14 | (structure) | $^1$H NMR (400 MHz, CHLOROFORM-d): δ 7.59-7.55 (m, 2H), 7.43-7.37 (m, 3H), 6.92-6.90 (d, J = 8.8 Hz, 2H), 6.83-6.81 (d, J = 8.8 Hz, 2H), 5.58 (s, 1H), 3.77 (s, 3H). |
| 15 | S-A15 | (structure) | $^1$H NMR (400 MHz, CHLOROFORM-d): δ 7.58-7.56 (m, 2H), 7.44-7.42 (m, 3H), 6.73-6.60 (m, 2H), 6.33-6.32 (m, 1H), 5.53 (s, 1H). |
| 16 | S-A16 | (structure) | $^1$H NMR (400 MHz, CHLOROFORM-d): δ 7.61-7.54 (m, 2H), 7.46-7.39 (m, 3H), 6.99-6.85 (m, 2H), 6.98-6.86 (m, 1H), 5.62 (s, 1H). |

| Reference Example | Compound Serial Number | Structural Formula | Spectrogram |
|---|---|---|---|
| 17 | S-A17 | ![structure] | ¹H NMR (400 MHz, CHLOROFORM-d): δ 7.63-7.51 (m, 2H), 7.47-7.33(m, 3H), 7.11-6.74 (m, 4H), 5.59 (s, 1 H). SFC: column: ChiralCel OJ—H (150 mm * 4.6 mm, 5 μm); mobile phase: [0.05% DEA EtOH]; B%: 5%-40% 5.5 min, 40% 3 min, 5% 1.5 min; Rt = 2.236 min; 49.0% ee. |
| 18 | S-A18 | ![structure] | ¹H NMR (400 MHz, CHLOROFORM-d): δ 7.63-7.54 (m, 2H), 7.46-7.35 (m, 3H), 7.16-7.06 (m, 1H), 7.04-6.89 (m, 3H), 5.68 (s, 1H). SFC: column: ChiralCel OJ—H (150 mm * 4.6 mm, 5 μm); mobile phase: [0.05% DEA EtOH]; B%: 5%-40% 5.5 min, 40% 3 min, 5% 1.5 min; Rt = 2.229 min; 19.7% ee. |
| 19 | S-A19 | ![structure] | ¹H NMR (400 MHz, CHLOROFORM-d): δ 7.65-7.53 (m, 2H), 7.49-7.35 (m, 3H), 7.27-7.18 (m, 2H), 7.02-6.75 (m, 2H), 5.62 (s, 1 H). SFC: column: ChiralPak AD-3 (150 mm * 4.6 mm, 3 μm); mobile phase: [0.05% DEA EtOH]; B%: 5%-40% 5.5 min, 40% 3 min, 5% 1.5 min; Rt = 3.968 min; 65.9% ee. |

Reference Example 20: Intermediate S-A1

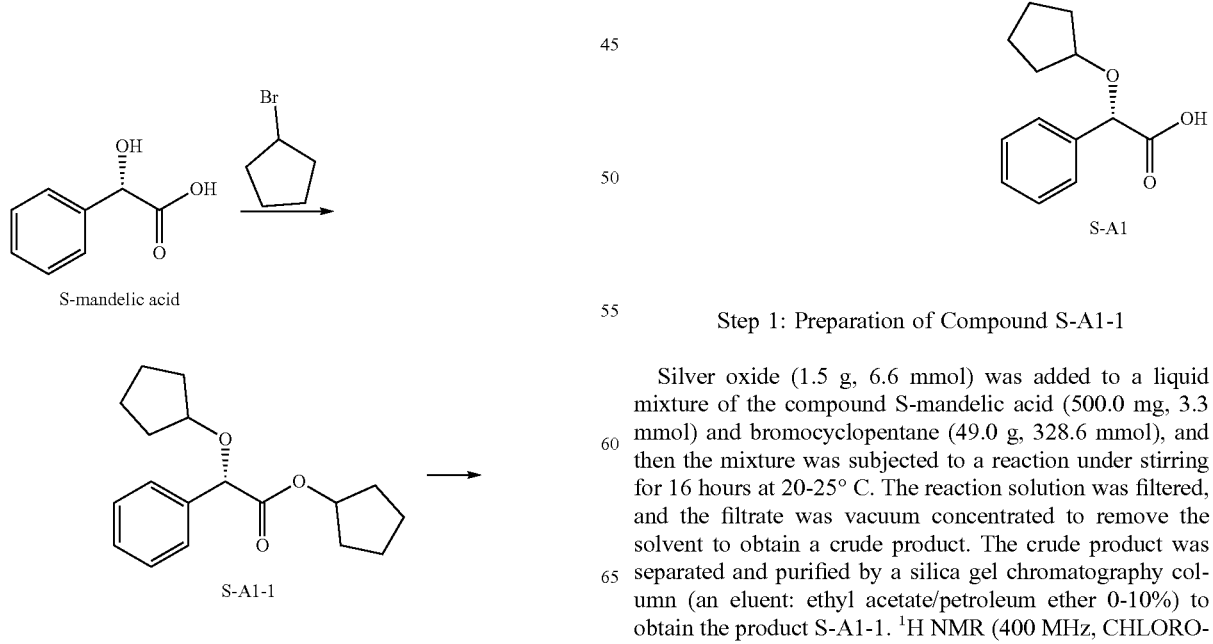

Step 1: Preparation of Compound S-A1-1

Silver oxide (1.5 g, 6.6 mmol) was added to a liquid mixture of the compound S-mandelic acid (500.0 mg, 3.3 mmol) and bromocyclopentane (49.0 g, 328.6 mmol), and then the mixture was subjected to a reaction under stirring for 16 hours at 20-25° C. The reaction solution was filtered, and the filtrate was vacuum concentrated to remove the solvent to obtain a crude product. The crude product was separated and purified by a silica gel chromatography column (an eluent: ethyl acetate/petroleum ether 0-10%) to obtain the product S-A1-1. ¹H NMR (400 MHz, CHLORO- FORM-d): δ 7.49-7.40 (m, 2H), 7.38-7.28 (m, 3H), 5.22-5.19 (m, 1H), 4.88 (s, 1H), 4.03-3.99 (m, 1H), 1.89-1.64 (m, 10H), 1.57-1.45 (m, 6H). MS m/z: 311.1 [M+Na]⁺.

The following compounds were synthesized in a similar manner to the compound S-A1-1:

| Compound Serial Number | Structural Formula | Spectrogram |
|---|---|---|
| R-A1-1 | | ¹H NMR (400 MHz, CHLOROFORM-d): δ 7.49-7.40 (m, 2H), 7.38-7.28 (m, 3H), 5.24-5.20 (m, 1H), 4.89 (s, 1H), 4.05-3.99 (m, 1H), 1.89-1.64 (m, 10H), 1.57-1.45 (m, 6H). MS m/z: 311.1 [M + Na]⁺. |
| S-A20-1 | | ¹H NMR (400 MHz, CHLOROFORM-d): δ 75.3-7.41 (m, 2H), 7.38-7.28 (m, 3H), 5.02 (s, 1H), 4.88-3.75 (m, 1H), 3.43-3.29 (m, 1H), 2.11-1.04 (m, 6H), 1.54-1.16 (m, 14H). |
| A31-1 | | ¹H NMR (400 MHz, CHLOROFORM-d): δ 7.48-7.39 (m, 2H), 7.09-7.01 (m, 2H), 5.25-5.18 (m, 1H), 4.86 (s, 1H), 4.05-3.97 (m, 1H), 1.88-1.67 (m, 11H), 1.59-1.50 (m, 5H). |

Step 2: Preparation of Compound S-A1

The compound S-A1-1 (340.0 mg, 1.2 mmol) was dissolved in a mixed solvent of tetrahydrofuran (6.0 mL) and water (3.0 mL), and lithium hydroxide monohydrate (283.0 mg, 11.8 mmol) was added. The reaction solution was stirred for 48 hours at 20-25° C. The reaction solution was adjusted to pH <3 with 1N hydrochloric acid and extracted with ethyl acetate (20 mL×3). The mixed organic phase was washed with saturated salt water (50 mL), dried with anhydrous sodium sulfate and concentrated in vacuum to obtain a crude product. The crude product was separated and purified by a silica gel chromatography column (an eluent: 0-37.5% petroleum ether/ethyl acetate) to obtain the product S-A1 (95.6% ee). ¹H NMR (400 MHz, CHLOROFORM-d): δ 7.45-7.34 (m, 5H), 4.93 (s, 1H), 4.07-4.03 (m, 1H), 1.78-1.69 (m, 6H), 1.62-1.48 (m, 2H).

The following compounds were synthesized in a similar manner to the compound S-A1:

| Reference Example | Compound Serial Number | Structural Formula | Spectrogram |
|---|---|---|---|
| 21 | R-A1 | | ¹H NMR (400 MHz, CHLOROFORM-d): δ 7.45-7.35 (m, 5H), 4.94 (s, 1H), 4.08-4.06 (m, 1H), 1.78-1.69 (m, 6H), 1.62-1.48 (m, 2H). |

| Reference Example | Compound Serial Number | Structural Formula | Spectrogram |
|---|---|---|---|
| 22 | S-A20 | 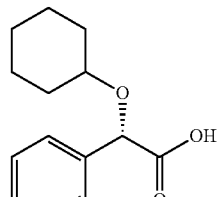 | ¹H NMR (400 MHz, CHLOROFORM-d): δ 7.51-7.31 (m, 5H), 5.05 (s, 1H), 3.63-3.36 (m, 1H), 1.90-1.67 (m, 3H), 1.60-1.35 (m, 3H), 1.30-1.19 (m, 4H). |
| 38 | A31 | 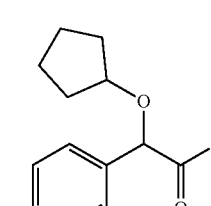 | ¹H NMR (400 MHz, CHLOROFORM-d): δ 7.49-7.37 (m, 2H), 7.12-7.00 (m, 2H), 4.92 (s, 1H), 4.08-4.02 (m, 1H), 1.82-1.67 (m, 8H). |

Reference Example 23: Intermediate A12

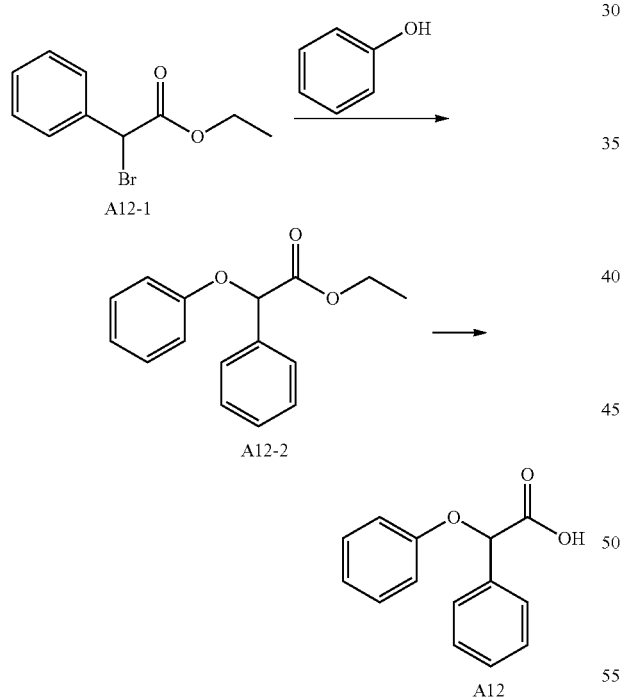

Step 1: Preparation of Compound A12-2

Phenol (193.9 mg, 2.1 mmol) was dissolved in N,N-dimethylformamide (10.0 mL), and then the compound A12-1 (500.0 mg, 2.1 mmol) and potassium carbonate (854.1 mg, 6.2 mmol) were added sequentially. After the reaction solution was heated to 80° C., stirring was continued to be performed for 16 hours. After cooling to room temperature, 20 mL of water was added to the reaction solution, and the aqueous phase was extracted with ethyl acetate (10 mL×3). The mixed organic phase was dried with anhydrous sodium sulfate, filtered and concentrated in vacuum to obtain a crude product. The crude product was separated and purified by a silica gel chromatography column (an eluent: 9% petroleum ether/ethyl acetate) to obtain the product A12-2. ¹H NMR (400 MHz. CHLOROFORM-d): δ 7.52-7.50 (m, 2H), 7.32-7.30 (m, 3H), 7.23-7.16 (m, 2H), 6.93-6.84 (m, 3H), 5.55 (s, 1H), 4.19-4.04 (m, 2H), 1.14-1.11 (t, J=7.2 Hz, 3H). MS m/z: 257.1 [M+1]⁺.

Step 2: Preparation of Compound A12

A12-2 (100.0 mg, 390.2 μmol) was dissolved in a mixed solvent of ethanol (2.0 mL) and water (0.5 mL). After lithium hydroxide monohydrate (14.0 mg, 585.3 μmol) was added, the reaction solution was continued to be stirred for 16 hours at 20° C. 2 mL of water was added to the reaction solution, and the reaction solution was adjusted to pH of 3 to 4 with 1N hydrochloric acid, and then extracted with ethyl acetate (10 mL). The organic phase was dried with anhydrous sodium sulfate, filtered and concentrated in vacuum to obtain a crude product A12. This compound was used in the next step without further purification. ¹H NMR (400 MHz, CHLOROFORM-d): δ 7.35-7.26 (m, 4H), 7.02-6.84 (m, 6H), 5.32 (s, 1H).

Reference Example 24: Intermediate S-A21-2

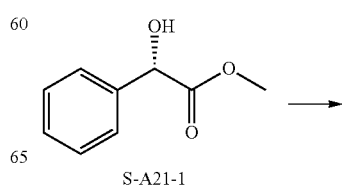

-continued

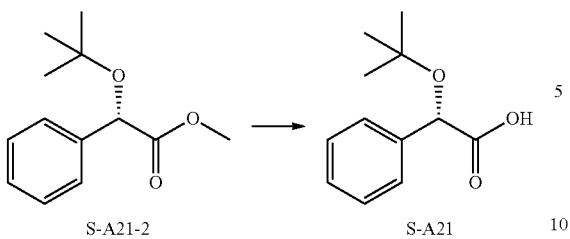

Step 1: Preparation of Compound S-A21-2

The compound S-A21-1 (831.0 mg, 5.0 mmol) was dissolved in dichloromethane (10.0 mL), then magnesium perchlorate (111.6 mg, 500.0 μmol) and di-tert-butyl dicarbonate (2.5 g, 11.5 mmol) were added sequentially. After the reaction solution was heated to 40° C., the reaction was continued to be performed under stirring for 40 hours. After cooling to room temperature, the reaction solution was poured into 25 mL of water and extracted with dichloromethane (10 mL×3). The mixed organic phase was washed with saturated salt water (50 mL), dried with anhydrous sodium sulfate, filtered and concentrated in vacuum to obtain a crude product. The crude product was separated and purified by a silica gel chromatography column (an eluent: 0-20% petroleum ether/ethyl acetate) to obtain the product S-A21-2. $^1$H NMR (400 MHz, CHLOROFORM-d): δ 7.49-7.47 (m, 2H), 7.35-7.31 (m, 3H), 5.10 (s, 1H), 3.71 (s, 3H), 1.27 (s, 9H).

Step 2: Preparation of Compound S-A21

S-A21-2 (300.0 mg, 1.4 mmol) was dissolved in methanol (11.0 mL), then potassium hydroxide (1.5 g, 26.7 mmol) was added, and the reaction solution was subjected to a reaction under stirring for 16 hours at 15° C. The reaction solution was adjusted to pH of 5-6 with 1N hydrochloric acid and extracted with dichloromethane (50 mL×3). The mixed organic phase was washed with saturated salt water (80 mL), dried with anhydrous sodium sulfate, filtered and concentrated in vacuum to obtain a crude product. The crude product was separated and purified by a silica gel chromatography column (an eluent: 0-33% petroleum ether/ethyl acetate) to obtain the product S-A21 (97.9% ee). $^1$H NMR (400 MHz, CHLOROFORM-d): δ 7.48-7.45 (m, 2H), 7.41-7.29 (m, 3H), 5.09 (s, 1H), 1.30 (s, 9H).

Reference Example 25: Intermediate S-A22

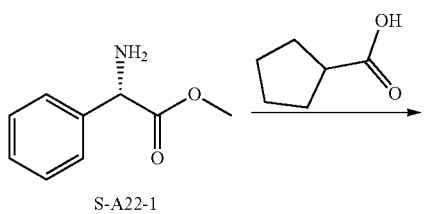

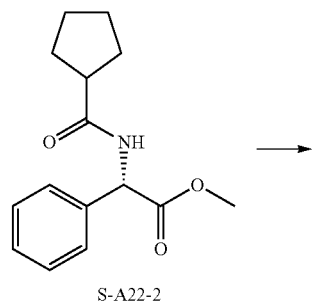

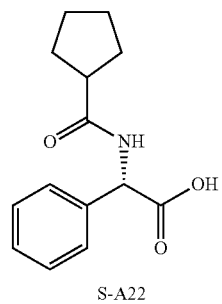

Step 1: Preparation of Compound S-A22-2

The hydrochloride of the compound S-A22-1 (650.0 mg, 3.2 mmol) was dissolved in dichloromethane (10.0 mL) under nitrogen protection. Cyclopentanecarboxylic acid (367.5 mg, 3.2 mmol, 350.03 uL), pyridine (1.0 g, 12.9 mmol, 1.0 mL) and HATU (1.6 g, 4.2 mmol) were sequentially added. After the reaction solution was continuously stirred at 10-15° C. for 12 hours, 30 mL of saturated sodium bicarbonate was added to the reaction solution for quenching the reaction, and the aqueous phase was extracted with dichloromethane (20 mL×3). The mixed organic phase was washed with saturated salt water (50 mL), dried with anhydrous sodium sulfate, filtered and concentrated in vacuum to obtain a crude product. The crude product was separated and purified by a silica gel chromatography column (an eluent: 0-33% petroleum ether/ethyl acetate) to obtain the product S-A22-2. $^1$H NMR (400 MHz. CHLOROFORM-d): δ 7.40-7.31 (m, 5H), 5.60-5.58 (d, J=7.2 Hz, 1H), 3.74 (s, 3H), 2.65-2.60 (m, 1H). 2.25-2.11 (m, 1H), 1.95-1.69 (m, 7H). MS m/z: 261.9 [M+1]$^+$.

Step 2: Preparation of Compound S-A22

S-A22-2 (400.0 mg, 1.5 mmol) was dissolved in tetrahydrofuran (10.0 mL). An aqueous solution (4.0 mL) of lithium hydroxide monohydrate (367.0 mg, 15.3 mmol) was added, and the reaction solution was stirred at 25° C. for 2 hours. The reaction solution was adjusted to pH of 5-6 with 1N hydrochloric acid and extracted with ethyl acetate (25 mL×3). The mixed organic phase was dried with anhydrous sodium sulfate, filtered and concentrated in vacuum to obtain a crude product S-A22. This product was used in the next reaction without purification. $^1$H NMR (400 MHz, METHANOL-$d_4$): δ 7.45-7.22 (m, 5H), 5.43 (s, 1H), 2.86-2.60 (m, 1H), 1.94-1.59 (m, 8H). MS m/z: 247.9 [M+1]$^+$.

Reference Example 26: Intermediate S-A23

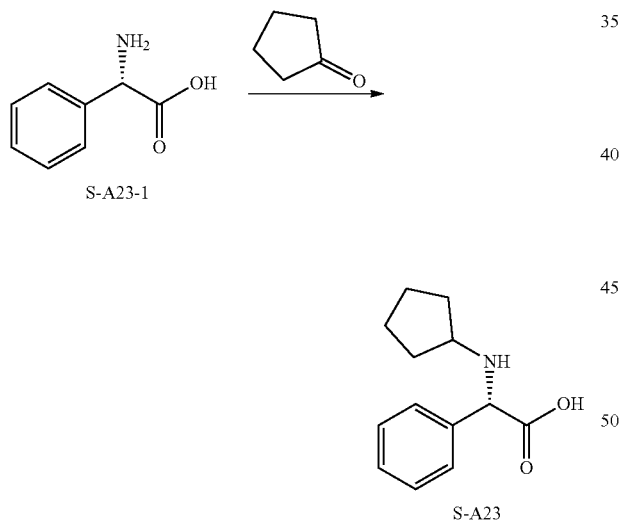

Step 1: Preparation of Compound S-A23

The compound S-A23-1 (500.0 mg, 3.3 mmol) and cyclopentanone (835.0 mg, 9.9 mmol) were dissolved in methanol (4.5 mL), and acetic acid (150.0 μL) and sodium cyanoborohydride (624.0 mg, 9.93 mmol) were successively added. The reaction solution was stirred at 10-15° C. for 12 hours and then concentrated in vacuum to obtain a crude product. 5 mL of water was added to the crude product, filtering was performed, and the product S-A23 was prepared and separated by high performance liquid chromatography. $^1$H NMR (400 MHz, CHLOROFORM-d) δ: 7.56-7.53 (m, 2H), 7.44-7.41 (m, 3H), 4.50 (s, 1H), 3.45-3.35 (m, 1H), 2.11-1.96 (m, 2H), 1.88-1.43 (m, 6H). MS m/z: 219.9 [M+1]$^+$.

The following compounds were synthesized in a similar manner to the compound S-A23:

| Reference Example | Compound Serial Number | Structural Formula | Spectrogram |
|---|---|---|---|
| 27 | S-A24 | | H NMR (400 MHz, CD$_3$OD): δ 7.63-7.52 (m, 5H), 5.15 (s, 3H), 3.97-2.50 (m, 1H), 3.08-2.36 (m, 3H), 2.12-1.55 (m, 8H). MS m/z: 233.9 [M + 1]$^+$. |

Reference Example 28: Synthesis of Intermediates C1, (−)-C1 and (+)-C1

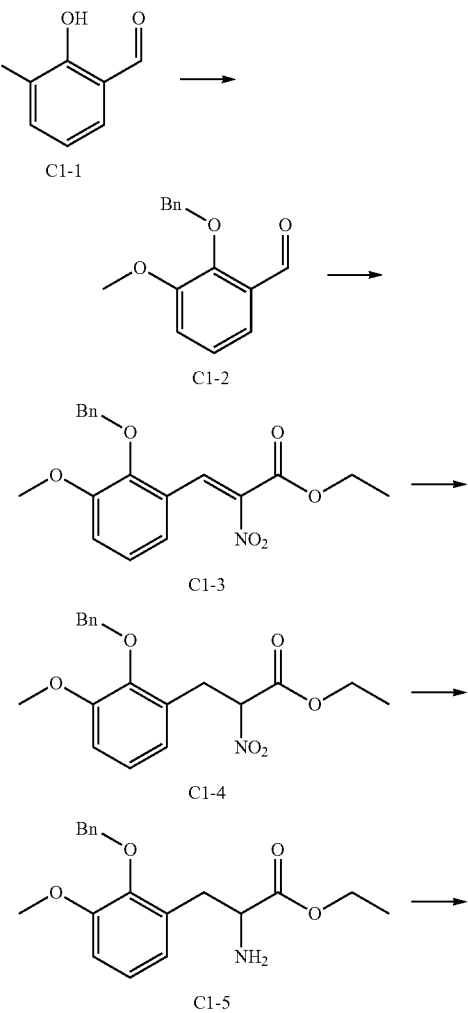

-continued

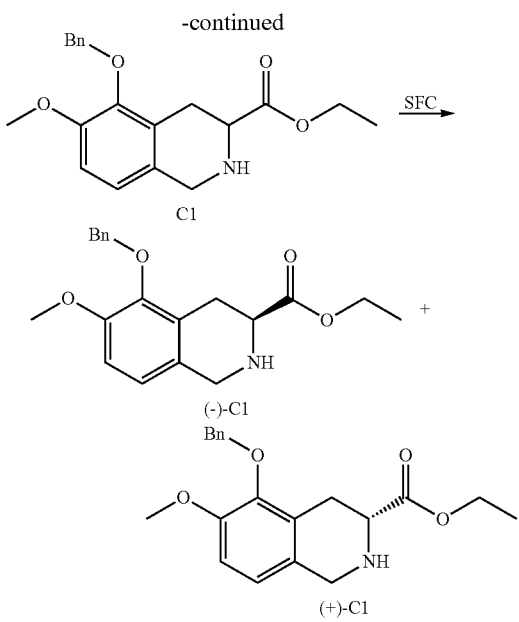

Step 1: Preparation of Compound C1-2

A compound C1-1 (200.0 g. 1.31 mol) was dissolved in absolute ethanol (1.50 L) under the protection of nitrogen. Anhydrous potassium carbonate (181.1 g, 1.31 mol) and benzyl bromide (268.9 g, 1.57 mol) were successively added under stirring at 15° C., and the reaction solution was heated to 100° C. and stirring was continued to be performed for 15 hours. After the reaction solution was cooled to room temperature, the reaction solution was filtered, and the filtrate was concentrated in vacuum to obtain an oily substance. After being re-dissolved with ethyl acetate (3.0 L), the oily substance was washed with a 2N sodium hydroxide solution (500 mL×2) and saturated salt water (600 mL×2), dried with anhydrous magnesium sulfate, filtered and concentrated in vacuum to obtain a crude product. The crude product was dispersed in petroleum ether and stirred for 1 hour, and filtered to obtain 247.0 g of the compound C1-2. $^1$H NMR (400 MHz, CHLOROFORM-d): δ 10.25 (s, 1H), 7.42-7.34 (m, 6H), 7.21-7.12 (m, 2H), 5.19 (s, 2H), 3.96 (s, 3H).

Step 2: Preparation of Compound C1-3

The compound C1-2 (220.0 g, 908.08 mmol), ethyl 2-nitroacetate (145.0 g, 1.09 mol) and diethylamine hydrochloride (149.3 g, 1.36 mol) were heated in a mixed solution of anhydrous toluene (2.1 L) to 130° C. to be subjected to reflux for 15 hours, and the water formed by the reaction was separated by using a Deane-Stark water knockout trap. After the reaction solution was cooled to room temperature, the reaction solution was concentrated in vacuum to remove toluene. The residue was re-dissolved in dichloromethane (500 mL), washed with a saturated saline solution (1000 mL×2), dried with anhydrous sodium sulfate, filtered and concentrated in vacuum to obtain the compound C1-3, which was directly used in the next reaction without purification.

Step 3: Preparation of Compound C1-4

The crude compound C1-3 (430.0 g, 1.2 mol) obtained in the above step 2 and isopropyl alcohol (2.2 g, 36.0 mmol) were dissolved in chloroform (4.5 L) under a nitrogen atmosphere, and the liquid mixture was cooled to 0° C. Thereafter, 100-200-mesh silica gel (1.8 kg) was added thereto with stirring, and then sodium borohydride (201.1 g, 5.3 mol) was added in batch within 1.5 hours. After the reaction solution was heated to 15° C., the reaction was continued to be performed under stirring for 12 hours. After acetic acid (210 mL) was slowly added, stirring was continued to be performed for 15 minutes, and the reaction solution was filtered, and the filter cake was washed with chloroform (500 mL). The residue obtained by concentrating the mixed filtrate under vacuum was separated and purified by a silica gel chromatography column (an eluent: 6-10% petroleum ether/ethyl acetate) to obtain the compound C1-4. $^1$H NMR (400 MHz, CHLOROFORM-d): δ 7.48-7.33 (m, 5H), 7.02-6.97 (m, 1H), 6.94-6.90 (m, 1H), 6.64-6.62 (dd, J=1.6, 7.6 Hz, 1H), 5.33-5.30 (dd, J=6.0, 9.2 Hz, 1H), 5.19-5.05 (m, 2H), 4.15-4.10 (q, J=7.2 Hz, 2H), 3.91 (s, 3H), 3.44-3.31 (m, 2H), 1.16-1.12 (t, J=7.2 Hz, 3H).

Step 4: Preparation of Compound C1-S

The compound C1-4 (8.2 g 22.82 mmol) was dissolved in acetic acid (100 mL) at 15° C., zinc powder (76.2 g, 212.04 mmol) was slowly added and the reaction temperature was maintained between 60-65° C. Thereafter, the reaction was continued to be performed under stirring at 60° C. for 2 hours. After the reaction solution was cooled to room temperature, the reaction solution was filtered, and the filter cake was washed with acetic acid (300 mL). The residue obtained by concentrating the mixed filtrate in vacuum was re-dissolved in dichloromethane (500 mL), washed with a saturated sodium bicarbonate aqueous solution (200 mL×3) and saturated saline solution (200 mL×2), dried with anhydrous sodium sulfate, filtered and concentrated in vacuum to obtain a crude product C1-5, which was directly used in the next step without purification. MS m/z: 330.1 [M+1]$^+$.

Step 5: Preparation of Compound C1

The compound C1-5 (48.9 g, 149.4 mmol) was dissolved in a 2N hydrochloric acid solution (500 mL) at 15° C. under the nitrogen atmosphere, and then a 37% aqueous solution of formaldehyde (36.4 g. 448.1 mmol) was added. After stirring is performed for 25 hours, the stirred material was filtered, and the filter cake was washed with water (100 mL) to obtain the hydrochloride of the compound C1. MS m/z: 342.1 [M+1]$^+$.

Step 6: Preparation of Compounds (−)-C1 and (+)-C1

The compound C1 (40.0 g, 117.2 mmol) was separated by a chiral column to obtain two isomers (−)-C1 and (+)-C1.

(−)-C1: $^1$H NMR (400 MHz, CHLOROFORM-d): δ 7.40-7.38 (m, 2H), 7.33-7.22 (m, 3H), 6.73-6.71 (m, 2H), 4.93-4.92 (m, 2H), 4.17-4.15 (q, J=7.2 Hz, 2H), 4.10-3.93 (m, 2H), 3.79 (s, 3H), 3.62-3.58 (m, 1H), 3.07-3.06 (m, 1H), 2.77-2.65 (m, 1H), 1.21 (t, J=7.2 Hz. 3H). MS m/z: 342.1 [M+1]$^+$. [α]=−23.4.

(+)-C1: $^1$H NMR (400 MHz, CHLOROFORM-d): δ 7.43-7.40 (m, 2H), 7.33-7.22 (m, 3H), 6.86 (s, 2H), 5.06-4.95 (q, J=11.2 Hz, 2H), 4.54-4.50 (m, 1H), 4.33-4.21 (m, 3H), 4.07-4.05 (m, 1H), 3.88 (s, 3H), 3.34-3.25 (m, 1H), 3.20-3.14 (m, 1H), 1.30-1.26 (t, J=7.2 Hz, 3H). MS m/z: 342.1 [M+1]$^+$. [α]=+9.8.

Reference Example 29: Synthesis of Intermediate C2

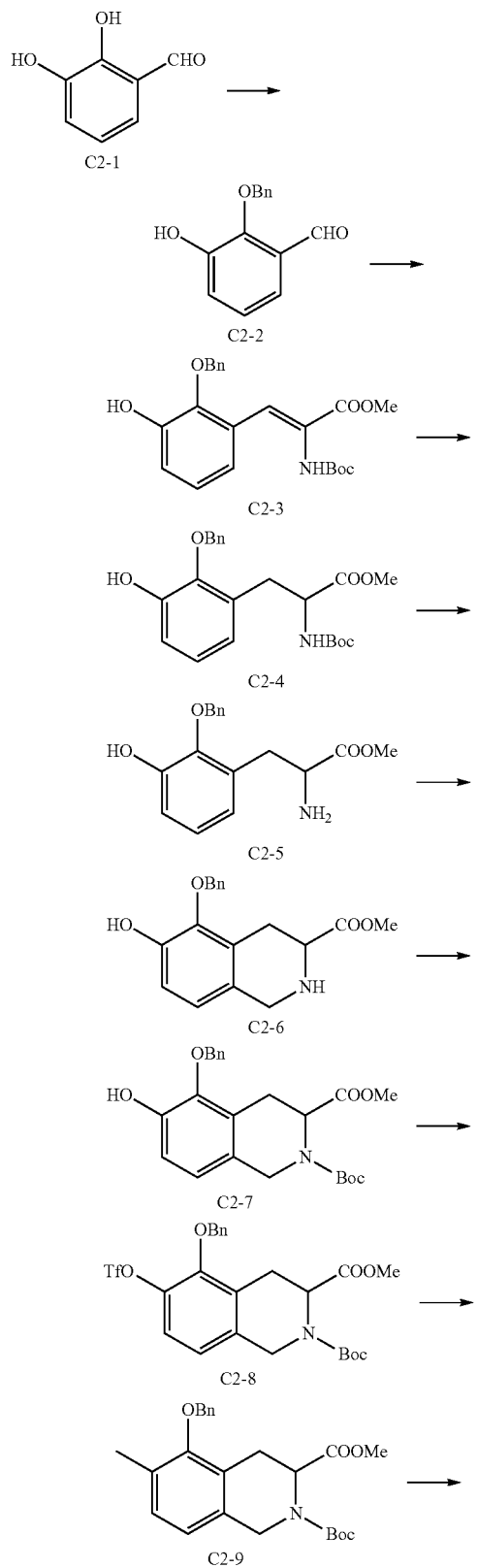

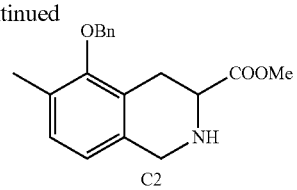

Step 1: Preparation of Compound C2-2

A compound C2-1 (5.0 g, 362 mmol) was dissolved in N,N-dimethylformamide (60 mL) under the nitrogen atmosphere, and a sodium hydrogen compound (1.5 g. 36.2 mmol, 60.0% purity) was added slowly, and after 0.5 hour, the temperature was lowered to 0° C., benzyl bromide (6.2 g, 36.2 mmol) was added dropwise to the reaction solution, and the reaction solution was slowly heated to 25° C. and then continuously stirred for 19.5 hours. The reaction solution was poured into ice water (50 mL), and ethyl acetate (200 mL) was added, and the mixture was separated, and the organic phase was washed with water (100 mL×3) and saturated saline water (50 mL), dried with anhydrous sodium sulfate, filtered and decompressed to remove the organic solvent. The crude product was separated and purified by a silica gel chromatography column (an eluent: 9-25% ethyl acetate/petroleum ether) to obtain the compound C2-2. $^1$H NMR (400 MHz, CHLOROFORM-d): δ 10.19 (s, 1H), 7.45-7.36 (m, 6H), 7.24-7.13 (m, 2H), 5.77 (s, 1H), 5.09 (s, 2H).

Step 2: Preparation of Compound C2-3

The Compound C2-2 (4.0 g, 17.5 mmol) and Boc-α-phosphonoglycine trimethyl ester (6.3 g, 21.0 mmol) were dissolved in tetrahydrofuran (60 mL) at 0° C. and tetramethylguanidine (4.4 g, 38.5 mmol) was added and the reaction solution was stirred at 25° C. for 20 hours. The reaction solution was adjusted to pH of 6-7 with 1M hydrochloric acid, and extracted by ethyl acetate (50 mL×3). The mixed organic phase was washed with a saturated saline solution (20 mL), dried with anhydrous sodium sulfate, filtered, and decompressed to remove the organic solvent, and the crude product was separated and purified by a silica gel chromatography column (an eluent: 9-25% ethyl acetate/petroleum ether) to obtain the compound C2-3. $^1$H NMR (400 MHz, CHLOROFORM-d): δ 7.42-7.37 (m, 5H), 7.16 (brs, 1H), 7.05-6.98 (m, 2H). 6.94-6.88 (m, 1H), 6.74 (brs, 1H), 5.58 (s, 1H). 4.91 (s, 2H), 3.88 (s, 3H), 1.41 (s, 9H).

Step 3: Preparation of Compound C2-4

The compound C2-3 (6.3 g, 15.8 mmol) was dissolved in methanol (60 mL) at 0° C. and then nickel chloride hexahydrate (1.9 g, 7.9 mmol) and sodium borohydride (1.8 g, 47.3 mmol) were added sequentially. The reaction solution was slowly heated to 25° C. and stirring was continued to be performed for 20 hours. Water (50 mL) was added to the reaction solution, and the reaction solution was decompressed to remove methanol, and extracted with ethyl acetate (50 mL×3). The mixed organic phase was washed with a saturated saline solution (30 mL), dried with anhydrous sodium sulfate, filtered, and decompressed to remove the organic solvent, and the crude product was separated and purified by a silica gel chromatography column (an eluent: 9-25% ethyl acetate/petroleum ether) to obtain the compound C2-4. ¹H NMR (400 MHz, CHLOROFORM-d): δ 7.40-7.31 (m, 5H), 6.93-6.86 (m, 1H), 6.79-6.77 (d, J=7.2 Hz, 1H), 6.62-6.60 (d, J=7.2 Hz, 1H), 5.41 (s, 1H), 4.89-4.81 (m, 2H), 4.52-4.47 (m, 1H), 3.57 (s, 3H), 3.06-3.03 (m, 1H), 2.99-2.94 (m, 1H), 1.35 (s, 9H). MS m/z: 423.9 [M+Na]⁺.

Step 4: Preparation of Compound C2-5

The compound C2-4 (1.1 g, 2.7 mmol) was dissolved in dichloromethane (20 mL), and trifluoroacetic acid (6.2 g, 54.0 mmol) was added, and the reaction solution was reacted at 25° C. for 1 hour. The organic solvent was removed under reduced pressure to obtain a trifluoroacetic acid salt of a crude compound C2-5. And the compound was used directly for the next reaction step without further purification. ¹H NMR (400 MHz, CHLOROFORM-d): δ 8.15 (brs, 2H), 7.38-7.33 (m, 5H), 6.94-6.89 (m, 2H), 6.62-6.60 (d, J=7.6 Hz), 1H), 4.96 (s, 2H), 4.36-4.33 (m, 1H), 3.71 (s, 3H), 3.15-3.10 (m, 1H), 2.93-2.87 (m, 1H). MS m/z: 301.9 [M+1]⁺.

Step 5: Preparation of Compound C2-6

The trifluoroacetic acid salt of the compound C2-5 (1.0 g, 2.4 mmol) was added to an aqueous solution of formaldehyde (1.2 g, 14.4 mmol, 37%), and 1M diluted hydrochloric acid (20 mL) was added, and the reaction solution was heated to 60° C., and continuously stirred for 1 hour. The organic solvent was removed under reduced pressure to obtain the hydrochloride salt of a crude compound C2-6. And the compound was used directly for the next reaction step without further purification. ¹H NMR (400 MHz, METHANOL-d₄): δ 7.47-7.44 (m, 2H), 7.38-7.36 (m, 3H), 6.90-6.85 (m, 2H), 5.12 (s, 2H), 4.37-4.25 (m, 3H), 3.90 (s, 3H), 3.33-3.30 (m, 1H), 2.89-2.80 (m, 1H). MS m/z: 314.0 [M+1]⁺.

Step 6: Preparation of Compound C2-7

The hydrochloride salt of the compound C2-6 (740.0 mg, 2.1 mmol) was dissolved in dichloromethane (7 mL), and then di-t-butyl dicarbonate (692.5 mg, 3.2 mmol) and triethylamine (856.2 mg, 8.5 mmol) were added sequentially, and the reaction solution was continuously stirred at 25° C. for 3 hours. The organic solvent was removed under reduced pressure, and the obtained crude product was separated and purified by a silica gel chromatography column (an eluent: 9-33% ethyl acetate/petroleum ether) to obtain the compound C2-7. ¹H NMR (400 MHz, CHLOROFORM-d): δ 7.44-7.39 (m, 5H), 6.88-6.80 (m, 2H), 5.34 (s, 1H), 5.21-4.88 (m, 3H), 4.76-4.63 (m, 1H), 4.51-4.38 (m, 1H), 3.67-3.65 (d, J=8.8 Hz, 3H), 3.57-3.34 (m, 1H), 3.07-2.99 (m, 1H), 1.48-1.44 (d, J=13.6 Hz, 9H). MS m/z: 436.1 [M+Na]⁺.

Step 7: Preparation of Compound C2-8

The compound C2-7 (500.0 mg, 1.2 mmol) was dissolved in N,N-dimethylformamide (10 mL), and then N,N-diisopropylethylamine (468.9 mg, 3.6 mmol) and N-phenyl bis (trifluoromethanesulfonimide) (648.0 mg, 1.8 mmol) were added. The reaction solution was continuously stirred at 25° C. for 16 hours. Ethyl acetate (100 mL) was added to the reaction solution, and the solution was washed with water (20 mL×3) and a saturated saline solution (20 mL), dried with anhydrous sodium sulfate, filtered, and decompressed to remove the organic solvent, and the resulting crude product was separated and purified by a silica gel chromatography column (an eluent: 9-25% ethyl acetate/petroleum ether) to obtain the compound C2-8. ¹H NMR (400 MHz, CHLOROFORM-d): δ 7.47-7.41 (m, 5H), 7.17-6.96 (m, 2H), 5.21-4.69 (m, 4H), 4.56-4.41 (m, 1H), 3.66-3.65 (d, J=6.0 Hz, 3H), 3.54-3.28 (m, 1H), 2.96-2.84 (m, 1H), 1.55-1.48 (d, J=27.6 Hz, 9H). MS m/z: 568.1 [M+Na]⁺.

Step 8: Preparation of Compound C2-9

The compound C2-8 (200.0 mg, 366.6 μmol) and methylboronic acid (109.7 mg, 1.8 mmol) were dissolved in dioxane (3 mL) under a nitrogen atmosphere, and Pd(dppf)Cl₂ (26.8 mg, 36.6 μmol) and potassium carbonate (152.0 mg, 1.1 mmol) were added sequentially, and the reaction solution was heated to 100° C. for a reaction for 2 hours. The organic solvent was removed under reduced pressure, and the resulting crude product was separated and purified by a silica gel chromatography column (an eluent: 9-25% ethyl acetate/petroleum ether) to obtain the compound C2-9. ¹H NMR (400 MHz, CHLOROFORM-d): δ 7.50-7.39 (m, 5H), 7.08-6.84 (m, 2H), 5.18-4.67 (m, 4H), 4.54-4.47 (m, 1H), 3.66-3.64 (d, J=9.2 Hz, 3H), 3.59-3.34 (m, 1H), 3.07-2.94 (m, 1H), 2.31 (s, 3H), 1.55-1.48 (d, J=28.4 Hz, 9H). MS m/z: 434.1 [M+Na]⁺.

Step 9: Preparation of Compound C2

The compound C2-9 (140.0 mg, 340.2 μmol) was dissolved in methanol (1 mL), and a 4M hydrochloric acid methanol solution (2 mL) was added, and the reaction solution was continuously stirred at 25° C. for 16 hours. The organic solvent was removed under reduced pressure to obtain a hydrochloride salt of the crude compound C2. ¹H NMR (400 MHz, METHANOL-d₄): δ 7.49-7.40 (m, 5H), 7.23-7.21 (d, J=8.0 Hz, 1H), 7.00-6.98 (d, J=8.0 Hz, 1H), 4.94 (s, 2H), 4.49-4.39 (m, 3H), 3.91 (s, 3H), 3.47-3.42 (m, 1H), 3.08-3.00 (m, 1H), 2.33 (s, 3H). MS m/z: 312.0 [M+1]⁺.

Reference Example 39: Synthesis of Intermediate C3

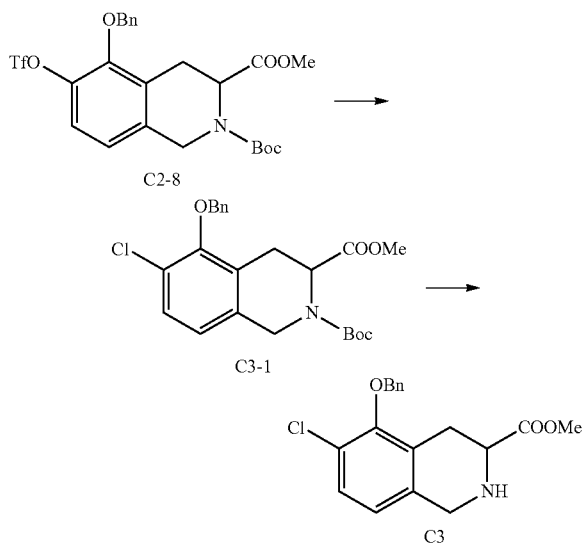

Step 1: Preparation of Compound C3-1

The compound C2-8 (190.0 mg, 348.3 µmol) was dissolved in dioxane (3 mL) under a nitrogen atmosphere, and then potassium chloride (51.9 mg, 696.9 µmol), Pd$_2$(dba)$_3$ (4.8 mg, 5.2 mol), di-tert-butyl (2',4',6'-triisopropyl-3,6-dimethoxybiphenyl-2-yl)phosphine (7.6 mg, 15.7 µmol) and potassium fluoride (10.1 mg, 174.1 µmol) were added sequentially. The reaction solution was heated to 130° C. and stirring was continued to be performed for 20 hours. The organic solvent was removed under reduced pressure, and the obtained crude product was separated and purified by a silica gel chromatography column (an eluent: 5-16% ethyl acetate/petroleum ether) to obtain the compound C3-1. $^1$H NMR (400 MHz, CHLOROFORM-d): δ 7.56-7.37 (m, 5H), 7.26-7.11 (m, 1H), 6.94-6.72 (m, 1H), 5.19-5.04 (m, 1H), 5.03-4.85 (m, 2H). 4.76-4.65 (m, 1H), 4.54-4.39 (m, 1H), 3.65-3.63 (d, J=8.0 Hz, 3H), 3.58-3.30 (m, 1H), 2.98-2.82 (m, 1H), 1.54-1.44 (m, 9H). MS m/z: 331.9 [M−100]$^+$.

Step 2: Preparation of Compound C3

The compound C3-1 (110.0 mg, 254.7 µmol) was dissolved in methanol (1 mL), and a 4M hydrogen chloride methanol solution (1 mL) was added, and the reaction solution was continuously stirred at 25° C. for 16 hours. The organic solvent was removed under reduced pressure to obtain a hydrochloride salt of the crude compound C3. $^1$H NMR (400 MHz, METHANOL-d$_4$): δ 7.54-7.37 (m, 6H), 7.13-6.91 (m, 1H), 5.20-5.08 (m, 2H), 4.55-4.33 (m, 3H), 3.93-3.90 (m, 3H), 3.54-3.38 (m, 1H), 3.06-2.90 (m, 1H). MS m/z: 332.0 [M+1]$^+$.

Reference Example 40: Synthesis of Intermediate C4

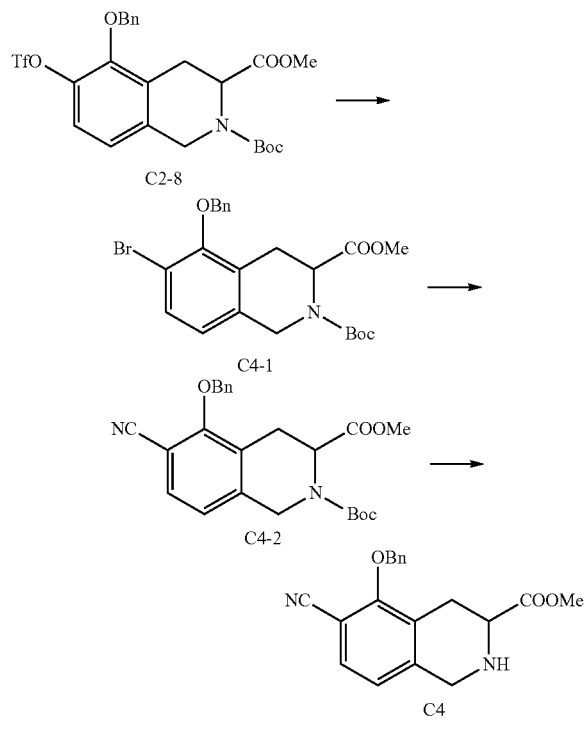

Step 1: Preparation of Compound C4-1

The compound C2-8 (260.0 mg, 476.6 µmol) was dissolved in dioxane (6 mL) under a nitrogen atmosphere, and potassium bromide (113.4 mg, 953.2 µmol), Pd$_2$(dba)$_3$ (13.1 mg, 14.3 µmol), di-tert-butyl (2',4',6'-triisopropyl-3,6-dimethoxybiphenyl-2-yl)phosphine (23.1 mg, 47.6 µmol) and potassium fluoride (13.8 mg, 238.3 µmol) were added sequentially, and the reaction solution was heated to 130° C. and stirring was continued to be performed for 20 hours. The organic solvent was removed under reduced pressure, and the obtained crude product was separated and purified by a silica gel chromatography column (an eluent: 5-10Y % ethyl acetate/petroleum ether) to obtain the compound C4-1. $^1$H NMR (400 MHz, CHLOROFORM-d): δ 7.59-7.33 (m, 6H), 6.90-6.77 (m, 1H), 5.22-5.06 (m, 1H), 5.03-4.84 (m, 2H), 4.79-4.63 (m, 1H), 4.54-4.37 (m, 1H), 3.65-3.63 (d, J=8.0 Hz, 3H), 3.59-3.32 (m, 1H), 3.02-2.85 (m, 1H), 1.54-1.45 (m, 9H). MS m/z: 377.9 [M−100]$^+$.

Step 2: Preparation of Compound C4-2

Under a nitrogen atmosphere, concentrated sulfuric acid (44.2 mg, 450.25 µmol) was added to N,N-dimethylacetamide (10.0 mL), and the reaction solution was stirred at 25° C. for 0.5 hour, and palladium acetate (0.1 g, 668.12 µmol) and XPhos (0.6 g, 1.30 mmol) were added. The temperature of the mixture was raised to 80° C. and stirring was continued to be performed for 0.5 hour. 1 mL of the above solution was added to a mixed solution of the compound C4-1 (50.0 mg, 104.9 µmol), zinc cyanide (18.5 mg, 157.4 µmol), zinc powder (686.4 µg, 10.50 µmol) and N,N-dimethylacetamide (2.0 mL). The reaction solution was heated to 90° C. and stirring was continued to be performed for 16 hours. After cooling, ethyl acetate (30.0 mL) was added into the reaction solution, and the mixture was washed with water (10.0 mL) for three times, washed with a saturated aqueous sodium chloride solution (20.0 mL), dried with anhydrous sodium sulfate, and filtered, and the filtrate was decompressed to remove the organic solvent. The obtained crude product was separated and purified by a silica gel preparation plate (20% ethyl acetate/petroleum ether) to obtain the compound C4-2. $^1$H NMR (400 MHz, CHLOROFORM-d): δ 7.55-7.37 (m, 6H), 7.01-6.95 (m, 1H), 5.23-5.12 (m, 2H), 4.88-4.43 (m, 3H), 3.65-3.63 (d, J=6.8 Hz, 3H), 3.59-3.35 (m, 1H), 2.93-2.77 (m, 1H), 1.57-1.43 (m, 9H). MS m/z: 323.0 [M−100]$^+$.

Step 3: Preparation of Compound C4

The compound C4-2 (76.0 mg, 179.9 µmol) was dissolved in methanol (1 mL), and a 4M hydrogen chloride methanol solution (1 mL) was added, and the reaction solution was continuously stirred at 25° C. for 2 hours. The organic solvent was removed under reduced pressure to obtain a hydrochloride salt of the crude compound C4. $^1$H NMR (400 MHz, METHANOL-d$_4$): δ 7.58-7.56 (d, J=8.0 Hz, 1H), 7.42-7.28 (m, 5H), 7.10-7.08 (d, J=8.0 Hz, 1H), 5.25-5.16 (m, 2H), 4.48-4.26 (m, 3H), 3.80 (s, 3H), 3.32-3.26 (m, 1H), 2.92-2.75 (m, 1H). MS m/z: 323.1 [M+1]$^+$.

Reference Example 41: Synthesis of Intermediate C5

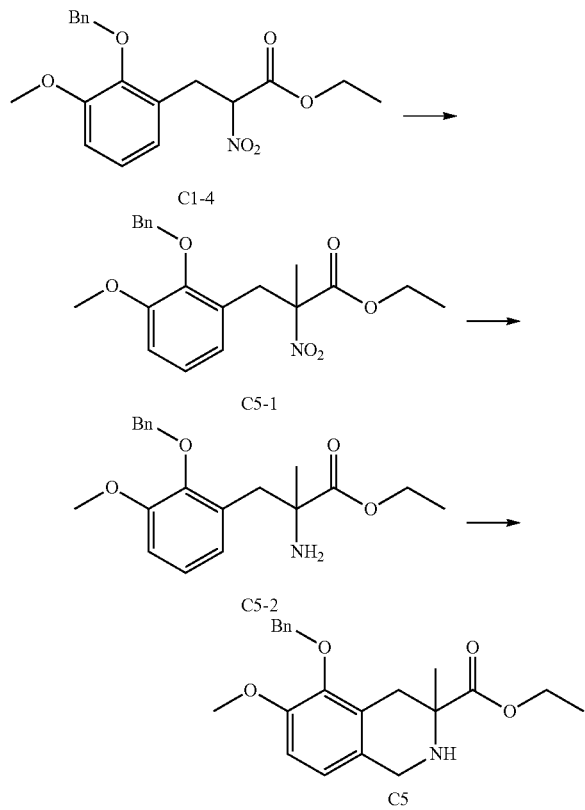

Step 1: Synthesis of Compound C5-1

The compound C1-4 (10.0 g, 27.8 mmol) was dissolved in N,N-dimethylformamide (30.0 mL), and sodium hydride (13.4 g, 33.5 mmol, 60% purity) was added under an ice-water bath, and stirring was continued to be performed for 30 minutes. Methyl iodide (35.3 g, 248.7 mmol) was added, and the reaction solution was slowly heated to 15-20° C. and stirring was continued to be performed for 16 hours. The reaction solution was poured into water (100.0 mL), and ethyl acetate (100.0 mL) was used for extraction for three times. The mixed organic phase was dried with anhydrous sodium sulfate, filtered and decompressed to remove the organic solvent. The obtained crude product was separated and purified by silica gel chromatography (an eluent: 0-17% ethyl acetate/petroleum ether) to obtain a crude compound C5-1. $^1$H NMR: (400 MHz, CHLOROFORM-d): δ 7.45-7.35 (m, 5H), 7.02-6.96 (m, 1H), 6.92-6.86 (m, 1H), 6.62-6.60 (m, 1H), 5.09-5.07 (d, J=10.8 Hz, 1H), 4.94-4.92 (d, J=10.8 Hz, 1H), 4.28-4.18 (m, 2H), 3.90 (s, 3H). 3.62-3.43 (m, 2H), 1.61 (s, 3H), 1.27-1.23 (t, J=7.2 Hz, 3H). MS m/z: 396.0 [M+Na]$^+$.

Step 2: Synthesis of Compound C5-2

The compound C5-1 (3.7 g. 9.8 mmol) was dissolved in ethanol (50.0 mL), and reduced iron powder (5.6 g. 99.6 mmol) and ammonium chloride (7.9 g, 147.0 mmol) were sequentially added, and the reaction solution was heated to 80° C., and stirring was continued to be performed for 16 hours. After cooling, the mixture was filtered with kieselguhr. And the filter cake was washed with ethanol (50.0 mL). The filtrate was decompressed to remove the organic solvent to obtain the crude compound C-2. The compound was used directly for the next reaction step without further purification. MS m/z: 344.1 [M+H]$^+$.

Step 3: Synthesis of Compound C5

The compound C5-2 (3.4 g, 9.8 mmol) was dissolved in a mixed solution of dichloromethane (50.0 mL) and trifluoroacetic acid (10.0 mL), and paraformaldehyde (3.5 g, 39.3 mmol) was added. The reaction solution was continuously stirred for 16 hours at 20-25° C. The organic solvent was removed under reduced pressure. Dichloromethane (50.0 ml) and water (50.0 ml) were added to the obtained crude product, and the mixture was adjusted to pH of 8-9 with saturated sodium carbonate, and then separated. The aqueous phase was extracted with dichloromethane (80.0 mL) for three times. The mixed organic phase was washed with a saturated saline solution (100.0 mL), and the organic solvent was removed under reduced pressure. The crude product was separated and purified by silica gel chromatography (an eluent: 0-10% methanol/dichloromethane), and then separated and purified through high performance liquid chromatography (column: Phenomenex luna C18 250*50 mm*10 μm; mobile phase: [water (0.1% TFA)-ACN]; B %: 15%-40%, 23 min), and most acetonitrile was removed under reduced pressure. The aqueous phase was adjusted to pH of 8-9 with saturated sodium carbonate, and extracted with dichloromethane (150.0 mL) for three times. The mixed organic phase was washed with a saturated saline solution (200.0 mL), and the organic solvent was removed under reduced pressure to obtain the compound C5. $^1$H NMR: (400 MHz, METHANOL-d$_4$): δ 7.52-7.51 (d, J=7.2 Hz, 2H), 7.44-7.31 (m, 3H), 6.82-6.72 (m, 2H), 5.08-4.88 (m, 2H), 4.16-4.07 (m, 2H), 4.06-3.93 (m, 2H), 3.86 (s, 3H), 3.39-3.35 (d, J=16.8 Hz, 1H), 2.62-2.57 (d, J=16.8 Hz, 1H), 1.40 (s, 3H), 1.22-1.18 (t, J=7.2 Hz, 3H). MS m/z: 356.1 [M+H]$^+$.

Reference Example 42: Synthesis of Intermediate (−)-C2

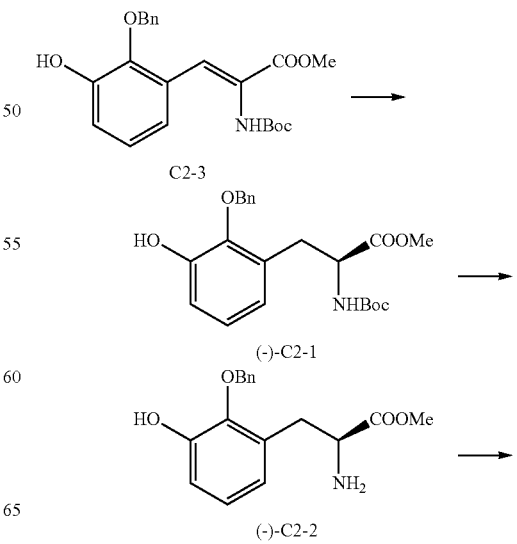

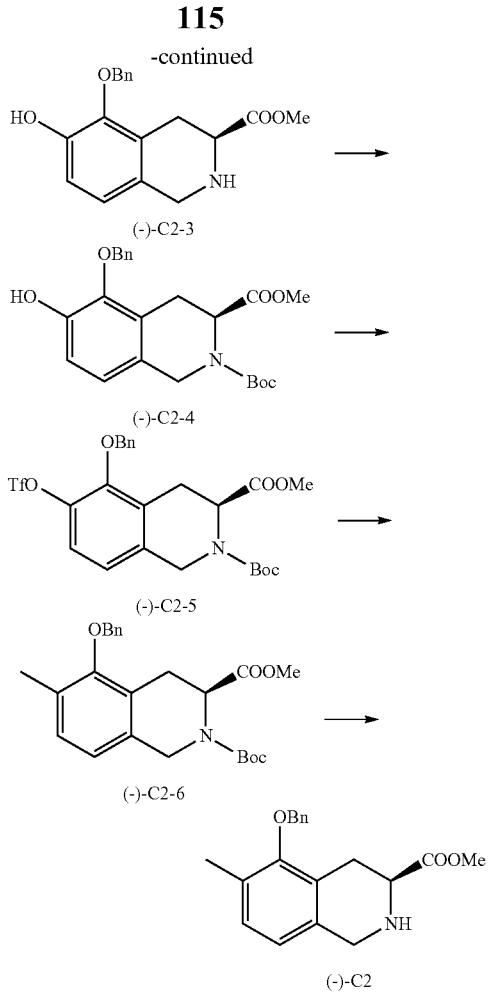

Step 1: Preparation of Compound (−)-C2-1

(S,S)-Et-DuPhos (202.9 mg, 559.8 μmol) was dissolved in methanol (20 mL) under an argon atmosphere, and Rh(COD)⁺OTf⁻ (231.9 mg, 495.2 mol) was added. Stirring was continuously performed for 15 minutes, and the solution was added to a methanol solution (1.0 L) of the compound C2-3 (86.0 g, 215.3 mmol) under an argon atmosphere, and argon replacement was performed for three times, hydrogen replacement was performed for three times, and the reaction solution was continuously stirred for 16 hours at 25° C. and in 15 Psi hydrogen. The organic solvent was removed under reduced pressure to obtain a crude product (−)-C2-1, which was used for the next reaction step without further purification. $^1$H NMR (400 MHz, CHLOROFORM-d): δ 7.41-7.28 (m, 5H), 6.94-6.86 (m, 1H), 6.80-6.78 (d, J=6.4 Hz, 1H), 6.62-6.61 (d, J=7.2 Hz, 1H), 5.32 (brs, 1H), 5.16-5.14 (m, 1H), 4.90-4.76 (m, 2H), 4.60-4.42 (m, 1H), 3.58 (s, 3H)), 3.15-2.87 (m, 2H), 1.32 (s, 9H). MS m/z: 424.1 [M+Na]⁺. SFC: column: Chiralpak AY (150 mm*4.6 mm, 3 μm); mobile phase: [0.05% DEA MeOH]; B %: 5%-40% 5 min, 40% 2.5 min, 40% 2.5 min; Rt=3.904 min; 98.9% ee.

Step 2: Preparation of Compound (−)-C2-2

The compound (−)-C2-1 (37.0 g, 92.2 mmol) was dissolved in ethyl acetate (200 mL), and then a hydrogen chloride ethyl acetate solution (4M, 200 mL) was added and the reaction solution was continuously stirred at 25° C. for 1.5 hours. The organic solvent was removed under reduced pressure to obtain a hydrochloride salt of the crude product (−)-C2-2. And the compound was directly used for the next reaction step without further purification. $^1$H NMR (400 MHz, METHANOL-d₄): δ 7.38-7.32 (m, 2H), 7.30-7.19 (m, 3H), 6.87-6.75 (m, 2H), 6.55-6.50 (m, 1H), 5.10-5.03 (m, 1H), 5.00-4.93 (m, 1H), 4.10-3.94 (m, 1H), 3.60 (s, 3H), 3.07-2.99 (m, 1H), 2.79-2.69 (m, 1H). MS m/z: 302.0 [M+1]⁺.

Step 3: Preparation of Compound (−)-C2-3

The compound (−)-C2-2 (21.0 g, 62.2 mmol) was dissolved in hydrochloric acid (I M, 187.3 mL), and an aqueous solution of formaldehyde (15.1 g, 186.5 mmol, 13.9 mL, 37%) was added, and the reaction solution was continuously stirred at 25° C. for 16 hours. The solution was filtered, and the filter cake was dried in vacuum to obtain a hydrochloride salt of the crude compound (−)-C2-3, which was directly used in the next reaction step without further purification. $^1$H NMR (400 MHz, METHANOL-d₄): δ 7.49-7.29 (m, 5H), 6.92-6.82 (m, 2H), 5.12 (s, 2H), 4.40-4.22 (m, 3H), 3.90 (s, 3H), 3.32-3.28 (m, 1H), 2.90-2.79 (m, 1H). MS m/z: 314.0 [M+1]⁺.

Step 4: Preparation of Compound (−)-C2-4

The compound (−)-C2-3 (16.0 g, 45.7 mmol) was dissolved in tetrahydrofuran (160.0 mL), triethylamine (5.6 g, 54.9 mmol, 7.6 mL) was added and stirred to be dissolved, and a tetrahydrofuran (50 mL) solution of Boc anhydride (10.0 g, 45.7 mmol, 10.5 mL) was added dropwise, and the reaction solution was continuously stirred for 16 hours at 25° C. The reaction solution was poured into 150 mL of water and extracted for three times with ethyl acetate (100 mL). The mixed organic phase was washed with 50 mL of saturated saline water, dried with anhydrous sodium sulfate, and filtered, and the organic solvent was removed under reduced pressure to obtain a crude product, and the crude product was separated and purified by silica gel chromatography (an eluent: 10-20% ethyl acetate/petroleum ether) to obtain the compound (−)-C2-4. MS m/z: 436.1 [M+Na]⁺.

Step 5: Preparation of Compound (−)-C2-5

The compound (−)-C2-4 (16.6 g, 40.2 mmol) was dissolved in DMF (200.0 mL), diisopropylethylamine (15.6 g, 120.5 mmol, 20.98 mL) and N-phenyl bis(trifluoromethanesulfonyl)imide (18.7 g, 52.2 mmol) were added and the reaction solution was continuously stirred at 25° C. for 16 hours. The reaction solution was poured into 200 mL of water and extracted with ethyl acetate (180 mL) for three times. The mixed organic phase was washed with 150 mL of a saturated saline solution, dried with anhydrous sodium sulfate, filtered, and decompressed to remove the organic solvent, and the obtained crude product was separated and purified by silica gel chromatography (an eluent: 10-20% ethyl acetate/petroleum ether) to obtain the compound (−)-C2-5. $^1$H NMR (400 MHz. CHLOROFORM-d): δ 7.42-7.28 (m, 5H), 7.10-7.04 (m, 1H), 6.94-6.85 (m, 1H), 5.10-5.01 (m, 0.5H), 4.97-4.88 (m, 1H), 4.86-4.78 (m, 1H), 4.72-4.57 (m, 1.5H), 4.51-4.29 (m, 1H), 3.57-3.56 (d, J=6.0 Hz, 3H), 3.48-3.15 (m, 1H), 2.87-2.70 (m, 1H), 1.48-1.32 (m, 9H). MS m/z: 446.1 [M−100]⁺.

Step 6: Preparation of Compound (−)-C2-6

The compound (−)-C2-5 (6.2 g, 11.4 mmol) and methylboronic acid (3.4 g, 56.8 mmol) were dissolved in dioxane (70 mL) under a nitrogen atmosphere, and Pd(dppf)Cl₂ (831.6 mg, 1.1 mmol) and potassium carbonate (4.7 g, 34.1 mmol) were sequentially added, and the reaction solution was heated to 100° C. for a reaction for 10 hours. The mixture was cooled, and filtered, and the filter cake was washed with 50 mL of ethyl acetate. The organic phase was mixed, and the organic solvent was removed under reduced pressure. The obtained crude product was separated and purified by a silica gel chromatography column (an eluent: 9-16% ethyl acetate/petroleum ether) to obtain the compound (−)-C2-6. ¹H NMR (400 MHz, CHLOROFORM-d): δ 7.52-7.34 (m, 5H), 7.07-7.05 (d, J=7.6 Hz, 1H), 6.91-6.81 (m, 1H), 5.19-4.64 (m, 4H), 4.55-4.41 (m, 1H), 3.65-3.62 (d, J=9.2 Hz, 3H). 3.58-3.30 (m, 1H), 3.08-2.89 (m, 1H), 2.30 (s, 3H), 1.56-1.44 (m, 9H). MS m/z: 434 [M+Na]⁺.

Step 7: Preparation of Compound (−)-C2

The compound (−)-C2-6 (4.58, 10.9 mmol) was dissolved in dioxane (20 mL), a 4M dioxane solution of hydrogen chloride (30 mL) was added, and the reaction solution was continuously stirred at 25° C. for 1.5 hours. The organic solvent was removed under reduced pressure to obtain a hydrochloride salt of a crude compound (−)-C2. ¹H NMR (400 MHz, METHANOL-d₄): δ 7.51-7.36 (m, 5H), 7.24-7.22 (d, J=7.6 Hz, 1H), 7.00-6.98 (d, J=7.6 Hz, 1H), 4.92 (s, 2H). 4.51-4.35 (m, 3H), 3.91 (s. 3H), 3.49-3.41 (m, 1H), 3.04-2.97 (m, 1H), 2.33 (s, 3H). MS m/z: 312.1 [M+1]⁺.

Reference Example 43: Synthesis of Intermediate (−)-C3

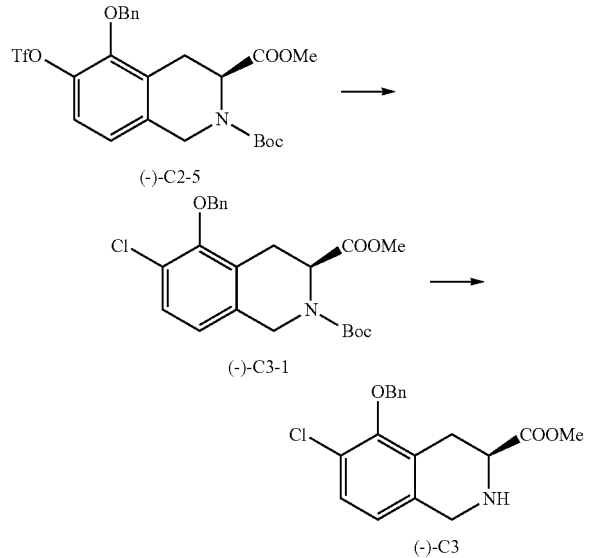

Step 1: Preparation of Compound (−)-C3-1

The compound (−)-C2-5 (1.0 g, 1.8 mmol) was dissolved in 1,4-dioxane (15.0 mL) under a nitrogen atmosphere, and then potassium chloride (275.0 mg, 3.7 mmol), potassium fluoride (54.0 mg, 929.5 μmol), Pd₂(dba)₃ (26.0 mg, 28.4 μmol) and di-tert-butyl(2',4',6'-triisopropyl-3,6-dimethoxybiphenyl-2-yl)phosphine (40.0 mg, 82.5 μmol) were added sequentially, and the reaction solution was heated to 130° C. and stirring was continued to be performed for 16 hours. The organic solvent was removed under reduced pressure, and the obtained crude product was separated and purified by silica gel column chromatography (an eluent: 0-20% methanol/ethyl acetate) to obtain the compound (−)-C3-1. ¹H NMR (400 MHz, CHLOROFORM-d): δ 7.54-7.51 (m, 2H), 7.48-7.35 (m, 3H), 7.29-7.23 (m, 1H), 6.92-6.85 (m, 1H), 5.17-5.15 (m, 0.5H), 5.05-4.87 (m, 2H), 4.78-4.61 (m, 1.5H), 4.53-4.34 (m, 1H), 3.65-3.63 (d, J=8.0 Hz, 3H), 3.57-3.53 (m, 0.5H), 3.36-3.31 (m, 0.5H), 3.01-2.77 (m, 1H), 1.56-1.46 (m, 9H). MS m/z: 454.1 [M+Na]⁺.

Step 2: Preparation of Compound (−)-C3

The compound (−)-C3-1 (590.0 mg, 1.4 mmol) was dissolved in dioxane (2.0 mL), and a dioxane solution of hydrogen chloride (4M, 3 mL) was added. The reaction solution was continuously stirred at 20-25° C. for 2.5 hours. The organic solvent was removed under reduced pressure to obtain a hydrochloride salt of the compound (−)-C3. And this compound was directly used in the next reaction step without further purification. ¹H NMR (400 MHz, METHANOL-d₄): δ 7.50-7.36 (m, 6H), 7.08-7.06 (d, J=8.0 Hz, 1H), 5.08 (s, 2H), 4.49-4.33 (m, 3H), 3.89 (s, 3H), 3.41-3.34 (m, 1H), 2.96-2.88 (m, 1H). MS m/z: 331.9 [M+1]⁺.

Reference Example 44: Synthesis of Intermediate (−)-C6

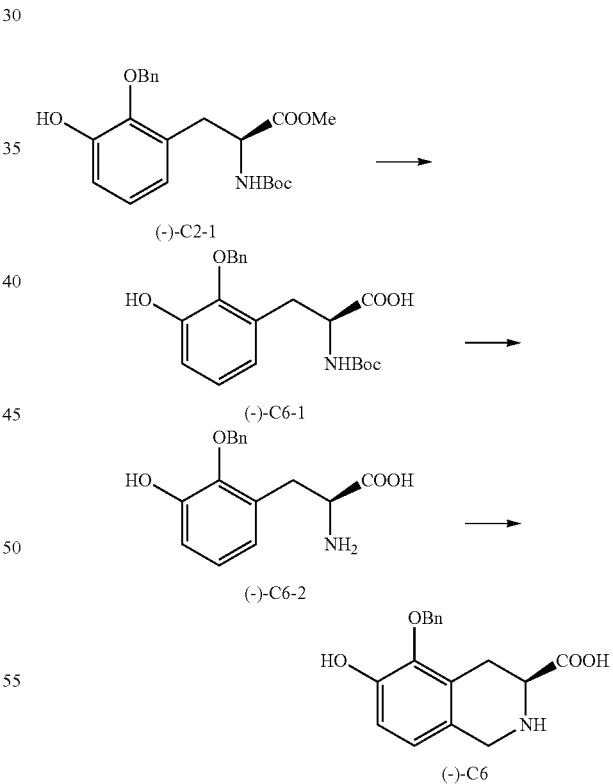

Step 1: Preparation of Compound (−)-C6-1

The compound (−)-C2-1 (6.0 g, 14.9 mmol) was dissolved in tetrahydrofuran (120.0 mL) and water (40.0 mL), and lithium hydroxide monohydrate (1.9 g, 44.8 mmol) was slowly added. The reaction solution was continuously stirred for 5 hours at 25° C. The reaction solution was adjusted to pH of 5-6 with 1M diluted hydrochloric acid, and extracted with ethyl acetate (40.0 mL) for three times. The mixed organic phase was washed with a saturated sodium chloride water solution (40.0 mL), dried with anhydrous sodium sulfate, filtered, and decompressed to remove the organic solvent to obtain the compound (−)-C6-1, which was directly used in the next reaction step without further purification. $^1$H NMR (400 MHz, CHLOROFORM-d): δ 7.48-7.30 (m, 5H), 7.00-6.67 (m, 3H), 5.38-5.37 (m H), 5.02-4.89 (m, 2H), 4.58-4.41 (m, 1H), 3.19-3.13 (m, 1H), 3.02-2.96 (m, 1H), 1.42-1.28 (m, 9H). MS m/z: 410.1 [M+Na]$^+$.

Step 2: Preparation of Compound (−)-C6-2

The compound (−)-C6-1 (7.0 g, 18.1 mmol) was dissolved in ethyl acetate (50.0 mL), and an ethyl acetate solution of hydrogen chloride (4M, 50.0 mL) was added. The reaction solution was continuously stirred at 25° C. for 2 hours. The organic solvent was removed under reduced pressure to obtain a hydrochloride salt of the compound (−)-C6-2, which was directly used in the next reaction step without further purification. $^1$H NMR (400 MHz, METHANOL-d$_4$): δ 7.51-7.46 (m, 2H), 7.39-7.31 (m, 3H), 6.97-6.89 (m, 2H), 6.69-6.67 (m, 1H), 5.24-5.19 (m, 1H), 5.14-5.09 (m, 1H), 4.19-4.14 (m, 1H), 3.31-3.26 (m, 1H), 2.83-2.77 (m, 1H). MS m/z: 287.9 [M+1]$^+$.

Step 3: Preparation of Compound (−)-C6

The compound (−)-C6-2 (5.0 g, 15.4 mmol) was dissolved in hydrochloric acid (1M, 83.0 mL), and an aqueous solution of formaldehyde (7.5 g, 92.6 mmol, 37%) was added, and the reaction solution was heated to 60° C. and stirring was continued to be performed for 1 hour. The solution was cooled with an ice water bath, and an aqueous solution (40.0 mL) of sodium acetate (10.1 g, 123.5 mmol) was added to the reaction system, and stirring was continued to be performed at 0° C. for 2 hours. The solution was filtered, and the filter cake was washed with water (50 mL) and dried in vacuum to obtain the compound (−)-C6. $^1$H NMR (400 MHz, METHANOL-d$_4$): δ 7.56-7.47 (m, 2H), 7.42-7.30 (m, 3H), 6.88-6.80 (m, 2H), 5.11-5.03 (m, 2H), 4.32-4.17 (m, 2H), 3.74-3.70 (m, 1H), 3.53-3.48 (m, 1H), 2.92-2.85 (m, 1H). MS m/z: 299.9 [M+1]$^+$.

Reference Example 45: Synthesis of Intermediate (−)-C7

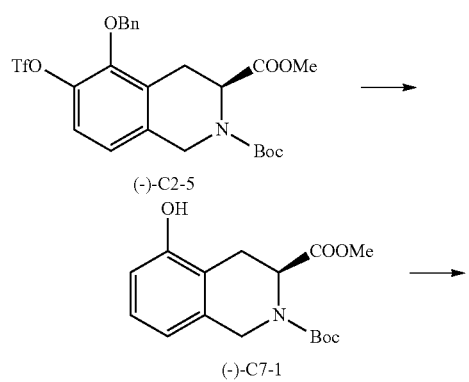

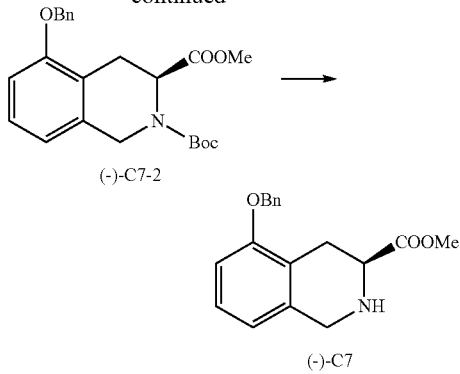

Step 1: Preparation of Compound (−)-C7-1

The compound (−)-C2-5 (4.0 g, 7.3 mmol) was dissolved in methanol (100 mL), and then triethylamine (1.5 g, 14.7 mmol, 2.0 mL) and wet palladium carbon (0.3 g, 10% purity) were added sequentially. The hydrogen replacement was performed for three times, and the reaction solution was continuously stirred at 25° C. in 15 Psi hydrogen for 16 hours. The reaction solution was filtered, and the organic solvent was removed under reduced pressure, and the resulting crude product was separated and purified by silica gel column chromatography (an eluent: 10-30% ethyl acetate/petroleum ether) to obtain the compound (−)-C7-1. $^1$H NMR (400 MHz, CHLOROFORM-d): δ 7.00-6.96 (t, J=7.6 Hz, 1H), 6.80-6.54 (m, 2H), 5.17-5.11 (m, 0.5H), 4.86 (s. 1H), 4.82-4.76 (m, 0.5H), 4.71-4.60 (m, 1H), 4.51-4.24 (m, 1H). 3.62-3.55 (m, 3H), 3.46-3.11 (m, 1H), 3.08-2.74 (m, 1H), 1.48-1.35 (m, 9H). MS m/z: 207.9 [M−100]$^+$.

Step 2: Preparation of Compound (−)-C7-2

The compound (−)-C7-1 (2.0 g, 6.5 mmol) was dissolved in tetrahydrofuran (50 mL), and cesium carbonate (4.2 g, 13.0 mmol) and benzyl bromide (1.7 g, 9.8 mmol, 1.2 mL) were sequentially added. The reaction solution was heated to 60° C. and continuously stirred for 3 hours. The organic solvent was removed under reduced pressure, and the obtained crude product was separated and purified by silica gel column chromatography (an eluent: 0-30% ethyl acetate/petroleum ether) to obtain the compound (−)-C7-2. $^1$H NMR (400 MHz, CHLOROFORM-d): δ 7.48-7.31 (m, 5H), 7.19-7.12 (m, 1H), 6.84-6.71 (m, 2H), 5.23-5.19 (m, 0.5H)), 5.10 (s, 2H), 4.90-4.69 (m, 1.5H), 4.58-4.40 (m, 1H), 3.68-3.63 (m, 3H), 3.61-3.37 (m, 1H), 3.14-2.93 (m, 1H). 1.57-1.44 (m, 9H). MS m/z: 420.0 [M+Na]$^+$.

Step 3: Preparation of Compound (−)-C7

The compound (−)-C7-2 (2.4 g, 6.0 mmol) was dissolved in dioxane (30 mL), and a dioxane solution of hydrogen chloride (4M. 8 mL) was added and the reaction solution was continuously stirred at 25° C. for 16 hours. The organic solvent was removed under reduced pressure to obtain a hydrochloride salt of the compound (−)-C7, which was directly used for the next reaction step without further purification. $^1$H NMR (400 MHz, METHANOL-d$_4$): δ 7.51-7.26 (m, 6H), 7.06-7.04 (d, J=8.4 Hz, 1H), 6.88-6.86 (d, J=7.8 Hz, 1H)), 5.18 (s, 2H), 4.54-4.41 (m, 3H), 3.93 (s, 3H), 3.54-3.46 (m, 1H), 3.05-2.96 (m, 1H). MS m/z: 298.0 [M+1]$^+$.

Reference Example 46: Synthesis of Intermediate (−)-C8

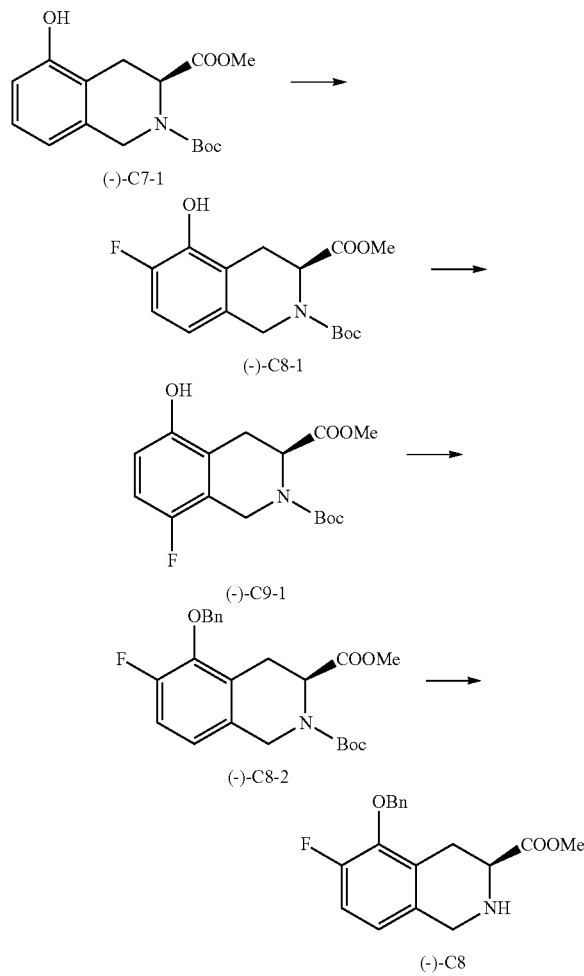

Step 1: Preparation of Compounds (−)-C8-1 and (−)-C9-1

The compound (−)-C7-1 (0.7 g, 2.3 mmol) was dissolved in acetonitrile (10 mL), and Select F (968.2 mg, 2.7 mmol) was added. The reaction solution was continuously stirred at 25° C. for 16 hours. 5 mL of methanol was added to the reaction solution, and decompressed to remove the organic solvent, and the crude product was separated and purified by silica gel column chromatography (an eluent: 10-25% ethyl acetate/petroleum ether), further separated and purified by high performance liquid chromatography (column: Xtimate C18 150*25 mm*5 microns; Mobile phase: [water (10 mM $NH_4HCO_3$)-ACN]; B %: 45%-70%, 9.5 min) to obtain the compound (−)-C8-1 and the compound (−)-C9-1.

Compound (−)-C8-1: $^1$H NMR (400 MHz, CHLOROFORM-d): δ 6.96-6.91 (t, J=9.2 Hz, 1H), 6.74-6.60 (m, 1H), 5.76 (brs, 1H), 5.31-4.96 (m, 0.5H), 4.86-4.85 (m, 0.5H), 4.74-4.66 (m, 1H), 4.49-4.38 (m, 1H), 3.69-3.66 (m, 3H), 3.53-3.30 (m, 1H), 3.10-2.94 (m, 1H), 1.61-1.43 (m, 9H). MS m/z: 225.9 [M−100]$^+$.

Compound (−)-C9-1: $^1$H NMR (400 MHz, CHLOROFORM-d): δ 6.80-6.75 (t, J=9.2 Hz, 1H), 6.63-6.53 (m, 1H), 5.94-5.75 (m, 1H), 5.29-5.01 (m, 1H), 4.85-4.75 (m, 1H), 4.47-4.37 (m, 1H), 3.69-3.66 (m, 3H), 3.56-3.24 (m, 1H), 2.98-2.85 (m, 1H), 1.56-1.51 (m, 9H). MS m/z: 226.0 [M−100]$^+$.

Step 2: Preparation of Compound (−)-C8-2

The compound (−)-C8-1 (30.0 mg, 92.2 μmol) was dissolved in tetrahydrofuran (5 mL), and cesium carbonate (60.1 mg, 184.4 μmol) and benzyl bromide (23.7 mg, 138.3 μmol, 16.4 μL) were added. The temperature of the reaction solution was raised to 60° C. and the stirring was continued to be performed for 16 hours. The organic solvent was removed under reduced pressure, and the obtained crude product was separated and purified by silica gel column chromatography (an eluent: 0-30% ethyl acetate/petroleum ether) to obtain the compound (−)-C8-2. $^1$H NMR (400 MHz, CHLOROFORM-d): δ 7.43-7.24 (m, 5H), 6.92-6.85 (m, 1H), 6.81-6.67 (m, 1H), 5.11-4.51 (m, 2.5H), 4.64-4.54 (m, 1.5H), 4.42-4.24 (m, 1H), 3.58-3.51 (m, 3H), 3.48-3.15 (m, 1H), 2.93-2.67 (m, 1H), 1.47-1.36 (m, 9H). MS m/z: 438.2 [M+Na]$^+$.

Step 3: Preparation of Compound (−)-C8

The compound (−)-C8-2 (35.0 mg, 77.5 μmol) was dissolved in ethyl acetate (2 mL), and an ethyl acetate solution of hydrogen chloride (4M, 2.4 mL) was added. The reaction solution was continuously stirred for 30 minutes at 25° C. The organic solvent was removed under reduced pressure to obtain a hydrochloride salt of the compound (−)-C8. $^1$H NMR (400 MHz, CHLOROFORM-d): δ 7.57-7.32 (m, 5H), 7.29-7.14 (m, 1H), 7.12-6.94 (m, 1H), 5.30-5.16 (m, 2H), 4.56-4.30 (m, 3H), 3.94 (s, 3H), 3.73-3.43 (m, 1H), 2.97-2.87 (m, 1H). MS m/z: 316.0 [M+1]$^+$.

Reference Example 47: Synthesis of Intermediate (−)-C9

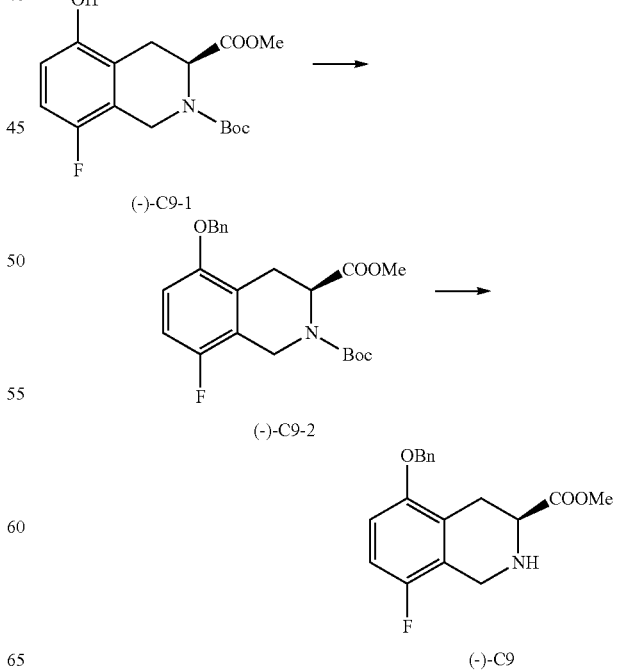

Step 1: Preparation of Compound (−)-C9-2

The compound (−)-C9-1 (80.0 mg, 245.9 μmol) was dissolved in tetrahydrofuran (5.0 mL), and cesium carbonate (160.2 mg, 491.8 μmol) and benzyl bromide (63.1 mg, 368.9 μmol) were added thereto, and the reaction liquid was heated to 60° C., and stirring was continued to be performed for 16 hours. After cooling, the organic solvent was removed under reduced pressure, and the obtained crude product was separated and purified by silica gel column chromatography (an eluent: 0-20% ethyl acetate/petroleum ether) to obtain the compound (−)-C9-2. $^1$H NMR (400 MHz, METHANOL-$d_4$): δ 7.46-7.31 (m, 5H), 6.90-6.82 (m, 1H), 6.73-6.70 (m, 1H), 5.35-5.22 (m, 0.5H), 5.07 (s, 2H), 5.01 (s, 0.5H), 4.93-4.70 (m, 1H), 4.53-4.30 (m, 1H), 3.74-3.65 (m, 3H), 3.65-3.45 (m, 1H), 3.06-2.83 (m, 1H), 1.58-1.48 (m, 9H). MS m/z: 438.1 [M+Na]$^+$.

Step 2: Preparation of Compound (−)-C9

The compound (−)-C9-2 (82.0 mg, 197.4 μmol) was dissolved in ethyl acetate (1.0 mL), and then an ethyl acetate solution of hydrogen chloride (4.0 M, 1.0 mL) was added. The reaction solution was continuously stirred for 3 hours at 20-25° C. The organic solvent was removed under reduced pressure to obtain a hydrochloride salt of the compound (−)-C9. And the compound was directly used for the next reaction step without further purification. $^1$H NMR (400 MHz, METHANOL-$d_4$): δ 7.45-7.29 (m, 5H), 7.10-7.02 (m, 2H), 5.15 (s, 2H), 4.58-4.31 (m, 3H), 3.92 (s, 3H), 3.52-3.46 (m, 1H), 3.03-2.95 (m, 1H). MS m/z: 315.9 [M+1]$^+$.

Reference Example 48: Synthesis of Intermediate (−)-C10

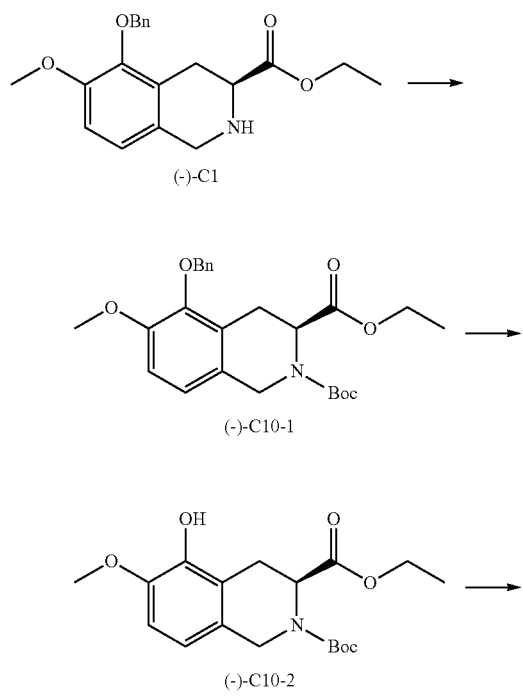

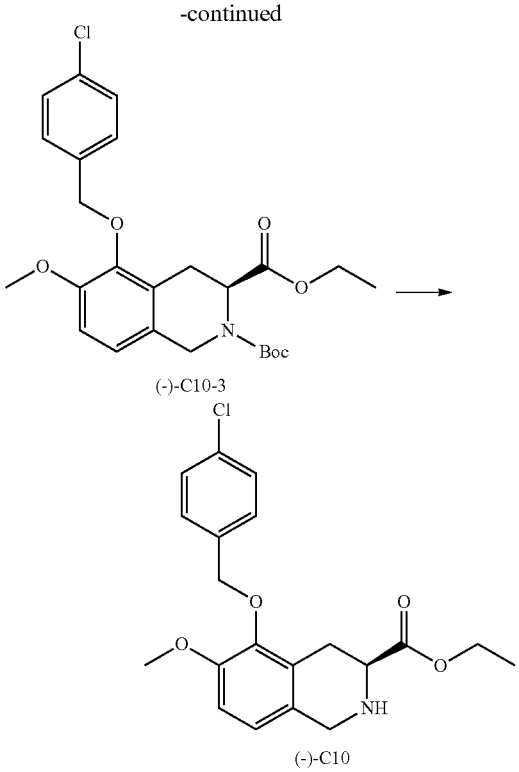

Step 1: Preparation of Compound (−)-C10-1

The compound (−)-C1 (1.0 g, 2.9 mmol) was dissolved in dichloromethane (12 mL), and then triethylamine (600.0 mg, 5.9 mmol) and di-tert-butyl dicarbonate (770.0 mg, 3.5 mmol) were sequentially added. And the reaction solution was continuously stirred at 15-20° C. for 5 hours. The organic solvent was removed under reduced pressure, and the obtained crude product was separated and purified by silica gel column chromatography (an eluent: 10-30% ethyl acetate/petroleum ether) to obtain the compound (−)-C10-1. $^1$H NMR (400 MHz, CHLOROFORM-d): δ 7.52-7.44 (m, 2H), 7.43-7.31 (m, 3H), 6.94-6.78 (m, 2H), 5.10-4.99 (m, 1.5H), 4.95-4.89 (m, 1H), 4.67-4.53 (m, 1.5H), 4.49-4.34 (m, 1H), 4.15-4.00 (m, 2H), 3.87 (s, 3H), 3.53-3.49 (m, 0.5H), 3.27-3.22 (m, 0.5H), 2.99-2.75 (m, 1H), 1.55-1.43 (m, 9H), 1.19-1.13 (m, 3H). MS m/z: 464.1 [M+Na]$^+$.

Step 2: Preparation of Compound (−)-C10-2

The compound (−)-C10-1 (1.0 g, 2.3 mmol) was dissolved in methanol (20.0 mL), and wet Pd/C (100.0 mg, 226.5 μmol, 5% purity) was added, and the hydrogen replacement was performed for three times, and the reaction solution was continuously stirred for 1.5 hours in a 15 Psi hydrogen atmosphere at 15-20° C. The reaction solution was filtered through kieselguhr. The organic solvent was removed under reduced pressure to obtain the compound (−)-C10-2. The compound is used directly for the next reaction step without further purification. $^1$H NMR (400 MHz, CHLOROFORM-d): δ 6.79-6.58 (m, 2H), 5.70 (brs, 1H), 5.14-5.12 (m, 0.5H), 4.79-4.59 (m, 1.5H), 4.50-4.34 (m, 1H), 4.16-4.02 (m, 2H), 3.87 (s, 3H), 3.50-3.44 (m, 0.5H), 3.33-3.28 (m, 0.5H), 3.14-2.90 (m, 1H), 1.57-1.42 (m, 9H), 1.20-1.17 (m, 3H). MS m/z: 374.1 [M+Na]$^+$.

Step 3: Preparation of Compound (−)-C10-3

The compound (−)-C10-2 (100.0 mg, 284.6 μmol) was dissolved in tetrahydrofuran (8.0 mL), and then a compound 4-chlorobenzyl bromide (88.0 mg, 428.3 μmol) and cesium carbonate (185.0 mg, 567.8) were added sequentially. The reaction solution was heated to 70° C. and stirring was continued to be performed for 16 hours. After cooling, the organic solvent was removed under reduced pressure, and the obtained crude product was separated and purified by silica gel column chromatography (an eluent: 0-30% ethyl acetate/petroleum ether) to obtain the compound (−)-C10-3. $^1$H NMR (400 MHz, CHLOROFORM-d): δ 7.47-7.32 (m, 4H), 6.93-6.77 (m, 2H), 5.09-5.07 (m, 0.5H), 5.02-4.82 (m, 2H), 4.68-4.55 (m, 1.5H), 4.48-4.34 (m, 1H), 4.16-3.99 (m, 2H), 3.86 (s, 3H), 3.53-5.48 (m, 0.5H), 3.26-3.21 (m, 0.5H), 2.97-2.77 (m, 1H), 1.54-1.41 (m, 9H), 1.21-1.09 (m, 3H). MS m/z: 498.2 [M+Na]$^+$.

The following compounds were synthesized in a similar manner to the compound (−)-C10-3:

| Serial Number | Compound Structural Formula | Spectrogram |
|---|---|---|
| (−)-C11-1 | 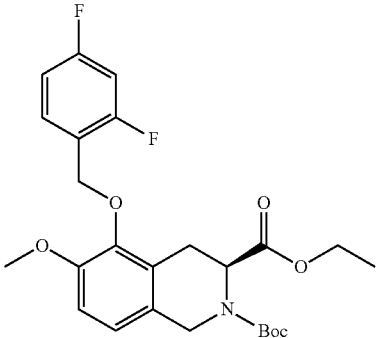 [SMILES: CCOC(=O)[C@@H]1Cc2c(ccc(OC)c2OCc2ccc(F)cc2F)CN1C(=O)OC(C)(C)C] | $^1$H NMR (400 MHz, CHLOROFORM-d): δ 7.61-7.37 (m, 1H), 6.94-6.81 (m, 4H), 5.10-5.03 (m, 1H), 5.01-4.94 (m, 1H), 4.77-4.56 (m, 2H), 4.51-4.36 (m, 1H), 4.17-4.02 (m, 2H), 3.88-3.87 (d, J = 3.6 Hz, 3H), 3.55-3.20 (m, 1H), 3.01-2.79 (m, 1H), 1.56-1.42 (m, 9H), 1.20-1.14 (m, 3H). MS m/z: 500.2 [M + Na]$^+$. |
| (−)-C12-1 | 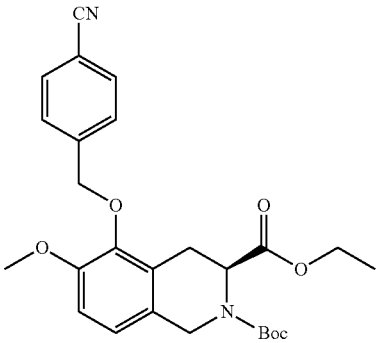 [SMILES: CCOC(=O)[C@@H]1Cc2c(ccc(OC)c2OCc2ccc(C#N)cc2)CN1C(=O)OC(C)(C)C] | $^1$H NMR (400 MHz, CHLOROFORM-d): δ 7.75-7.59 (m, 4H), 6.96-6.81 (m, 2H), 5.14-4.95 (m, 2H), 4.74-4.59 (m, 2H), 4.48-4.40 (t, J = 17.2 Hz, 1H), 4.10-4.05 (m, 2H), 3.86 (s, 3H), 3.58-3.28 (m, 1H), 3.01-2.82 (m, 1H), 1.57-1.44 (m, 9H), 1.19-1.13 (m, 3H). MS m/z: 489.2 [M + Na]$^+$. |
| (−)-C13-1 | 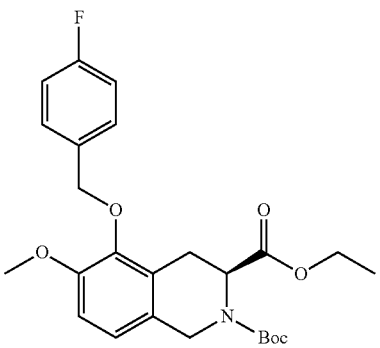 [SMILES: CCOC(=O)[C@@H]1Cc2c(ccc(OC)c2OCc2ccc(F)cc2)CN1C(=O)OC(C)(C)C] | $^1$H NMR (400 MHz, CHLOROFORM-d): δ 7.47-7.41 (m, 2H), 7.09-7.04 (m, 2H), 6.89-6.81 (m, 2H), 5.07-4.88 (m, 2.5H), 4.62-4.56 (m, 1.5H), 4.41-4.33 (m, 1H), 4.10-4.04 (m, 2H), 3.87 (s, 3H), 3.50-3.48 (m, 0.5H), 3.23-3.19 (m, 0.5H), 2.95-2.82 (m, 1H), 1.57-1.44 (m, 9H), 1.19-1.13 (m, 3H). MS m/z: 482.2 [M + Na]$^+$. |
| (−)-C14-1 | 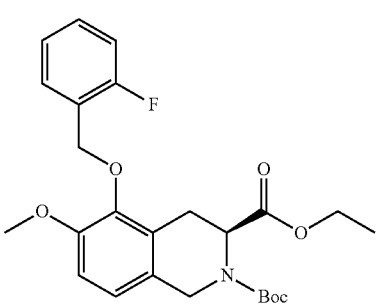 [SMILES: CCOC(=O)[C@@H]1Cc2c(ccc(OC)c2OCc2ccccc2F)CN1C(=O)OC(C)(C)C] | $^1$H NMR (400 MHz, CHLOROFORM-d): δ 7.62-7.51 (m, 1H), 7.38-7.29 (m, 1H), 7.23-7.13 (m, 1H), 7.11-7.03 (m, 1H), 6.94-6.77 (m, 2H), 5.14-4.99 (m, 2H), 4.82-4.56 (m, 2H), 4.50-4.37 (m, 1H), 4.11-4.02 (m, 2H), 3.87 (s, 3H), 3.55-3.22 (m, 1H), 3.00-2.79 (m, 1H), 1.54-1.43 (m, 9H), 1.19-1.13 (m, 3H). MS m/z: 482.2 [M + Na]$^+$. |

-continued

| Serial Number | Compound Structural Formula | Spectrogram |
|---|---|---|
| (−)-C15-1 | 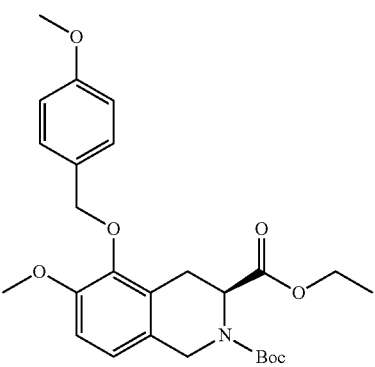 [SMILES: CCOC(=O)[C@@H]1Cc2c(ccc(OC)c2OCc2ccc(OC)cc2)CN1C(=O)OC(C)(C)C] | $^1$H NMR (400 MHz, CHLOROFORM-d): δ 7.41-7.36(m, 2H), 6.96-6.77 (m, 4H), 5.06-4.95 (m, 1.5H). 4.87-4.81 (m, 1H), 4.66-4.52 (m, 1.5H), 4.51-4.33 (m, 1H), 4.11-4.01 (m, 2H), 3.88-3.83 (d, J = 19.2 Hz, 6H), 3.55-3.14 (m, 1H), 2.98-2.76 (m, 1H), 1.54-1.42 (m, 9H), 1.21-1.11 (m, 3H). MS m/z: 494.2 [M + Na]$^+$. |
| (−)-C16-1 | 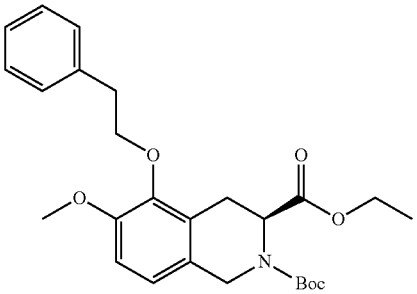 [SMILES: CCOC(=O)[C@@H]1Cc2c(ccc(OC)c2OCCc2ccccc2)CN1C(=O)OC(C)(C)C] | $^1$H NMR (400 MHz, CHLOROFORM-d): δ 7.35-7.28 (m, 4H), 7.26-7.20 (m, 1H), 6.92-6.70 (m, 2H), 5.04-5.01 (m, 0.5H), 4.69-4.54 (m, 1.5H), 4.49-4.35 (m, 1H), 4.26-3.96 (m, 4H), 3.81 (s, 3H), 3.37-3.03 (m, 3H), 2.95-2.68 (m, 1H), 1.53-1.40 (m, 9H), 1.20-1.08 (m, 3H). MS m/z: 478.2 [M + Na]$^+$. |
| (−)-C17-1 | 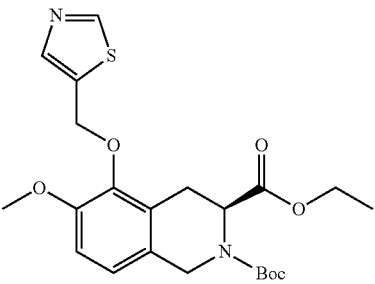 [SMILES: CCOC(=O)[C@@H]1Cc2c(ccc(OC)c2OCc2cncs2)CN1C(=O)OC(C)(C)C] | $^1$H NMR (400 MHz, CHLOROFORM-d): δ 8.85 (s, 1H), 7.86 (s, 1H), 6.98-6.78 (m, 2H), 5.35-5.13 (m, 2H), 5.11-4.58 (m, 2H), 4.50-4.38 (m, 1H), 4.13-4.01 (m, 2H), 3.89 (s, 3H), 3.55-3.21 (m, 1H), 3.05-2.73 (m, 1H), 1.56-1.46 (m, 9H), 1.21-1.13(m, 3H). MS m/z: 471.1 [M + Na]$^+$. |
| (−)-C18-1 | 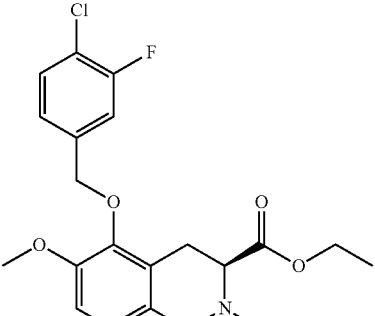 | $^1$H NMR (400 MHz, CHLOROFORM-d): δ 7.43-7.39 (m, 1H), 7.38-7.33 (m, 1H), 7.25-7.12 (m, 1H), 6.97-6.78 (m, 2H), 5.10-5.09 (m, 0.5H), 5.01-4.95 (m, 1H), 4.91-4.83 (m, 1H), 4.69-4.58 (m, 1.5H), 4.49-4.36 (m, 1H), 4.16-4.01 (m, 2H), 3.86 (s, 3H), 3.53-3.48 (m, 0.5H), 3.30-3.25 (m, 0.5H), 2.99-2.81 (m, 1H), 1.55-1.43 (m, 9H), 1.18-1.13 (m, 3H). MS m/z: 516.1 [M + Na]$^+$. |

-continued

| Serial Number | Compound Structural Formula | Spectrogram |
|---|---|---|
| (−)-C19-1 | 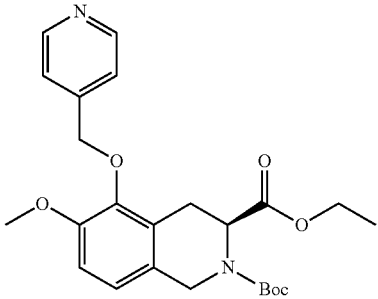 [SMILES: CCOC(=O)[C@@H]1Cc2c(ccc(OC)c2OCc2ccncc2)CN1C(=O)OC(C)(C)C] | ¹H NMR (400 MHz, CHLOROFORM-d): δ 8.65-8.63 (d, J = 6.0 Hz, 2H), 7.42-7.36 (m, 2H), 6.93-6.81 (m, 2H), 5.13-5.04 (m, 1.5H), 4.96-4.92 (m, 1H), 4.76-4.60 (m, 1.5H), 4.48-4.41 (m, 1H), 3.14-4.04 (m, 2H), 3.84 (s, 3H), 3.56-3.33 (m, 1H), 3.02-2.93 (m, 1H). 1.53-1.46 (m, 9H), 1.17-1.12 (m, 3H). MS m/z: 443.2 [M + 1]⁺. |
| (−)-C20-1 | 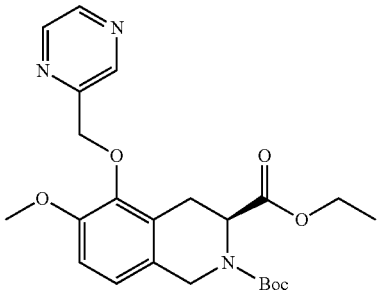 | ¹H NMR (400 MHz, CHLOROFORM-d): δ 8.97 (s, 1H), 8.57 (s, 2H), 6.94-6.82 (m, 2H), 5.22-5.09 (m, 2.5H), 4.74-4.61 (m, 1.5H), 4.49-4.41 (m, 1H), 4.1-4.05 (m, 2H), 3.84 (s, 3H), 3.58-3.35(m, 1H), 3.05-2.92 (m, 1H), 1.53-1.46 (m, 9H), 1.18-1.13 (q, J = 6.8 Hz, 3H). MS m/z: 552.1 [M + Na]⁺. |
| (−)-C21-1 | 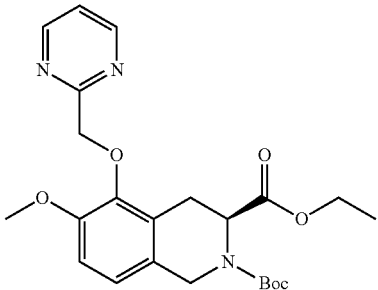 [SMILES: CCOC(=O)[C@@H]1Cc2c(ccc(OC)c2OCc2ncccn2)CN1C(=O)OC(C)(C)C] | ¹H NMR (400 MHz, CHLOROFORM-d): δ 8.79-8.76 (m, 2H), 7.30-7.26 (m, 1H), 6.70-6.53 (m, 2H), 5.06-5.03 (m, 2H), 4.69-4.29 (m, 3H), 4.15-3.98 (m, 2H), 3.79 (s, 3H), 3.48-2.80 (m, 2H), 1.39-1.34 (m, 9H), 1.18-1.07 (m, 3H). MS m/z: 444.1 [M + 1]⁺. |
| (−)-C22-1 | 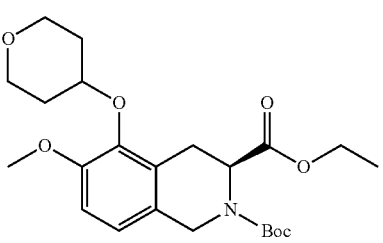 [SMILES: CCOC(=O)[C@@H]1Cc2c(ccc(OC)c2OC2CCOCC2)CN1C(=O)OC(C)(C)C] | ¹H NMR (400 MHz, CHLOROFORM-d): δ 6.95-6.75 (m, 2H), 5.09-5.07 (m, 0.5H), 4.74-4.57 (m, 1.5H), 4.53-4.38 (m, 1H), 4.32-4.27 (m, 1H), 4.16-3.97 (m, 4H), 3.83 (s, 3H), 3.56-3.29 (m, 3H), 3.14-2.88 (m, 1H), 2.02-1.72 (m, 4H), 1.54-1.45 (m, 9H), 1.21-1.15(m, 3H). MS m/z: 458.2 [M + Na]⁺. |
| (−)-C23-1 | 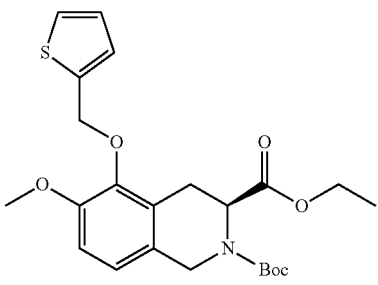 [SMILES: CCOC(=O)[C@@H]1Cc2c(ccc(OC)c2OCc2cccs2)CN1C(=O)OC(C)(C)C] | ¹H NMR (400 MHz, CHLOROFORM-d): δ 7.34-7.27 (m, 1H), 7.07-6.98 (m, 2H), 6.91-6.80 (m, 2H), 5.23-5.09 (m, 2H), 4.96-4.92 (m, 0.5H), 4.65-4.56 (m, 1.5H), 4.46-4.33 (m, 1H), 4.14-4.04 (m, 2H), 3.88 (s, 3H), 3.55-3.19 (m, 1H), 2.89-2.78 (m, 1H), 1.52-1.44 (m, 9H), 1.19-1.14 (m, 3H). MS m/z: 470.1 [M + Na]⁺. |

Step 4: Preparation of Compound (−)-C10

The compound (−)-C10-3 (120.0 mg, 252.1 μmol) was dissolved in ethyl acetate (1.0 mL), and then an ethyl acetate solution of hydrogen chloride (4.0 M, 1.0 mL) was added. The reaction solution was continuously stirred for 16 hours at 15-20° C. The organic solvent was removed under reduced pressure to obtain a hydrochloride salt of the compound (−)-C10. And the compound was directly used for the next reaction step without further purification. $^1$H NMR (400 MHz, METHANOL-d$_4$): δ 7.46-7.33 (m, 4H), 7.12-6.95 (m, 2H), 5.12-5.02 (m, 2H), 4.42-4.23 (m, 5H), 3.91 (s, 3H), 3.35-3.31 (m, 1H), 2.88-2.80 (m, 1H), 1.36-1.32 (t, J=7.2 Hz, 3H). MS m/z: 376.0 [M+1]$^+$.

The following compounds were synthesized in a similar manner to the compound (−)-C10:

| Reference Example | Compound Serial Number | Structural Formula | Spectrogram |
|---|---|---|---|
| 49 | (−)-C11 | | $^1$H NMR (400 MHz, METHANOL-d$_4$): δ 7.56-7.48 (m, 1H), 7.11-6.97 (m, 4H), 5.20-5.12 (m, 2H), 4.44-4.27 (m, 5H), 3.93 (s, 3H), 3.42-3.35 (m, 1H), 2.90-2.83 (m, 1H), 1.38-1.35 (t, J = 7.2 Hz, 3H). MS m/z: 378.1 [M + 1]$^+$. |
| 50 | (−)-C12 | | $^1$H NMR (400 MHz, METHANOL-d$_4$): δ 7.79-7.77 (d, J = 8.4 Hz, 2H), 7.67-7.65 (d, J=8.4 Hz, 2H), 7.12-7.00 (m, 2H), 5.20-5.15 (m, 2H), 4.43-4.25 (m, 5H), 3.91 (s, 3H), 3.39-3.35 (m, 1H), 2.95-2.88 (m, 1H), 1.37-1.33 (t, J = 7.2 Hz, 3H). MS m/z: 367.0 [M + 1]$^+$. |
| 51 | (−)-C13 | | $^1$H NMR (400 MHz, METHANOL-d$_4$): δ 7.46-7.42 (m, 2H), 7.15-7.03 (m, 3H), 7.02-6.95 (m, 1H), 5.12-5.00 (m, 2H), 4.44-4.20 (m, 5H), 3.91 (s, 3H), 3.35-3.27 (m, 1H), 2.86-2.79 (m, 1H), 1.36-1.32 (t, J = 7.2 Hz, 3H). MS m/z: 360.1 [M + 1]$^+$. |
| 52 | (−)-C14 | | $^1$H NMR (400 MHz, METHANOL-d$_4$): δ 7.54-7.38 (m, 2H), 7.23-6.99 (m, 4H), 5.19 (s, 2H), 4.43-4.25 (m, 5H), 3.93 (s, 3H), 3.43-3.38 (m, 1H), 2.91-2.84 (m, 1H), 1.38-1.34 (t, J = 7.2 Hz, 3H). MS m/z: 360.1 [M + 1]$^+$. |

-continued

| Reference Example | Compound Serial Number | Structural Formula | Spectrogram |
|---|---|---|---|
| 53 | (−)-C15 | | $^1$H NMR (400 MHz, METHANOL-d$_4$): δ 7.36-7.25 (m, 2H), 6.96-6.89 (m, 3H), 6.74-6.71 (d, J = 8.4 Hz, 1H), 4.93-4.90 (m, 1H), 4.61 (s, 1H), 4.45-4.35 (m, 5H), 3.88 (s, 3H), 3.80 (s, 3H), 3.50-3.45 (m, 1H), 3.00-2.93 (m, 1H), 1.41-1.36 (t, J = 6.8 Hz, 3H). MS m/z: 372.2 [M + 1]$^+$. |
| 54 | (−)-C16 | | $^1$H NMR (400 MHz, METHANOL-d$_4$): δ 7.32-7.26 (m, 4H), 7.25-7.18 (m, 1H), 7.03-6.91 (m, 2H), 4.44-4.28 (m, 5H), 4.27-4.19 (m, 2H), 3.85 (s, 3H), 3.18-3.07 (m, 1H), 3.05-3.01 (m, 2H), 2.67-2.59 (m, 1H), 1.38-1.35 (t, J =7.2 Hz, 3H). MS m/z: 356.2 [M + 1]+. |
| 55 | (−)-C17 | | $^1$H NMR (400 MHz, METHANOL-d$_4$): δ 9.73 (s, 1H), 8.25 (s, 1H), 7.25-6.99 (m, 2H), 5.59-5.35 (m, 2H), 4.52-4.28 (m, 5H), 3.95 (s, 3H), 3.58-3.41 (m, 1H), 3.06-3.01 (m, 1H), 1.40-1.36 (t, J = 7.2 Hz, 3H). MS m/z: 349.0 [M + 1]$^+$. |
| 56 | (−)-C18 | | $^1$H NMR (400 MHz, METHANOL-d$_4$): δ 7.50-7.46 (t, J = 8.0 Hz, 1H), 7.38-7.35 (m, 1H), 7.24-7.21 (d, J = 8.0 Hz, 1H), 7.10-6.96 (m, 2H), 5.14-5.01 (m, 2H), 4.45-4.23 (m, 5H), 3.90 (s, 3H), 3.40-3.34 (m, 1H), 2.93-2.86 (m, 1H). 1.36-1.32 (t. J = 7.2 Hz, 3H). MS m/z: 394.1 [M + 1]$^+$. |
| 57 | (−)-C19 | | $^1$H NMR (400 MHz, CHLOROFORM-d): δ 8.97-8.95 (d, J = 6.0 Hz, 2H), 8.12-8.07 (m, 2H), 7.05-6.94 (m, 2H), 5.39-5.29 (m, 2H), 4.56-4.52 (m, 1H), 4.45-4.41 (m, 1H), 4.32-4.24 (m, 3H), 3.82 (s, 3H), 3.54-3.48 (m, 1H), 3.28-3.22 (m, 1H), 1.30-1.26 (m, 3H). MS m/z: 343.1 [M + 1]$^+$. |

| Reference Example | Compound Serial Number | Structural Formula | Spectrogram |
|---|---|---|---|
| 58 | (−)-C20 | | ¹H NMR (400 MHz, CHLOROFORM-d): δ 8.98 (s, 1H), 8.78 (br s, 1H), 8.65 (s, 1H), 6.95 (s, 2H), 5.32 (s, 2H), 4.52-4.26 (m, 5H), 3.53-3.48 (m, 1H), 3.26-3.18 (m, 1H), 1.31-1.28(m, 3H). |
| 59 | (−)-C21 | | MS m/z: 344.1 [M + 1]⁺. |
| 60 | (−)-C22 | | ¹H NMR (400 MHz, METHANOL-d₄): δ 7.10-6.93 (m, 2H), 4.56-4.53 (m, 1H), 4.45-4.30 (m, 5H), 4.00-3.95 (m, 2H), 3.86 (s, 3H), 3.54-3.42 (m, 3H), 3.08-3.00 (m, 1H), 2.05-1.86 (m, 2H), 1.81-1.63 (m, 2H), 1.38-1.35 (t, J = 7.2 Mz, 3H). MS m/z: 336.1 [M + 1]⁺. |
| 61 | (−)-C23 | | ¹H NMR (400 MHz, METHANOL-d₄): δ 6.96-6.91 (m, 1H), 6.72-6.70 (d, J = 8.0 Hz, 1H), 4.42-4.36 (m, 4H), 3.86 (s, 3H), 3.52-3.44 (m, 1H), 3.00-2.86 (m, 1H), 2.04-1.99 (m, 1H), 1.39-1.35 (t, J = 7.6 Hz, 3H). MS m/z: 252.1 [M + 1]⁺. |
Reference Example 62: Synthesis of Intermediate (−)-C24
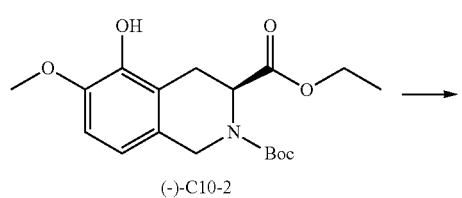
(−)-C10-2
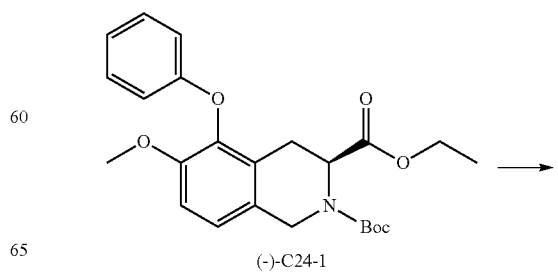
(−)-C24-1
→

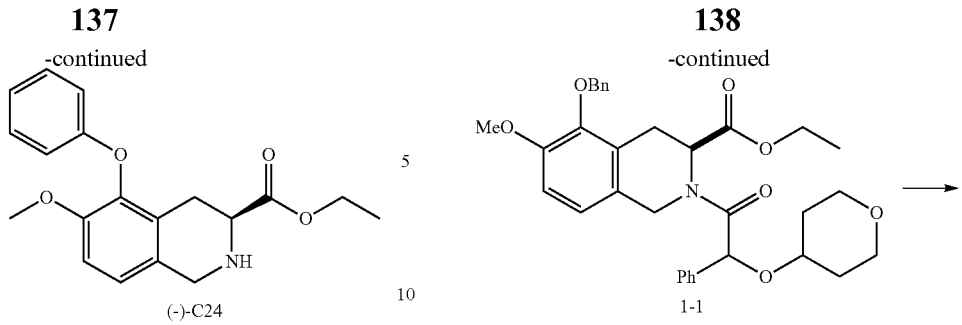

(-)-C24

Step 1: Preparation of Compound (−)-C24-1

The compound (−)-C10-2 (100.0 mg, 284.6 μmol) and phenylboronic acid (70.1 mg, 574.9 μmol) were dissolved in dichloromethane (10 mL), and copper acetate (54.0 mg, 297.3 μmol), a 4 Å molecular sieve (321 mg), TEMPO (90.0 mg, 572.3 μmol) and pyridine (226.0 mg, 2.9 mmol) were added, and the reaction solution was continuously stirred at 15-20° C. for 64 hours. The reaction solution was poured into water (30 mL), the mixture was separated, the water phase was extracted with dichloromethane (30 mL) for three times, the mixed organic phase was washed with a saturated sodium chloride water solution (50 mL), and the organic solvent was removed under reduced pressure. The resulting crude product was separated and purified by silica gel column chromatography (an eluent: 0-30% ethyl acetate/ petroleum ether) to obtain the compound (−)-C24-1. $^1$H NMR (400 MHz, CHLOROFORM-d): δ 7.26-7.21 (m, 2H), 7.06-6.96 (m, 2H), 6.89-6.76 (m, 3H), 5.06-5.05 (m, 0.5H), 4.76-4.63 (m, 1.5H), 4.58-4.46 (m, 1H), 4.12-3.87 (m, 2H), 3.75 (s, 3H), 3.40-3.13 (m, 1H), 2.96-2.75 (m, 1H), 1.56-1.38 (m, 9H), 1.16-1.02 (m, 3H). MS m/z: 450.2 [M+Na]$^+$.

Step 2: Preparation of Compound (−)-C24

The compound (−)-C24-1 (125.0 mg, 292.4 μmol) was dissolved in ethyl acetate (1.0 mL), and then an ethyl acetate solution of hydrogen chloride (4.0 M, 1.0 mL) was added. The reaction solution was continuously stirred for 16 hours at 20-25° C. The organic solvent was removed under reduced pressure to obtain a hydrochloride salt of the compound (−)-C24. And the compound was directly used for the next reaction step without further purification. $^1$H NMR (400 MHz, METHANOL-d$_4$): δ 7.28-724 (m, 2H), 7.21-7.14 (m, 2H), 7.04-6.95 (m, 1H), 6.79-6.76 (m, 2H), 4.53-4.37 (m, 3H), 4.35-4.21 (m, 2H), 3.74 (s, 3H), 3.40-3.32 (m, 1H), 2.97-2.90 (m, 1H), 1.29-1.26 (t, J=7.2 Hz, 3H). MS m/z: 325.1 [M+1]$^+$.

Examples 1 and 2: Preparation of Compounds 1 and 2

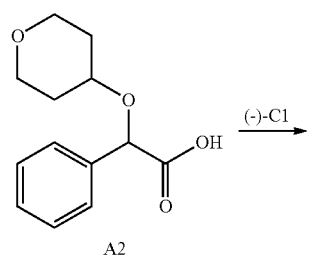

A2 (-)-C1

1-1

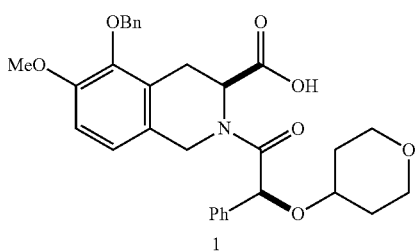

1

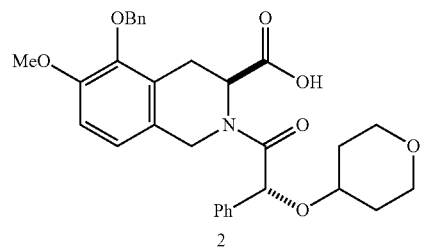

2

Step 1: Preparation of Compound 1-1

The compound (−)-C1 (150.0 mg, 439.4 μmol) was dissolved in anhydrous dichloromethane (6.0 mL), and then HATU (200.0 mg, 527.2 μmol), pyridine (104.0 mg, 1.32 mmol) and A2 (156.0 mg, 659.1 μmol) were added sequentially. After the reaction solution was stirred at 25° C. for 16 hours, the organic solvent was removed through concentration in vacuum. The resulting crude product was separated and purified by a silica gel chromatography column (an eluent: 50-100% ethyl acetate/petroleum ether) to obtain the compound 1-1. $^1$H NMR (400 MHz, CHLOROFORM-d): δ 7.64-7.31 (m, 10H), 6.93-6.32 (m, 2H), 5.51-5.29 (m, 1H), 5.13-4.81 (m, 3H), 4.27-3.90 (m, 4H), 3.90-3.79 (m, 2H), 3.53-3.35 (m, 2H), 1.87-1.49 (m, 5H), 1.33-1.04 (m, 3H). MS m/z: 560.2 [M+1]$^+$.

The following compounds were synthesized in a similar manner to the compound 1-1:

| Compound Serial Number | Structural Formula | Spectrogram |
|---|---|---|
| 3-1 | | ¹H NMR (400 MHz, CHLOROFORM-d): δ 7.53-7.31 (m, 10H), 6.95-6.49 (m, 2H), 5.41-5.28 (m, 1H), 5.24-4.60 (m, 4H), 4.53-4.19 (m, 1H), 4.16-3.89 (m, 2H), 3.87-3.82 (m, 3H), 3.80-3.48 (m, 5H), 3.45-3.26 (m, 4H), 1.20-0.86 (m, 3H). MS m/z: 534.2 [M + 1]⁺. |
| 5-1 | | ¹H NMR (400 MHz, CHLOROFORM-d): δ 7.59-7.32 (m, 10H), 6.93-6.43 (m, 2H), 5.35-4.79 (m, 5H), 4.69-4.39 (m, 1H), 4.22-3.99 (m, 2H), 3.86 (d, J = 7.2 Hz, 3H), 3.72-3.49 (m, 2H), 3.35-3.10 (m, 1H), 1.82-1.35 (m, 5H), 1.10 (t, J = 7.2 Hz, 1H), 1.23-1.07 (m, 1H), 1.02-0.85 (m, 4H). MS m/z: 532.2 [M + 1]⁺. |
| 7-1 | | ¹H NMR (400 MHz, CHLOROFORM-d): δ 7.55-7.31 (m, 10H), 6.92-6.43 (m, 2H), 5.50-5.33 (m, 1H), 5.08-4.81 (m, 3H), 4.62-4.43 (m, 1H), 4.35-4.19 (m, 1H), 4.10-3.94 (m, 2H), 3.85 (d, J = 3.5 Hz. 4H), 3.51-2.81 (m, 2H), 1.22-0.92 (m, 4H). MS m/z: 558.1 [M + 1]⁺. |
| 9-1 | | ¹H NMR (400 MHz, CHLOROFORM-d): δ 7.56-7.30 (m, 10H), 6.90-6.36 (m, 2H), 5.37-5.27 (m, 1H), 5.14-4.75 (m, 4H), 4.59-4.30 (m, 2H), 4.07-3.89 (m, 3H), 3.87-3.82 (m, 4H), 3.79-3.63 (m, 1H), 3.56-3.22 (m, 1H), 3.17-2.95 (m, 1H), 2.81 (s, 1H), 2.19-2.08 (m, 1H), 2.03-1.88 (m, 1H), 1.21-0.85 (m, 3H). MS m/z: 546.1 [M + 1]⁺. |
| 13-1 | | ¹H NMR (400 MHz, CHLOROFORM-d): δ 7.55-7.31 (m, 10H), 6.95-6.40 (m, 2H), 5.30-5.13 (m, 1H), 5.09-4.22 (m, 10H), 4.12-4.04 (m, 1H), 3.87-3.86 (d, J = 4.0 Hz, 3H), 3.51-3.08 (m, 1H), 3.05-2.81 (m, 1H), 2.55-2.12 (m, 1H), 1.22-0.93 (m, 3H). MS m/z: 546.1 [M + 1]⁺. |
| 15-1 | | ¹H NMR (400 MHz, CHLOROFORM-d): δ 7.54-7.35 (m, 10H), 6.67-6.59 (m, 4H), 6.03-5.73 (m, 1H), 5.35-4.82 (m, 3H), 4.81-4.49 (m, 1H), 4.42-4.18 (m, 1H), 4.11-3.94 (m, 1H), 3.89-3.84 (m, 3H), 3.84-3.62 (m, 1H), 3.55-3.31 (m, 1H), 2.99-2.53 (m, 1H), 1.19-0.97 (m, 3H). MS m/z: m/z: 606.0 [M + 1]⁺. |
| 51-1 | | ¹H NMR (400 MHz, CHLOROFORM-d): δ 10H), 6.90-6.41 (m, 2H), 5.23-5.15 (m, 1H), 5.13-4.95 (m, 2H), 4.95-4.62 (m, 2H), 4.57-4.45 (m, 1H), 4.36-4.21 (m, 1H), 4.09-3.97 (m, 1H), 3.88-3.82 (m, 3H), 3.80-3.43 (m, 1H), 3.34-3.04 (m, 1H), 3.01-2.45 (m, 5H), 1.24-1.03 (m, 3H). MS m/z: 566.0 [M + 1]⁺. |

-continued

| Compound Serial Number | Structural Formula | Spectrogram |
|---|---|---|
| 53-1 | | $^1$H NMR (400 MHz, CHLOROFORM-d): δ 7.51-7.32 (m, 7H), 7.11-6.96 (m, 2H), 6.89-6.74 (m, 1H), 6.70-6.41 (m, 1H), 5.47-4.78 (m, 5H), 4.64-4.41 (m, 1H), 4.35-4.16 (m, 1H), 4.09-3.95 (m, 1H). 3.88-3.83 (m, 3H), 3.74-3.47 (m, 1H), 3.32-3.07 (m, 1H), 3.02-2.66 (m, 1H), 2.01-1.85 (m, 1H), 1.85-1.61 (m, 7H), 1.24-0.90 (m, 3H). MS m/z: 562.1 [M + 1]$^+$. |
| 55-1 | | $^1$H NMR (400 MHz, CHLOROFORM-d): δ 7.52-7.25 (m, 10H), 6.90-6.32 (m, 2H), 5.49-5.18 (m, 2H), 5.07-4.74 (m, 3H), 4.57-4.38 (m, 1H), 4.34-3.94 (m, 3H), 3.89-3.79 (m, 3H), 3.67-3.37 (m, 1H), 3.25-2.87 (m, 1H), 2.15-1.89 (m, 4H), 1.37-1.04 (m, 5H), 0.72-0.37 (m, 2H). MS m/z: 556.3 [M + 1]$^+$. |
| 57-1 | | $^1$H NMR (400 MHz, CHLOROFORM-d): δ 7.55-7.45 (m, 4H), 7.44-7.34 (m, 6H), 6.89-6.62 (m, 2H), 5.61-5.20 (m, 2H), 5.13-4.75 (m, 4H), 4.67-4.42 (m, 1H), 4.11-3.96 (m, 1H), 3.89-3.83 (m, 3H), 3.64-3.39 (m, 1H), 3.25-2.90 (m, 1H), 2.05-1.79 (m, 4H), 1.78-1.62 (m, 4H), 1.44-1.31 (m, 3H), 1.24-1.09 (m, 3H). MS m/z: 580.2 [M + Na]. |
| 59-1 | | $^1$H NMR (400 MHz, CHLOROFORM-d): δ 7.50-7.18 (m, 10H), 6.80-6.55 (m, 2H), 5.49-5.40 (m, 1H), 5.28-3.99 (m, 8H), 3.81-3.72 (m, 3H), 3.50-2.62 (m, 2H), 1.91-1.12 (m, 9H), 0.46-0.24 (m, 1H), 0.03-0.03 (m, 1H). MS m/z : 556.1 [M + 1]$^+$. |
| 63-1 | | MS m/z: 574.3 [M + 1]$^+$. |
| 65-1 | | MS m/z: 574.3 [M + 1]$^+$. |

-continued

| Compound Serial Number | Structural Formula | Spectrogram |
|---|---|---|
| 67-1 | | ¹H NMR (400 MHz, CHLOROFORM-d): δ 7.54-7.31 (m, 10H), 7.09-6.45 (m, 2H), 5.40-5.04 (m, 3H), 4.82-4.47 (m, 3H), 4.41-4.22 (m, 1H), 3.71-3.53 (m, 2H), 3.52-3.30 (m, 1H), 3.29-3.24 (m, 1H), 2.98-2.83 (m, 2H), 2.75-2.51 (m, 2H), 2.32-2.25 (m, 3H). MS m/z: 536.1 [M + H]⁺. |
| 69-1 | | ¹H NMR (400 MHz, CHLOROFORM-d): δ 7.43-7.25 (m, 10H), 6.97-6.35 (m, 2H), 5.59-5.18 (m, 2H), 5.13-4.94 (m, 1H), 4.87-4.56 (m, 2H), 4.55-4.34 (m, 1H), 3.61-3.51 (m, 2H), 3.23-3.08 (m, 1H), 2.98 (s, 1H), 2.94-2.78 (m, 1H), 2.19-2.15 (d, J = 18.4 Hz, 3H), 1.96-1.62 (m, 8H), 1.30-1.24 (m, 3H). MS m/z: 550.2 [M + Na]⁺. |
| 71-1 | | ¹H NMR (400 MHz, CHLOROFORM-d): δ 7.59-7.28 (m, 10H), 7.11-6.41 (m, 2H), 5.60-5.15 (m, 2H), 5.13-4.48 (m, 4H), 3.69-3.58 (m, 3H), 3.37-3.17 (m, 1H), 3.15-3.00 (m, 1H), 2.98 (s, 2H), 2.30-2.23 (m, 3H), 1.77-1.55 (m, 8H). MS m/z: 566.2 [M + Na]⁺. |
| 73-1 | | ¹H NMR (400 MHz, CHLOROFORM-d): δ 7.51-7.30 (m, 10H), 7.27-7.12 (m, 10H), 6.92-6.42 (m, 1H), 5.27-4.07 (m, 7H), 3.67-3.65 (d, J = 7.6 Hz, 2H), 3.55 (s, 1H), 3.32-3.13 (m, 1H), 2.99-2.45 (m, 5H). MS m/z 578.1 [M + Na]⁺. |
| 75-1 | | ¹H NMR (400 MHz, CHLOROFORM-d): δ 7.53-7.36 (m, 10H), 7.11-6.38 (m, 2H), 5.46-5.25 (m, 2H), 5.21-5.06 (m, 1H), 5.02-4.84 (m, 2H), 4.61-4.37 (m, 1H), 3.72-3.55 (m, 3H), 3.31-3.13 (m, 1H), 3.00-2.73 (m, 1H), 2.03-1.65 (m, 8H), 1.42-1.32 (m, 3H). MS m/z: 570.1 [M + Na]⁺. |
| 77-1 | | ¹H NMR (400 MHz, CHLOROFORM-d): δ 7.60-7.33 (m, 11H), 7.14-6.36 (m, 1H), 5.60-5.37 (m, 3H), 5.21-4.44 (m, 5H), 3.80-3.49 (m, 4H), 3.24-3.09 (m, 1H), 1.94-1.46 (m, 8H). MS m/z: 564.1 [M + 1]⁺. |
| 79-1 | | MS m/z: 536.2 [M + Na]⁺. |

| Compound Serial Number | Structural Formula | Spectrogram |
|---|---|---|
| 81-1 | (structure shown) | MS m/z: 530.2 [M + 1]$^+$. |
| 83-1 | (structure shown) | $^1$H NMR (400 MHz, CHLOROFORM-d): δ 7.55-7.30 (m, 10H), 7.21-7.12 (m, 1H), 6.89-6.35 (m, 2H), 5.50-4.10 (m, 7H), 3.75-3.61 (m, 3H), 3.41-3.30 (m, 1H), 3.15-3.02 (m, 1H), 2.99-2.50 (m, 4H). MS m/z: 522.1 [M + 1]$^+$. |
| 85-1 | (structure shown) | MS m/z: 502.1 [M + 1]$^+$. |

Step 2: Preparation of Compounds 1 and 2

The compound 1-1 (200.0 mg, 357.4 μmol) was dissolved in a mixed solution of tetrahydrofuran (3.0 mL) and water (1.5 mL) at 25° C., and then lithium hydroxide monohydrate (85.0 mg, 2.0 mmol) was added. After stirring for 72 hours, 1 M hydrochloric acid was added to the reaction solution to have a pH <4. The aqueous phase was extracted with ethyl acetate (15.0 mL×3). The mixed organic phase was washed with a saturated saline solution (30.0 mL), dried with anhydrous sodium sulfate, and concentrated in vacuum to obtain a crude product. The crude product was separated and purified by a chromatography column (an eluent: 50-100% ethyl acetate/petroleum ether) to obtain a white solid (130.0 mg). Then two diastereoisomers 1 (99.4% de) and 2 (96.4% de) were obtained through SFC separation (AD (250 mm*30 mm, 10 μm); mobile phase: [0.1% NH$_3$H$_2$O EtOH]; B %: 30%-30%).

Compound 1: 1H NMR (400 MHz, DMSO-d$_6$): δ 7.54-7.21 (m, 10H), 6.99-6.60 (m, 2H), 5.55 (s, 1H), 5.18-4.64 (m, 4H), 4.43-4.24 (m, 1H), 3.88-3.56 (m, 4H), 3.27-3.14 (m, 2H). 2.92-2.64 (m, 1H), 2.37-2.24 (m, 1H), 2.04-1.82 (m, 2H), 1.63-1.41 (m, 2H). MS m/z: 532.1 [M+1]$^+$. SFC: Column: Chiralpak AD-3 (150 mm*4.6 mm, 3 μm); mobile phase: [0.05% DEA ethanol]; B %: 5%-40% 5 min, 40% 2.5 min, 5% 2.5 min; Rt=4.704 min; 99.4% de.

Compound 2: $^1$H NMR (400 MHz, DMSO-d$_6$): δ 7.52-7.25 (m, 10H), 6.97-6.72 (m, 2H), 5.56-5.44 (m, 1H), 5.08-4.66 (m, 4H), 4.51-4.25 (m, 1H), 3.88-3.60 (m, 6H), 3.25-3.16 (m, 2H), 2.83-2.63 (m, 1H), 2.20-1.76 (m, 3H), 1.62-1.36 (m, 2H). MS m/z: 532.1 [M+1]$^+$. SFC: column: Chiralpak AD-3 (150 mm*4.6 mm, 3 μm); mobile phase: [0.05% DEA ethanol]; B %: 5%-40%/5 min, 40% 2.5 min, 5% 2.5 min; Rt=5.497 min; 96.4% de.

The following compounds were synthesized by using a method similar to compounds 1 and 2:

| Example | Compound Serial Number | Structural Formula | Spectrogram |
|---|---|---|---|
| 3 | 3 | (structure shown) | $^1$H NMR (400 MHz, METHANOL-d$_4$): δ 7.49-7.28 (m, 10H). 6.90-6.64 (m, 2H), 5.45-5.27 (m, 1H), 5.04-4.67 (m, 4H), 4.45-4.25 (m, 1H), 3.78 (d, J = 8.0 Hz, 3H), 3.69-3.49 (m, 4H), 3.24 (d. J = 8.0 Hz, 3H), 2.80-2.64 (m, 1H), 2.34-2.17 (m, 1H). MS m/z: 506.1 [M + l]$^+$. SFC: column: ChiralCel OJ—H (150 mm * 4.6 mm, 5 μm); mobile phase [0.05% DEA MeOH]; B%: 5%-40% 5.5 min, 40% 3 min, 5% 1.5 min; Rt = 3.203 min; 97.2% de. |

| Example | Compound Serial Number | Structural Formula | Spectrogram |
|---|---|---|---|
| 4 | 4 | (structure: 5-OBn, 6-MeO tetrahydroisoquinoline-3-carboxylic acid, N-acyl with Ph-CH(O-CH2CH2-OMe)-C(O)-) | $^1$H NMR (400 MHz, METHANOL-d$_4$): δ 7.48-7.25 (m, 10H), 6.90-6.67 (m, 2H), 5.41-5.24 (m, 1H), 5.02-4.58 (m, 4.5H), 4.29 (d, J = 16.0 Hz, 0.5H). 3.77 (d, J = 4.0 Hz, 3H), 3.61-3.45 (m, 4H), 3.23 (d, J = 8.0 Hz, 3H), 2.69-2.52 (m, 1H), 2.43-2.29 (m, 1H). MS m/z: 506.1 [M + 1]$^+$. SFC: column: ChiralCel OJ—H (150 mm * 4.6 mm, 5 μm); mobile phase [0.05% DEA MeOH]; B%: 5%-40% 5.5 min, 40% 3 min, 5% 1.5 min; Rt = 3.504 min; 86.4% de. |
| 5 | 5 | (structure: 5-OBn, 6-MeO tetrahydroisoquinoline-3-carboxylic acid, N-acyl with Ph-CH(O-n-Bu)-C(O)-) | $^1$H NMR (400 MHz, METHANOL-d$_4$): δ 7.51-7.26 (m, 10H), 6.95-6.64 (m, 2H), 5.40-5.23 (m, 1H), 4.97-4.73 (m, 3H), 4.52-4.28 (m, 1H), 3.78 (d, J = 2.8 Hz, 3H), 3.69-3.48 (m, 2H), 2.81-2.60 (m, 1H), 2.27-1.93 (m, 1H), 1.61-1.27 (m, 5H), 0.88 (q, J = 8.0 Hz, 3H). MS m/z: 504.1 [M + 1]$^+$. SFC: column: Chiralpak AD-3 (150 mm * 4.6mm, 3 μm); mobile phase: [0.05% DEA EtOH]; B%: 5%-40% 5 min, 40% 2.5 min, 5% 2.5 min; Rt = 5.200 min; 96.6% de. |
| 6 | 6 | (structure: 5-OBn, 6-MeO tetrahydroisoquinoline-3-carboxylic acid, N-acyl with Ph-CH(O-n-Bu)-C(O)-, other diastereomer) | $^1$H NMR (400 MHz, METHANOL-d$_4$): δ 7.60-7.30 (m, 10H), 7.00-6.77 (m, 2H), 5.43-5.27 (m, 1H), 5.09-4.70 (m, 4H), 4.64-4.30 (m, 1H), 3.67-3.50 (m, 3H), 2.81-2.60 (m, 1H), 2.43-2.06 (m, 1H), 1.68-1.23 (m, 5H), 0.98-0.81 (m, 3H). MS m/z: 504.1 [M + 1]$^+$. SFC: column: Chiralpak AD-3 (150 mm * 4.6 mm, 3 μm); mobile phase: [0.05% DEA EtOH]; B%: 5%-40% 5 min, 40% 2.5 min, 5% 2.5 min; Rt = 5.660 min; 91.7% de. |
| 7 | 7 | (structure: 5-OBn, 6-MeO tetrahydroisoquinoline-3-carboxylic acid, N-acyl with Ph-CH(O-CH2-CF3)-C(O)-) | $^1$H NMR (400 MHz, METHANOL-d$_4$): δ 7.54-7.29 (m, 10H), 6.96-6.67 (m, 2H), 5.75-5.57 (m, 1H), 5.13-4.66 (m, 4H), 4.38-3.96 (m, 3H), 3.79 (d, J = 4.0 Hz, 3H), 2.90-2.64 (m, 1H), 2.41-1.99 (m, 1H). MS m/z: 530.1 [M + 1]$^+$. SFC: column: Chiralpak AD-3 (150 mm * 4.6 mm, 3 μm); mobile phase: [0.05% DEA EtOH]; B%: 5%-40% 5 min, 40% 2.5 min, 5% 2.5 min; Rt = 4.128 min; 96.4% de. |
| 8 | 8 | (structure: 5-OBn, 6-MeO tetrahydroisoquinoline-3-carboxylic acid, N-acyl with Ph-CH(O-CH2-CF3)-C(O)-, other diastereomer) | $^1$H NMR (400 MHz, METHANOL-d$_4$): δ 7.51-7.25 (m, 10H), 6.98-6.70 (m, 2H), 5.74-5.56 (m, 1H), 5.07-4.60 (m, 4H), 4.48-4.00 (m, 3H), 3.79 (d, J = 8.0 Hz, 3H), 2.82-2.57 (m, 1H), 2.37-2.05 (m, 1H). MS m/z: 530.0 [M + 1]$^+$. SFC: column: Chiralpak AD-3 (150 mm * 4.6 mm, 3 μm); mobile phase: [0.05% DEA EtOH]; B%: 5%-40% 5 min, 40% 2.5 min, 5% 2.5 min; Rt = 5.081 min; 95.1% de. |
| 9 | 9 | (structure: 5-OBn, 6-MeO tetrahydroisoquinoline-3-carboxylic acid, N-acyl with Ph-CH(O-tetrahydrofuran-3-yl)-C(O)-) | $^1$H NMR (400 MHz, METHANOL-d$_4$): δ 7.51-7.26 (m, 10H), 6.92-6.65 (m, 2H), 5.53-5.35 (m, 1H), 5.10-4.63 (m, 4H), 4.46-4.25 (m, 2H), 3.88-3.56 (m, 7H), 2.82-2.63 (m, 1H), 2.38-1.86 (m, 3H). MS m/z: 518.1 [M + 1]$^+$. SKC: column: Chiralpak AD-3 (100 mm * 4.6 mm, 3 μm); mobile phase [0.05% DEA EtOH]: B%: 5%-40% 4.5 min, 40% 2.5 min, 5% 1 min; Rt = 3.603 min; 98.1 % de. |

| Example | Compound Serial Number | Structural Formula | Spectrogram |
|---|---|---|---|
| 10 | 10 | | $^1$H NMR (400 MHz, METHANOL-d$_4$): δ 7.51-7.26 (m, 10H), 6.90-6.63 (m, 2H), 5.50-5.35 (m, 1H), 4.96-4.66 (m, 3H), 4.49-4.19 (m, 2H), 3.90-3.52 (m, 7H), 3.44-3.38 (m, 1H), 2.69-2.55 (m, 1H), 2.46-2.32 (m, 3H). MS m/z: 518.1 [M + 1]$^+$. SFC: column: Chiralcel OJ-3 (100 mm * 4.6 mm, 3 μm); mobile phase [0.05% DEA EtOH]; B%: 5%-40% 4.5 min, 40% 2.5 min, 5% 1 min; Rt = 2.676 min; 97.7% de. |
| 11 | 11 | | $^1$H NMR (400 MHz, METHANOL-d$_4$): δ 7.49-7.28 (m, 10H), 6.91-6.70 (m, 2H), 5.49-5.32 (m, 1H), 5.11-4.06 (m, 6H), 4.04-3.48 (m, 7H), 2.68 (s, 1H), 2.38-1.84 (m, 3H). MS m/z: 518.1 [M + 1]$^+$. SFC: column: Chiralpak AD-3 (100 mm * 4.6 mm, 3 μm); mobile phase [0.05% DEA EtOH]: B%: 5%-40% 4.5 min, 40% 2.5 min, 5% 1 min; Rt = 4.416 min; 99.4% de. |
| 12 | 12 | | $^1$H NMR (400 MHz, METHANOL-d$_4$): δ 7.52-7.25 (m, 10H), 6.91-6.68 (m, 2H), 5.39 (d, J = 20.0 Hz, 1H), 5.07-4.65 (m, 4H), 4.62-4.20 (m, 2H), 3.90-3.55 (m, 8H), 2.68 (s, 1H), 2.37-2.00 (m, 2H). MS m/z: 518.1 [M + 1]$^+$. SFC: column: Chiralcel OJ-3 (100 mm * 4.6 mm, 3 μm); mobile phase [0.05% DEA EtOH; B%: 5%-40% 4.5 min, 40% 2.5 min, 5% 1 min: Rt = 3.221 min; 98.7% de. |
| 13 | 13 | | $^1$H NMR (400 MHz, METHANOL-d$_4$): δ 7.50-7.29 (m, 10H), 6.96-6.67 (m, 2H), 5.53-5.30 (m, 1H), 5.06-4.71 (m, 3H), 4.69-4.13 (m, 7H), 3.80-3.78 (d, J = 6.0 Hz, 3H), 2.37-2.00 (m, 2H). MS m/z: 504.1 [M + 1]$^+$. SFC: column: Chiralpak AD-3 (100 mm * 4.6 mm, 3 μm); mobile phase [0.05% DEA EtOH]: B%: 5%-40% 4.5 min, 40% 2.5 min, 5% 1 min; Rt = 3.645 min; 92.2% de. |
| 14 | 14 | | $^1$H NMR (400 MHz, METHANOL-d$_4$): δ 7.50-7.29 (m, 10H), 6.96-6.67 (m, 2H), 5.53-5.30 (m, 1H), 5.06-4.71 (m, 3H), 4.69-4.13 (m, 7H), 3.79-3.77 (d, J = 8.0 Hz, 3H), 2.37-2.00 (m, 2H). MS m/z: 504.0 [M + 1]$^+$. SFC: column: Chiralpak AD-3 (100 mm * 4.61 mm, 3 μm); mobile phase [0.05%DEA EtOH]; B%: 5%-40% 4.5 min, 40% 2.5 min, 5% 1 min; Rt = 4.230 min; 96.3% de. |
| 15 | 15 | | $^1$H NMR (400 MHz, DMSO-d$_6$): δ 7.61-7.35 (m, 10H), 7.19-7.15 (m, 2H), 6.90-6.78 (m, 2H), 6.33-6.14 (m, 1H), 5.08-4.74 (m, 4H), 4.31-4.12 (m, 1H), 3.80-3.77 (d, J = 12.8 Hz, 3H), 2.75-2.68 (m, 1H), 2.34-1.80 (m, 1H). MS m/z: 578.0 [M + 1]$^+$. SFC: column: Chiralcel OJ-3 (100 mm * 4.6 mm, 3 μm); mobile phase [0.05% DEA EtOH]: B%: 5%-40% 4.5 min, 40% 2.5 min, 5% 1 min; Rt = 2.620 min; 100.0% de. |

-continued

| Example | Compound Serial Number | Structural Formula | Spectrogram |
|---|---|---|---|
| 16 | 16 | (structure) | ¹H NMR (400 MHz, DMSO-d₆): δ 7.54-7.35 (m, 10H), 7.19-7.15 (m, 2H), 6.91-6.75 (m, 2H), 6.26-6.20 (m, 1H), 4.99-4.70 (m, 4H). 4.67-4.28 (m, 1H), 3.80-3.77 (d, J = 13.6 Hz, 3H), 2.75-2.68 (m, 1H), 2.34-1.80 (m, 1H). MS m/z: 578.1 [M + 1]⁺. SFC: column: Chiralcel OJ-3 (100 mm * 4.6 mm, 3 μm); mobile phase [0.05% DEA EtOH]; B%: 5%-40% 4.5 min, 40% 2.5 min, 5% 1 min; Rt = 2.912 min; 90.0% de. |
| 51 | 51 | (structure) | ¹H NMR (400 MHz, DMSO-d₆): δ 7.63-7.27 (m, 10H), 7.02-6.72 (m, 2H), 5.61-5.37 (m, 1H), 5.18-4.73 (m, 4H), 4.43-4.05 (m, 2H), 3.85-3.84 (d, J = 4.0 Hz, 3H), 2.86 (s, 3H), 2.77-2.65 (m, 2H), 2.44-2.03 (m, 1H). MS m/z: 538.1 [M + 1]⁺. SFC: column: Chiralpak AD-3 (100 mm * 4.6 mm, 3 μm); mobile phase: B: [0.05% DEA EtOH]; B%: 5%-40% 4.5 min, 40% 2.5 min, 5% 1 min; Rt = 2.971 min; 98.6% de. |
| 52 | 52 | (structure) | ¹H NMR (400 MHz, DMSO-d₆): δ 7.60-7.33 (m, 10H), 7.04-6.77 (m, 2H), 5.56-5.37 (m, 1H), 5.03-4.84 (m, 3H), 4.70-4.54 (m, 1H), 4.43-4.05 (m, 2H), 3.85 (s, 3H), 2.88 ( s, 2H), 2.79-2.63 (m, 3H), 2.45-2.30 (m, 1H). MS m/z: 538.1 [M + 1]⁺. SFC: column: Chiralpak AD-3 (100 mm*4.6 mm, 3 μm): mobile phase: B: [0.05% DEA EtOH]; B%: 5%-40% 4.5 min, 40% 2.5 min, 5% 1 min; Rt = 3.431 min; 98.2% de. |
| 53 | 53 | (structure) | ¹H NMR (400 MHz, DMSO-d₆): δ 7.48-7.32 (m, 7H), 7.19-7.16 (m, 2H), 6.95-6.70 (m, 2H), 5.40-5.36 (d, J = 16.0 Hz, 1H), 5.13-4.70 (m, 4H), 4.45-4.25 (m, 1H), 4.05-4.01 (d, J = 20.0 Hz, 1H), 3.80 (s, 3H), 2.84-2.79 (m, 1H), 2.43-2.30 (m, 1H), 1.76-1.55 (m, 6H), 1.50-1.46 (m, 2H). MS m/z: 534.1 [M + 1]⁺. SFC: column: Chiralpak AD-3 (150 mm * 4.6 mm, 3 μm); mobile phase: B: [0.05% DEA IPA]; B%: 5%-40% 5.5 min, 40% 3 min, 5% 1.5 min; Rt = 5.399 min; 97.7% de. |
| 54 | 54 | (structure) | ¹H NMR (400 MHz, DMSO-d₆): δ 7.51-7.30 (m, 7H), 7.20-7.16 (t, J = 8.8 Hz, 2H), 6.96-6.73 (m, 2H), 5.36-5.31 (d, J = 20.0 Hz, 1H), 5.08-4.70 (m, 4H), 4.47-4.26 (m, 1H), 4.00 (br s, 1H), 3.80 (s, 3H), 2.79-2.65 (m, 1H), 2.37-2.21 (m, 1H), 1.76-1.54 (m, 6H), 1.48 (br s, 2H). MS m/z: 534.1 [M + 1]⁺. SFC: column: Chiralpak AD-3 (150 mm * 4.6 mm, 3 μm): mobile phase: B: [0.05% DEA IPA]; B%: 5%-40% 5.5 mm, 40% 3 mm, 5% 1.5 min: Rt = 5.959 min: 96.9% de. |
| 55 | 55 | (structure) | ¹H NMR (400 MHz, DMSO-d₆): δ 7.48-7.28 (m, 10H), 7.02-6.55 (m, 2H), 5.38-5.28 (m, 1H), 5.13-4.60 (m, 4H), 4.47-3.99 (m, 2H), 3.79 (s, 3H), 3.25-3.22 (m, 1H), 2.87-2.64 (m, 1H), 2.00-1.83 (m, 4H), 1.28-1.15 (m, 2H), 0.58-0.35 (m, 2H). MS m/z: 531.1 [M + 1]⁺. SFC: column: Chiralpak AD-3 (100 mm * 4.6 mm, 3 μm); mobile phase: B: [0.05% DBA IPA]; B%: 5%-40% 4.5 min, 40% 2.5 min, 5% 1 min; Rt = 4.466 min; 97.8% de. |

| Example | Compound Serial Number | Structural Formula | Spectrogram |
|---|---|---|---|
| 56 | 56 | (structure: 5-OBn, 6-MeO tetrahydroisoquinoline-3-carboxylic acid, N-acyl with Ph-CH(O-bicyclo[2.1.1]) group) | $^1$H NMR (400 MHz, DMSO-d$_6$): δ 7.46-7.25 (m, 10H), 6.96-6.68 (m, 2H), 5.38-5.23 (m, 1H), 4.95-4.60 (m, 4H), 4.42-4.22 (m, 1H), 4.11-3.97 (m, 1H), 3.79-3.78 (d, J = 3.6 Hz, 3H), 3.25-3.13 (m, 1H), 2.80-2.67 (m, 1H), 2.03-1.76 (m, 4H), 1.30-1.13 (m, 2H), 0.55-0.24 (m, 2H). MS m/z: 528.3 [M + 1]$^+$. SFC: column: Chiralpak AD-3 (100 mm * 4.6 mm, 3 μm); mobile phase: B: [0.05% DEA IPA]; B%: 5%-40% 4.5 min, 40% 2.5 min, 5% 1 min: Rt = 5.247 min; 98.6% de. |
| 57 | 57 | (structure: similar core, N-acyl with Ph-CH(O-1-methylcyclopentyl)) | $^1$H NMR (400 MHz, DMSO-d$_6$): δ 7.51-7.13 (m, 10H), 6.96-6.52 (m, 2H), 5.35-5.32 (d, J = 12.0 Hz, 1H), 5.05-4.66 (m, 4H), 4.61-4.22 (m, 1H), 3.78-3.77 (d, J = 4.0 Hz, 3H), 2.72-2.57 (m, 1H), 2.36-2.34 (m, 1H), 1.96-1.37 (m, 8H), 1.35-1.19 (m, 3H). MS m/z: 552.3 [M + Na]$^+$. SFC: column: ChiralCel OJ—H (150 mm * 4.6 mm, 3 μm); mobile phase: B: [0.05% DEA MeOH]; B%: 5%-40% 5.5 min, 40% 3 min, 5% 1.5 min; Rt = 2.860 min; 100.0% de. |
| 58 | 58 | (structure: similar core, N-acyl with Ph-CH(O-1-methylcyclopentyl), opposite stereo) | $^1$H NMR (400 MHz, DMSO-d$_6$): δ 7.50-7.28 (m, 10H), 6.92-6.68 (m, 2H), 5.29-5.28 (d, J = 4.0 Hz, 1H), 5.05-4.72 (m, 4H), 4.38-4.17 (m, 1H), 3.79-3.77 (d, J = 8.0 Hz, 3H), 3.30-3.06 (m, 1H), 2.71-2.65 (m, 1H), 1.93-1.42 (m, 8H), 1.34-1.21 (m, 3H). MS m/z: 552.5 [M + Na]$^+$. SEC: column: ChiralCel OJ—H (150 mm * 4.6 mm, 3 μm); mobile phase: B: [0.05% DEA MeOH]; B%: 5%-40% 5.5 min, 40% 3 min, 5% 1.5 min; Rt = 3.100 min; 90.9% de. |
| 59 | 59 | (structure: similar core, N-acyl with Ph-CH(O-bicyclic)) | $^1$H NMR (400 MHz, DMSO-d$_6$): δ 7.45-7.22 (m, 10H), 6.96-6.67 (m, 2H), 5.43-5.41 (d, J = 10.0 Hz, 1H), 5.18-4.67 (m, 4H), 4.47-4.22 (m, 1H), 3.97-3.89 (m, 1H), 3.77 (s, 3H), 3.21-2.35 (m, 2H), 1.80-1.16 (m, 6H), 0.44-0.30 (m, 1H), 0.06-0.07 (m, 1H). MS m/z: 528.1 [M + 1]$^+$. SFC: column: ChiralPak AS-3 (150 mm * 4.6 mm, 3 μm); mobile phase: B: [0.05% DEA EEtOH]; B%: 5%-40% 5.5 min, 40% 3 min, 5% 1.5 min; Rt = 3.612 min; 97.4% de. |
| 60 | 60 | (structure: similar core, N-acyl with Ph-CH(O-bicyclic)) | $^1$H NMR (400 MHz, DMSO-d$_6$): δ 7.51-7.21 (m, 10H), 6.99-6.62 (m, 2H), 5.57-5.42 (m, 1H), 5.15-4.68 (m, 4H), 4.52-4.21 (m, 1H), 4.04-3.88 (m, 1H), 3.79 (s, 3H), 3.30-2.18 (m, 2H), 1.91-1.23 (m, 6H), 0.48-0.30 (m, 1H), 0.03-0.03 (m, 1H), MS m/z: 528.3 [M + 1]$^+$. SFC: column: ChiralPak AS-3 (150 mm * 4.6 mm, 3 μm); mobile phase: B: [0.05% DEA EEtOH]; B%: 5%-40% 5.5 mm, 40% 3 mm, 5% 1.5 min; Rt = 3.691 min; 76.4% de. |
| 61 | 61 | (structure: similar core, N-acyl with Ph-CH(O-bicyclic)) | $^1$H NMR(400 MHz, DMSO-d$_6$): δ 7.52-7.24 (m, 10H), 6.98-6.66 (m, 2H), 5.41-5.33 (m, 1H), 5.09-4.72 (m, 4H), 4.59-4.26 (m, 1H), 3.91-3.78 (m, 1H), 3.78-3.74 (m, 3H), 2.92-2.24 (m, 2H), 1.81-1.21 (m, 6H), 0.45-0.24 (m, 1H), 0.04-0.03 (m, 1H). MS m/z: 528.2 [M + 1]$^+$. SFC: column: ChiralCel OJ—H (150 mm * 4.6 mm, 5 μm); mobile phase: B: [0.05% DEA MeOH]; B%: 5%-40% 5.5 min, 40% 3 min, 5% 1.5 min; Rt = 3.720 min; 92.7% de. |

| Example | Compound Serial Number | Structural Formula | Spectrogram |
|---|---|---|---|
| 62 | 62 | (structure) | $^1$H NMR (400 MHz, DMSO-$d_6$): δ 7.52-7.26 (m, 10H), 6.97-6.70 (m, 2H), 5.47-5.42 (d, J = 18.4 Hz, 1H), 5.04-4.66 (m, 4H), 4.53-4.26 (m, 1H), 3.98-3.89 (m, 1H), 3.79 (s, 3H), 3.14-2.23 (m, 2H), 1.90-1.14 (m, 6H), 0.46-0.32 (m, 1H), 0.04-0.06 (m, 1H). MS m/z: 528.1 [M + 1]$^+$. SFC: column: ChiralCel OJ—H (150 mm * 4.6 mm, 5 μm); mobile phase: B: [0.05% DEA MeOH]; B%: 5%-40% 5.5 min, 40% 3 min, 5% 1.5 min; Rt = 4.395 min; 98.9% de. |
| 63 | 63 | (structure) | $^1$H NMR (400 MHz, DMSO-$d_6$): δ 7.56-7.26 (m, 10H), 7.02-6.65(m, 2H), 5.52-5.45 (m, 1H), 5.12-4.69 (m, 4H), 4.51-4.31 (m, 1H), 3.84 (s, 3H), 3.69-3.50 (m, 2H), 3.29-3.24 (m, 1H), 2.87-2.80 (m, 0.5H), 2.40-2.30 (m, 0.5H), 1.99-1.40 (m, 8H). MS m/z: 568.1 [M + Na]$^+$. SFC: column: Chiralcel OJ-3 (100 mm * 4.6 mm, 3 μm); mobile phase: B: [0.05% DEA MeOH]; B%: 5%-40% 4.5 min, 40% 2.5 min, 5% 1 min; Rt = 2.605 min; 98.2% de. |
| 64 | 64 | (structure) | $^1$H NMR (400 MHz, DMSO-$d_6$): δ 7.59-7.30 (m, 10H), 7.01-6.73 (m, 2H), 5.49-5.42 (m, 1H), 5.22-4.71 (m, 4H), 4.49-4.31 (m, 1H), 3.84 (s, 3H), 3.64-3.61 (m, 2H), 3.34-3.25 (m, 1H), 2.81-2.75 (m, 0.5H), 2.13-2.09 (m, 0.5H), 1.98-1.39 (m, 8H). MS m/z: 568.1 [M + Na]$^+$. SFC: column: Chiralcel OJ-3 (100 mm * 4.6 mm, 3 μm); mobile phase: B: [0.05% DEA MMeOH]; B%: 5%-40% 4.5 min, 40% 2.5 min, 5% 1 min; Rt = 3.227 min; 98.6% de. |
| 65 | 65 | (structure) | $^1$H NMR (400 MHz, DMSO-$d_6$): δ 7.49-7.27 (m, 10H), 6.90-6.58 (m, 2H), 5.50-5.28 (m, 1H), 5.06-4.67 (m, 4H), 4.63-4.38 (m, 2H), 3.76 (s, 3H), 3.33-3.32 (m, 1H), 2.75-2.52 (m, 1H), 2.14-2.09 (m, 1H), 2.03-1.64 (m, 4H), 1.31-1.02 (m, 4H). MS m/z: 546.2 [M + 1]$^+$. SFC: column: Chiralcel OJ-3 (100 mm * 4.6 mm, 3 μm); mobile phase: B: [0.05% DEA MeOH]; B%: 5%-40% 5 min, 40% 2.5 min, 5% 2.5 min; Rt = 3.403 min; 100.0% de. |
| 66 | 66 | (structure) | $^1$H NMR (400 MHz, DMSO-$d_6$): δ 7.55-7.25 (m, 10H), 6.93-6.64 (m, 2H), 5.46-5.36 (m, 1H), 5.09-5.07 (m, 0.5H), 4.87-4.73 (m, 3H), 4.53-4.47 (m, 2H), 4.33-4.28 (m, 0.5H), 3.77 (s, 3H), 3.31-3.30 (m, 1H), 2.65-2.59 (m, 1H), 2.21-2.08 (m, 1H), 2.05-1.60 (m, 4H), 1.31-1.03 (m, 4H). MS m/z: 546.2 [M + 1]$^+$. SFC: column: Chiralcel OJ-3 (100 mm * 4.6 mm, 5 μm); mobile phase: B: [0.05% DBA MeOH]; B%: 5%-40% 5 mm, 40% 2.5 min, 5% 2.5 min; Rt = 4.786 min; 93.9% de. |
| 67 | 67 | (structure) | $^1$H NMR (400 MHz, DMSO-$d_6$): δ 7.55-7.29 (m, 10H), 7.05-6.63 (m, 2H), 5.53-5.37 (m, 1H), 5.24-4.07 (tn, 6H), 2.94-2.74 (m, 2H), 2.73-2.52 (m, 3H), 2.42-2.23 (m, 1H), 2.19-2.17 (d, J = 8.0 Hz, 3H). MS m/z: 522.3 [M + 1]$^+$. SFC: column: Chiralpak AD-3 (100 mm * 4.6 mm, 3 μm); mobile phase: B: [0.05% DEA IPA]; B%: 5%-40% 4.5 min, 40% 2.5 min, 5% 1 min; Rt = 3.357 min; 98.3% de. |

| Example | Compound Serial Number | Structural Formula | Spectrogram |
|---|---|---|---|
| 68 | 68 | (structure: 5-OBn, 6-methyl tetrahydroisoquinoline-3-carboxylic acid, N-acylated with Ph-CH(O-3,3-difluorocyclobutyl)-C(O)-) | ¹H NMR (400 MHz, DMSO-d₆): δ 7.55-7.26 (m, 10H), 7.07-6.69 (m, 2H), 5.53-5.32 (m, 1H), 5.14-4.05 (m, 6H), 2.93-2.55 (m, 5H), 2.47-2.30 (m, 1H), 2.19-2.18 (d, J = 3.2 Hz, 3H). MS m/z: 522.3 [M + 1]⁺. SFC: column: Chiralpak AD-3 (100 mm * 4.6 mm, 3 μm): mobile phase: B: [0.05% DEA IPA]; B%: 5%-40% 4.5 min, 40% 2.5 min, 5% 1 min; Rt = 3.994 min; 99.0% de. |
| 69 | 69 | (structure: 5-OBn, 6-methyl tetrahydroisoquinoline-3-carboxylic acid, N-acylated with Ph-CH(O-(1-methylcyclopentyl))-C(O)-) | ¹H NMR (400 MHz, DMSO-d₆): δ 7.52-7.18 (m, 10H), 7.06-6.55 (m, 2H), 5.42-5.06 (m, 2H), 4.88-4.30 (m, 4H), 2.83-2.78 (m, 1H), 2.48-2.27 (m, 1H), 2.19-2.17 (d, J = 6.0 Hz, 3H), 1.96-1.45 (m, 8H), 1.36-1.25 (m, 3H). MS m/z: 536.3 [M + Na]⁺. SFC: column: ChiralPak AD-3 (150 mm * 4.6 mm, 3 μm); mobile phase: B: [0.05% DEA IPA]; B%: 5%-40% 5.5 min, 40% 3 min, 5% 1.5 min; Rt = 4.854 min; 100% de. |
| 70 | 70 | (structure: 5-OBn, 6-methyl tetrahydroisoquinoline-3-carboxylic acid, N-acylated with Ph-CH(O-(1-methylcyclopentyl))-C(O)-, diastereomer) | ¹H NMR (400 MHz, DMSO-d₆): δ 7.56-7.26 (m, 10H), 7.08-6.64 (m, 2H), 5.35-4.71 (m, 4H), 4.65-4.25 (m, 2H), 3.13-3.10 (m, 1H), 2.84-2.80 (m, 1H), 2.19-2.16 (d, J = 10.0 Hz, 3H), 1.92-1.44 (m, 8H), 1.36-1.19 (m, 3H). MS m/z: 536.3 [M + Na]⁺. SFC: column: ChiralPak AD-3 (150 mm * 4.6 mm, 3 μm); mobile phase: B: [0.05% DEA IPA]; B%: 5%-40% 5.5 min, 40% 3 min, 5% 1.5 min; Rt = 5.312 min; 100% de. |
| 71 | 71 | (structure: 5-OBn, 6-methyl tetrahydroisoquinoline-3-carboxylic acid, N-acylated with Ph-CH(O-(4-hydroxycyclohexyl))-C(O)-) | ¹H NMR (400 MHz, DMSO-d₆): δ 7.53-7.25 (m, 10H), 7.02-6.61 (m, 2H), 5.41-5.38 (d, J = 8.8 Hz, 1H), 5.19-4.83 (m, 2H), 4.79-4.33 (m, 4H), 3.60-3.51 (m, 2H), 3.50-3.48 (m, 1H), 2.18 (s, 3H), 1.87-1.39 (m, 8H). MS m/z: 530.2 [M + H]⁺. SFC condition: SFC: column: ChiralPak AD-3 (150 mm * 4.6 mm, 3 μm); mobile phase: B: [0.05% DEA Ethanol]; B%: 5%-40% 5.5 min, 40% 3 min, 5% 1.5 min; Rt = 5.030 min; 100% de. |
| 72 | 72 | (structure: 5-OBn, 6-methyl tetrahydroisoquinoline-3-carboxylic acid, N-acylated with Ph-CH(O-(4-hydroxycyclohexyl))-C(O)-, diastereomer) | ¹H NMR (400 MHz, DMSO-d₆): δ 7.56-7.25 (m, 10H), 6.98-6.95 (m, 1H), 6.88-6.61 (m, 1H), 5.54-5.32 (m, 1H), 5.24-4.32 (m, 6H), 3.63-3.49 (m, 1H), 2.83-2.77 (m, 1H), 2.42-2.32 (m, 1H), 2.18 (s, 3H), 1.90-1.44 (m, 8H). MS m/z: 530.2 [M + H]⁺. SFC condition: SFC: column: ChiralPak AD-3 (150 mm * 4.6 mm, 3 μm); mobile phase: B: [0.05% DEA Ethanol]; B%: 5%-40% 5.5 min, 40% 3 min, 5% 1.5 min; Rt = 5.789 min; 98.7% de. |
| 73 | 73 | (structure: 5-OBn, 6-Cl tetrahydroisoquinoline-3-carboxylic acid, N-acylated with Ph-CH(O-3,3-difluorocyclobutyl)-C(O)-) | ¹H NMR(400 MHz, DMSO-d₆): δ 7.57-7.25 (m, 11H), 7.05-6.75 (m, 1H), 5.53-5.34 (m, 1H), 5.22-5.09 (m, 0.5H), 4.96-4.67 (m, 3.5H), 4.41-4.27 (m, 1H), 4.11 (brs, 1H), 2.96-2.74 (m, 3H), 2.64-2.52 (m, 2H), 2.27-2.22 (m, 1H). MS m/z: 542.1 [M + 1]⁺. SFC: column: ChiralCel OJ—H (150 mm*4.6 mm, 5 μm); mobile phase: B: [0.05% DEA Methanol]; B%: 5%-40% 5.5 min, 40% 3 min, 5% 1.5 min; Rt = 3.192 min; 82.4% de. |

| Example | Compound Serial Number | Structural Formula | Spectrogram |
|---|---|---|---|
| 74 | 74 | (structure: 6-Cl, 5-OBn tetrahydroisoquinoline-3-carboxylic acid, N-acyl with Ph-CH(O-3,3-difluorocyclobutyl)-C(=O)) | $^1$H NMR (400 MHz, DMSO-d$_6$): δ 7.59-7.22 (m, 11H), 7.07-6.79 (m, 1H), 5.49-5.31 (m, 1H), 5.12-4.60 (m, 4.5H), 4.41-4.36 (d, J = 18.0 Hz, 0.5H), 4.14 (brs, 1H), 2.94-2.70 (m, 3H), 2.64-2.53 (m, 2H), 2.43-2.31 (m, 1H). MS m/z: 442.4 [M + 1]$^+$. SKC: column: ChiralCel OJ—H (150 mm * 4.6 mm, 5 μm); mobile phase: B: [0.05% DEA Methanol]; B%: 5%-40% 5.5 min, 40% 3 min, 5% 1.5 min; Rt = 3.698 min; 97.1% de. |
| 75 | 75 | (structure: 6-Cl, 5-OBn THIQ-3-COOH, N-acyl with Ph-CH(O-(1-methylcyclopentyl))-C(=O)) | $^1$H NMR (400 MHz, DMSO-d$_6$): δ 7.52-7.17 (m, 11H), 7.03-7.01 (d, J = 8.4 Hz, 0.5H), 6.72-6.70 (d, J = 8.4 Hz, 0.5H), 5.37-5.35 (d, J = 6.4 Hz, 1H), 5.22-5.06 (m, 1H), 4.93-4.74 (m, 3H), 4.61-4.27 (m, 1H), 3.29-3.26 (m, 1H), 2.81-2.75 (m, 1H), 1.96-1.41 (m, 8H), 1.36-1.24 (m, 3H). MS m/z: 556.3 [M + Na]$^+$. SFC: column: Chiralpak AD-3 (150 mm * 4.6 mm, 3 μm); mobile phase: B: [0.05% DEA IPA]; B%: 5%-40% 5 min, 40% 2.5 min, 5% 2.5 min; Rt = 4.620 min; 100% de. |
| 76 | 76 | (structure: 6-Cl, 5-OBn THIQ-3-COOH, N-acyl with Ph-CH(O-(1-methylcyclopentyl))-C(=O), diastereomer) | $^1$H NMR (400 MHz, DMSO-d$_6$): δ 7.54-7.24 (m, 11H), 7.08-6.79 (m, 1H), 5.33-5.32 (d, J = 4.8 Hz, 1H), 5.12-4.83 (m, 3H), 4.76-4.68 (m, 1H), 4.44-4.21 (m, 1H), 3.14-3.10 (d, J = 16.0 Hz, 1H), 2.85-2.79 (m, 1H), 1.90-1.46 (m, 8H), 1.35-1.23 (m, 3H). MS m/z: 556.2 [M + Na]$^+$. SFC: column: Chiralpak AD-3 (150 mm * 4.6 mm, 3 μm); mobile phase: B: [0.05% DEA IPA]; B%: 5%-40% 5 min, 40% 2.5 min, 5% 2.5 min; Rt = 4.947 min; 96.3% de. |
| 77 | 77 | (structure: 6-Cl, 5-OBn THIQ-3-COOH, N-acyl with Ph-CH(O-(4-hydroxycyclohexyl))-C(=O)) | $^1$H NMR (400 MHz, DMSO-d$_6$): δ 7.58-7.17 (m, 11H), 7.04-6.73 (m, 1H), 5.39-5.37 (d, J = 5.2 Hz, 1H), 5.14-5.13 (d, J = 5.6 Hz, 0.5H), 4.99-4.80 (m, 3H), 4.70-4.67 (d, J = 10.4 Hz, 0.5H), 4.60-4.31 (m, 2H), 3.57-3.38 (m, 1H), 2.71-2.59 (m, 1H), 2.35-2.07 (m, 1H), 1.88-1.33 (m, 8H), MS m/z: 550.1 [M + 1]$^+$. SFC: column: Chiralpak AD-3 (150 mm * 4.6 mm, 3 μm); mobile phase: B: [0.05% DEA Ethanol]; B%: 5%-40% 5 min, 40% 2.5 min, 5% 2.5 min; Rt = 4.795 min; 97.6% de. |
| 78 | 78 | (structure: 6-Cl, 5-OBn THIQ-3-COOH, N-acyl with Ph-CH(O-(4-hydroxycyclohexyl))-C(=O), diastereomer) | $^1$H NMR (400 MHz, DMSO-d$_6$): δ 7.56-7.24 (m, 11H), 7.04-6.68 (m, 1H), 5.52-5.32 (m, 1H), 5.18-5.17 (d, J = 3.6 Hz, 0.5H), 4.98-4.70 (m, 3.5H), 4.62-4.31 (m, 2H), 3.62-3.51 (m, 1H), 2.86-2.66 (m, 1H), 2.42-2.28 (m, 1H), 1.89-1.37 (m, 8H). MS m/z: 550.2 [M + 1]$^+$. SFC: column: Chiralpak AD-3 (150 mm * 4.6 mm, 3 μm); mobile phase: B: [0.05% DEA Ethanol]; B%: 5%-40% 5 min, 40% 2.5 min, 5% 2.5 min; Rt = 5.778 min; 98.2% de. |
| 79 | 79 | (structure: 5-OBn THIQ-3-COOH, N-acyl with Ph-CH(O-(1-methylcyclopentyl))-C(=O)) | $^1$H NMR (400 MHz, DMSO-d$_6$): δ 7.48-7.19 (m, 10H), 7.15-6.99 (m, 1H), 6.86-6.47 (m, 2H), 5.39-5.06 (m, 4H), 4.91-4.75 (m, 1H), 4.55-4.24 (m, 1H), 2.94-2.53 (m, 2H), 1.97-1.43 (m, 8H), 1.36-1.24 (m, 3H), MS m/z: 522.3 [M + Na]$^+$. SFC: column: Chiralpak AD-3 (150 mm * 4.6 mm, 3 μm); mobile phase: B: [0.05% DEA Ethanol]; B%: 5%-40% 5.5 min, 40% 3 min, 5% 1.5 min; Rt = 4.325 min; 100% de. |

| Example | Compound Serial Number | Structural Formula | Spectrogram |
|---|---|---|---|
| 80 | 80 | (structure) | $^1$H NMR (400 MHz, DMSO-$d_6$): δ 7.52-7.25 (m, 10H), 7.19-7.01 (m, 1H), 6.94-6.60 (m, 2H), 5.40-4.88 (m, 5H), 4.51-4.15 (m, 1H), 3.19-2.63 (m, 2H), 1.96-1.38 (m, 8H), 1.35-1.14 (m, 3H). MS m/z: 522.3 [M + Na]$^+$. SFC: column: Chiralpak AD-3 (150 mm * 4.6 mm, 3 μm); mobile phase: B: [0.05% DBA Ethanol]; B%: 5%-40% 5.5 min, 40% 3 min, 5% 1.5 min; Rt = 4.785 min; 98.0% de. |
| 81 | 81 | (structure) | $^1$H NMR (400 MHz, DMSO-$d_6$): δ 7.59-7.22 (m, 10H), 7.13-6.97 (m, 1H), 6.87-6.52 (m, 2H), 5.56-4.82 (m, 5H), 4.62-4.22 (m, 2H), 3.60-3.50 (m, 1H), 2.76-2.55 (m, 1H), 1.89-1.34 (m, 8H). MS m/z: 516.3 [M + 1]$^+$. SFC: column: Chiralpak AD-3 (150 mm * 4.6 mm, 3 μm); mobile phase: B: [0.05% DEA IPA]; B%: 40%; Rt = 2.046 min; 100% de. |
| 82 | 82 | (structure) | $^1$H NMR (400 MHz, DMSO-$d_6$): δ 7.53-7.18 (m, 10H), 7.13-6.97 (m, 1H), 6.86-6.43 (m, 2H), 5.60-4.21 (m, 7H), 3.66-3.46 (m, 1H), 2.69-2.60 (m, 1H), 1.95-1.31 (m, 8H). MS m/z: 516.1 [M + 1]$^+$. SFC: Chiralpak AD-3 (150 mm * 4.6 mm, 3 μm); mobile phase: B: [0.05% DEA IPA]; B%: 40%: Rt = 5.382 min; 99.58% de. |
| 83 | 83 | (structure) | $^1$H NMR (400 MHz, DMSO-$d_6$): δ 7.52-7.26 (m, 10H), 7.10-7.02 (m, 1H), 6.88-6.56 (m, 2H), 5.61-4.63 (m, 5H), 4.47-4.01 (m, 2H), 3.03-2.54 (m, 5H), 2.37-2.13 (m, 1H). MS m/z: 508.1 [M + 1]$^+$. SFC: column: Chiralpak AD-3 (150 mm * 4.6 mm, 3 μm): mobile phase: B: [0.05% DEA Ethanol]; B%: 5%-40% 5.5 min, 40% 3 min, 5% 1.5 min; Rt = 3.861 min; 100% de. |
| 84 | 84 | (structure) | $^1$H NMR (400 MHz, DMSO-$d_6$): δ 7.59-7.39 (m, 10H), 7.22-7.13 (m, 1H), 6.99-6.70 (m, 2H), 5.64-4.74 (m, 7H), 3.06-2.33 (m, 6H), MS m/z: 508.1 [M + 1]$^+$. SFC: column: Chiralpak AD-3 (150 mm * 4.6 mm, 3 μm); mobile phase: B: [0.05% DEA Ethanol]; B%: 5%-40% 5.5 min, 40% 3 min, 5% 1.5 min; Rt = 4.692 min; 99.6% de. |
| 85 | 85 | (structure) | $^1$H NMR (400 MHz, DMSO-$d_6$): δ 7.48-7.27 (m, 10H), 7.18-7.05 (m, 1H), 6.95-6.82 (m, 1H), 6.82-6.55 (m, 1H), 5.39-5.31 (m, 1H), 5.25 (brs, 1H), 5.16-5.02 (m, 3H), 4.96-4.82 (m, 1H), 4.40-4.22 (m, 1H), 3.76-3.61 (m, 5H), 2.93-2.81 (m, 1H), 2.45-2.33 (m, 1H), 1.94-1.66 (m, 2H). MS m/z: 488.2 [M + 1]$^+$. SFC: column: Chiralpak AD-3 (50 mm * 3 mm, 3 μm); mobile phase: B: [0.05% DEA IPA]; B%: 5%-40% 2.5 min, 40% 0.35 min, 5% 0.15 min; Rt = 2.285 min; 95.1% de. |

| Example | Compound Serial Number | Structural Formula | Spectrogram |
|---|---|---|---|
| 86 | 86 | | $^1$H NMR (400 MHz, DMSO-$d_6$): δ 7.49-7.27 (m, 10H), 7.18-7.06 (m, 1H), 6.93-6.83 (m, 1H), 6.82-6.63 (m, 1H), 5.38-5.22 (m, 1H), 5.22-5.14 (m, 1H), 5.12-5.03 (m, 3H), 5.01-4.74 (m, 1H), 4.58-4.26 (m, 1H), 3.67-3.56 (m, 5H), 2.85-2.74 (m, 1H), 2.44-2.31 (m, 1H), 1.91-1.68 (m, 2H). MS m/z: 488.1 [M + 1]$^+$. SFC: column: Chiralpak AD-3 (50 mm * 3 mm, 3 μm); mobile phase: B: [0.05% DEA IPA]; B%: 5%-40% 2.5 min, 40% 0.35 min, 5% 0.15 min; Rt = 2.126 min; 72.96% de. |

Examples 17 and 18: Preparation of Compounds 17 and 18

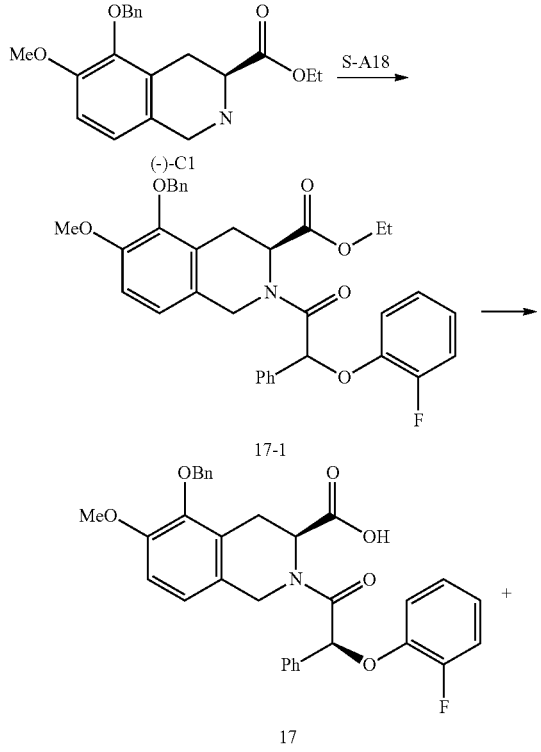

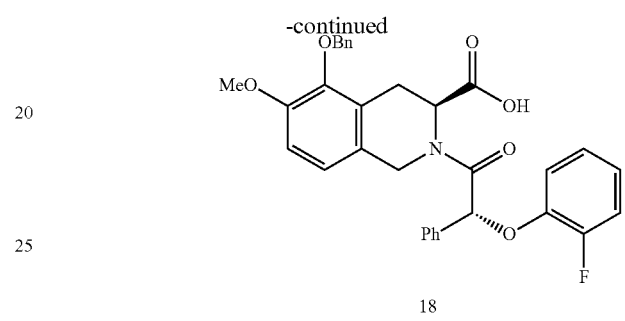

Step 1: Preparation of Compound 17-1

The compound (−)-C1 (150.0 mg, 439.4 μmol) was dissolved in dichloromethane (5.0 mL), and then HATU (251.0 mg, 660.1 μmol), pyridine (70.0 mg, 885.0 μmol) and S-A18 (120.0 mg, 487.4 μmol) were added sequentially. After the reaction solution was stirred at 25° C. for 16 hours, the organic solvent was removed through concentrating in vacuum to obtain a crude product. The crude product was separated and purified by a silica gel chromatography column (an eluent: 0-50% petroleum ether/ethyl acetate) to obtain the product 17-1. $^1$H NMR (400 MHz, CHLOROFORM-d): δ 7.68-7.57 (m, 2H), 7.50-7.34 (m, 8H), 7.21-6.94 (m, 4H), 6.87-6.79 (m, 1H), 6.73-6.50 (m, 1H), 6.06-5.96 (m, 1H), 5.43-5.11 (m, 1H), 5.08-4.70 (m, 4H), 4.56-4.30 (m, 1H), 4.08-3.92 (m, 1H), 3.87-3.81 (m, 3H), 3.68-3.41 (m, 1H), 3.27-3.08 (m, 0.5H), 2.98-2.74 (m, 0.5H), 1.08-0.80 (m, 3H). MS m/z: 570.1 [M+1]$^+$.

The following compounds were synthesized in a similar manner to the compound 17-1:

| Compound Serial number | Structural formula | Spectrogram |
|---|---|---|
| 19-1 | | $^1$H NMR (400 MHz, CHLOROFORM-d): δ 7.67-7.52 (m, 2H), 7.49-7.27 (m, 10H), 7.13-6.96 (m, 3H), 6.87-6.77 (m, 1H), 6.80-6.54 (m, 1H), 6.09-5.95 (m, 1H), 5.12-5.08 (m, 1H), 5.07-4.70 (m, 3H), 4.71-4.41 (m, 1H), 4.19-4.10 (m, 2H), 3.84 (m, 3H), 3.56-3.13 (m, 1H), 2.06 (s, 2H), 1.27 (t, J = 8.0 Hz, 3H). MS m/z: 552.3 [M + 1]$^+$. |

-continued

| Compound Serial number | Structural formula | Spectrogram |
|---|---|---|
| 21-1 | 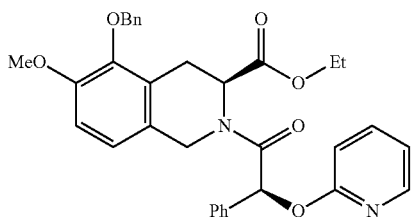 [SMILES: CCOC(=O)[C@@H]1Cc2c(ccc(OC)c2OCc2ccccc2)CN1C(=O)[C@@H](Oc1ccccn1)c1ccccc1] | ¹H NMR (400 MHz, CHLOROFORM-d): δ 8.19-7.91 (m, 1H), 7.71-7.54 (m, 3H), 7.51-7.31 (m, 8H), 6.96-6,65 (m, 5H), 5.47-5.13 (m, 1H), 5.10-4.80 (m, 3H), 4.69 (d, J = 16.0 Hz, 0.2H), 4.58-4.33 (m, 0.8H), 4.09-3.91 (m, 2H), 3.88-3.80 (m, 3H), 3.50-3.30 (m, 1H), 2.88-2.63 (m, 1H), 1.10-0.93 (m, 3H). MS m/z: 553.2 [M + 1]⁺. |
| 23-1 | 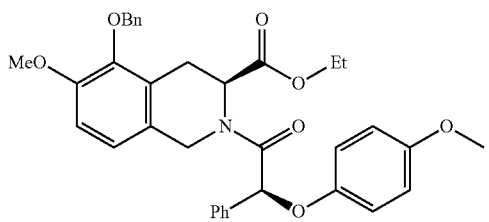 [SMILES: CCOC(=O)[C@@H]1Cc2c(ccc(OC)c2OCc2ccccc2)CN1C(=O)[C@@H](Oc1ccc(OC)cc1)c1ccccc1] | ¹H NMR (400 MHz, CHLOROFORM-d): δ 7.47-7.30 (m, 10H), 7.03-6,97 (m, 2H), 6.85-6.79 (m, 4H), 5.96-5.87 (m, 1H), 5,05-4.74 (m, 3H), 4.54-4.37 (m, 1H), 4.08-3.92 (m, 1H), 3.84 (d, J = 8.0 Hz, 3H), 3.78-3.72 (m, 5H), 3.68-3.44 (m, 1H), 3.28-2.87 (m, 1H), 1.07-0.88 (m, 3H). MS m/z: 582.1 [M + 1]⁺. |
| 25-1 | 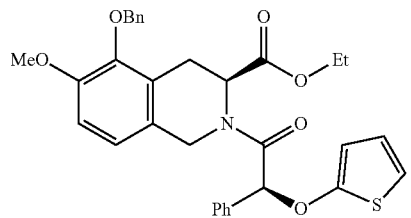 [SMILES: CCOC(=O)[C@@H]1Cc2c(ccc(OC)c2OCc2ccccc2)CN1C(=O)[C@@H](Oc1cccs1)c1ccccc1] | ¹H NMR (400 MHz, CHLOROFORM-d): δ 7.63-7.31 (m, 10H), 6.92-6.57 (m, 4H), 6.46-6.35 (m, 1H), 5.94-5.83 (m, 1H), 5.29-4.66 (m, 4H), 4.60-4.35 (m, 1H), 4.10-3.96 (m, 1H), 3.89-3.82 (m, 3H), 3.80-3.62 (m, 1H), 3.54-3.27 (m, 1H), 2.97-2.54 (m, 1H), 1.18-0.86 (m, 3H). MS m/z: 558.1 [M + 1]⁺. |
| 27-1 | 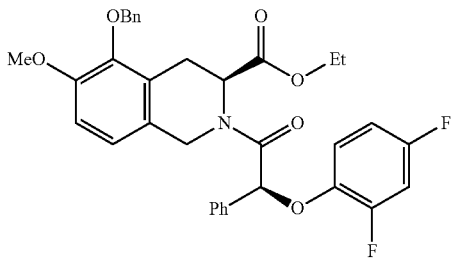 [SMILES: CCOC(=O)[C@@H]1Cc2c(ccc(OC)c2OCc2ccccc2)CN1C(=O)[C@@H](Oc1ccc(F)cc1F)c1ccccc1] | ¹H NMR (400 MHz, CHLOROFORM-d): δ 7.61-7.54 (m, 2H), 7.49-7.33 (m, 8H), 7.21-7.04 (m, 1H), 6.96-6.50 (m, 4H), 5.97-5.89 (m, 1H), 5.29-4.73 (m, 4H), 4.71-4.30 (m, 2H), 4.11-3.96 (m, 1H), 3.86 (d, J = 4.0 Hz, 3H), 3.74-3.47 (m, 1H), 3.27-2.89 (m, 1H), 1.13-0.88 (m, 3H). MS m/z: 588.1 [M + 1]⁺. |
| 29-1 | 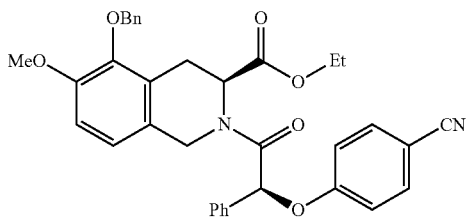 [SMILES: CCOC(=O)[C@@H]1Cc2c(ccc(OC)c2OCc2ccccc2)CN1C(=O)[C@@H](Oc1ccc(C#N)cc1)c1ccccc1] | ¹H NMR (400 MHz, CHLOROFORM-d): δ 7.65-7.52 (m, 4H), 7.46-7.34 (m, 8H), 7.17-7.05 (m, 2H), 6.89-6.46 (m, 2H), 6.05-5.90 (m, 1H), 5.12-4.74 (m, 4H), 4.72-4.29 (m, 2H), 4.09-3.91 (m, 1H), 3.87-3.84 (m, 3H), 3.49-2.76 (m, 2H), 1.20-1.00 (m, 3H). MS m/z: 577.1 [M + 1]⁺. |
| 31-1 | 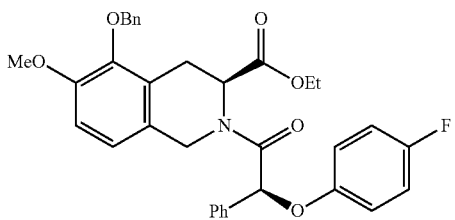 [SMILES: COc1ccc2c(c1OCc1ccccc1)C[C@@H](C(=O)O)N(C(=O)[C@@H](Oc1ccc(F)cc1)c1ccccc1)C2] | ¹H NMR (400 MHz, CHLOROFORM-d): δ 7.64-7.53 (m, 2H), 7.47-7.35 (m, 8H), 7.06-6.95 (m, 4H), 6.88-6.50 (m, 2H), 5.92 (d, J = 8.0 Hz, 1H), 5.35-5.12 (m, 1H), 5.10-4.60 (m, 4H), 4.57-4.34 (m, 1H), 4.08-3.93 (m, 1H), 3.89-3.83 (m, 3H), 3.72-3.42 (m, 1H), 3.34-2.76 (m, 1H), 1.10-0.77 (m, 3H). MS m/z: 570.1 [M + 1]⁺. |

| Compound Serial number | Structural formula | Spectrogram |
|---|---|---|
| 33-1 | | $^1$H NMR (400 MHz, CHLOROFORM-d): δ 7.61-7.50 (m, 2H), 7.46-7.31 (m, 9H), 7.25-7.20 (m, 1H), 7.06-6.93 (m, 2H), 6.87-6.78 (m, 1H), 6.77-6.49 (m, 1H), 5.98-5.90 (m, 1H), 5.35-4.58 (m, 5H), 4.55-4.28 (m, 1H), 4.06-3.91 (m, 1H), 3.87-3.83 (m, 3H), 3.74-3.59 (m, 1H), 3.50-3.15 (m, 1H), 1.07-0.90 (m, 3H). MS m/z: 586.1 [M + 1]$^+$. |
| 35-1 | | $^1$H NMR (400 MHz, CHLOROFORM-d): δ 7.86-7.73 (m, 4H), 7.72-7.57 (m, 3H), 7.51-7.35 (m, 12H), 6.92-6.57 (m, 2H), 6.20-6.11 (m, 1H), 5.33-5.00 (m, 2H), 5.00-4.84 (m, 2H), 4.83-4.72 (m, 1H), 4.66-4.39 (m, 1H), 4.19-4.01 (m, 1H), 3.86-3.81 (m, 3H), 3.76-3.45 (m, 1H), 3.43-3.12 (m, 1H), 1.16 (t, J = 8.0 Hz, 1H), 0.99-0.83 (m, 2H). MS m/z: 602.1 [M + 1]$^+$. |
| 37-1 | | $^1$H NMR (400 MHz, CHLOROFORM-d): δ 7.50-7.20 (m, 10H), 6.84 (m, 1H), 6.66 (d, J = 8.0 Hz, 0.5H), 6.43 (d, J = 12.0 Hz, 0.5H), 5.50-5.48 (m, 0.5H), 5.32 (d, J = 8.0 Hz, 1H), 5.07-4.76 (m, 3H), 4.60 (d, J = 16.0 Hz, 0.5H), 4.51-4.45 (m, 1H), 4.18-4.07 (m, 2H), 3.84 (d, J = 12 Hz, 3H), 3.66-3.61 (m, 0.5H), 3.55-3.40 (m, 1H), 3.17-3.11 (m, 0.5H), 2.99-2.93 (m, 0.5H), 2.74-2.68 (m, 0.5H), 1.90-1.70 (m, 5H), 1.60-1.57 (m, 3H), 1.29-1.17 (m, 3H). MS m/z: 544.4 [M + 1]$^+$. |
| 38-1 | | $^1$H NMR (400 MHz, CHLOROFORM-d): δ 7.53 (d, J = 4 Hz, 1H), 7.48-7.30 (m, 9H), 6.95-6.61 (m, 2H), 5.40-5.15 (m, 1.5H), 4.76-4.57 (m, 3.5H), 4.10-4.01 (m, 3H), 3.86 (d, J = 8.0 Hz, 3H), 3.34-3.14 (m, 1H), 3.00-2.94 (m, 1H), 1.90-1.58 (m, 9H), 1.29-1.17 (m, 3H). MS m/z: 544.3 [M + 1]$^+$. |
| 39-1 | | $^1$H NMR (400 MHz, CHLOROFORM-d): δ 7.53-7.45 (m, 2H), 7.44-7.28 (m, 7H), 7.24-7.14 (m, 1H), 6.83 (d, J = 8.0 Hz, 1H), 6.64 (d, J = 8.0 Hz, 0.5H), 6.40 (d, J = 8.0 Hz, 0.5H), 5.62-5.43 (m, 2H), 5.07-4.82 (m, 3H), 4.64-4.40 (m, 1.5H), 4.20-4.05 (m, 1.5H), 3.89-3.79 (m, 3H), 3.64-3.38 (m, 2H), 1.39 (s, 3H), 1.34-1.16 (m, 9H). MS m/z: 532.3 [M + 1]$^+$. |
| 40-1 | | $^1$H NMR (400 MHz, CHLOROFORM-d): δ 7.64-7.56 (m, 2H), 7.55-7.49 (m, 2H), 7.47-7.31 (m, 7H), 6.95-6.57 (m, 1H), 5.31 (s, 2H), 5.05-4.76 (m, 3H), 4.64-4,56 (m, 1H), 4.05-3.87 (m, 2H), 3.78-3.86 (m, 3H), 3.51-3.29 (m, 2H), 3.02-2.83 (m, 1H), 1.94-1.41 (m, 8H), 1.54-1.13 (m, 3H). MS m/z: 543.2 [M + 1]$^+$. |

| Compound Serial number | Structural formula | Spectrogram |
|---|---|---|
| 42-1 | (structure: tetrahydroisoquinoline with OBn, MeO, CO-OEt, N-acyl with Ph and NHC(O)-cyclopentyl) | $^1$H NMR (400 MHz, CHLOROFORM-d): δ 7.59-7.28 (m, 10H), 6.96-6.48 (m, 2H), 6.07-5.84 (m, 1H), 5.03-4.76 (m, 3H), 4.64-4.48 (m, 1H), 4.18-3.98 (m, 3H), 3.87-3.82 (m, 3H), 3.57-3.17 (m, 1H), 2.95-2.42 (m, 2H), 1.96-1.57 (m, 8H), 1.30-1.09 (m, 3H). MS m/z: 571.2 [M + 1]$^+$. |
| 44-1 | (structure: tetrahydroisoquinoline with OBn, MeO, CO-OEt, N-acyl with Ph and O-cyclohexyl) | $^1$H NMR (400 MHz, CHLOROFORM-d): δ 55-7.27 (m, 10H), 6.92-6.33 (m, 2H), 5.56-5.26 (m, 2H), 5.05-4.79 (m, 3H), 4.68-4.40 (m, 2H), 4.20-4.02 (m, 1H), 3.84 (d, J = 8.0 Hz, 3H), 3.64-3.44 (m, 2H), 3.19-2.62 (m, 1H), 2.05-1.72 (m, 4H), 1.51-1.22 (m, 6H), 1.19 (t, J = 8.0 Hz, 1.5H), 0.85 (t, J = 8.0 Hz, 1.5H). MS m/z: 558.2 [M + 1]$^+$. |
| 45-1 | (structure: tetrahydroisoquinoline with OBn, MeO, CO-OEt, N-acyl with Ph and N(cyclopentyl)(Me)) | MS m/z: 557.1 [M + 1]$^+$. |

Step 2: Preparation of Compounds 17 and 18

At 25° C., the compound 17-1 (218.0 mg, 382.7 μmol) was dissolved in tetrahydrofuran (5.0 mL), and an aqueous solution (2.0 mL) of lithium hydroxide monohydrate (93.0 mg, 2.2 mmol) was added. The solution was reacted for 40 hours while stirring at 15-20° C., then the reaction solution was diluted with water (15.0 mL) and adjusted to pH <4 with 1 M hydrochloric acid. The aqueous phase was extracted with ethyl acetate (50.0 mL×3). The mixed organic phase was washed with saturated saline water (50.0 mL), dried with anhydrous sodium sulfate, and concentrated in vacuum to obtain a crude product. The crude product was separated and purified by a chromatography column (an eluent: 0-80°/% petroleum ether/ethyl acetate) to obtain the product, which was separated by SFC (column: AD (250 mm*30 mm, 5 μm); mobile phase [0.1% NH$_3$H$_2$O EtOH]; B %: 35%-35%) to obtain two diastereomers, the main product compound 17 and a small amount of compound 18.

Compound 17: $^1$H NMR (400 MHz, DMSO-d$_6$) δ 7.69-7.30 (m, 11H), 725-7.13 (m, 1H), 7.06-6.77 (m, 4H), 6.52-6.23 (m, 1H), 5.11-4.75 (m, 4H). 4.27 (d, J=16.0 Hz, 1H), 3.84-3.74 (m, 3H), 2.88-2.64 (m, 1H), 2.43-2.29 (m, 1H). MS m/z: 564.1 [M+Na]$^+$. SFC: Column: Chiralpak AD-3 (150 mm*4.6 mm, 3 μm); mobile phase: B: [0.05% DEA Ethanol]; B %: 5%-40% 5.5 min, 40% 3 min, 5% 1.5 min; Rt=5.339 min; 97.5% de.

Compound 18: $^1$H NMR (400 MHz, DMSO-d$_6$) δ 7.63-7.28 (m, 10H), 7.25-6.99 (m, 3H), 6.97-6.73 (m, 3H), 6.47-6.28 (m, 1H), 5.04-4.73 (m, 4H), 4.56-4.27 (m, 1H), 3.82-3.75 (m, 3H), 2.83-2.59 (m, 1H), 2.42-2.22 (m, 1H). MS m/z: 564.1 [M+Na]$^+$. SFC: Column: Chiralpak AD-3 (150 mm*4.6 mm, 3 μm); Mobile phase: B: [0.05% DEA Ethanol]; B %: 5%-40% 5.5 min, 40% 3 min, 5% 1.5 min; Rt=5.745 min; 94.5% de.

The following compounds were synthesized by using a method similar to the compounds 17 and 18:

| Example | Compound Serial Number | Structural Formula | Spectrogram |
|---|---|---|---|
| 19 | 19 | (structure) | $^1$H NMR (400 MHz, METHANOL-d$_4$): δ 7.64-7.51 (m, 2H), 7.47-7.30 (m, 8H), 7.28-7.19 (m, 2H), 7.05 (d, J = 8 Hz, 1H), 6.97-6.81 (m, 4H), 6.44-6.20 (m, 1H), 5.08-4.74 (m, 4H), 4.26 (d, J = 20.0 Hz, 1H), 3.88-3.70 (m, 3H), 2.90-2.65 (m, 1H), 2.53-2.50 (m, 1H). MS m/z: 524.3 [M + 1]$^+$. SFC: column: ChiralCel OJ-H (150 mm * 4.6 mm, 5 μm); mobile phase: B: [0.05% DEA Methanol]; B%: 5%-40% 5.5 min, 40% 3 min, 5% 1.5 min; Rt = 5.584 min; 100.0% de. |
| 20 | 20 | (structure) | $^1$H NMR (400 MHz, METHANOL-d$_4$): δ 7.63-7.49 (m, 2H), 7.48-7.30 (m, 8H), 7.25 (t, J = 8.0 Hz, 2H), 7.06-6.82 (m, 5H), 6.41-6.16 (m, 1H), 5.03-4.76 (m, 4H), 4.55 (d, J = 16 Hz, 0.6H), 4.32 (d, J = 20 Hz, 0.4H), 3.88-3.71 (m, 3H), 3.50-3.40 (m, 1H), 2.80-2.62 (m, 1H). MS m/z: 524.3 [M + 1]$^+$. SFC: column: ChiralCel OJ-H (150 mm * 4.6 mm, 5 μm); mobile phase: B: [0.05% DEA Methanol]; B%: 5%-40% 5.5 min, 40% 3 min, 5% 1.5 min; Rt = 5.720 min; 99.1% de. |
| 21 | 21 | (structure) | $^1$H NMR (400 MHz, METHANOL-d$_4$): δ 8.23-7.84 (m, 1H), 7.69 (s, 2H), 7.58-7.23 (m, 9H), 7.08-6.72 (m, 5H), 5.06-5.01 (m, 1H), 4.96-4.56 (m, 3H), 4.46-4.27 (m, 1H), 3.86-3.69 (m, 3H), 3.20-3.10 (m, 1H), 2.67-2.59 (m, 1H). MS m/z: 525.1 [M + 1]$^+$. SFC: column: ChiralCel OJ-3 (100 mm * 4.6 mm, 3 μm); mobile phase: B: [0.05% DEA Ethanol]; B%: 5%-40% 4.5 min, 40% 2.5 min, 5% 1 min; Rt = 3.192 min; 97.7% de. |
| 22 | 22 | (structure) | $^1$H NMR (400 MHz, METHANOL-d$_4$): δ 8.15-7.98 (m, 1H), 7.78-7.54 (m, 3H), 7.52-7.27 (m, 8H), 7.06-6.68 (m, 5H), 5.60-5.25 (m, 0.5H), 5,10-4.59 (m, 4H), 4.22-4.18 (m, 0.5H), 3.88-3.76 (m, 3H), 3.22-3.17 (m, 1H), 2.94-2.88 (m, 0.5H), 2.79-2.62 (m, 0.5H). MS m/z: 525.1 [M + 1]$^+$. SFC: column: ChiralCel OJ-3 (100 mm * 4.6 mm, 3 μm); mobile phase: B: [0.05% DEA Ethanol]; B%: 5%-40% 4.5 min, 40% 2.5 min, 5% 1 min; Rt = 3.465 min; 91.2% % de. |
| 23 | 23 | (structure) | $^1$H NMR (400 MHz, DMSO-d$_6$): δ 7.64-7.33 (m, 10H), 7.04-6.78 (m, 6H), 6.31-6.08 (m, 1H), 5.11-4.77 (m, 4H), 4.38-4.23 (m, 1H), 3.86-3.61 (m, 6H), 3.18 (s, 2H), 2.89-2.62 (m, 1H), 2.37-1.90 (m, 1H), MS m/z: 554.1 [M + 1]$^+$. SFC: column: ChiralPak AD-3 (150 mm * 4.6 mm, 3 μm); mobile phase: B: [0.05% DEA Ethanol]; B%: 5%-40% 5.5 min, 40% 3 min, 5% 1.5 min: Rt = 6.612 min; 100.0% de. |
| 24 | 24 | (structure) | $^1$H NMR (400 MHz, DMSO-d$_6$): δ 7.64-7.25 (m, 10H), 7.03-6.71 (m, 6H), 6.15-6.01 (m, 1H), 5.14-4.32 (m, 5H), 3.83-3.62 (m, 6H), 3.52 (d, J = 12.0 Hz, 1H), 3.17 (d, J = 4.0 Hz, 1H), 2.73-2.57 (m, 1H), 2.39-1.91 (m, 1H). MS m/z: 554.1 [M + 1]$^+$. SFC: column: ChiralPak AD-3 (150 mm * 4.6 mm, 3 μm); mobile phase: B: [0.05% DEA Ethanol]; B%: 5%-40% 5.5 min, 40% 3 min, 5% 1.5 min; Rt = 7.593 min; 99.1% de. |
| 25 | 25 | (structure) | $^1$H NMR (400 MHz, DMSO-d$_6$): δ 7.61 (s, 1H), 7.46-7.31 (m, 9H), 6.95-6.81 (m, 2H), 6.76-6.65 (m, 2H), 6.51-6.30 (m, 1H), 6.30-6.14 (m, 1H), 5.09-4.77 (m, 4H), 4.32-4.16 (m, 1H), 3.79 (d, J = 12.4 Hz, 3H), 2.84-2.65 (m, 1H), 2.36-1.90 (m, 1H). MS m/z: 530.0 [M + 1]$^+$. SFC: column: ChiralPak AD-3 (100 mm * 4.6 mm, 3 μm); mobile phase: B: [0.05% DEA iso-propanol]; B%: 5%-40% 4.5 mm, 40% 2.5 min, 5% 1 min; Rt = 5.171 min: 96.0% de. |

-continued

| Example | Compound Serial Number | Structural Formula | Spectrogram |
|---|---|---|---|
| 26 | 26 | (structure: tetrahydroisoquinoline with OBn, MeO substituents, N-acyl with Ph and O-thiophene) | ¹H NMR (400 MHz, DMSO-d₆): δ 7.65-7.23 (m, 10H), 6.96-6.62 (m, 4H), 6.48-6.30 (m, 1H), 6.28-6.11 (m, 1H), 5.15-4.63 (m, 4H), 4.57-4.23 (m, 1H), 3.77 (s, 3H), 2.86-2.69 (m, 1H), 1.97 (s, 1H). MS m/z: 530.0 [M + 1]⁺. SEC: column: ChiralPak AD-3 (100 mm * 4.6 mm, 3 μm); mobile phase: B: [0.05% DEA iso-propanol]; B%: 5%-40% 4.5 min, 40% 2.5 min, 5% 1 min; Rt = 6.112 min; 90.9% de. |
| 27 | 27 | (structure: tetrahydroisoquinoline with OBn, MeO substituents, N-acyl with Ph and O-2,4-difluorophenyl) | ¹H NMR (400 MHz, DMSO-d₆): δ 7.67-7.52 (m, 2H), 7.51-7.09 (m, 10H), 7.00-6.75 (m, 3H), 6.51-6.29 (m, 1H), 5.11-4.76 (m, 4H), 4.33-4.14 (m, 1H), 3.80 (d, J = 10.8 Hz, 3H), 2.89-2.64 (m, 1H), 2.39-1.92 (m, 1H). MS m/z: 560.0 [M + 1]⁺. SEC: column: ChiralPak AD-3 (100 mm * 4.6 mm, 3 μm); mobile phase: B: [0.05% DEA iso-propanol]; B%: 5%-40% 4.5 min, 40% 2.5 min, 5% 1 min; Rt = 4.386 min; 99.1% de. |
| 28 | 28 | (structure: tetrahydroisoquinoline with OBn, MeO substituents, N-acyl with Ph and O-2,4-difluorophenyl, opposite stereochemistry) | ¹H NMR (400 MHz, DMSO-d₆): δ 7.67-7.52 (m, 2H), 7.51-7.09 (m, 10H), 7.00-6.75 (m, 3H), 6.51-6.29 (m, 1H), 5.11-4.76 (m, 4H), 4.33-4.14 (m, 1H), 3.80 (d, J = 10.8 Hz, 3H), 2.89-2.64 (m, 1H), 2.39-1.92 (m, 1H). MS m/z: 560.0 [M + 1]⁺. SEC: column: ChiralPak AD-3 (100 mm * 4.6 mm, 3 μm); mobile phase: B: [0.05% DEA iso-propanol]; B%: 5%-40% 4.5 min, 40% 2.5 min, 5% 1 min; Rt = 5.051 min; 94.3% de. |
| 29 | 29 | (structure: tetrahydroisoquinoline with OBn, MeO substituents, N-acyl with Ph and O-4-cyanophenyl) | ¹H NMR (400 MHz, DMSO-d₆): δ 7.77-7.67 (m, 2H), 7.67-7.50 (m, 2H), 7.49-7.29 (m, 9H), 7.12-6.91 (m, 1H), 6.88 (s, 2H), 6.63-6.27 (m, 1H), 5.10-4.57 (m, 4H), 4.34-4.12 (m, 1H), 3.85-3.75 (m, 3H), 2.96-2.61 (m, 1H), 2.37-1.92 (m, 1H). MS m/z: 571.1 [M + Na]⁺. SFC: column: Chiralcel OJ-3 (100 mm * 4.6 mm, 3 μm); mobile phase: B: [0.05% DEA ethanol]; B%: 5%-40% 4.5 min, 40% 2.5 min, 5% 1 min; Rt = 3.079 min; 99.5% de. |
| 30 | 30 | (structure: tetrahydroisoquinoline with OBn, MeO substituents, N-acyl with Ph and O-4-cyanophenyl, opposite stereochemistry) | ¹H NMR (400 MHz, DMSO-d₆): δ 7.78-7.59 (m, 3H), 7.55-7.31 (m, 9H), 7.22-7.05 (m, 2H), 6.96-6.75 (m, 2H), 6.62-6.37 (m, 1H), 5.21-4.76 (m, 4H), 4.52-4.28 (m, 1H), 3.85-3.76 (m, 3H), 3.52 (s, 1H), 2.90-2.61 (m, 1H). MS m/z: 571.1 [M + 1]⁺. SEC: column: Chiralcel OJ-3 (100 mm * 4.6 mm, 3 μm); mobile phase: B: [0.05% DEA ethanol]; B%: 5%-40% 4.5 min, 40% 2.5 min, 5% 1 min; Rt = 4.142 min; 97.4% de. |
| 31 | 31 | (structure: tetrahydroisoquinoline with OBn, MeO substituents, N-acyl with Ph and O-4-fluorophenyl) | ¹H NMR (400 MHz, DMSO-d₆): δ 7.63-7.34 (m, 10H), 7.17-6.75 (m, 6H), 6.40-6.08 (m, 1H), 5.07-4.71 (m, 4H), 4.27 (d, J = 16.0 Hz, 1H), 3.83-3.75 (m, 3H), 2.83-2.63 (m, 1H), 2.36-2.18 (m, 1H). MS m/z: 564.1 [M + Na]⁺. SFC: column: Chiralcel OJ-3 (100 mm * 4.6 mm, 3 μm); mobile phase: B: [0.05% DEA ethanol]; B%: 5%-40% 4.5 min, 40% 2.5 min, 5% 1 min; Rt = 2.899 min; 100.0% de. |

-continued

| Example | Compound Serial Number | Structural Formula | Spectrogram |
|---|---|---|---|
| 32 | 32 | (structure: 5-OBn, 6-OMeO tetrahydroisoquinoline-3-carboxylic acid, N-acylated with Ph-CH(O-4-F-C6H4)-C(O)-) | $^1$H NMR (400 MHz, DMSO-d$_6$): δ 7.61-7.31 (m, 10H), 7.12-6.70 (m, 6H), 6.29-6.10 (m, 1H), 5.06-4.76 (m, 4H), 4.63-4.27 (m, 1H), 3.81-3.75 (m, 3H), 2.74-2.59 (m, 1H), 2.39-2.27 (m, 1H). MS m/z: 564.1 [M + Na]$^+$. SFC: column: Chiralcel OJ-3 (100 mm * 4.6 mm, 3 μm); mobile phase: B: [0.05% DEA ethanol]; B%: 5%-40% 4.5 min, 40% 2.5 min, 5% 1 min; Rt = 3.654 min; 97.9% de. |
| 33 | 33 | (structure: 5-OBn, 6-OMeO tetrahydroisoquinoline-3-carboxylic acid, N-acylated with Ph-CH(O-4-Cl-C6H4)-C(O)-) | $^1$H NMR (400 MHz, DMSO-d$_6$): δ 7.63-7.12 (m, 13H), 6.99-6.71 (m, 3H), 6.46-6.09 (m, 1H), 5.08-4.60 (m, 4H), 4.27 (d, J = 16.0 Hz,1H), 3.83-3.72 (m, 3H), 2.86-2.61 (m, 1H), 2.45-2.22 (m, 1H). MS m/z: 558.1 [M + 1]$^+$. SFC: column: Chiralpak AD-3 (100 mm * 4.6 mm, 3 μm); mobile phase: B: [0.05% DEA ethanol]; B%: 5%-40% 4.5 min, 40% 2.5 min, 5% 1 min; Rt = 4.897 min: 100.0% de. |
| 34 | 34 | (structure: 5-OBn, 6-OMeO tetrahydroisoquinoline-3-carboxylic acid, N-acylated with Ph-CH(O-4-Cl-C6H4)-C(O)-) | $^1$H NMR (400 MHz, DMSO-d$_6$): δ 7.62-7.55 (m, 1H), 7.52-7.28 (m, 11H), 7.07-6.78 (m, 4H), 6.41-6.14 (m, 1H), 5.03-4.76 (m, 4H), 4.56-4.25 (m, 1H), 3.87-3.73 (m, 3H), 2.71-2.62 (m, 1H), 2.41-2.26 (m, 1H). MS m/z: 558.1 [M + 1]$^+$. SFC: column: Chiralpak AD-3 (100 mm * 4.6 mm, 3 μm); mobile phase: B: [0.05% DEA ethanol]; B%: 5%-40% 4.5 min, 40% 2.5 min, 5% 1 min; Rt = 5.999 min; 100.0% de. |
| 35 | 35 | (structure: 5-OBn, 6-OMeO tetrahydroisoquinoline-3-carboxylic acid, N-acylated with Ph-CH(O-2-naphthyl)-C(O)-) | $^1$H NMR (400 MHz, DMSO-d$_6$): δ 7.93-7.73 (m, 3H), 7.72-7.66 (m, 1H), 7.65-7.52 (m, 2H), 7.51-7.28 (m, 10H), 7.24-7.07 (m, 1H), 7.02-6.85 (m, 2H), 6.61-6.37 (m, 1H), 5.24-4.73 (m, 4H), 4.38-4.20 (m, 1H), 3.78-3.72 (m, 3H), 2.93-2.62 (m, 1H), 2.44-2.23 (m, 1H). MS m/z: 574.1 [M + Na]$^+$. SFC: column: Chiralpak AD-3 (100 mm * 4.6 mm, 3 μm); mobile phase: B: [0.05% DEA iso-propanol]; B%: 40%; Rt = 4.484 min; 98.3% de. |
| 36 | 36 | (structure: 5-OBn, 6-OMeO tetrahydroisoquinoline-3-carboxylic acid, N-acylated with Ph-CH(O-2-naphthyl)-C(O)-) | $^1$H NMR (400 MHz, DMSO-d$_6$): δ 7.89-7.73 (m, 3H), 7.69-7.56 (m, 2H), 7.49-7.15 (m, 12H), 7.01-6.76 (m, 2H), 6.59-6.29 (m, 1H), 5.18-4.75 (m, 4H), 4.66-4.21 (m, 1H), 3.80 (s, 3H), 2.82-2.63 (m, 1H), 2.46-2.15 (m, 1H). MS m/z: 574.1 [M + Na]$^+$. SFC: Chiralpak AD-3 (100 mm * 4.6 mm, 3 μm); mobile phase: B: [0.05% DEA iso-propanol]; B%: 40%; Rt = 5.502 min; 96.9% de. |
| 37 | 37 | (structure: 5-OBn, 6-OMeO tetrahydroisoquinoline-3-carboxylic acid, N-acylated with Ph-CH(O-cyclopentyl)-C(O)-) | $^1$H NMR (400 MHz, DMSO-d$_6$): δ 7.53-7.16 (m, 10H), 7.00-6.80 (m, 1.5H), 6.68 (d, J = 8.0 Hz, 0.5H), 5.36 (d, J = 12.0 Hz, 1H), 5.01-4.66 (m, 3H), 4.41 (d, J = 24.0 Hz, 0.5H), 4.30 (d, J = 24 Hz, 0.5H), 4.13-3.95 (m, 1H), 3.79 (s, 3H), 2.84-2.79 (m, 1H), 2.68-2.64 (m, 1H), 2.39-2.27 (m, 1H), 1.80-1.38 (m, 8H). MS m/z: 516.3 [M + 1]$^+$. SFC: column: Chiralpak AD-3 (100 mm * 4.6 mm, 3 μm); mobile phase: B: [0.05% DEA iso-propanol]; B%: min; 5%-40% 4.5 min, 40% 2.5 min. 5% 1 min: Rt = 4.198 100.0% de. |
| 38 | 38 | (structure: 5-OBn, 6-OMeO tetrahydroisoquinoline-3-carboxylic acid, N-acylated with Ph-CH(O-cyclopentyl)-C(O)-) | $^1$H NMR (400 MHz, DMSO-d$_6$): δ 7.47-7.25 (m, 10H), 6.97-6.85 (m, 1.5H), 6.75 (d, J = 42.0 Hz, 0.5H), 5.32 (d, J = 24.0 Hz, 1H), 4.97-4.66 (m, 3H), 4.46-4.27 (m, 1H), 4.08-3.96 (m, 1H), 3.80 (s, 3H), 3.26-3.13 (m, 1H), 2.79-2.74 (m, 0.7H), 2.69-2.66 (m, 0.3H), 2.35-2.33 (m, 0.5H), 2.14-2.08 (m, 0.5H), 1.80-1.38 (m, 8H). MS m/z: 516.3 [M + 1]$^+$. SFC: column: Chiralpak AD-3 (100 mm * 4.6 mm, 3 μm); mobile phase: B: [0.05% DEA iso-propanol]; B%: 5%-40% 4.5 min, 40% 2.5 min, 5% 1 min; Rt = 4.776 min; 100.0% de. |

| Example | Compound Serial Number | Structural Formula | Spectrogram |
|---|---|---|---|
| 39 | 39 | [Structure: tetrahydroisoquinoline with MeO, OBn, COOH, N-acyl with Ph and OtBu] | $^1$H NMR (400 MHz, DMSO-d$_6$): δ 7.50-7.20 (m, 10H), 6.97-6.88 (m, 1H). 6.83 (d, J = 8.0 Hz, 0.5H), 6.59 (d, J = 8.0 Hz, 0.5H), 5.41 (s, 1H), 5.30-5.26 (m, 0.5H), 4.94-4.61 (m, 3.5H), 4.45 (d, J = 16.0 Hz, 0.5H), 4.26 (d, J = 16.0 Hz, 0.5H), 3.79 (d, J = 8.0 Hz, 3H), 3.16-3.11 (m, 0.5H), 2.80-2.75 (m, 0.5H), 2.41-2.35 (m, 0.5H), 2.34-2.30 (s, 0.5H), 1.28-1.20 (m, 9H). MS m/z: 526.1 [M + Na]$^+$. SFC: column: Chiralcel OJ-3 (100 mm * 4.6 mm, 3 μm); mobile phase: B: [0.05% DEA ethanol]; B%: 5%-40% 4.5 min, 40% 2.5 min, 5% 1 min; Rt = 1.836 min; 90.3% de. |
| 40 | 40 | [Structure: tetrahydroisoquinoline with MeO, OBn, COOH, N-acyl with Ph and NH-cyclopentyl] | $^1$H NMR (400 MHz, DMSO-d$_6$): δ 7.74-7.58 (m, 2H), 7.54-7.26 (m, 8H), 7.06-6.69 (m, 2H), 5.62 (s, 1H), 5.24-4.69 (m, 4H), 4.32 (d, J = 16.0 Hz, 0.5H), 3.89-3.83 (m, 0.5H), 3.80 (d, J = 8.0 Hz, 3H), 3.20-3.07 (m, 2H), 2.90-2.65 (m, 1H), 1.87-1.40 (m, 8H). MS m/z: 515.2 [M + 1]$^+$. SFC: column: Chiralcel OJ-3 (100 mm * 4.6 mm, 3 μm); mobile phase: B: [0.05% DEA ethanol]; B%: 5%-40% 4.5 min, 40% 2.5 min, 5% 1 min; Rt = 4.375 min; 98.6% de. |
| 41 | 41 | [Structure: tetrahydroisoquinoline with MeO, OBn, COOH, N-acyl with Ph and NH-cyclopentyl] | $^1$H NMR (400 MHz, DMSO-d$_6$): δ 7.66-7.15 (m, 10H), 6.99-6.59 (m, 2H), 5.33 (t, J = 4.0 Hz, 2H), 5.01-4.71 (m, 3H), 4.36-4.19 (m, 1H), 3.80 (d, J = 8.0 Hz, 3H), 3.17-3.15 (m, 2H), 2.66-2.68 (m, 1H), 1.74-1.39 (m, 8H). MS m/z: 515.2 [M + 1]$^+$. SEC: column: Chiralcel OJ-3 (100 mm * 4.6 mm, 3 μm); mobile phase: B: [0.05% DEA ethanol]; B%: 5%-40% 4.5 min, 40% 2.5 min, 5% 1 min; Rt = 5.107 min; 83.4% de. |
| 42 | 42 | [Structure: tetrahydroisoquinoline with MeO, OBn, COOH, N-acyl with Ph and NH-C(O)-cyclopentyl] | $^1$H NMR (400 MHz, DMSO-d$_6$): δ 8.49-8.23 (m, 1H), 7.57-7.23 (m, 10H), 6.99-6.72 (m, 2H), 6.15-5.83 (m, 1H), 5.13-4.59 (m, 4H), 4.41-4.10 (m, 1H), 3.78 (d, J = 12.0 Hz, 3H), 2.89-2.63 (m, 2H), 2.35-2.24 (m, 0.5H), 2.02-1.91 (m, 0.5H), 1.74-1.39 (m, 8H). MS m/z: 543.3 [M + 1]$^+$. SEC: column: ChiralPak AD-3 (150 mm * 4.6 mm, 3 μm); mobile phase: B: [0.05% DEA ethanol]; B%: 5%-40% 5.5 min, 40% 3.0 min, 5% 1.5 min; Rt = 5.926 min; 100.0% de. |
| 43 | 43 | [Structure: tetrahydroisoquinoline with MeO, OBn, COOH, N-acyl with Ph and NH-C(O)-cyclopentyl] | $^1$H NMR (400 MHz, DMSO-d$_6$): δ 8.38 (d, J = 8.0 Hz, 1H), 7.47-7.22 (m, 10H), 6.95-6.70 (m, 2H), 6.18-5.84 (m, 1H), 5.10-4.61 (m, 4H), 4.49-4.19 (m, 1H), 3.79 (d, J = 8.0 Hz, 3H), 2.80-2.59 (m, 2H), 2.40-2.24 (m, 0.5H), 2.02-1.88 (m, 0.5H), 1.75-1.35 (m, 8H). MS m/z: 543.2 [M + 1]$^+$. SEC: column: ChiralPak AD-3 (150 mm * 4.6 mm, 3 μm); mobile phase: B: [0.05% DEA ethanol]; B%: 5%-40% 5.5 min, 40% 3.0 min, 5% 1.5 min; Rt = 7.558 min; 100.0% de. |
| 44 | 44 | [Structure: tetrahydroisoquinoline with MeO, OBn, COOH, N-acyl with Ph and O-cyclohexyl] | $^1$H NMR (400 MHz, DMSO-d$_6$): δ 7.47-7.28 (m, 10H), 6.98-6.57 (m, 2H), 5.47 (d, J = 8.0 Hz, 1H) 5.23-4.59 (m, 4H), 4.46-4.23 (m, 1H), 3.79 (s, 3H), 3.24-3.16 (m, 1H), 2.91-2.62 (m, 1H), 2.42-2.28 (m, 1H), 1.94-1.62 (m, 4H), 1.55-1.06 (m, 6H). MS m/z: 530.1 [M + 1]$^+$. SFC: column: ChiralCel OJ-H (150 mm * 4.6 mm, 5 μm); mobile phase: B: [0.05% DEA ethanol]; B%: 5%-40% 5.5 min, 40% 3.0 min, 5% 1.5 min; Rt = 3.221 min; 90.6% de. |

| Example | Compound Serial Number | Structural Formula | Spectrogram |
|---|---|---|---|
| 45 | 45 | (structure: tetrahydroisoquinoline with OBn, MeO, carboxylic acid, N-acyl with Ph and N-cyclopentyl-N-methyl group) | $^1$H NMR (400 MHz, DMSO-d$_6$): δ 7.82-7.29 (m, 10H), 7.03-6.73 (m, 2H), 5.84-5.63 (m, 1H), 5.45-4.62 (m, 4H), 4.36-4.25 (m, 0.5H), 3.91-3.84 (m, 0.5H), 3.83-3.75 (m, 3H), 3.27-2.75 (m, 2H), 2.37-1.34 (m, 12H). MS m/z: 529.1 [M + 1]$^+$. SFC: column: Chiralpak IC-3 (150 mm * 4.6 mm, 3 μm); mobile phase: B: [0.05% DEA Methanol]; B%: 40%; Rt = 8.541 min; 13.6% de. |

Example 46: Preparation of Compound 46

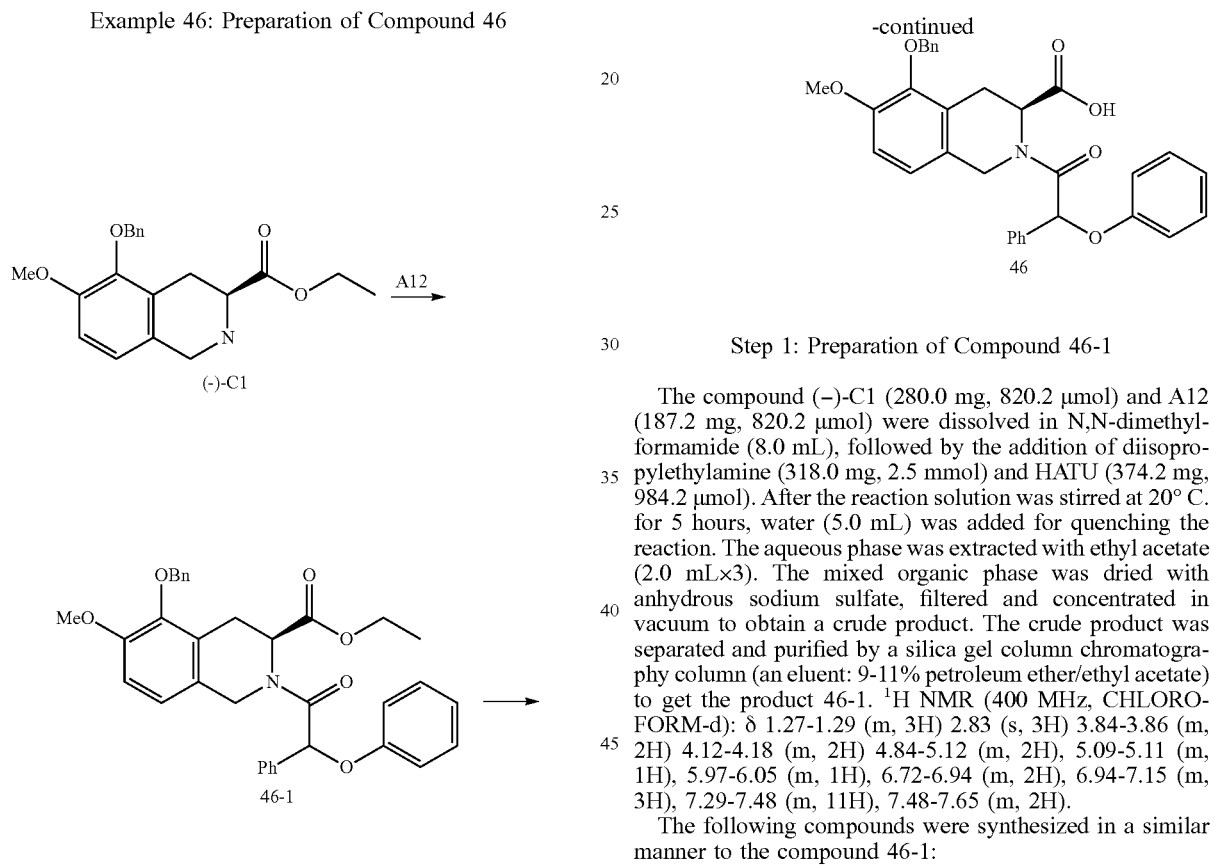

Step 1: Preparation of Compound 46-1

The compound (−)-C1 (280.0 mg, 820.2 μmol) and A12 (187.2 mg, 820.2 μmol) were dissolved in N,N-dimethylformamide (8.0 mL), followed by the addition of diisopropylethylamine (318.0 mg, 2.5 mmol) and HATU (374.2 mg, 984.2 μmol). After the reaction solution was stirred at 20° C. for 5 hours, water (5.0 mL) was added for quenching the reaction. The aqueous phase was extracted with ethyl acetate (2.0 mL×3). The mixed organic phase was dried with anhydrous sodium sulfate, filtered and concentrated in vacuum to obtain a crude product. The crude product was separated and purified by a silica gel column chromatography column (an eluent: 9-11% petroleum ether/ethyl acetate) to get the product 46-1. $^1$H NMR (400 MHz, CHLOROFORM-d): δ 1.27-1.29 (m, 3H) 2.83 (s, 3H) 3.84-3.86 (m, 2H) 4.12-4.18 (m, 2H) 4.84-5.12 (m, 2H), 5.09-5.11 (m, 1H), 5.97-6.05 (m, 1H), 6.72-6.94 (m, 2H), 6.94-7.15 (m, 3H), 7.29-7.48 (m, 11H), 7.48-7.65 (m, 2H).

The following compounds were synthesized in a similar manner to the compound 46-1:

| Compound serial number | Structural formula | Spectrogram |
|---|---|---|
| 47-1 | (structure: tetrahydroisoquinoline with OBn, MeO, ethyl ester, N-acyl with Ph and O-cyclopentyl group) | $^1$H NMR (400 MHz, CHLOROFORM-d): δ 7.15-7.44 (m, 10H), 6.65-6.82 (m, 1H), 6.52-6.60 (m, 1H), 5.15-5.27 (m, 2H), 4.75-4.98 (m, 3H), 4.30-4.46 (m, 1H), 3.90-4.16 (m, 3H), 3.74-3.89 (m, 3H), 2.97-3.21 (m, 1H), 2.77-2.96 (m, 1H), 1.36-1.92 (m, 9H), 0.97-1.26 (m, 3H), 0.77 (t, J = 7.15 Hz, 1H). |

| Compound serial number | Structural formula | Spectrogram |
|---|---|---|
| 48-1 | 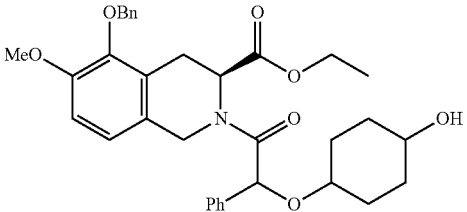 [SMILES: CCOC(=O)[C@@H]1Cc2c(ccc(OC)c2OCc2ccccc2)CN1C(=O)C(OC1CCC(O)CC1)c1ccccc1] | MS m/z: 574.3 [M + 1]+. |
| 87-1 | 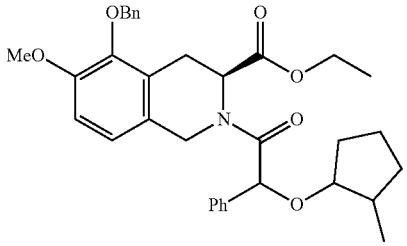 [SMILES: CCOC(=O)[C@@H]1Cc2c(ccc(OC)c2OCc2ccccc2)CN1C(=O)C(OC1CCCC1C)c1ccccc1] | ¹H NMR (400 MHz, CHLOROFORM-d): δ 7.60-7.24 (m, 10H), 6.96-6.41 (m, 2H), 5.50-5.15 (m, 2H), 5.06-4.93 (m, 1H), 4.81-4.55 (m, 2H), 4.51-4.31 (m, 1H), 4.23-3.97 (m, 2H), 3.85-3.83 (d, J = 5.2 Hz, 3H), 3.76-3.45 (m, 1H), 3.44-3.40 (m, 1H), 3.16-2.81 (m, 1H), 2.16-1.56 (m, 7H), 1.17-0.87 (m, 6H). MS m/z: 558.3 [M + 1]+. |
| 88-1 | 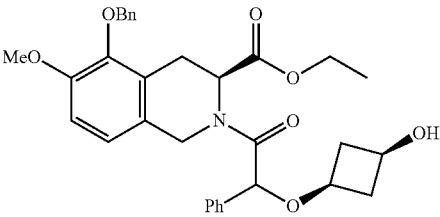 [SMILES: CCOC(=O)[C@@H]1Cc2c(ccc(OC)c2OCc2ccccc2)CN1C(=O)C(O[C@H]1C[C@@H](O)C1)c1ccccc1] | ¹H NMR (400 MHz, CHLOROFORM-d): δ 7.46-7.26 (m, 10H), 7.03-6.53 (m, 2H), 5.36-4.89 (m, 4H), 4.76-4.21 (m, 2H), 4.16-3.92 (m, 2H), 3.84 (s, 3H), 3.81-3.62 (m, 2H), 3.24-2.93 (m, 1H), 2.93-2.83 (m, 1H), 2.74-2.52 (m, 2H), 2.00-1.79 (m, 2H), 1,19-0.87 (m, 3H). MS m/z: 546.1 [M + 1]+. |
| 89-1 | 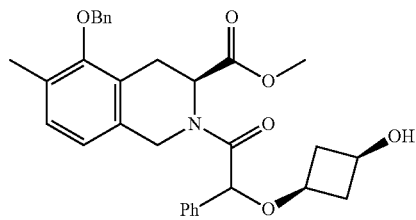 [SMILES: COC(=O)[C@@H]1Cc2c(ccc(C)c2OCc2ccccc2)CN1C(=O)C(O[C@H]1C[C@@H](O)C1)c1ccccc1] | ¹H NMR (400 MHz, CHLOROFORM-d): δ 7.55-7.29 (m, 10H), 7.08-6.49 (m, 2H), 5.42-5.13 (m, 2H), 5.11-4.83 (m, 1H), 4.81-4.61 (m, 2H), 4.58-4.42 (m, 1H), 4.02-3.71 (m, 2H), 3.70-3.55 (m, 2H), 3.53-3.25 (m, 1H), 3.23 (s, 1H), 3.10-2.84 (m, 1H), 2.32-2.22 (m, 3H), 1.97-1.76 (m, 4H). MS m/z: 516.2 [M + 1]+. |
| 90-1 | 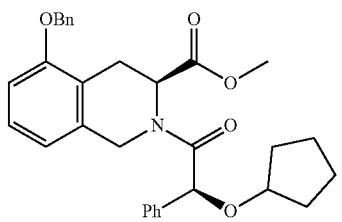 [SMILES: COC(=O)[C@@H]1Cc2c(cccc2OCc2ccccc2)CN1C(=O)[C@@H](OC1CCCC1)c1ccccc1] | ¹H NMR (400 MHz, CHLOROFORM-d): δ 7.70-7.63 (m, 1H), 7.54-7.30 (m, 10H), 7.18-6.84 (m, 1H), 6.79-6.38 (m, 1H), 5.64-5.34 (m, 2H), 5.16-4.96 (m, 2H), 4.94-4.64 (m, 1H), 4.63-4.48 (m, 1H), 4.35-4.20 (m, 1H), 3.73-3.66 (m, 1H), 3.62-3.50 (m, 1H), 3.21-3.03 (m, 2H), 2.96-2.79 (m, 1H), 1.97-1.74 (m, 8H). MS m/z: 500.2 [M + 1]+. |
| 91-1 | 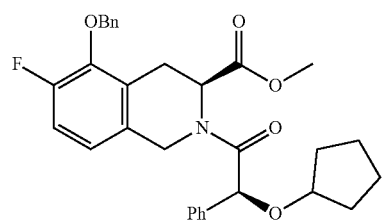 [SMILES: COC(=O)[C@@H]1Cc2c(ccc(F)c2OCc2ccccc2)CN1C(=O)[C@@H](OC1CCCC1)c1ccccc1] | MS m/z: 518.2 [M + 1]+. |

| Compound serial number | Structural formula | Spectrogram |
|---|---|---|
| 92-1 | (structure with OBn, F, methyl ester, tetrahydroisoquinoline, N-acyl with Ph and cyclopentyloxy) | $^1$H NMR (400 MHz, CHLOROFORM-d): δ 7.49-7.28 (m, 9H), 7.27-7.22 (m, 1H), 6.91-6.59 (m, 2H), 5.70-5.53 (m, 1H), 5.44-5.30 (m, 1H), 5.14-4.83 (m, 3H), 4.54-4.35 (m, 1H), 4.28-4.09 (m, 1H), 3.66-3.62 (m, 1H), 3.57-3.42 (m, 1H), 3.14 (s, 2H), 2.95-2.76 (m, 1H), 1.96-1.58 (m, 8H), MS m/z: 518.3 [M + 1]$^+$. |
| 93-1 | (structure with 4-chlorobenzyloxy, methoxy, ethyl ester, tetrahydroisoquinoline, N-acyl with Ph and cyclopentyloxy) | $^1$H NMR (400 MHz, CHLOROFORM-d): δ 7.54-7.28 (m, 9H), 6.92-6.42 (m, 2H), 5.54-5.47 (m, 2H), 5.13-4.76 (m, 3H), 4.65-4.44 (m, 1H), 4.32-4.02 (m, 2H), 3.85-3.82 (d, J = 10.0 Hz, 3H), 3.67-3.59 (m, 0.5H), 3.51-3.39 (m, 1H), 3.21-3.16 (m, 0.5H), 2.97-2.89 (m, 0.5H), 2.73-2.67 (m, 0.5H), 1.96-1.59 (m, 8H), 1.18-1.15 (t, J = 7.2 Hz, 1.5H), 0.86-0.82 (t, J = 7.2 Hz, 1.5H). MS m/z: 578.3 [M + 1]$^+$. |
| 94-1 | (structure with 2,4-difluorobenzyloxy, methoxy, ethyl ester, tetrahydroisoquinoline, N-acyl with Ph and cyclopentyloxy) | $^1$H NMR (400 MHz, CHLOROFORM-d): δ 7.57-7.38 (m, 5H), 7.36-7.29 (m, 2H), 6.96-6.80 (m, 3H), 5.56-5.43 (m, 1H), 5.38-5.29 (m, 2H), 5.10-4.89 (m, 3H), 4.52-4.48 (m, 1H), 4.32-4.30 (m, 1H), 4.21-4.10 (m, 1H), 3.86-3.83 (d, J = 9.6 Hz, 3H), 3.55-3.41 (m, 1H), 3.26-2.93 (m, 1H), 1.97-1.76 (m, 8H), 1.25-0.83 (m, 3H). MS m/z: 580.1 [M + 1]$^+$. |
| 95-1 | (structure with 4-cyanobenzyloxy, methoxy, ethyl ester, tetrahydroisoquinoline, N-acyl with Ph and cyclopentyloxy) | $^1$H NMR (400 MHz, CHLOROFORM-d): δ 7.65-7.46 (m, 4H), 7.44-7.21 (m, 5H), 6.85-6.40 (m, 2H), 5.46-5.24 (m, 2H), 5.23-4.97 (m, 1H), 5.14-4.79 (m, 3H), 4.60-4.34 (m, 1H), 4.24-3.96 (m, 2H), 3.78-3.70 (m, 3H), 3.60-3.33 (m, 1H), 2.93-2.63 (m, 1H), 1.85-1,54 (m, 8H), 1.12-0.74 (m, 3H). MS m/z: 569.3 [M + 1]$^+$. |

| Compound serial number | Structural formula | Spectrogram |
|---|---|---|
| 96-1 | | ¹H NMR (400 MHz, CHLOROFORM-d): δ 7.48-7.38 (m, 4H), 7.35-7.28 (m, 2H), 7.27-7.21 (m, 1H), 7.09-7.04 (m, 2H), 6.91-6.42 (m, 2H), 5.54-5.29 (m, 2H), 5.17-4.77 (m, 3H), 4.65-4.41 (m, 1H), 4.35-4.13 (m, 2H), 3.85-3.83 (d, J = 9.6 Hz, 3H), 3.68-3.60 (m, 0.5H), 3.50-3.38 (m, 1H), 3.25-3.08 (m, 0.5H), 2.97-2.91 (m, 0.5H), 2.71-2.66 (m, 0.5H), 1.98-1.61 (m, 8H), 1.20-0.83 (m, 2H). MS m/z: 562.1 [M + 1]⁺. |
| 97-1 | | ¹H NMR (400 MHz, CHLOROFORM-d): δ 7.52-7.43 (m, 2H), 7.43-7.36 (m, 2H), 7.36-7.28 (m, 3H), 7.20-7.05 (m, 2H), 6.89-6.79 (m, 1H), 6.67-6.39 (m, 1H), 5.52-4.89 (m, 5H), 4.64-4.27 (m, 2H), 4.18-4.05 (m, 1H), 3.85-3.83 (d, J = 7.2 Hz, 3H), 3.67-3.59 (m, 0.5H), 3.54-3.44 (m, 1H), 3.20-2.95 (m, 1H), 2.77-2.69 (m, 0.5H), 1.96-1.87 (m, 1H), 1.86-1.71 (m, 7H), 1.19-0.83 (m, 3H). MS m/z: 562.1 [M + 1]⁺. |
| 98-1 | | ¹H NMR (400 MHz, CHLOROFORM-d): δ 7.42-7.28 (m, 5H), 7.27-7.21 (m, 4H), 6.68-6.63 (m, 1H), 6.58-6.53 (m, 1H), 5.59 (s, 2H), 5.51-5.44 (m, 1H), 5.28-5.25 (d, J = 9.2 Hz, 2H), 5.17-5.15 (t, J = 6.0 Hz, 1H), 4.95-4.86 (m, 1H), 4.44-4.34 (m, 2H), 3.77 (s, 6H), 3.76 (s, 6H), 3.62-3.54 (m, 1H), 3.46-3.40 (m, 1H), 1.79-1.70 (m, 8H), 1.14-1,11 (m, 3H). MS m/z: 574.3 [M + 1]⁺. |
| 99-1 | | ¹H NMR (400 MHz, CHLOROFORM-d): δ 7.51-7.38 (m, 2H), 7.35-7.27 (m, 6H), 7.27-7.20 (m, 2H), 6.87-6.37 (m, 2H), 5.46-5.44 (m, 0.5H), 5.36-5.28 (m, 1H), 5.17-5.12 (m, 0.5H), 4.91-4.88 (d, J = 17.6 Hz, 0.5H), 4.64-4.42 (m, 1.5H), 4.31-3.99 (m, 4H), 3.79-3.77 (d, J = 6.8 Hz, 3H), 3.67-3.59 (m, 0.5H), 3.52-3.41 (m, 0.5H), 3.34-3.29 (m, 0.5H), 3.14-3.03 (m, 2.5H), 2.90-2.84 (m, 0.5H), 2.71-2.65 (m, 0.5H), 1.94-1,58 (m, 8H), 1.20-1.17 (t, J = 7.0 Hz, 1.5H), 0.86-0.82 (t, J = 7.2 Hz, 1.5H), MS m/z: 558.3 [M + 1]⁺. |

| Compound serial number | Structural formula | Spectrogram |
|---|---|---|
| 100-1 | | $^1$H NMR (400 MHz, CHLOROFORM-d): δ 7.51-7.38 (m, 2H), 7.35-7.27 (m, 6H), 7.27-7.20 (m, 2H), 6.87-6.37 (m, 2H), 5.46-5.44 (m, 0.5H), 5.36-5.28 (m, 1H), 5.19-5.17 (m, 0.5H), 5.04-4.91 (m, 0.5H), 4.64-4.42 (m, 1.5H), 4.31-3.99 (m, 2H), 3.73-3.70 (m, 3H), 3.67-3.29 (m, 1H), 3.14-3.03 (m, 1H), 2.90-2.65 (m, 1H), 1.94-1.58 (m, 8H), 1.14-0.79 (m, 3H). MS m/z: 558.3 [M + 1]$^+$. |
| 101-1 | | $^1$H NMR (400 MHz, CHLOROFORM-d): δ 7.50-7.36 (m, 3H), 7.36-7.28 (m, 3H), 7.26-7.21 (m, 1H), 7.19-7.10 (m, 1H), 6.95-6.40 (m, 2H), 5.52-5.50 (m, 0.5H), 5.36-5.29 (m, 1.5H), 5.16-5.14 (t, J = 5.2 Hz, 0.5H), 5.01-4.77 (m, 2.5H), 4.68-4.57 (m, 0.5H), 4.54-4.43 (m, 1H), 4.30-4.29 (m, 0.5H), 4.21-3.99 (m, 2H), 3.84-3.82 (d, J = 10.0 Hz, 3H), 3.68-3.60 (m, 0.5H), 3.51-3.37 (m, 1H), 3.24-3.19 (m, 0.5H), 2.99-2.94 (m, 0.5H), 2.76-2.71 (m, 0.5H), 1.95-1.58 (m, 8H), 1.20-1.16 (t, J = 7.2 Hz, 1.5H), 0.86-0.84 (t, J = 7.2 Hz, 1.5H). MS m/z: 596.1 [M + 1]$^+$. |
| 102-1 | | $^1$H NMR (400 MHz, CHLOROFORM-d): δ 8.64-8.63 (m, 2H), 7.41-7.47 (m, 4H), 7.34-7.31 (m, 2H), 7.21-7.26 (m, 1H), 6.90-6.82 (m, 1H), 6.70-6.50 (m, 1H), 5.52-5.24 (m, 2H), 5.06-4.90 (m, 2.5H), 4.65-4.45 (m, 1.5H), 3.40-4.00 (m, 2H), 3.83-3.81 (m, 3H), 3.68-3.65 (m, 1H), 3.52-3.46 (m, 1H), 3.31-2.99 (m, 1H), 1.89-1.60 (m, 8H), 1.30-1.27 (m, 1H), 0.87-0.83 (m, 2H). MS m/z: 545.2 [M + 1]$^+$. |
| 103-1 | | $^1$H NMR (400 MHz, CHLOROFORM-d): δ 8.96-8.92 (m, 1H), 8.57-8.56 (m, 2H), 7.47-7.41 (m, 2H), 7.34-7.30 (m, 2H), 7.26-7.22 (m, 1H), 6.91-6.82 (m, 1H), 6.69-6.67 (d, J = 8.8 Hz, 0.5H), 6.51-6.49 (d, J = 8.8 Hz, 0.5H), 5.53-5.51 (m, 0.5H), 5.35-5.33 (m, 1H), 5.21-5.16 (m, 1.5H), 5.12-5.03 (m, 1H), 4.97-4.92 (m, 0.5H), 4.65-4.61 (m, 0.5H), 4.54-4.46 (m, 1H), 4.32-4.28 m, 0.5H), 4.21-4.17 (m, 0.5H), 4.15-4.07 (m, 1H), 3.82-3.80 (m, 3H), 3.66-3.62 (m, 0.5H), 3.56-3.45 (m, 1H), 3.31-3.25 (m, 0.5H), 3.07-2.97 (m, 0.5H), 2.85-2.84 (m, 0.5H), 1.93-1.73 (m, 6H), 1.57-1.42 (m, 2H), 1.31-1.24 (m, 2H), 1.21-1.15 (m, 1.5H), 0.86-0.83 (t, J = 6.8 Hz, 1.5H) |

| Compound serial number | Structural formula | Spectrogram |
|---|---|---|
| 104-1 | | $^1$H NMR (400 MHz, CHLOROFORM-d): δ 7.32 (m, 5H), 6.88-6.37 (m, 2H), 5.35-5.32 (m, 1H), 5.25-5.08 (m, 2H), 4.94-4.93 (m, 1H), 4.68-4.44 (m, 1H), 4.37-4.14 (m, 4H), 3.81-3.79 (d, J = 8.4 Hz, 3H), 3.49-3.40 (m, 2H), 1.86-1.76 (m, 12H), 0.91-0.82 (m, 3H). MS m/z: 538.1 [M + 1]$^+$. |
| 105-1 | | $^1$H NMR (400 MHz, CHLOROFORM-d): δ 8.85-8.80 (m, 1H), 7.87-7.82 (m, 1H), 7.45-7.26 (m, 5H), 6.85-6.45 (m, 2H), 5.55-4.05 (m, 9H), 3.89-3.83 (m, 3H), 3.50-2.70 (m, 2H), 1.90-1.42 (m, 8H), 1.23-0.84 (m, 3H). MS m/z: 551.2 [M + 1]$^+$. |
| 106-1 | | MS m/z: 546.1 [M + 1]$^+$. |

Step 2: Preparation of Compound 46

At 25° C., the compound 46-1 (123.0 mg, 223.0 μmol) was dissolved in ethanol (2.0 mL), and then lithium hydroxide monohydrate (10.7 mg, 446.0 μmol) was added. The mixture was reacted for 4 hours while stirring at 20° C., then the reaction solution was diluted with 5 mL of water and adjusted to pH <4 with 1 M hydrochloric acid. The aqueous phase was extracted with ethyl acetate (5.0 mL×3). The mixed organic phase was dried with anhydrous sodium sulfate, and concentrated in vacuum to obtain a crude product. The crude product was separated and purified by a chromatography column (an eluent: 0-80% petroleum ether/ethyl acetate) to obtain the product 46.

Compound 46: $^1$H NMR (400 MHz, DMSO-d$_6$) δ 2.61-3.11 (m, 2H), 3.71-3.91 (m, 3H), 4.05-4.33 (m, 1H), 4.78-5.06 (m, 4H), 5.06-5.24 (m, 1H), 6.30-6.42 (m, 1H), 6.80-6.86 (m, 1H), 6.88-6.98 (m, 4H), 7.25 (brt, J=7.47 Hz, 2H), 7.35-7.47 (m, 8H), 7.44-7.48 (m, 1H), 7.53-7.66 (m, 2H). MS m/z: 524.2 [M+1]$^+$.

The following compounds were synthesized in a similar manner to the compound 46:

| Example | Compound serial number | Structural formula | Spectrogram |
|---|---|---|---|
| 47 | 47 | 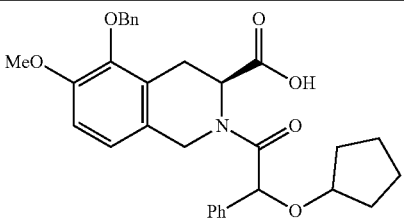 | $^1$H NMR (400 MHz, CHLOROFORM-d): δ 7.27-7.50 (m, 10H), 6.86-6.98 (m, 1H), 6.65-6.78 (m, 1H), 5.33-5.40 (m, 1H), 5.16-5.22 (m, 1H), 5.19 (br d, J = 3.91 Hz, 1H), 5.13 (br d, J = 4.40 Hz, 1H), 4.72-4.99 (m, 4H), 4.27-4.46 (m, 1H), 3.85-4.13 (m, 1H), 3.75-3.85 (m, 3H), 3.29-3.49 (m, 1H), 3.08-3.29 (m, 1H), 2.75-2.95 (m, 1H), 2.26-2.47 (m, 1H), 2.05-2.15 (m, 1H), 1.42-1.82 (m, 8H). MS m/z: 516.3 [M + 1]$^+$. |
| 48 | 48 | 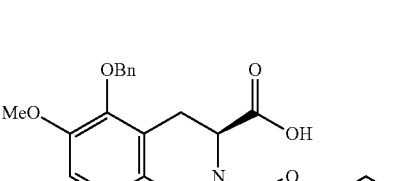 | $^1$H NMR (400 MHz, DMSO-d6): δ 7.42-7.28 (m, 10H), 6.96-6.57 (m, 2H), 5.45-5.38 (m, 1H), 4.92-4.71 (m, 4H), 4.43-4.31 (m, 1H), 3.78 (s, 3H), 3.21-3.05 (m, 1H), 2.94-2.66 (m, 1H), 2.36-2.03 (m, 2H), 2.02-1.67 (m, 4H), 1.54-1.11 (m, 4H). MS m/z: 546.2 [M + 1]$^+$. |

Examples 49 and 50: Preparation of Compounds 49 and 50

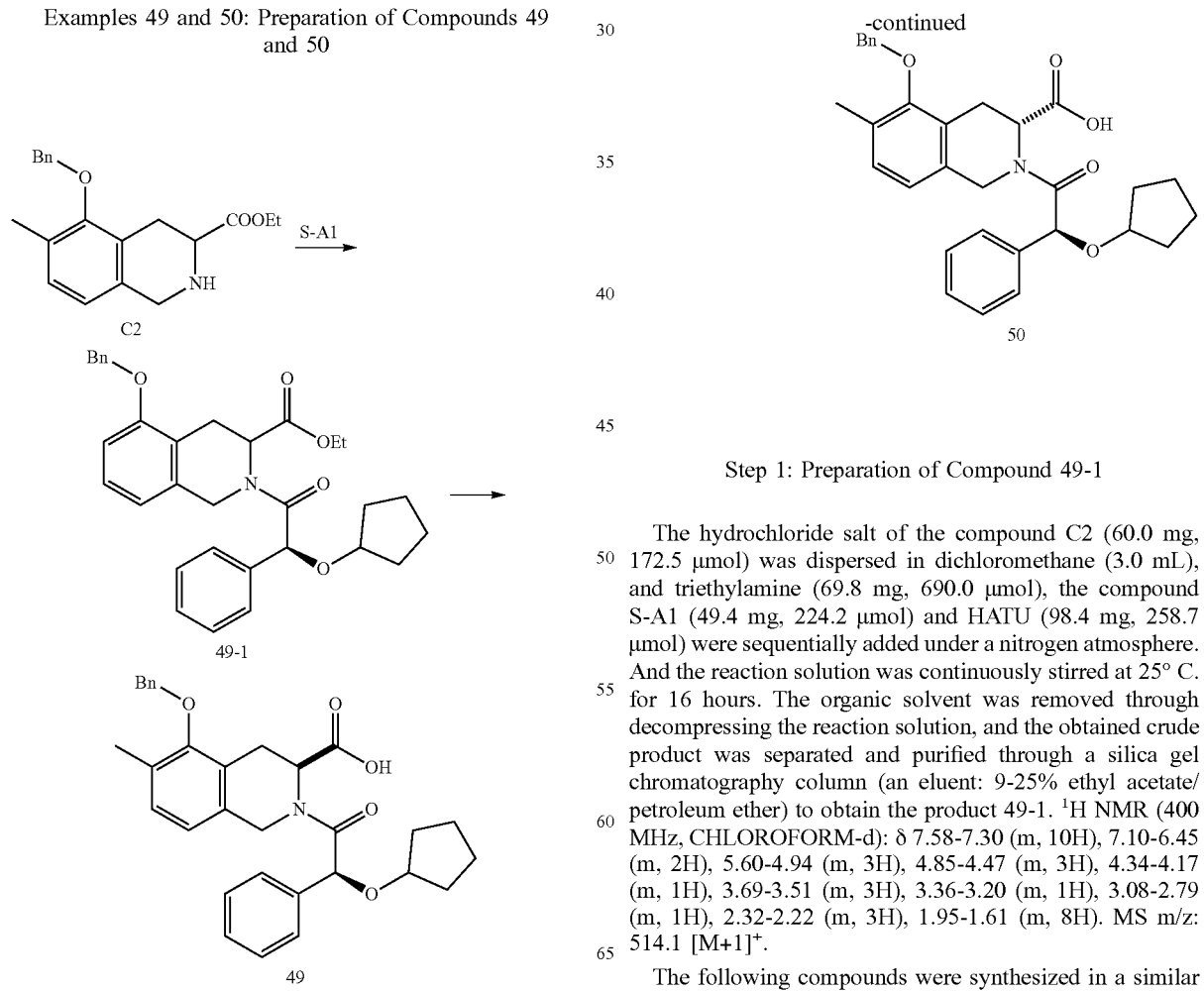

Step 1: Preparation of Compound 49-1

The hydrochloride salt of the compound C2 (60.0 mg, 172.5 μmol) was dispersed in dichloromethane (3.0 mL), and triethylamine (69.8 mg, 690.0 μmol), the compound S-A1 (49.4 mg, 224.2 μmol) and HATU (98.4 mg, 258.7 μmol) were sequentially added under a nitrogen atmosphere. And the reaction solution was continuously stirred at 25° C. for 16 hours. The organic solvent was removed through decompressing the reaction solution, and the obtained crude product was separated and purified through a silica gel chromatography column (an eluent: 9-25% ethyl acetate/ petroleum ether) to obtain the product 49-1. $^1$H NMR (400 MHz, CHLOROFORM-d): δ 7.58-7.30 (m, 10H), 7.10-6.45 (m, 2H), 5.60-4.94 (m, 3H), 4.85-4.47 (m, 3H), 4.34-4.17 (m, 1H), 3.69-3.51 (m, 3H), 3.36-3.20 (m, 1H), 3.08-2.79 (m, 1H), 2.32-2.22 (m, 3H), 1.95-1.61 (m, 8H). MS m/z: 514.1 [M+1]$^+$.

The following compounds were synthesized in a similar manner to the compound 49-1:

| Compound Serial Number | Structural Formula | Spectrogram |
| --- | --- | --- |
| 107-1 | Bn-O, Cl, COOMe, N, O, Ph, O-cyclopentyl | $^1$H NMR (400 MHz, CHLOROFORM-d): δ 7.45-7.30 (m, 10H), 7.25-7.11 (m, 1H), 6.91-6.62 (m, 1H), 5.41-5.26 (m, 2H), 5.13-4.84 (m, 3H), 4.80-4.63 (m, 1H), 4.54-4.43 (m, 1H), 3.68-3.58 (m, 3H), 3.31-3.18 (m, 1H), 2.98-2.70 (m, 1H), 1.86-1.72 (m, 6H), 1.66-1.60 (m, 2H). MS m/z: 534.1 [M + 1]$^+$. |
| 109-1 | Bn-O, NC, COOMe, N, O, Ph, O-cyclopentyl | $^1$H NMR (400 MHz, CHLOROFORM-d): δ 7.51-7.34 (m, 11H), 7.00-6.52 (m, 1H), 5.37-5.29 (m, 2H), 5.25-5.06 (m, 2H), 5.04-4.93 (m, 1H), 4.58-4.48 (m, 1H), 4.33-4.15 (m, 1H), 3.69-3.59 (m, 2H), 3.50-3.15 (m, 1H), 3.13 (s, 1H), 2.95-2.67 (m, 1H), 1.86-1.68 (m, 8H). MS m/z: 525.2 [M + 1]$^+$. |
| 113-1 | Bn-O, O-, COOEt, N, O, Ph, O-cyclopentyl | $^1$H NMR (400 MHz, CHLOROFORM-d): δ 7.53-7.29 (m, 10H), 6.74-6.37 (m, 2H), 5.21 (s, 1H), 4.98-4.90 (m, 2H), 4.51-4.10 (m, 5H), 3.88-3.82 (m, 3H), 3.05-2.78 (m, 2H), 1.94-1.60 (m, 8H), 1.42-1.32 (m, 3H), 1.24-1.16 (m, 3H). MS m/z: 558.3 [M + 1]$^+$. |

Step 2: Preparation of Compounds 49 and 50

The compound 49-1 (80.0 mg, 155.7 μmol) was dissolved in tetrahydrofuran (3.0 mL) and water (1.0 mL), then lithium hydroxide monohydrate (37.3 mg, 1.5 mmol) was added and the reaction solution was continuously stirred for 16 hours at 25° C. The reaction solution was adjusted to pH of 5-6 with 1.0M hydrochloric acid, and extraction was performed with ethyl acetate (10 mL×3). The mixed organic phase was washed with 10 mL of a saturated saline solution, dried with anhydrous sodium sulfate, and decompressed to remove the organic solvent. The resulting crude product was separated and purified by a silica gel column chromatography column (an eluent: 50-100% ethyl acetate/petroleum ether) to obtain the product which was separated by SFC (column: AD (250 mm*30 mm, 10 μm); mobile phase [0.1% NH$_3$H$_2$O MeOH]; B %: 20%-20%) to obtain two diastereomers: the compound 49 and the compound 50.

Compound 49: $^1$H NMR (400 MHz, DMSO-d$_6$): δ 7.58-7.21 (m, 10H), 7.02-6.57 (m, 2H), 5.49-5.09 (m, 1H). 4.89-4.47 (m, 4H), 4.41-4.37 (d, J=16.8 Hz, 1H), 4.18-4.00 (m, 1H), 3.22-3.18 (m, 1H), 2.38-2.25 (m, 1H). 2.18-2.17 (d, J=4.8 Hz, 3H), 1.80-1.42 (m, 8H). MS m/z: 500.2 [M+1]$^+$. SFC: column: Chiralpak AD-3 (100 mm*4.6 mm, 3 μm); mobile phase: B: [0.05% DEA Methanol]; B %: 5%-40% 4.5 min, 40% 2.5 min, 5% 1.0 min; Rt=3.207 min; 97.2% de.

Compound 50: $^1$H NMR (400 MHz, DMSO-d$_6$): δ 7.54-7.23 (m, 10H), 7.05-6.69 (m, 2H), 5.35-5.30 (d, J=18.0 Hz, 1H). 5.17-4.80 (m, 2H), 4.79-4.29 (m, 3H), 4.04 (s, 1H), 3.22-3.18 (m, 1H), 2.81-2.65 (m, 1H). 2.19 (s, 3H), 1.81-1.42 (m, 8H). MS m/z: 500.1 [M+1]$^+$. SFC: column: Chiralpak AD-3 (100 mm*4.6 mm, 3 μm); mobile phase: B: [0.05% DEA Methanol]; B %: 5%-40% 4.5 min, 40% 2.5 min, 5% 1.0 min; Rt=3.813 min; 96.4% de.

The following compounds were synthesized by using a method similar to the compounds 49 and 50:

| Example | Compound Serial number | Structural formula | Spectrogram |
| --- | --- | --- | --- |
| 107 | 107 | Bn-O, Cl, OH, N, O, Ph, O-cyclopentyl | $^1$H NMR (400 MHz, DMSO-d$_6$): δ 7.56-6.62 (m, 12H), 5.44-5.30 (m, 1H), 5.23-5.00 (m, 1H), 4.96-4.36 (m, 4H), 4.16-3.97 (m, 1H), 3.68-3.50 (m, 1H), 2.92-2.85 (m, 1H), 1.79-1.43 (m, 8H). MS m/z: 520.1 [M + 1]$^+$. SEC: column: ChiralPak AD-3 (150 mm * 4.6 mm, 3 μm); mobile phase: B: [0.05% DEA ethanol]; B%: 5%-40% 5.5 min, 40% 3.0 min, 5% 1.5 min; Rt = 4.552 min; 99.8% de. |

| Example | Compound Serial number | Structural formula | Spectrogram |
|---|---|---|---|
| 108 | 108 | | $^1$H NMR (400 MHz, DMSO-d$_6$): δ 7.60-6.79 (m, 12H), 5.33-5.30 (d, J = 10.8 Hz, 1H), 5.16-4.67 (m, 4H), 4.62-4.34 (m, 1H), 4.05-4.01 (m, 1H), 3.71-3.47 (m, 1H), 2.25-1.96 (m, 1H), 1.79-1.37 (m, 8H). MS m/z: 520.1 [M + 1]$^+$. SFC: column: ChiralPak AD-3 (150 mm * 4.6 mm, 3 μm); mobile phase: B: [0.05% DEA EtOH]; B%: 5%-40% 5.5 min, 40% 3.0 min, 5% 1.5 min; Rt = 4.992 min; 98.3% de. |
| 109 | 109 | | $^1$H NMR (400 MHz, DMSO-d$_6$): δ 7.60-7.26 (m, 10H), 7.18-6.77 (m, 2H), 5.39-5.26 (m, 1H), 5.21-4.88 (m, 4H), 4.73-4.43 (m, 1H), 4.05-4.01 (m, 1H), 3.09-3.06 (m, 1H), 3.05-3.03 (m, 1H), 1.88-1.48 (m, 8H). MS m/z: 511.3 [M + 1]$^+$. SFC: column: ChiralPak AD-3 (150 mm * 4.6 mm, 3 μm); mobile phase: B: [0.05% DEA IPA]; B%: 5%-40% 5.5 min, 40% 3.0 min, 5% 1.5 min; Rt = 5.069 min; 89.4% de. |
| 110 | 110 | | $^1$H NMR (400 MHz, DMSO-d$_6$): δ 7.59-6.94 (m, 12H), 5.38-5.26 (m, 1H), 5.21-4.91 (m, 4H), 4.76-4.48 (m, 1H), 4.05-4.01 (m, 1H), 3.48-3.44 (m, 2H), 1.73-1.50 (m, 8H). MS m/z: 511.3 [M + 1]$^+$. SFC: column: ChiralPak AD-3 (150 mm * 4.6 mm, 3 μm); mobile phase: B: [0.05% DEA IPA]; B%: 5%-40% 5.5 min, 40% 3.0 min, 5% 1.5 min; Rt = 6.378 min; 100.0% de. |
| 111 | 111 | | $^1$H NMR (400 MHz, DMSO-d$_6$): δ 7.57-7.28 (m, 10H), 7.21-6.83 (m, 2H), 5.47-4.83 (m, 4H), 4.69-4.63 (m, 1H), 4.51-4.46 (m, 1H), 4.11-4.05 (m, 1H), 3.33-3.25 (m, 2H), 1.76-1.46 (m, 8H). MS m/z: 511.2 [M + 1]$^+$. SFC: column: (R,R)Whelk-01 (100 mm * 4.6 mm, 3 μm); mobile phase: B: [0.05% DEA EtOH]; B%: 5%-40% 5.5 min, 40% 3.0 min, 5% 1.5 min; Rt = 5.889 min; 94.2% de. |
| 112 | 112 | | $^1$H NMR (400 MHz, DMSO-d$_6$): δ 7.60-6.91 (m, 12H), 5.43-5.28 (m, 2H), 5.12-4.87 (m, 4H), 4.55-4.48 (m, 1H), 2.07-1.93 (m, 2H), 1.70-1.44 (m, 8H). MS m/z: 511.3 [M + 1]$^+$. SFC: column: (R,R)Whelk-01 (100 mm * 4.6 mm, 3 μm); mobile phase: B: [0.05% DEA EtOH]; B%: 5%-40% 5.5 min, 40% 3.0 min, 5% 1.5 min; Rt = 5.694 min; 61.9% de. |
| 113 | 113 | | $^1$H NMR (400 MHz, DMSO-d$_6$): δ 7.70-7.18 (m, 10H), 6.85-6.81 (m, 1H), 6.59-6.55 (m, 1H), 5.22 (s, 1H), 4.94-4.79 (m, 2H), 4.56-4.03 (m, 3H), 3.79 (s, 3H), 2.98-2.75 (m, 2H), 1.80-1.40 (m, 8H), 1.27-1.18 (m, 3H). MS m/z: 530.2 [M + 1]$^+$. SEC: column: ChiralPak AD-3 (150 min * 4.6 mm, 3 μm); mobile phase: B: [0.05% DEA IPA]; B%; 40%; Rt = 1.589 min; 98.0% de. |

| Example | Compound Serial number | Structural formula | Spectrogram |
|---|---|---|---|
| 114 | 114 | | $^1$H NMR (400 MHz, DMSO-d$_6$): δ 7.73-7.19 (m, 10H), 6.85-6.83 (d, J = 8.4 Hz, 1H), 6.63-6.61 (d, J = 8.0 Hz, 1H), 5.15 (s, 1H), 4.97-4.81 (m, 2H), 4.69-4.66 (d, J = 12.8 Hz, 1H), 4.05-3.95 (m, 2H), 3.80 (s, 3H), 3.03-2.78 (m, 2H), 1.85-1.37 (m, 8H). 1.21 (s, 3H). MS m/z: 530.2 [M + 1]$^+$. SFC: column: ChiralPak AD-3 (150 mm * 4.6 mm, 3 μm); mobile phase: B: [0.05% DEA IPA]; B%: 40%; Rt = 2.841 min; 99.1% de. |
| 115 | 115 | | $^1$H NMR (400 MHz, DMSO-d$_6$): δ 7.58-7.23 (m, 10H), 6.84-6.82 (d, J = 8.0 Hz, 1H), 6.59-6.57 (d, J = 7.2 Hz, 1H), 5.22 (s, 1H), 4.94-4.77 (m, 2H), 4.50-4.42 (m, 1H), 4.32-4.07 (m, 2H), 3.79 (s, 3H), 2.96-2.79 (m, 2H), 1.81-1.39 (m, 8H), 1.21 (s, 3H). MS m/z: 530.2 [M + 1]$^+$. SFC: column: Chiralpak AS-3 (150 mm * 4.6 mm, 3 μm); mobile phase: B: [0.05% DEA EtOH]; B%: 5%-40% 5.0 min, 40% 2.5 min, 5% 2.5 min; Rt = 3.082 min; 97.1% de. |
| 116 | 116 | | $^1$H NMR (400 MHz, DMSO-d$_6$): δ 7.57-7.24 (m, 10H), 6.85-6.83 (d, J = 8.4 Hz, 1H), 6.63-6.61 (d, J = 8.4 Hz, 1H), 5.15 (s, 1H), 4.96-4.80 (m, 2H). 4.70-4.67 (d, J = 14.4 Hz, 1H), 4.05-3.95 (m, 2H), 3.80 (s, 3H), 3.00-2.77 (m, 2H), 1.82-1.43 (m, 8H), 1.21 (s, 3H). MS m/z: 530.2 [M + 1]$^+$. SFC: column: Chiralpak AS-3 (150 mm * 4.6 mm, 3 μm); mobile phase: B: [0.05% DEA EtOH]; B%: 5%-40% 5.0 mm, 40% 2.5 min, 5% 2.5 min; Rt = 3.714 min; 100% de. |

Example 117: Preparation of Compound 117

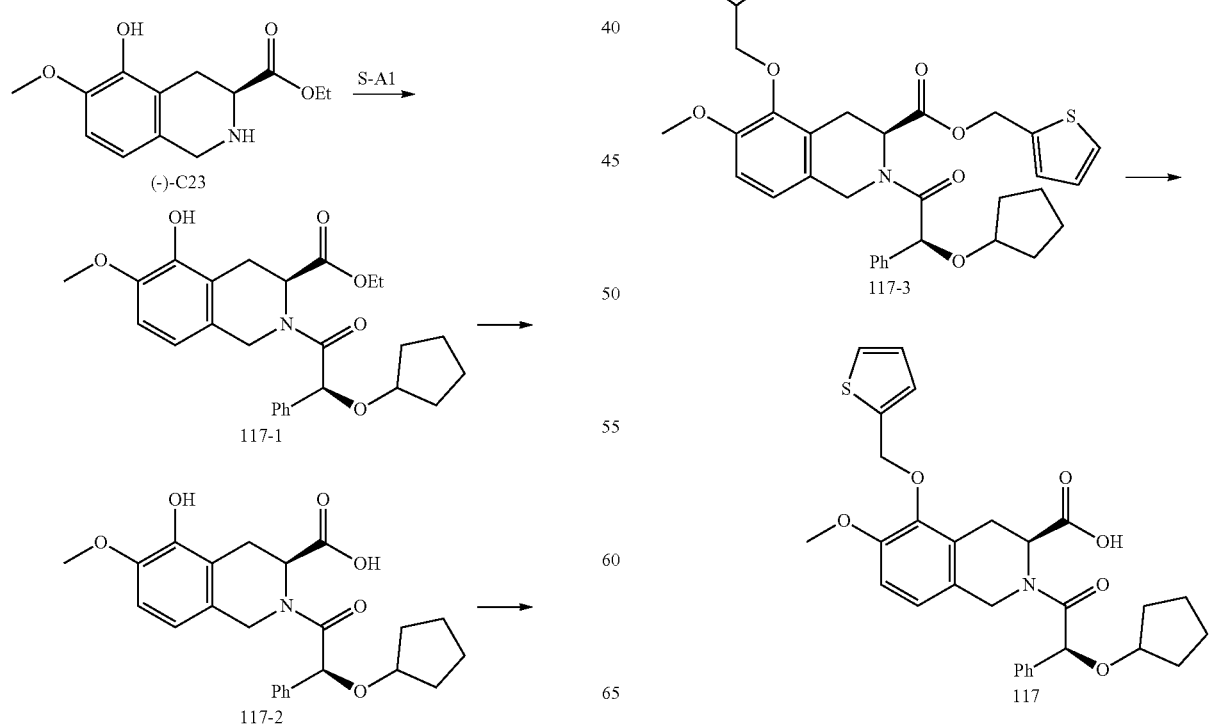

Step 1: Preparation of Compound 117-1

The compound (–)-C23 (I 10 mg, 437.76 μmol) and S-A1 (115.71 mg, 525.31 μmol) were dissolved in anhydrous dichloromethane (5 mL), and HATU (166.45 mg, 437.76 μmol) and diisopropylethylamine (169.73 mg, 1.31 mmol, 228.75 μL) were added, and the reaction solution was continuously stirred at 25° C. for 16 hours. 10 mL of water was added to the reaction solution, and the mixture was separated, and the aqueous phase was extracted with dichloromethane (10 mL) for three times. The organic phase was mixed and the organic solvent was removed under reduced pressure, and the resulting crude product was separated and purified by silica gel column chromatography (petroleum ether:ethyl acetate=2:1) to obtain the compound 117-1. $^1$H NMR (400 MHz, CHLOROFORM-d): δ 7.48-7.22 (m, 5H), 7.07-6.93 (m, 1H), 6.75-6.58 (m, 1H), 5.81-4.06 (m, 7H), 3.85-3.83 (d, J=8.4 Hz, 3H), 3.79-3.44 (m, 1H), 3.27-2.83 (m, 1H), 1.89-1.59 (m, 8H), 1.27-0.85 (m, 3H). MS m/z: 454.2 [M+1]$^+$.

Step 2: Preparation of Compound 117-2

The compound 117-1 (45 mg, 99.22 μmol) was dissolved in a mixed solvent of tetrahydrofuran (1 mL) and water (2 mL), and lithium hydroxide monohydrate (83.27 mg, 1.98 mmol) was added, and the reaction solution was continuously stirred at 25° C. for 16 hours. 10 mL of water was added to the reaction solution, and the mixture was extracted with ethyl acetate (10 mL) for three times. The organic phase was mixed and the organic solvent was removed under reduced pressure, and the resulting crude product was separated and purified by silica gel column chromatography (petroleum ether:ethyl acetate=2:1) to obtain the compound 117-2. $^1$H NMR (400 MHz, CHLOROFORM-d): δ 7.31-7.21 (m, 5H), 7.05-6.98 (m, 1H), 6.69-6.56 (m, 1H). 5.61-5.51 (m, 1H). 5.27-5.10 (m, 1H), 4.93-4.56 (m, 1H), 4.42-4.35 (m, 1H), 4.08-4.03 (m, 1H), 3.78-3.76 (d, J=8.8 Hz, 3H), 3.40-3.17 (m, 1H), 3.08-2.73 (m, 1H), 1.74-1.71 (m, 8H). MS m/z: 426.1 [M+1]$^+$.

Step 3: Preparation of Compound 117-3

The compound 117-2 (30 mg. 70.51 μmol) was dissolved in N,N-dimethylformamide (I mL), potassium carbonate (19.49 mg, 141.02 μmol) was added, and the reaction solution was stirred at 25° C. for 30 minutes, and 2-chloromethylthiophene (18.70 mg, 141.02 μmol) was added, and the reaction solution was heated to 70° C. and stirring was continued to be performed for 1 hour. 5 mL of water was added to the reaction solution, and the mixture was extracted with ethyl acetate (5 mL) for three times. The organic phase was mixed and the organic solvent was removed under reduced pressure, and the resulting crude product was separated and purified by silica gel column chromatography (petroleum ether:ethyl acetate=10:1) to obtain the compound 117-3. MS m/z: 618.1 [M+1]$^+$.

Step 4: Preparation of Compound 117

The compound 117-3 (45 mg, 72.84 μmol) was dissolved in a mixed solution of tetrahydrofuran (2 mL) and water (1 mL), and lithium hydroxide monohydrate (30.57 mg, 728.42 μmol) was added, and the reaction solution was continuously stirred at 25° C. for 16 hours. And 5 mL of water was added, and the mixture was extracted with ethyl acetate (10 mL) for three times. The organic phase was mixed and the organic solvent was removed under reduced pressure, and the resulting crude product was separated and purified by a silica gel preparation plate (petroleum ether:ethyl acetate=5:1) to obtain the compound 117. $^1$H NMR (400 MHz, DMSO-d$_6$): δ 8.41 (brs, 2H), 7.55-7.51 (m, 1H), 7.36-723 (m, 4H), 7.07-7.06 (m, 1H), 7.01-6.98 (m, 1H), 6.85-6.80 (m, 1H), 5.32-5.25 (m, 1H), 5.08-4.90 (m, 3H), 4.82-4.73 (m, 1H), 4.40-4.31 (m, 1H), 4.14-4.02 (m, 1H), 3.78 (s, 3H), 2.73-2.66 (m, 1H), 2.33-2.24 (m, 1H), 2.15-1.99 (m, 1H), 1.73-1.85 (m, 6H), 1.45-1.23 (m, 1H). MS m/z: 522.1 [M+1]$^+$. SFC: column: Chiralcel OD-3 (100 mm*4.6 mm, 3 μm); mobile phase: B: [0.1% DEA EtOH]; B %: 5%-40% 4.5 min, 40% 2.5 min, 5% 1.0 min; Rt=3.370 min; de=87.16%.

Example 118: Preparation of Compound 118

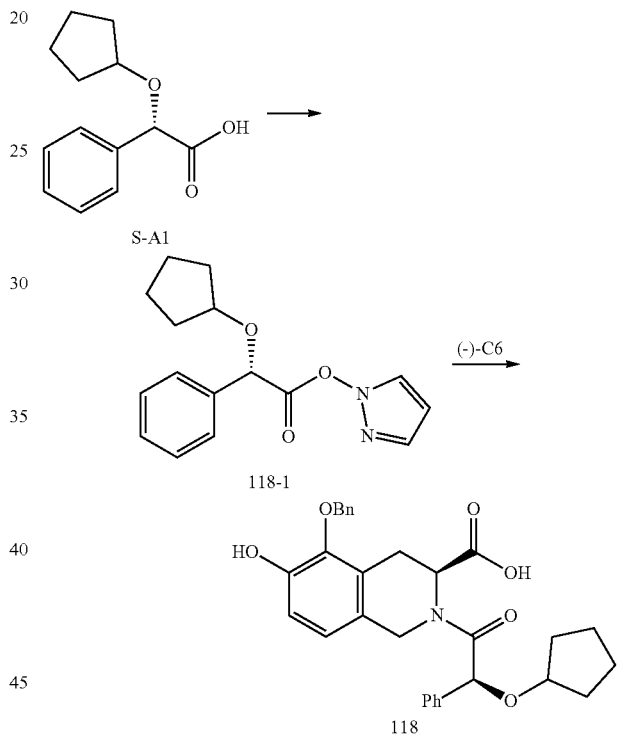

Step 1: Preparation of Compound 118-1

The compound S-A1 (25.3 g, 114.9 mmol) was dissolved in anhydrous dichloromethane (250.0 mL), N,N-dimethylformamide (0.5 mL) was added, and oxalyl chloride (17.5 g, 137.8 mmol, 12.07 mL) was added dropwise under a nitrogen atmosphere. The reaction solution was stirred at 20-25° C. for 30 minutes, and the organic solvent was removed under reduced pressure. The obtained crude product was dissolved in dichloromethane (200.0 mL) to prepare a solution. Pyrazole (8.6 g, 126.3 mmol) and N-methylmorpholine (15.1 g, 149.3 mmol, 16.4 mL) were dissolved in anhydrous dichloromethane (100.0 mL), and the above solution was slowly added dropwise under a nitrogen atmosphere. The reaction solution was continuously stirred at 20-25° C. for 16 hours. The stirred material was washed with a 1.0 M sulfuric acid solution (300 mL) twice, washed with saturated sodium bicarbonate (300 mL) twice, washed with water (300 mL), washed with a saturated aqueous sodium chloride solution (500 mL), dried with anhydrous sodium sulfate, and filtered. The organic solvent was removed under reduced pressure, and n-hexane (150 mL) was added to the obtained crude product, and the mixture was stirred at 70° C. for 30 minutes, and slowly cooled to 0° C., and allowed to stand for 2 hours. Then the mixture was filtered, and the filter cake was washed with n-hexane (80 mL), and dried in vacuum to obtain the compound 118-1. $^1$H NMR (400 MHz, CHLOROFORM-d): δ 8.24-8.23 (d, J=2.4 Hz, 1H). 7.73 (s, 1H), 7.60-7.58 (d, J=6.8 Hz, 2H), 7.41-7.27 (m, 3H), 6.44-6.43 (m, 1H), 6.36 (s, 1H), 4.21-3.98 (m, 1H), 1.87-1.67 (m, 6H), 1.56-1.42 (m, 2H). MS m/z: 271.0 [M+1]$^+$. SFC: column: ChiralCel OJ-H (150 mm*4.6 mm, 5 µm); mobile phase: B: [0.05% DEA EtOH]; B %/o: 5%-40%-5%; Rt=1.936 min; 99.4% de.

Step 2: Preparation of Compound 118

The compound (−)-C6 (50.0 mg, 167.0 µmol) was dissolved in N,N-dimethylformamide (2.0 mL), and 1,1,3,3-tetramethylguanidine (23.1 mg, 200.4 µmol) was added. After the liquid mixture was stirred at 25° C. for 1 hour, the compound 118-1 (54.2 mg, 200.4 µmol) was added, and the reaction solution was continuously stirred at 25° C. for 18 hours. Ethyl acetate (30 mL) was added to the reaction solution, and the mixture was washed with water (25 mL) twice, and washed with a saturated sodium chloride aqueous solution (20 mL) once. The organic phase was dried with anhydrous sodium sulfate, filtered and decompressed to remove the organic solvent. The obtained crude product was separated and purified by a silica gel preparation plate (ethyl acetate/petroleum ether=1/1) to obtain the compound 118. $^1$H NMR (400 MHz, DMSO-d$_6$): δ 7.54-7.23 (m, 10H), 6.74-6.43 (m, 2H), 5.39-5.26 (m, 1H), 5.12-4.55 (m, 4H), 4.51-4.25 (m, 1H), 4.16-3.97 (m, 1H), 3.46-3.42 (m, 1H), 2.21-2.16 (m, 1H), 1.80-1.40 (m, 8H). MS m/z: 502.2 [M+1]$^+$. SFC: column: ChiralCel OJ-H (150 mm*4.6 mm, 5 µm); mobile phase: B: [0.05% DEA EtOH]; B %: 5%-40% 5.5 min, 40% 3.0 min, 5% 1.5 min; Rt=4.009 min; 96.5% de.

Experimental Example 1: In Vitro Evaluation hAT2 Receptor Binding Assay
Solution and Buffer
Buffer
50 mM Tris
100 mM NaCl
5 mM MgCl$_2$
0.1% BSA
Protease inhibitor mixture, free of ethylenediaminetetraacetic acid-1 tablets (Roche #11873580001) (50 mL plus one piece)
pH 7.4
Experimental Methods and Steps
Compound Preparation
The reference ligand PD123319 and the test compound were prepared into a 750 µM mother liquor by DMSO; each compound was prepared into a solution of 8 concentration gradients (up to a concentration of 750 µM, 3-fold dilution) and 10 µl of the solution was added to a master of a 384-well plate per well.
The SPA beads were prepared to a mother liquor of 25 mg/ml by the buffer;
The isotope [$^{125}$I]-Sar1-Ile8-Angiotensin II was prepared into a mother liquor of 50 µCi/ml by adding pure water.

Membrane Preparation
The cell membrane overexpressing hAT2 in HEK-293 cells was prepared to 2.5 mg/ml by the buffer.

Experiment Steps 200 nl of compound was aspirated from the mother plate with ECHO to each well of the 384-well test plate. ZPE was added to an equal volume of DMSO. (The concentration of the test compound in the reaction was diluted by 250 times).
A 50 ml membrane solution containing 10 µg/µl of magnetic beads and 0.05 µg/µl of AT2 was prepared, placed on a shaker and uniformly mixed. (100 rpm, 30 min). The test plate finally contained an hAT2 membrane with 1.25 µg/well and magnetic beads with 250 µg/well.
A 3.2 ml membrane liquid mixture was added to the compound test plate by using a Multidrop Combi pipette, and 25 µl was added to each well.
A 0.2 nM solution was prepared with 50 µCi/ml of isotope [$^{125}$I]-Sar1-Ile8-Angiotensin II mother liquor by the buffer, and 0.2 nM of $^{125}$I was added to the compound test plate with a Multidrop Combi pipette. A volume of 25 µl was added to each well. The final concentration of $^{125}$I isotope is 0.1 nM.
The prepared test plate was placed on a shaker overnight at room temperature at 200 rpm.
The test plate was centrifuged with a centrifuge at 1200 rpm for 1 min.
The centrifuged test plate was read with Microbeta.
The experimental results are shown in Table 1.

TABLE 1

| Compound Serial Number | hAT2 IC$_{50}$ (nM) |
| --- | --- |
| EMA-401 | 53.2 |
| 1 | 66.4 |
| 2 | 850.5 |
| 3 | 196.7 |
| 4 | 836.0 |
| 5 | 17.7 |
| 6 | 382.7 |
| 7 | 35.2 |
| 8 | 513.1 |
| 9 | 47.6 |
| 10 | 60.7 |
| 11 | >3000 |
| 12 | >3000 |
| 13 | 153.8 |
| 14 | >3,000 |
| 15 | 96.4 |
| 16 | 16.5 |
| 17 | 143.3 |
| 18 | 54.1 |
| 19 | 249.8 |
| 20 | 175.6 |
| 21 | 195.3 |
| 22 | 1342.0 |
| 23 | >3000 |
| 24 | 191.9 |
| 25 | 72.1 |
| 26 | 95.1 |
| 27 | 245.3 |
| 28 | 29.8 |
| 29 | 230.8 |
| 30 | 372.9 |
| 31 | 59.6 |
| 32 | 78.3 |
| 33 | 647.7 |
| 34 | 227.2 |
| 35 | 1242.0 |
| 36 | 97.1 |
| 37 | 4.1 |

TABLE 1-continued

| Compound Serial Number | hAT2 IC$_{50}$ (nM) |
|---|---|
| 38 | 691.1 |
| 39 | 18.5 |
| 40 | 9.1 |
| 41 | 216.4 |
| 42 | 161.0 |
| 43 | >3000 |
| 44 | 8.0 |
| 45 | 487.0 |
| 46 | 186.3 |
| 47 | 17.0 |
| 48 | 21.4 |
| 49 | 4.0 |
| 50 | 269.5 |
| 51 | 3.2 |
| 52 | 126.3 |
| 53 | 84.1 |
| 54 | >3,000 |
| 55 | 4.4 |
| 56 | 224.5 |
| 57 | 5.8 |
| 58 | 155.3 |
| 59 | 22.7 |
| 60 | 2.5 |
| 61 | 72.7 |
| 62 | 270.2 |
| 63 | 10.3 |
| 64 | 375.3 |
| 65 | 157.4 |
| 66 | >3,000 |
| 67 | 1.6 |
| 68 | 67.0 |
| 69 | 1.7 |
| 70 | 65.6 |
| 71 | 1090.0 |
| 72 | 5.3 |
| 73 | 3.7 |
| 74 | 129.4 |
| 75 | 3.9 |
| 76 | 72.7 |
| 77 | 880.8 |
| 78 | 7.4 |
| 79 | 5.8 |
| 80 | 322.7 |
| 81 | 10380.0 |
| 82 | 20.8 |
| 83 | 3.2 |
| 84 | 481.1 |
| 85 | 83.5 |
| 86 | 878.9 |
| 87 | 22.4 |
| 88 | 55.2 |
| 89 | 29.7 |
| 90 | 10.3 |
| 91 | 7.0 |
| 92 | 4.8 |
| 93 | 10.5 |
| 94 | 7.2 |
| 95 | 59.6 |
| 96 | 3.7 |
| 97 | 6.1 |
| 98 | 5.6 |
| 99 | 11.0 |
| 100 | 10.8 |
| 101 | 30.6 |
| 102 | 22.1 |
| 103 | 12.3 |
| 104 | 40.0 |
| 105 | 13.8 |
| 106 | 22.9 |
| 107 | 13.2 |
| 108 | 234.0 |
| 109 | 1055.0 |
| 110 | 552.5 |
| 111 | 15.9 |
| 112 | 116.3 |
| 113 | >3,000 |
| 114 | 412.5 |
| 115 | 115.3 |
| 116 | NA |
| 117 | 9.1 |
| 118 | 30.4 |

Conclusion: the results show that the active isomers of the compounds of the present disclosure have good in vitro activity compared to that of EMA-401.

Experimental Example 2: Determination of Kinetic Solubility

The to-be-tested compound was dissolved in DMSO to prepare a 10 mmol/L stock solution. 980 μL of dissolution medium was pipetted into a 2 mL screw-capped glass vial by using a pipette (Eppendorf Research Company). 20 μL of the stock solution of each test compound and the QC sample were added to a buffer solution corresponding to a kinetic detection solution of pH 7.4. The final concentrations of the test compound and DMSO solution were 200 μM and 2%, respectively. The cover of the medicine bottle was screwed. The theoretical maximum concentration is 200 μM. The mixture was shaken at 880 rpm for 24 hours at room temperature. The vial was centrifuged for 30 minutes at 13,000 rpm. 200 μL of the supernatant was added to a 96-well plate by using a digital pipette. The solubility of the test compound was determined by high performance liquid chromatography, and the experimental results are shown in Table 2.

TABLE 2

| Compound | Solubility (μM)@pH = 7.4 |
|---|---|
| EMA401 | 191.7 |
| 37 | >200.0 |
| 49 | >200.0 |
| 51 | 189.96 |
| 63 | 190.32 |
| 90 | 182.68 |
| 103 | >200.0 |
| 107 | 181.07 |
| 111 | >200.0 |

Conclusion: the results show the compounds of the present disclosure have good solubility (at pH 7.4).

Example 3: Human Liver Microsome CYP Inhibition Experiment

The research project used a specific probe substrate for each isoenzyme to evaluate the inhibitory effect of the test compound on human liver microsomal cytochrome P450 isoenzymes (CYPIA2. CYP2C9, CYP2C19, CYP2D6, and CYP3A4).

Mixed human liver microsomes (pooled HLM, n≥50) were purchased from Corning Inc. (Steuben, N.Y., USA) or other qualified suppliers, and were stored in a refrigerator below −60° C. before use.

The diluted series of to-be-tested compound working solutions were added to an incubation system containing cofactors of human liver microsomes, a probe substrate and a circulation system, and the methanol content was about 1% (v/v) of the final incubation system. A control containing no the to-be-tested compound and containing a solvent was used as a control for enzyme activity (100%). The concentration of the analyte in the sample was determined by liquid chromatography-tandem mass spectrometry (LC/MS/MS). The calculation was performed by using the average of the concentrations of the samples (a blank solvent, a positive control inhibitor, or the to-be-tested compound). Non-linear regression analysis was performed by using SigmaPlot (V.11) on the average percent activity of the compound to be tested to the concentration. The $IC_{50}$ value was calculated by a three-parameter or four-parameter inflection logarithmic equation. The experimental results are shown in Table 3.

TABLE 3

| Test Compound | Cytochrome P450 isoenzyme $IC_{50}$ (μM) | | | | |
|---|---|---|---|---|---|
| | CYP1A2 | 2C9 | 2C19 | 2D6 | 3A4 |
| EMA-401 | 13.0 | 7.28 | 17.6 | >50 | 9.19 |
| 37 | >50 | 30.5 | >50 | >50 | >50 |
| 49 | >50 | 16.0 | >50 | >50 | >50 |
| 51 | >50 | 34.4 | >50 | >50 | >50 |
| 63 | >50 | >50 | >50 | >50 | >50 |
| 90 | >50 | 21.6 | >50 | >50 | >50 |
| 103 | >50 | >50 | >50 | >50 | >50 |
| 107 | >50 | 14.5 | >50 | >50 | >50 |

Conclusion: the compounds of the present disclosure have no inhibitory effect on five GYP isoenzymes, or the inhibitory effects are weak, indicating that there is less possibility of drug-drug interaction in humans.

Example 4: Two-Way Permeability Study of Compounds in CACO-2 Cells

The two-way permeability of the to-be-tested compound in Caco-2 cells was measured, and whether the to-be-tested compound was transported by efflux or not was tested.

Experimental Method

Preparation of Stock Solution

The compound is dissolved in dimethyl sulfoxide (DMSO) or other suitable solvent to prepare a stock solution of the appropriate concentration.

A suitable internal standard (IS) is dissolved in acetonitrile (ACN) or other organic solvent to be used as a stop solution. The specific information will be described in the research report.

Nadolol, metoprolol, digoxin, estrone 3-sulfate potassium (E3S) and GF120918 were used as a hypotonic control compound, a hypertonic control compound, a P-glycoprotein (P-gp) substrate, a breast cancer resistance protein (BCRP) substrate, and an efflux transporter inhibitor in this study. Stock solutions of these compounds are prepared with DMSO and stored at ≤−30° C., and used within 6 months.

Preparation of Administration Solution and Receiving Solution

In this study, HBSS (Hanks Balanced Salt Solution) containing 10 mM HEPES (2-[4-(2-hydroxyethyl)-1-piperazine]ethanesulfonic acid) was used as a transport buffer (pH 7.40*0.05). The preparation method of the administration solution and the receiving solution is shown in Table 4 below.

TABLE 4

| Solution Name | Composition | DMSO Final Concentration (v/v) |
|---|---|---|
| administration solution | 1) to-be-tested compounds with concentrations of 2, 10 and 100 μM were prepared with a transport buffer containing or containing no 10 μM GF120918, respectively<br>2) digoxin with a concentration of 10 μM was prepared with a transport buffer containing or containing no 10 μM GF120918<br>3) E3S with a concentration of 5 μM was prepared with a transport buffer containing or containing no 10 μM GF120918<br>4) nadolol with a concentration of 2 μM and metoprolol with a concentration of 2 μM are prepared with a transport buffer containing no GF120918 | ≤0.7% |
| Receiving Solution | transport buffer containing or containing no 10 μM GF120918 | ≤0.2% |

Cell Culture

Caco-2 cells were cultured in an MEM medium (Minimum Essential Media) under the conditions of 37±1° C., 5% $CO_2$ and saturated humidity. The cells were then seeded in a Corning Transwell-96 well plate at a density of $1 \times 10^5$ cells/$cm^2$, and then the cells were placed in a carbon dioxide incubator for culture for 21-28 days for transport experiments. The medium was changed once every 5-6 days during culture.

Transport Experiment

Compounds were administered at concentrations of 2, 10 and 100 μM and were administered in both directions (A-B and B-A directions) with or without 10 μM GF120918, and there are three parallels for each administration concentration. Digoxin and E3S were tested at the concentration of 10 μM and 5 μM, respectively, and administered bidirectionally with or without 10 μM GF120918. The test concentrations of nadolol and metoprolol were 2 μM, and nadolol and metoprolol were administered unidirectionally (the A-B direction) without 10 μM GF120918. The three control compounds were also made in three parallels.

The administration solution, receiving solution and transport buffer were pre-incubated for 30 minutes at 37° C. The cell layer was rinsed twice with the transport buffer. The administration solution and the receiving solution were separately added to the corresponding cell plate wells (75 μL and 250 μL, respectively, for each of the top and base end wells). After sampling, the cell plates were incubated for 120 minutes in an incubator at 37±1° C., 5% $CO_2$ and saturated humidity.

Sample collection information is shown in Table 5 below.

TABLE 5

| Sample Type | Receiving Volume Per Hole (μL) | Stop Solution Volume (μL) | Transport Buffer Volume (μL) |
|---|---|---|---|
| A-B Administration End | 50 | 250 | 100 |
| A-B Receiving End | 150 | 250 | 0 |

TABLE 5-continued

| Sample Type | Receiving Volume Per Hole (μL) | Stop Solution Volume (μL) | Transport Buffer Volume (μL) |
|---|---|---|---|
| A-B Cell Lysis | 50 | 200 | 150 |
| B-A Administration End | 50 | 250 | 100 |
| B-A Receiving End | 50 | 250 | 100 |
| B-A Cell Lysis | 50 | 200 | 150 |
| T0 | 50 | 250 | 100 |

After all the compounds were subjected to vortex oscillation, the compounds after vortex oscillation were centrifuged at 3220×g, and 20° C. for 20 minutes, the appropriate volume of the supernatant was transferred to a sample analysis plate, and after the plate was sealed, the compounds were stored at 2-8° C. if the compounds were not immediately analyzed. The analysis was carried out by the method of LC/MS/MS, and the specific compound treatment method is shown in the research report.

Cell Membrane Integrity Test

The Lucifer Yellow Rejection Assay was used to test the integrity of Caco-2 cells. Six cell wells were randomly selected from each cell plate, and 100 μM Lucifer Yellow was added respectively. The Lucifer Yellow Rejection Assay and the transport experiment were performed simultaneously. After 120 minutes of incubation, a Lucifer Yellow sample was taken and the relative fluorescence unit (RFU) of the Lucifer Yellow in the sample was detected at a 425/528 nm (excitation/emission) spectrum.

Sample Analysis

The concentrations of the to-be-tested compound and the control compounds nadolol, metoprolol, digoxin and E3S in the samples were determined by liquid chromatography-tandem mass spectrometry (LC/MS/MS). The retention time of the analyte and internal standard, chromatogram acquisition and chromatogram integration were processed by using the software Analyst (AB Sciex, Framingham, Mass., USA). The experimental results are shown in Table 6.

TABLE 6

| Compound Serial Number | Papp (AB) ($10^{-6}$ cm/s) | Papp (BA) ($10^{-6}$ cm/s) | Efflux ratio |
|---|---|---|---|
| EMA-401 | 0.11 | 6.40 | 58.39 |
| 37 | 0.27 | 8.68 | 32.50 |
| 49 | 1.15 | 14.56 | 12.6 |
| 57 | 0.67 | 17.69 | 26.33 |
| 90 | 1.10 | 10.89 | 9.91 |
| 107 | 0.48 | 6.24 | 13.05 |

Conclusion: The test results show that the permeability of the compound of the present disclosure is improved relative to EMA-401, which is advantageous for the absorption of the compound.

Example 5: Plasma Protein Binding Rate (PPB) Test

In vitro protein binding rates of 0.2 μM, 2 μM, 10 μM of test compounds with Sprague-Dawley rats, beagle dogs, human plasma were determined by equilibrium dialysis.

Experimental Method

The experiment will use a 96-well equilibrium dialysis plate (HTDialysis device) to determine the plasma protein binding rate of the to-be-tested compound and the control compounds.

Prior to the start of the experiment, the dialysis membrane was pretreated according to the instructions for use and the dialysis unit was assembled as required.

Blank plasma was taken from CD-1 mice, Sprague-Dawley rats, Beagle dogs, cynomolgus monkeys and humans (an anticoagulant is EDTA-K2, which is a commercial product purchased, or is collected and prepared by the Drug Evaluation Department of Wuxi AppTech, and is stored in a refrigerator below −60° C. before use). A certain volume of the to-be-tested compound or the control compound working solution was added to prepare plasma samples of the compound to be tested at a concentration of 0.2, 2, 10 μM and plasma samples of the control compound at a concentration of 2 μM (n=1). The organic phase content was ≤1%. First, a certain volume of a plasma sample containing the to-be-tested compound and the control compound was taken out into the sample receiving plate as a sample at zero time (T0 sample, n=3); secondly, a plasma sample containing the to-be-tested compound and the control compound was added to one side of the dialysis membrane (plasma end, n=3), and a certain volume of dialysis buffer (buffer end, n=3) was added to the other side of the dialysis membrane; then the dialysis plate was placed in a humidified incubator with 5% $CO_2$ for incubation for 4 hours at 37±1° C.

After the incubation, a certain volume of the dialyzed buffer sample (F sample) and the dialyzed plasma sample (T sample) were transferred to the sample receiving plate, and all samples were subjected to protein precipitation for LC/MS/MS analysis. And the dissociation rate of the compound (% Unbound) was calculated by the following formula: % Unbound=100*[F]/[T], % Bound=100−% Unbound. Wherein, % Unbound is the dissociation rate of the compound; % Bound is the binding rate of the compound; [F] is the concentration of the compound at the buffer end of the dialysis plate; [T] is the concentration of the compound at the plasma end of the dialysis plate; and the experimental results are shown in Table 7.

TABLE 7

| Compound Serial Number | Plasma Protein Binding (%) | |
|---|---|---|
| | Human Plasma | SD Rat Plasma |
| EMA-401 | 99.8% | 99.9% |
| 37 | 99.6% | 99.9% |
| 49 | 99.8% | 99.9% |
| 51 | 99.3% | 94.5% |
| 57 | 99.5% | 99.8% |
| 63 | 98.4% | 98.9% |
| 103 | 94.0% | 95.5% |
| 111 | 99.8% | 99.8% |

The results indicate that the results showed that the plasma protein binding rate of the test compound was improved relative to EMA-401, which was beneficial to the drug reaching the target of drug action.

The invention claimed is:
1. A compound of a formula (II) and a pharmaceutically acceptable salt thereof,

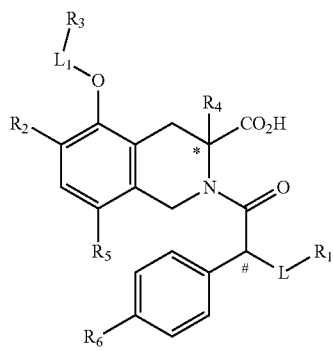

(II)

wherein,
L is selected from —O—, —S—, —N(R)—, —N(R)C(=O)— and —C(=O)O—;
$L_1$ is selected from a single bond, —$CH_2$— and —$CH_2CH_2$—;
$R_1$ is selected from the group consisting of $C_{1-6}$ alkyl, $C_{1-6}$ heteroalkyl, $C_{3-7}$ cycloalkyl, 3-7 membered heterocycloalkyl, 6-10 membered aryl and 5-6 membered heteroaryl, wherein each is optionally substituted by one, two or three R groups;
$R_2$ is selected from H, halogen, OH, $NH_2$ and CN; or selected from the group consisting of $C_{1-6}$ alkyl and $C_{1-6}$ heteroalkyl, wherein each is optionally substituted by one, two or three R groups;
$R_3$ is selected from the group consisting of phenyl, 5-6 membered heteroaryl and 5-6 membered heterocycloalkyl, wherein each is optionally substituted by one, two or three R groups;
$R_4$ is selected from H, or selected from $C_{1-3}$ alkyl optionally substituted by one, two or three R groups;
$R_5$ is selected from H, F, Cl, Br, I, and OH;
$R_6$ is selected from H, F, Cl, Br, I, and OH;
R is selected from H, halogen, OH, $NH_2$, CN, or selected from the group consisting of $C_{1-3}$ alkyl optionally substituted by one, two or three R' groups and $C_{1-3}$ heteroalkyl optionally substituted by one, two or three R' groups;
R' is selected from F, Cl, Br, I, OH, CN and $NH_2$;
a carbon atom with "*" is a chiral carbon atom, and is present in a single enantiomer form of (R) or (S) or in a form rich in one enantiomer,
a carbon atom with "#" is a chiral carbon atom, and is present in a single enantiomer form of (R) or (S) or in a form rich in one enantiomer,
the "hetero" of the 3-7 membered heterocycloalkyl, 5-6 membered heteroaryl, $C_{1-6}$ heteroalkyl, $C_{1-3}$ heteroalkyl and 5-6 membered heterocycloalkyl is independently selected from —C(=O)NH—, —NH—, N, —O—, —S—, —C(=O)O— and —C(=O)—; and
in any one of the above cases, the number of heteroatoms or heteroatom groups is independently selected from 1, 2 or 3.

2. The compound or the pharmaceutically acceptable salt thereof according to claim 1, wherein R is selected from H, halogen, OH, $NH_2$ and CN; or selected from the group consisting of $C_{1-3}$ alkyl optionally substituted by one, two or three R' groups and $C_{1-3}$ alkoxy optionally substituted by one, two or three R' groups.

3. The compound or the pharmaceutically acceptable salt thereof according to claim 2, wherein R is selected from H, F, Cl, Br, I, OH, $NH_2$, CN, Me, Et, $CF_3$ and

4. The compound or the pharmaceutically acceptable salt thereof according to claim 1, wherein L is selected from —O—, —S—, —NH—, —N($CH_3$)—, —NHC(=O)—, —N($CH_3$)C(=O)— and —C(=O)O—.

5. The compound or the pharmaceutically acceptable salt thereof according to claim 1, wherein $R_1$ is selected from the group consisting of $C_{1-4}$ alkyl, $C_{1-6}$ heteroalkyl, $C_{3-7}$ cycloalkyl, 3-7 membered heterocycloalkyl, 6-10 membered aryl and 5-6 membered heteroaryl, wherein each is optionally substituted by one, two or three R groups.

6. The compound or the pharmaceutically acceptable salt thereof according to claim 5, wherein $R_1$ is selected from the group consisting of $C_{1-4}$ alkyl, cyclobutyl, cyclopentyl, cyclohexyl, bicyclo[3.1.0]hexyl, oxetanyl, tetrahydrofuranyl, tetrahydropyranyl, phenyl, naphthyl, thienyl, pyrazolyl, imidazolyl, oxazolyl, thiazolyl, morpholinyl, piperazinyl, piperidinyl, pyridyl, pyrazinyl and pyrimidinyl, wherein each is optionally substituted by one, two or three R groups.

7. The compound or the pharmaceutically acceptable salt thereof according to claim 6, wherein $R_1$ is selected from

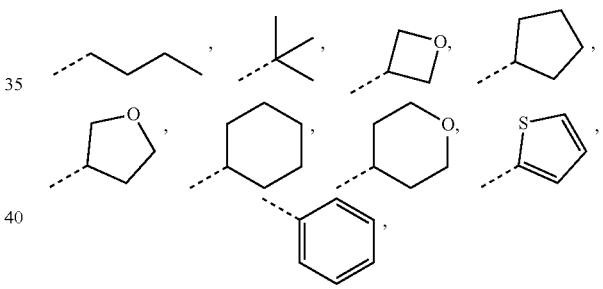

the group consisting of Me, Et,

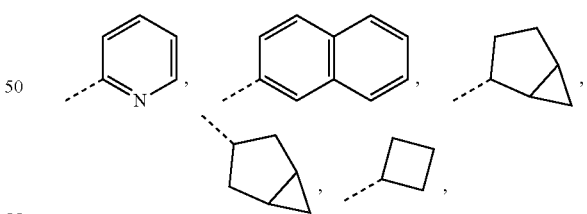

wherein each is optionally substituted by one, two or three R groups.

8. The compound or the pharmaceutically acceptable salt thereof according to claim 7, wherein $R_1$ is selected from Me, Et,

-continued

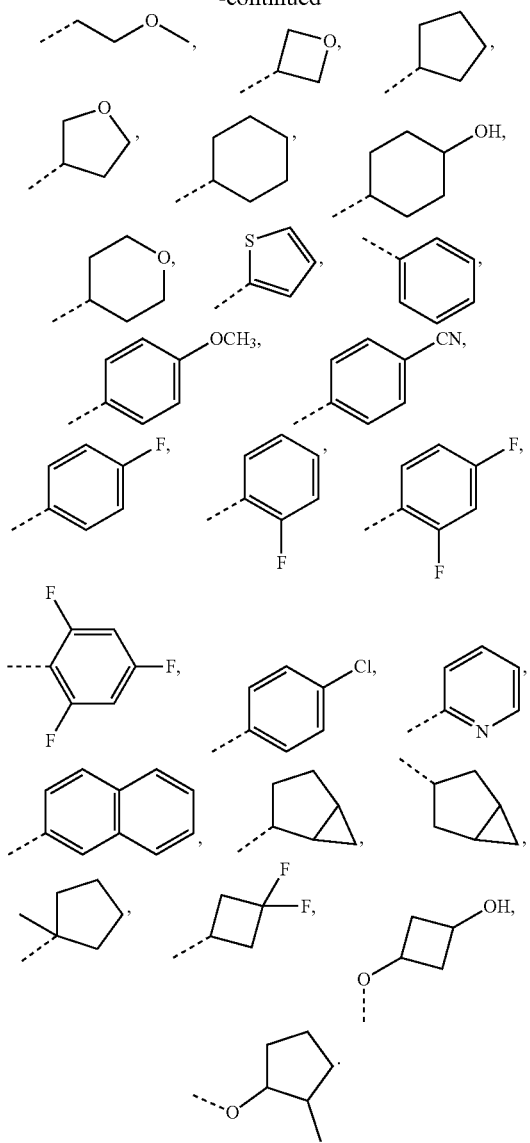

-continued

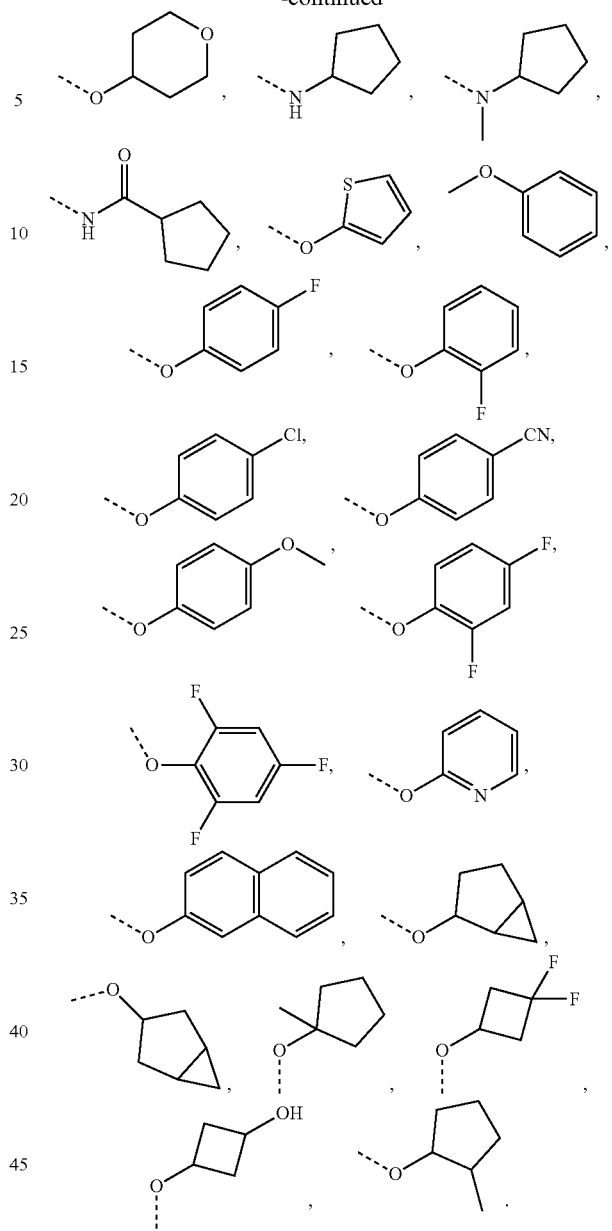

9. The compound or the pharmaceutically acceptable salt thereof according to claim 1, wherein the structural unit

is selected from

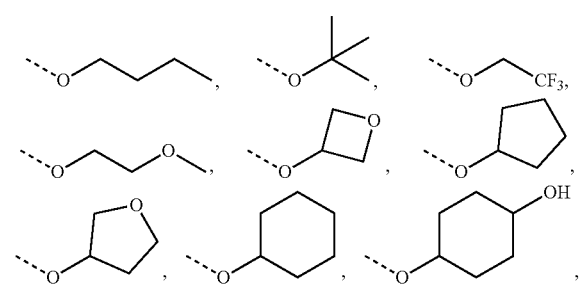

10. The compound or the pharmaceutically acceptable salt thereof according to claim 1, wherein $R_2$ is selected from H, halogen, OH, $NH_2$ and CN; or selected from the group consisting of $C_{1-3}$ alkyl, $C_{1-3}$ alkoxyl, $C_{1-3}$ alkylthio and $C_{1-3}$ alkylamino, wherein each is optionally substituted by one, two or three R groups.

11. The compound or the pharmaceutically acceptable salt thereof according to claim 10, wherein $R_2$ is selected from H, F, Cl, Br, I, OH, $NH_2$, CN, Me, and

12. The compound or the pharmaceutically acceptable salt thereof according to claim 1, wherein $R_3$ is selected from the group consisting of phenyl, pyridyl, pyrimidinyl, pyrazinyl, thienyl, thiazolyl, isothiazolyl, oxazolyl, isoxazolyl, tetrahydropyranyl, piperidinyl and morpholinyl, wherein each is optionally substituted by one, two or three R groups.

13. The compound or the pharmaceutically acceptable salt thereof according to claim 12, wherein $R_3$ is selected from

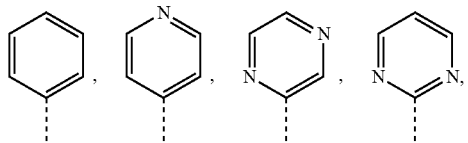

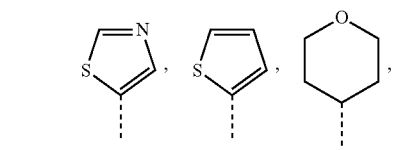

wherein each is optionally substituted by one, two or three R groups.

14. The compound or the pharmaceutically acceptable salt thereof according to claim 13, wherein $R_3$ is selected from

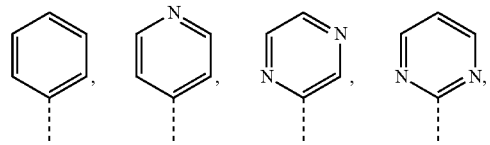

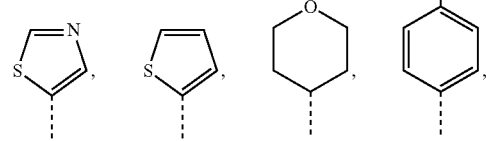

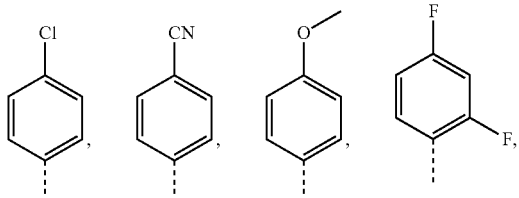

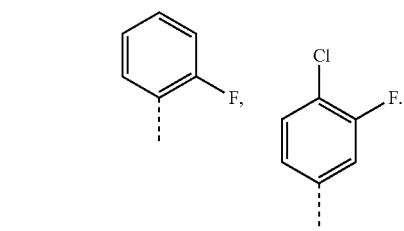

15. The compound or the pharmaceutically acceptable salt thereof according to claim 1, wherein the structural unit

is selected from

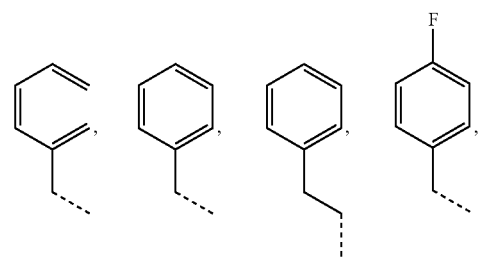

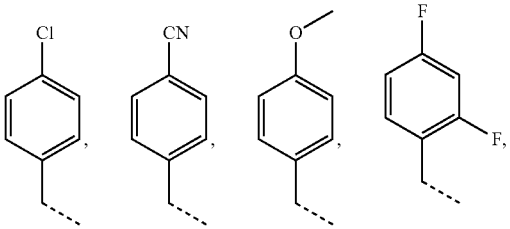

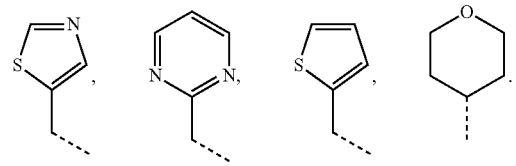

16. The compound or the pharmaceutically acceptable salt thereof according to claim 1, wherein $R_4$ is selected from H and Me.

17. The compound or the pharmaceutically acceptable salt thereof according to claim 1, selected from the group consisting of

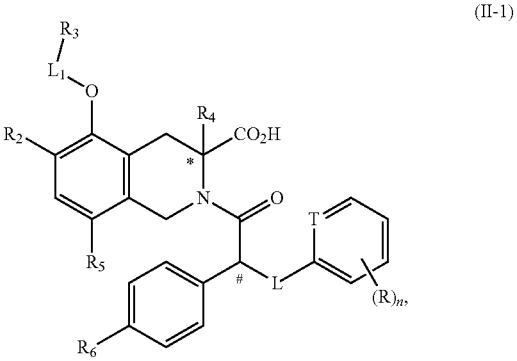

(II-1)

-continued

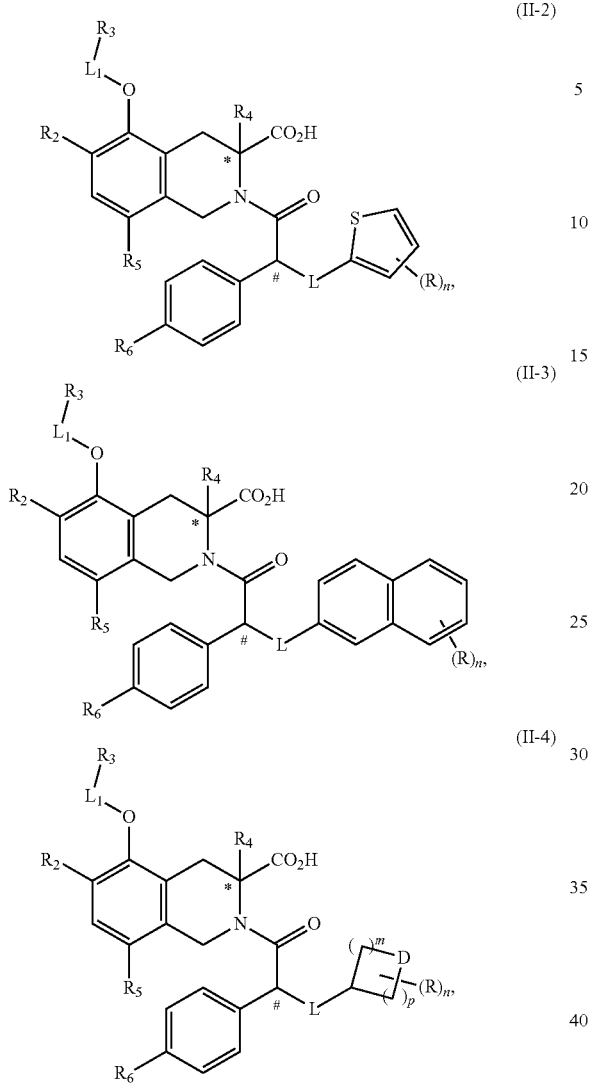

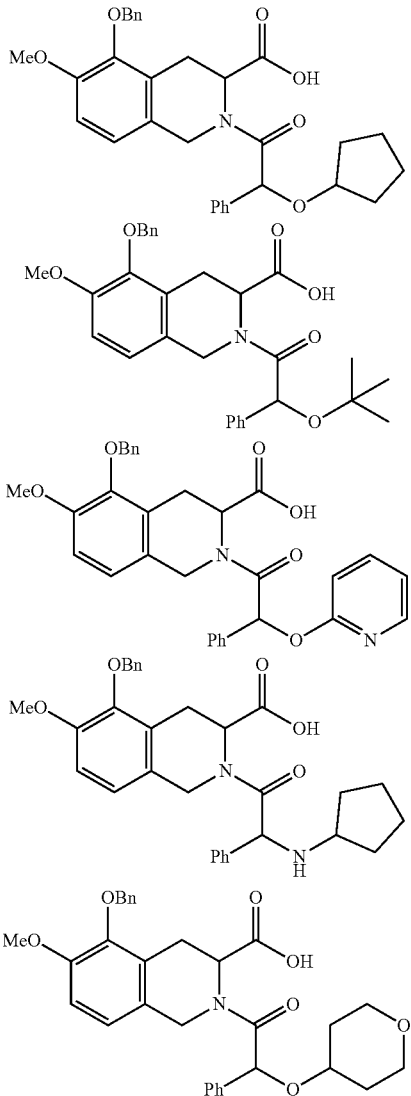

wherein,
R, $R_2$, $R_3$, $R_4$, $R_5$, $R_6$, $L_1$ and L are defined as in claims 1-5 and 9-16;
T is selected from N or CH;
D is selected from $CH_2$ or O;
m and p are each independently selected from 0, 1, 2 or 3, and m and p are not simultaneously selected from 0 or 3;
n is selected from 0, 1, 2 or 3;
and n is not selected from 3 when m is selected from 0 and D is selected from O.

18. A compound of the following formula, which is selected from

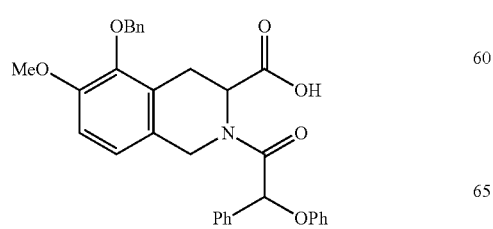

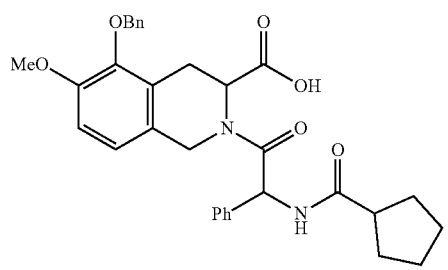

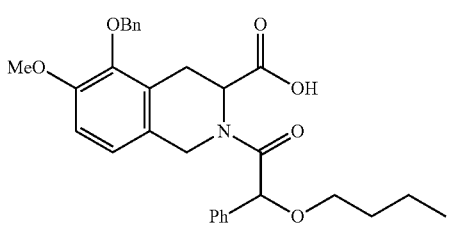

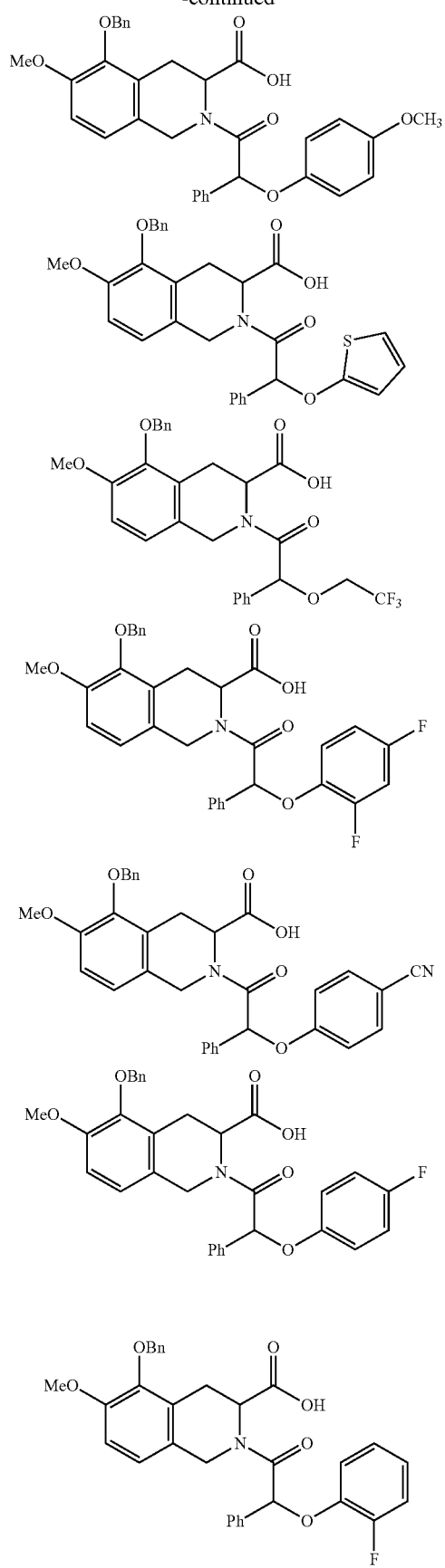
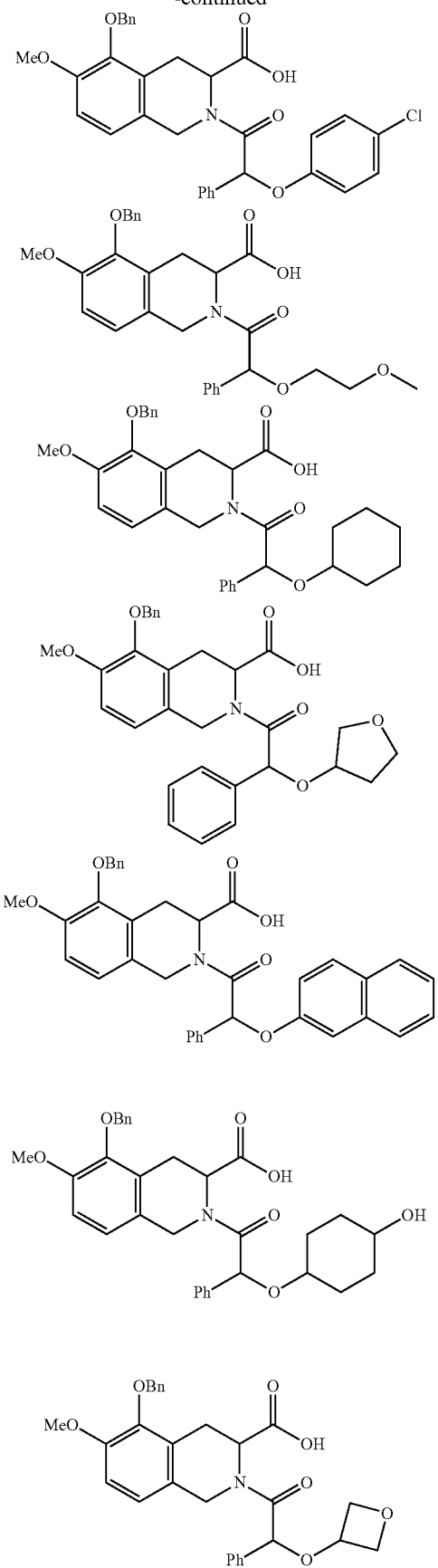

219
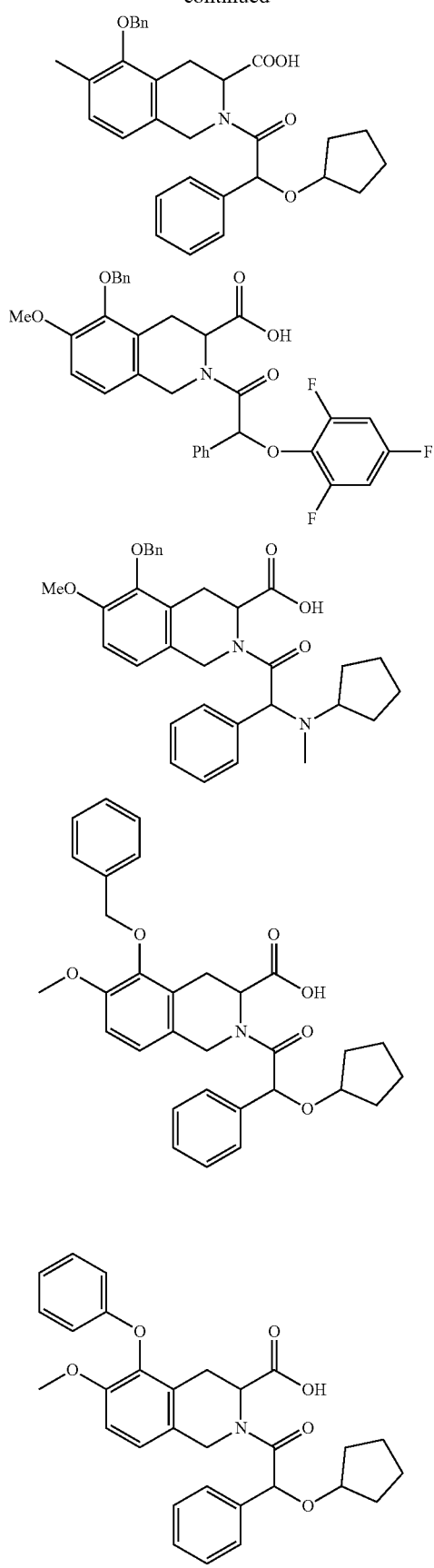
220
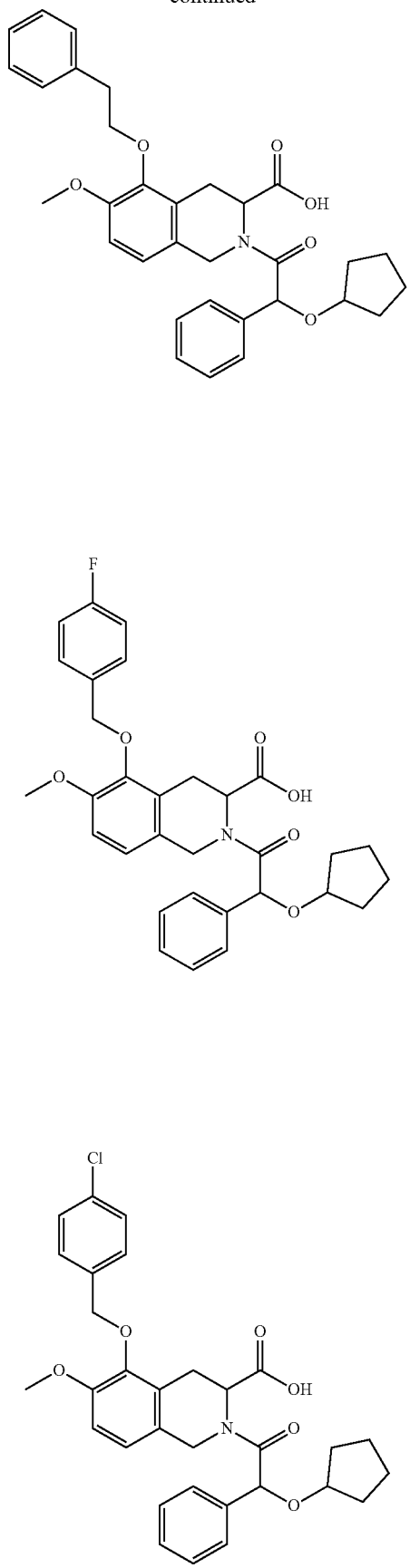

221
-continued
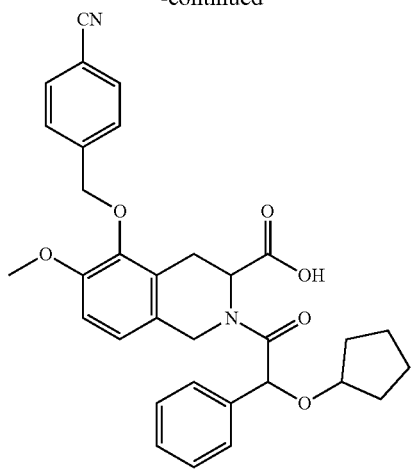
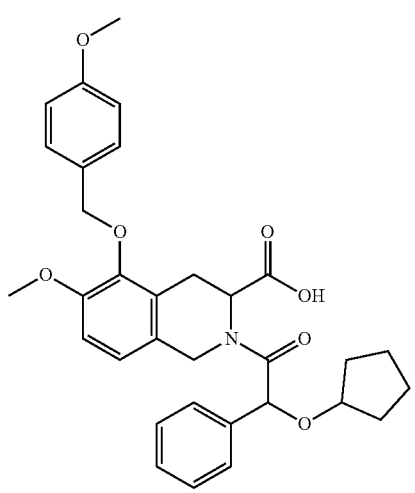
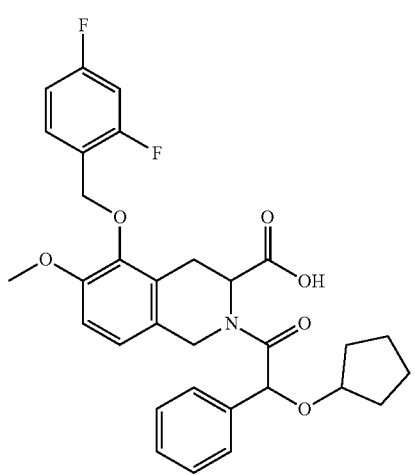
222
-continued
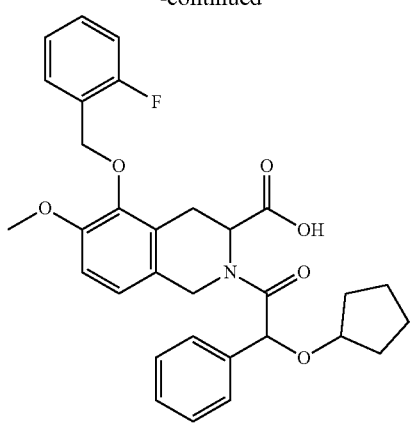
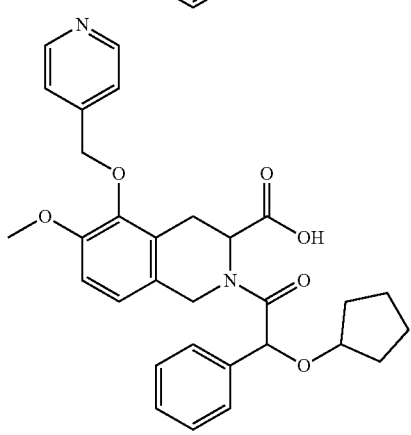
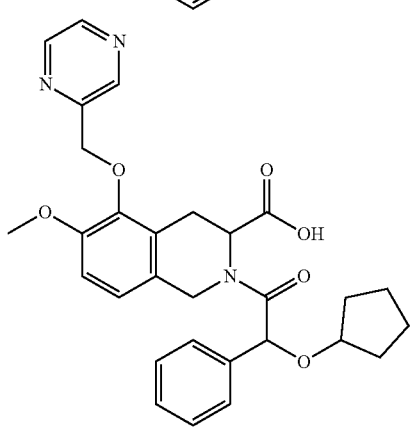
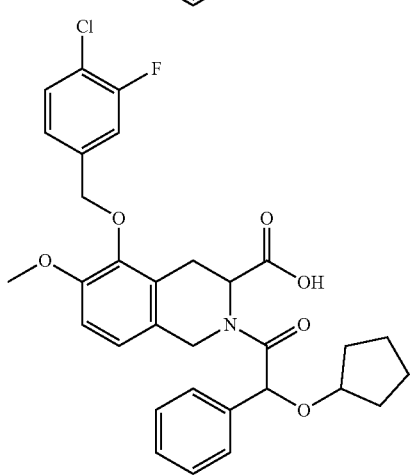

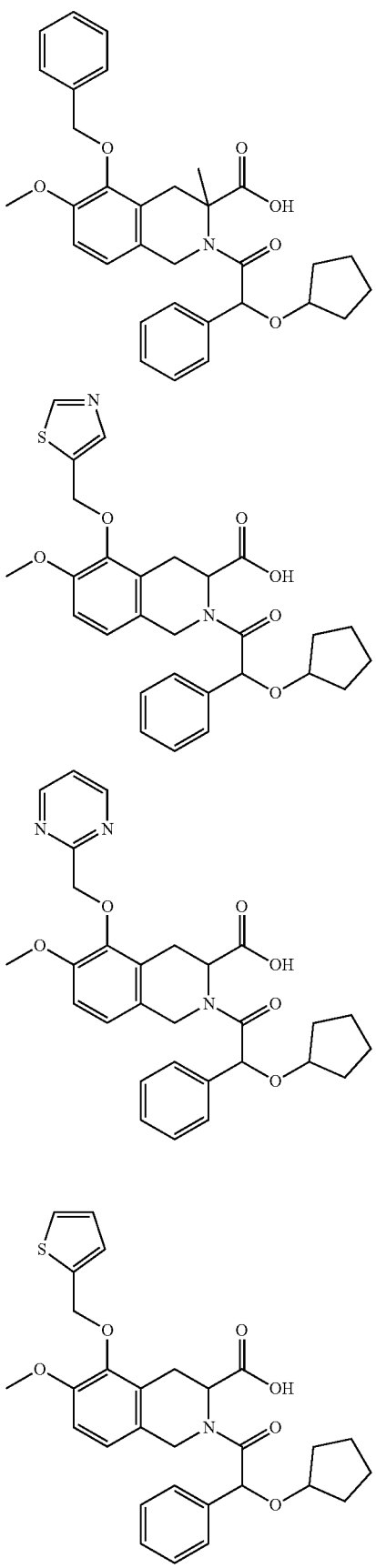
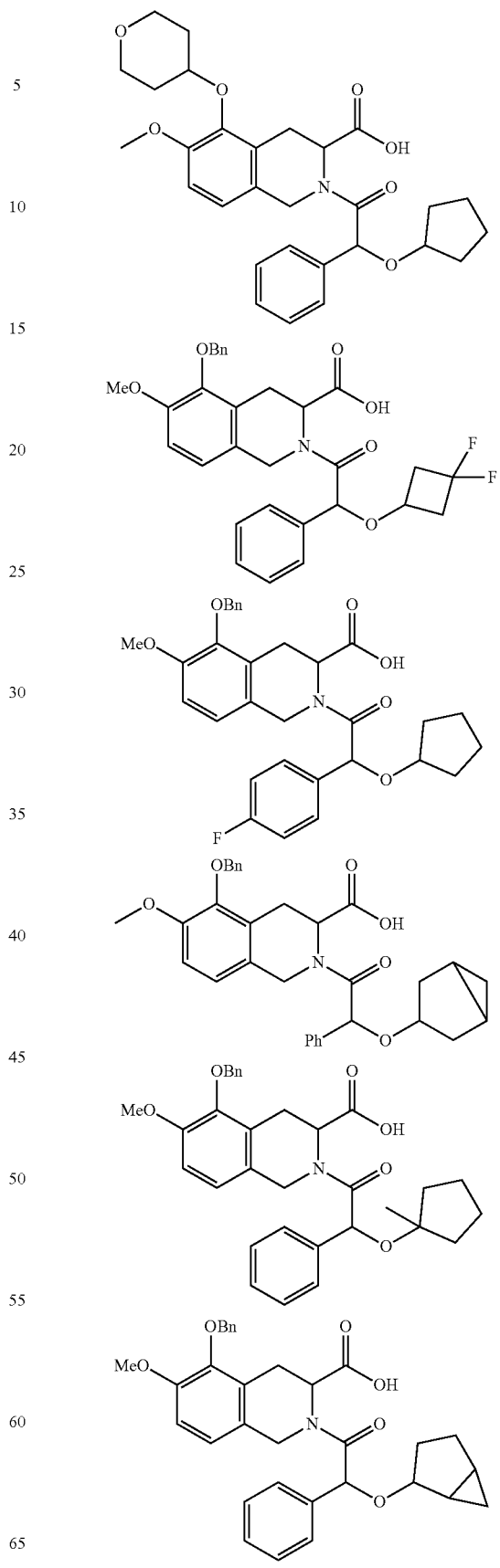

225
-continued
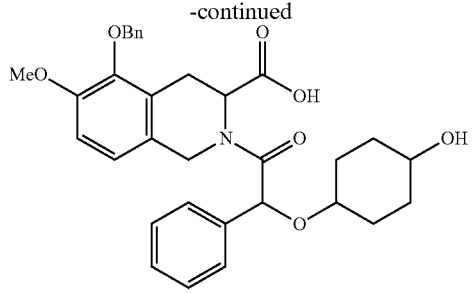
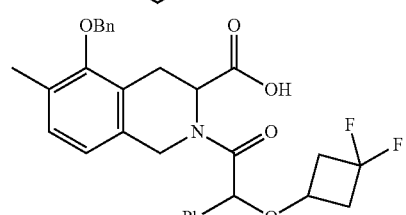
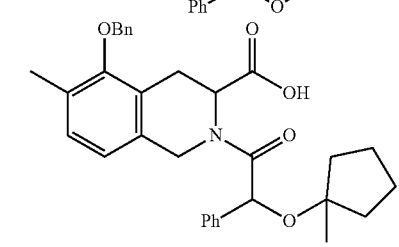
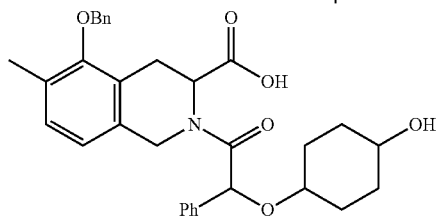
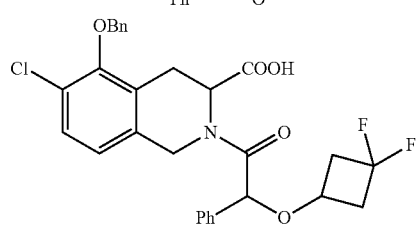
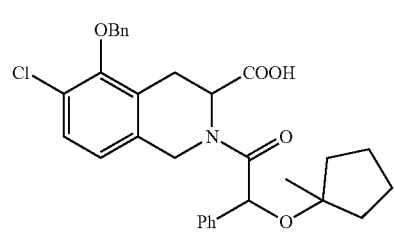
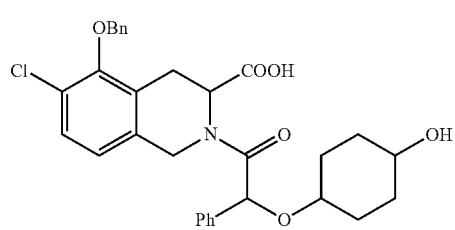
226
-continued
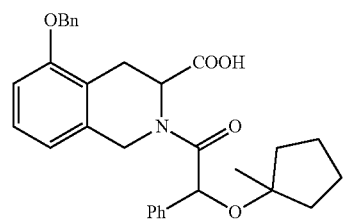
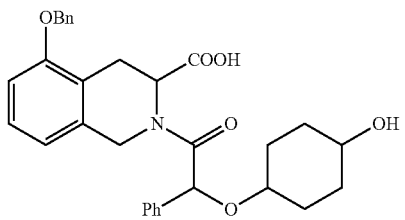
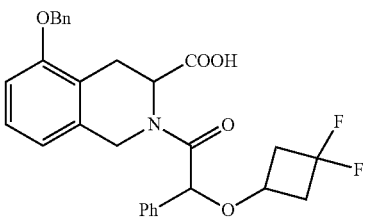
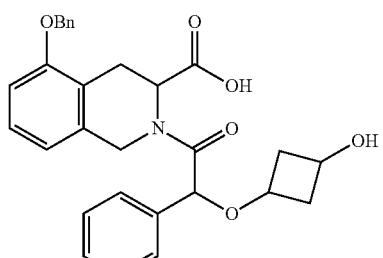
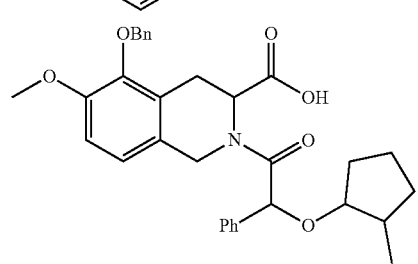
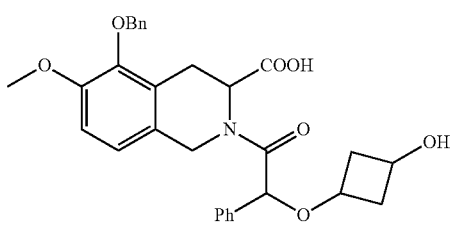
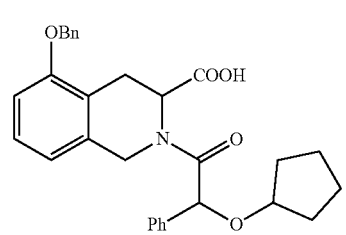

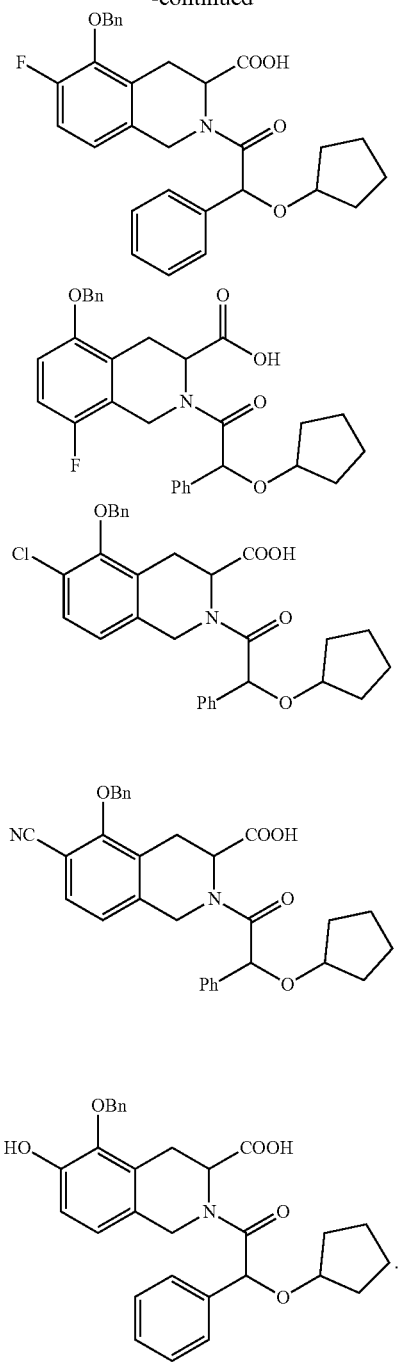
19. The compound according to claim 18, which is selected from
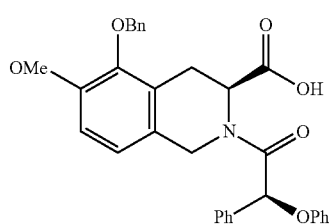
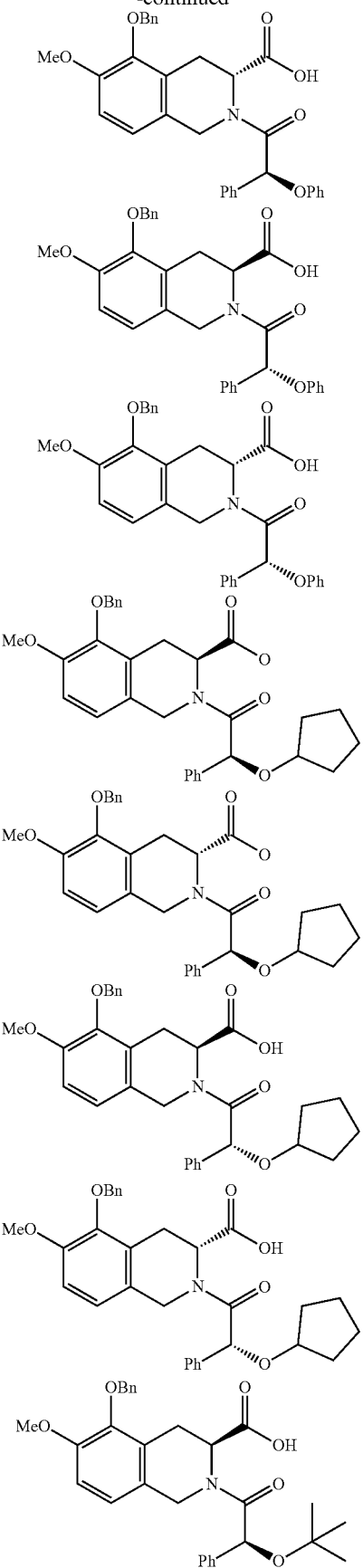

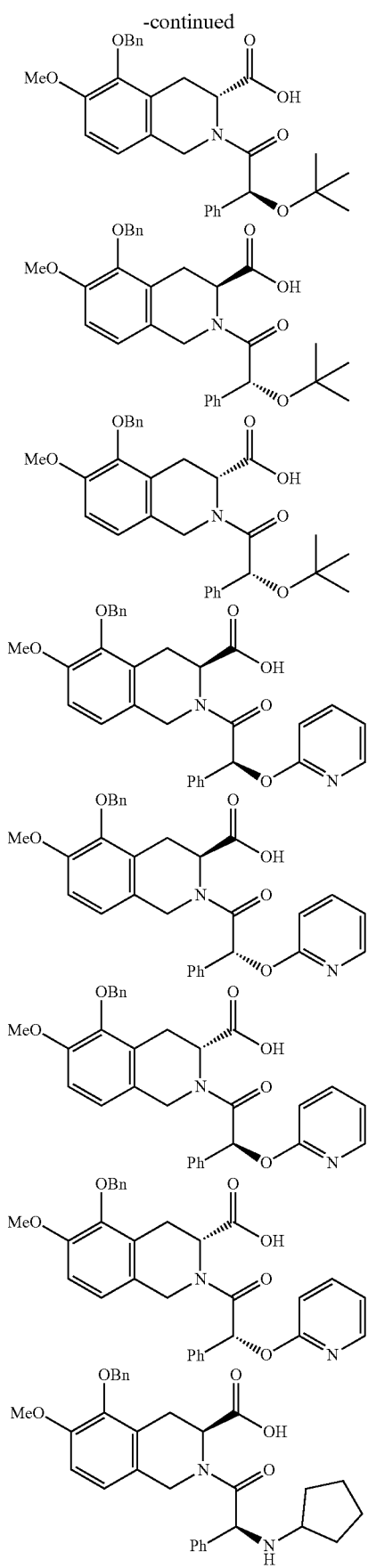
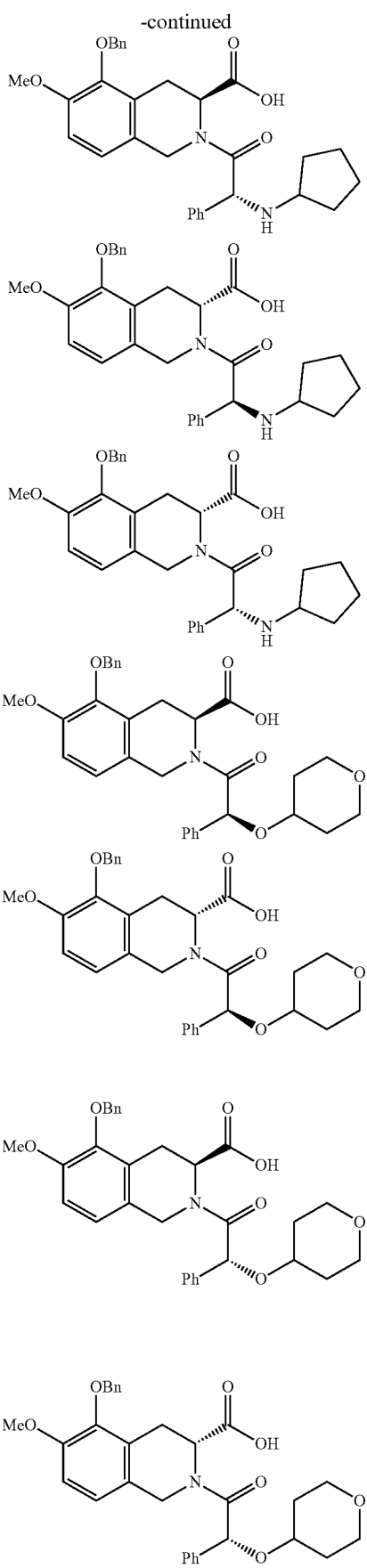

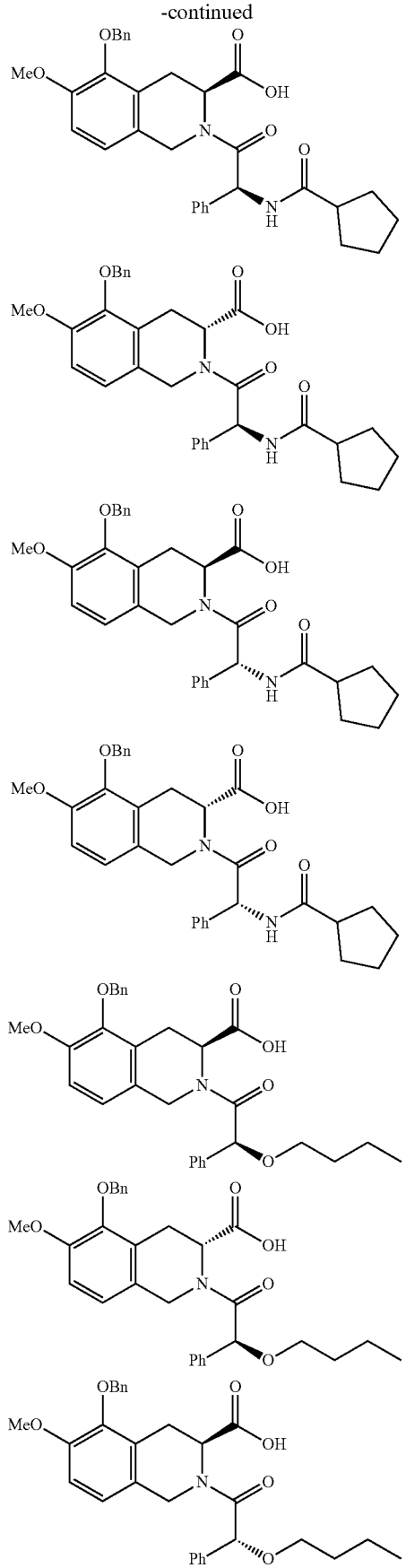
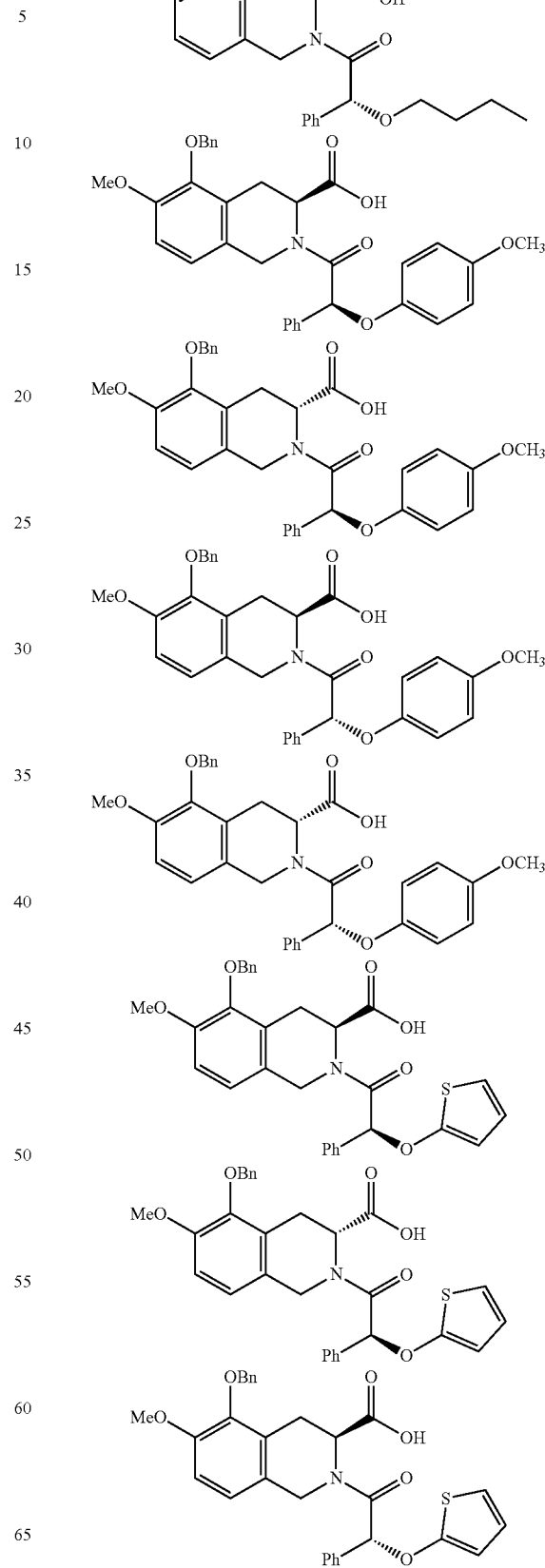

233
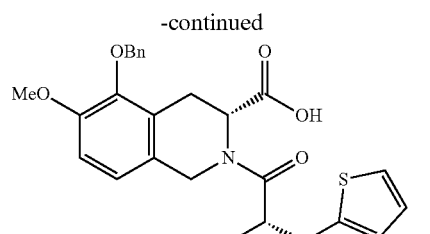
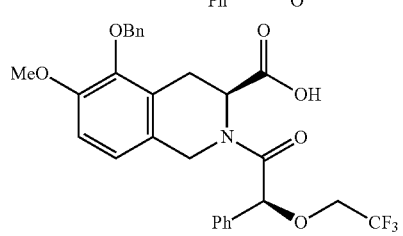
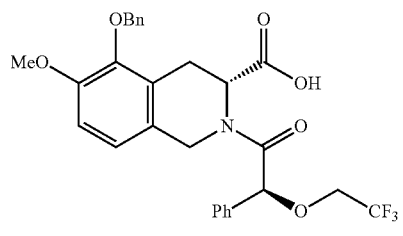
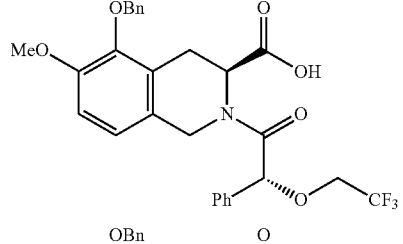
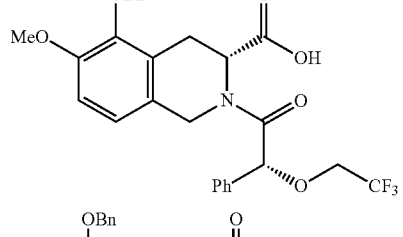
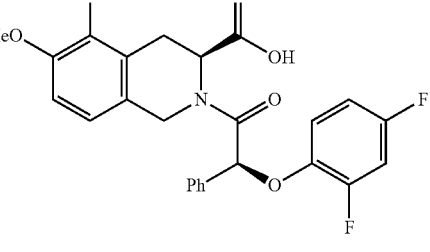
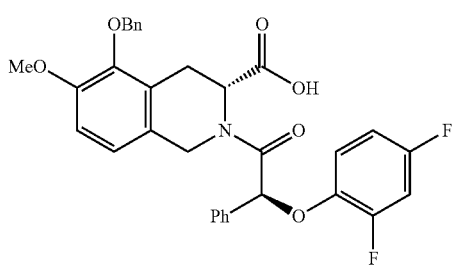
234
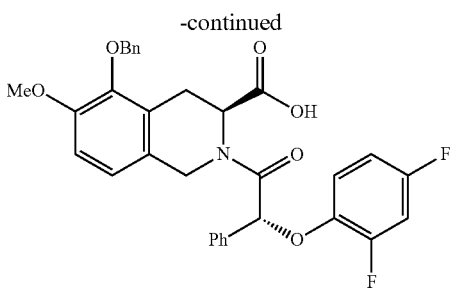
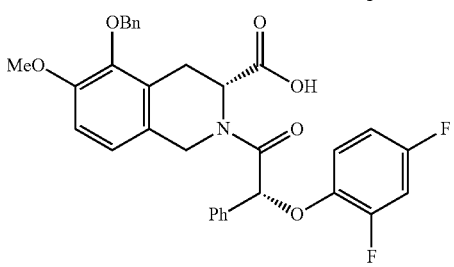
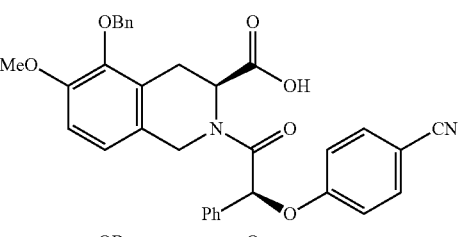
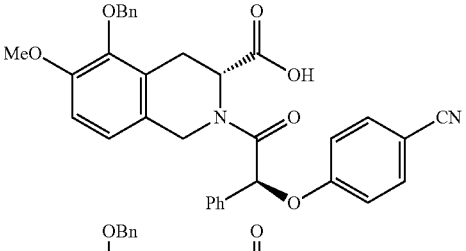
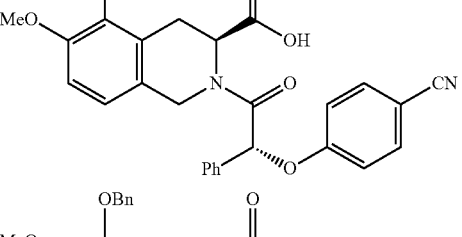
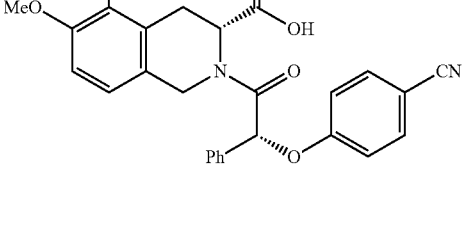
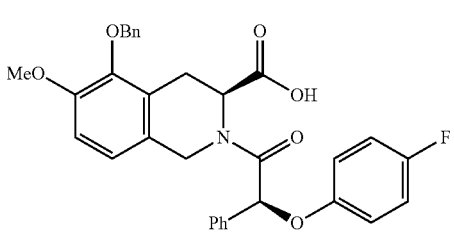

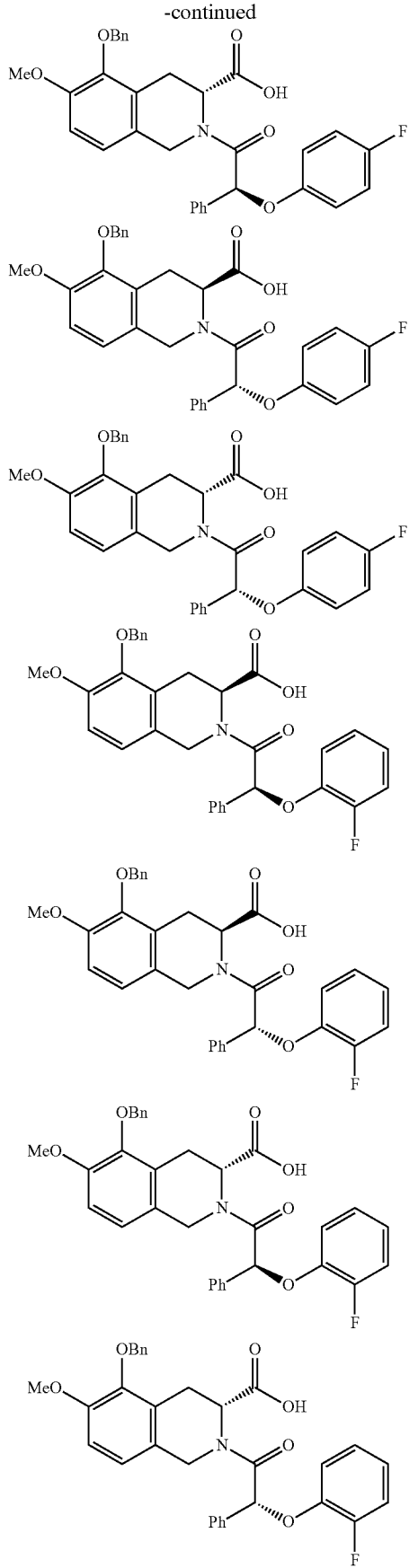
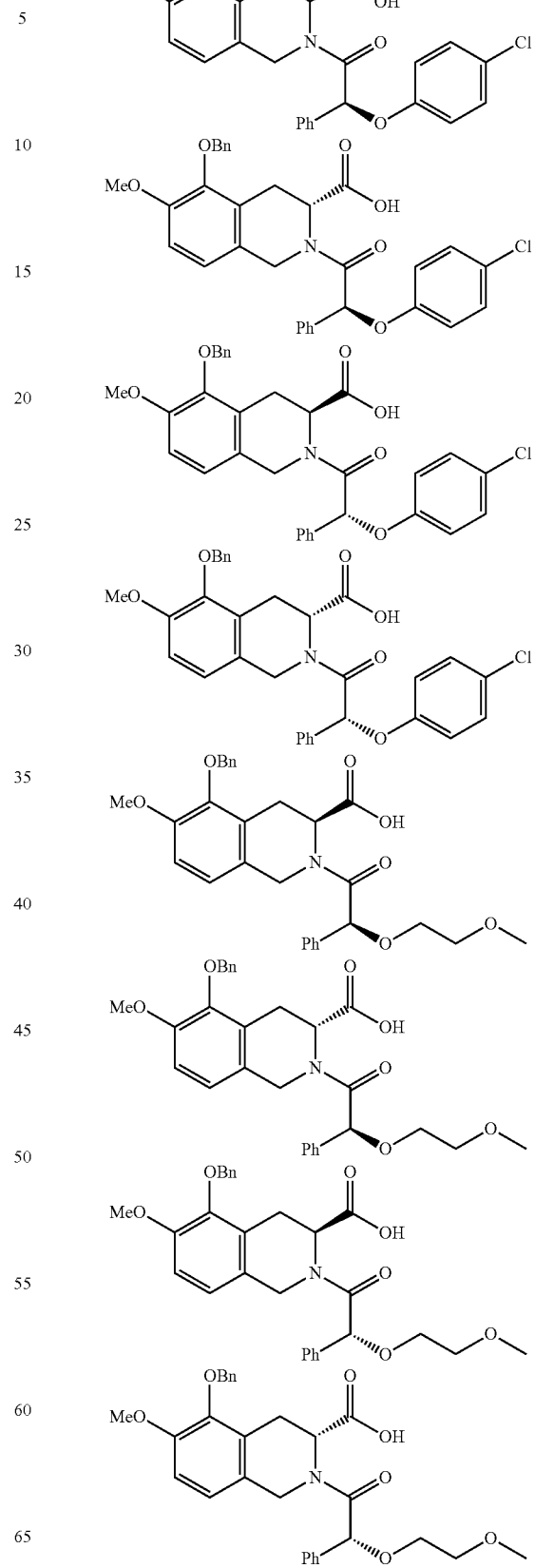

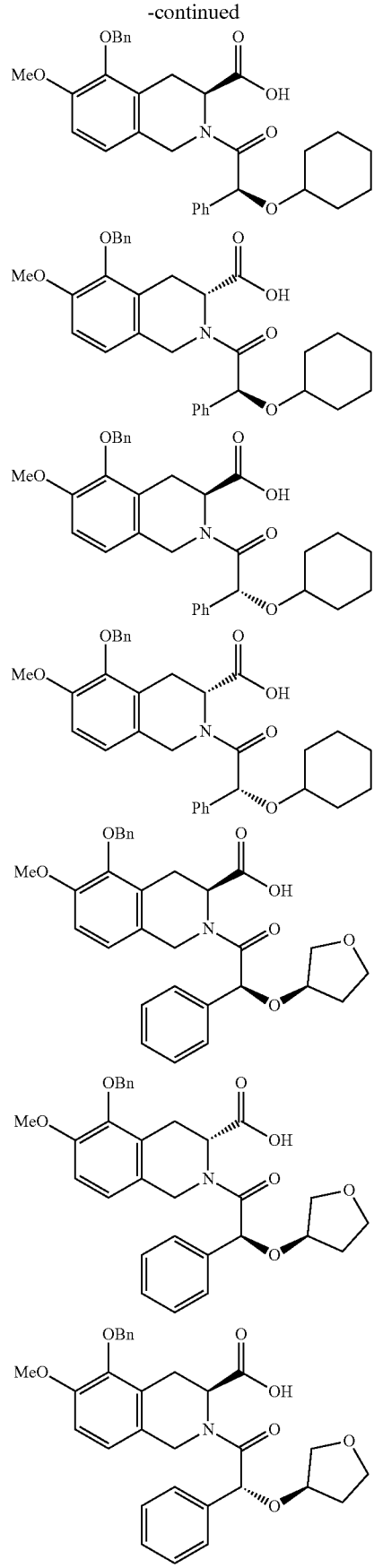
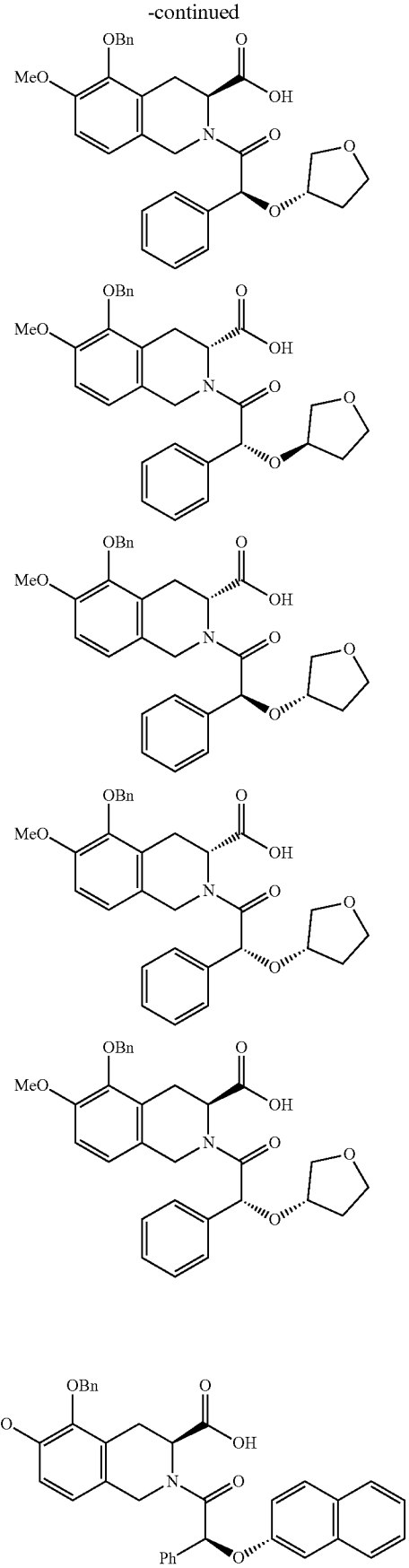

-continued
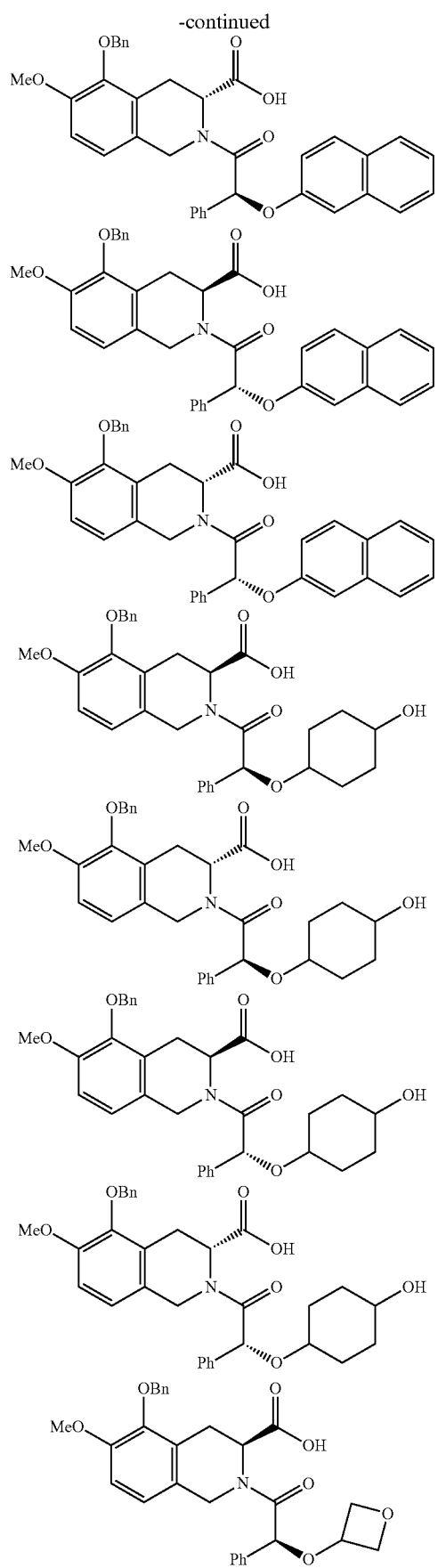
-continued
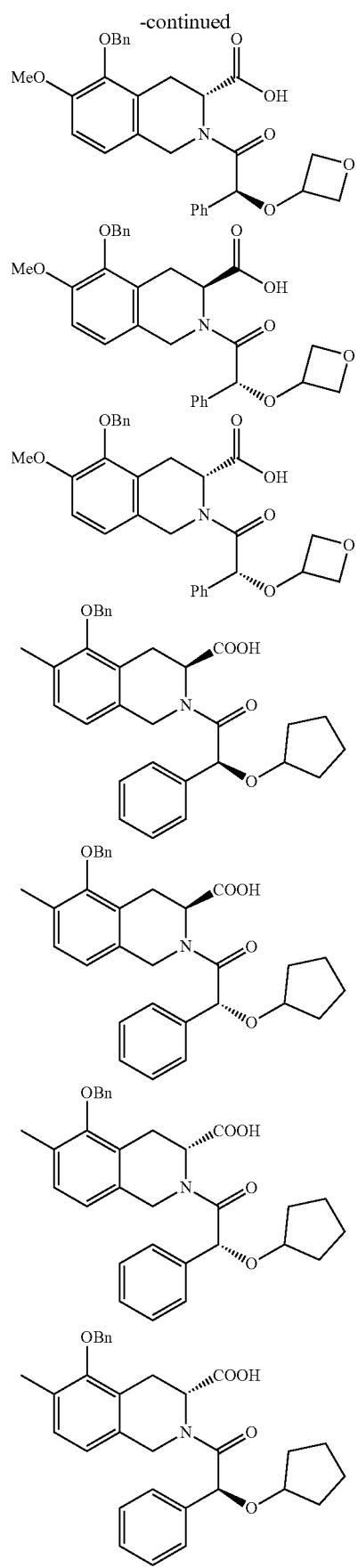

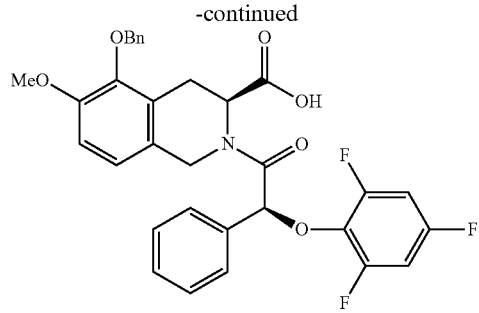
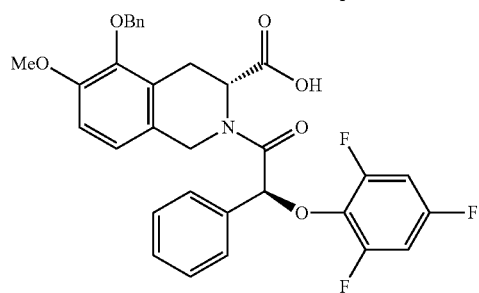
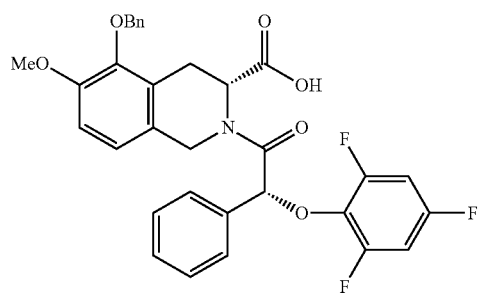
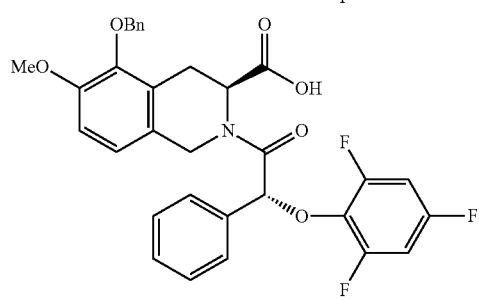
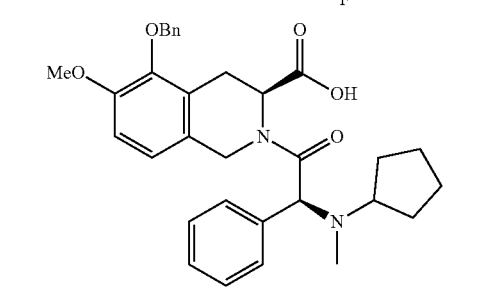
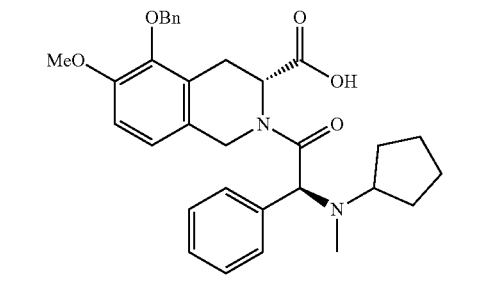
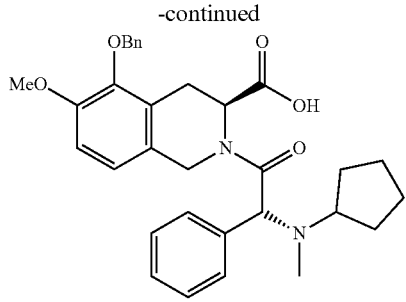
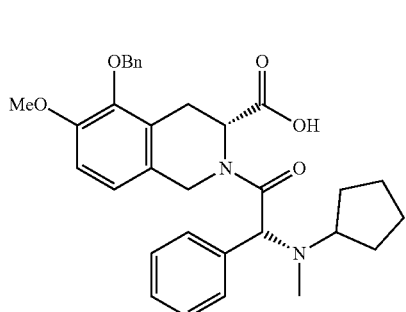
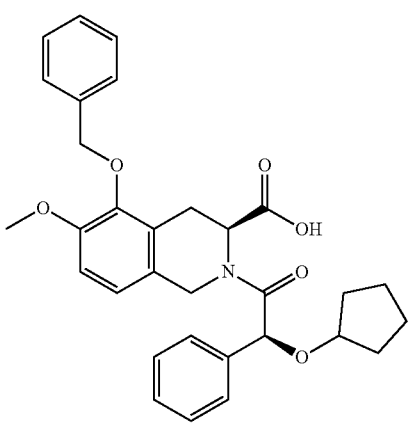
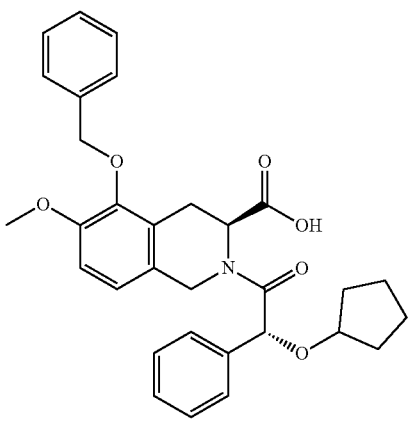

243
-continued
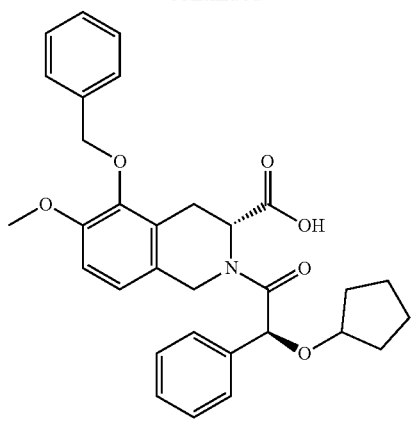
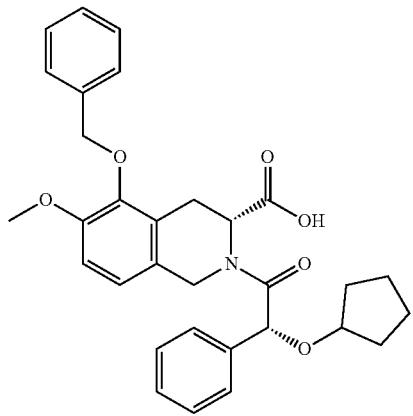
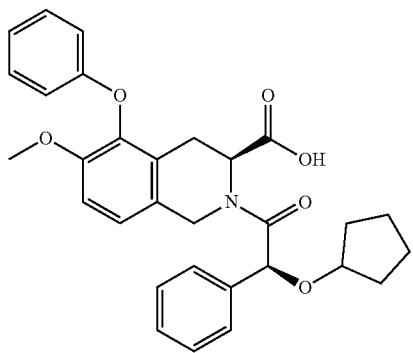
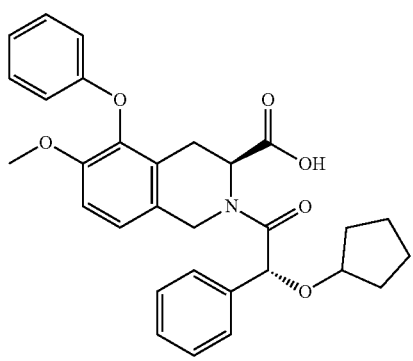
244
-continued
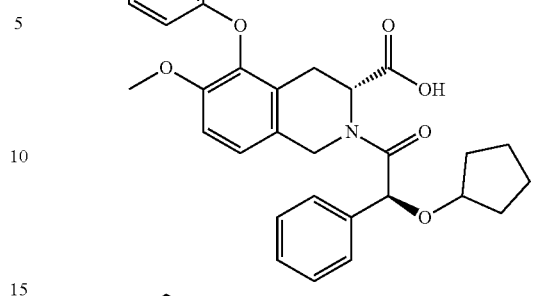
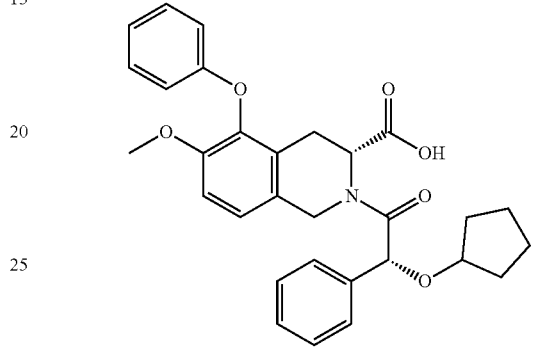
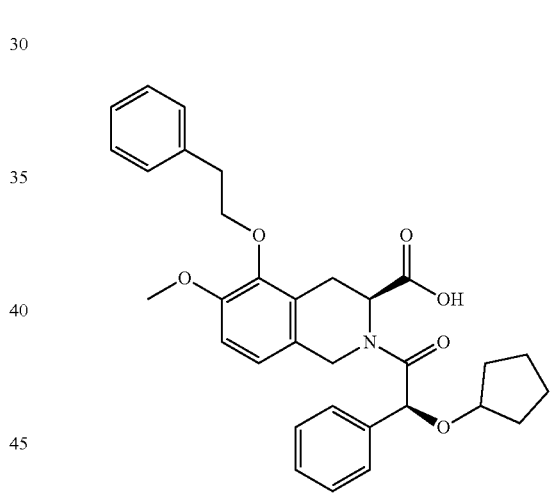

245
-continued
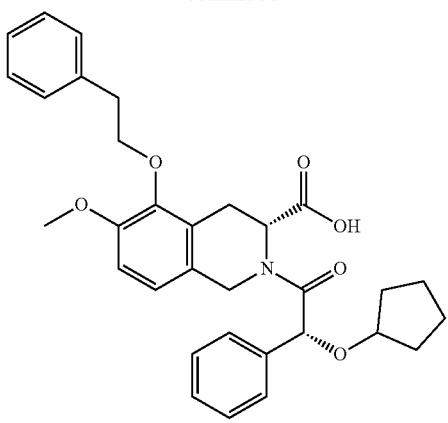
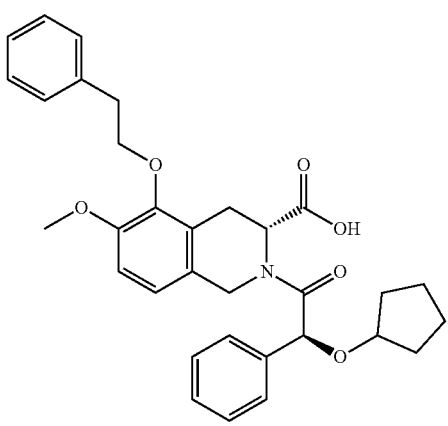
246
-continued
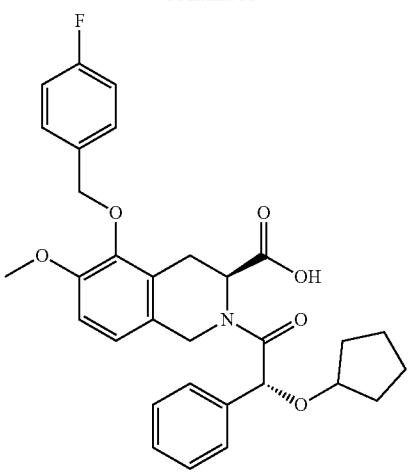
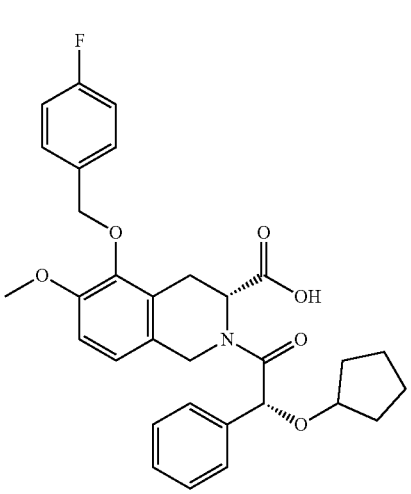
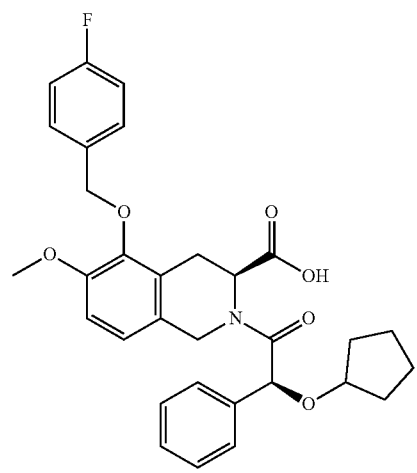
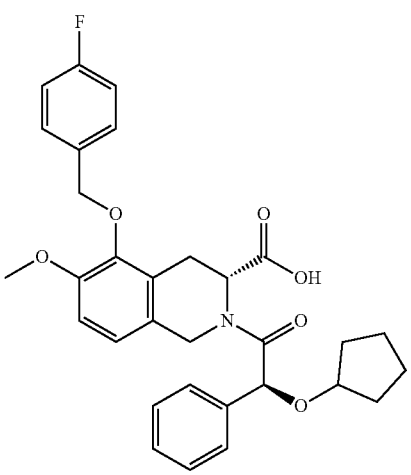

247
-continued
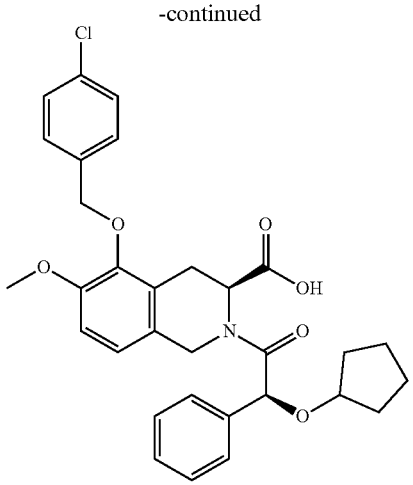
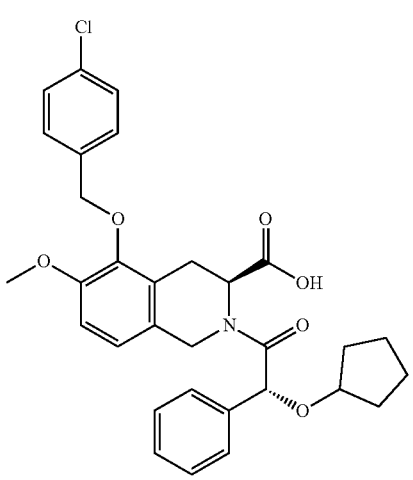
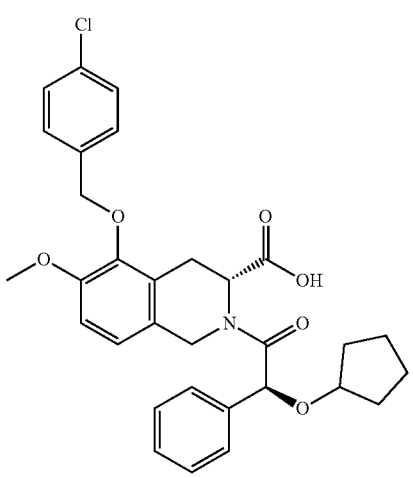
248
-continued
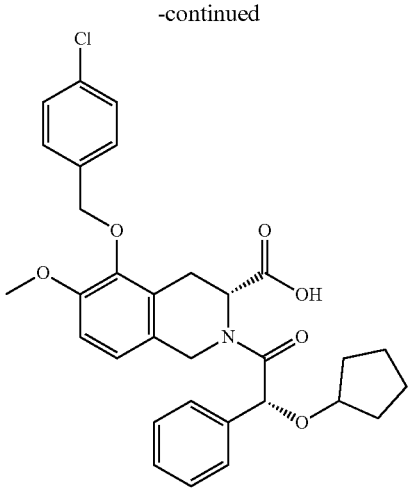
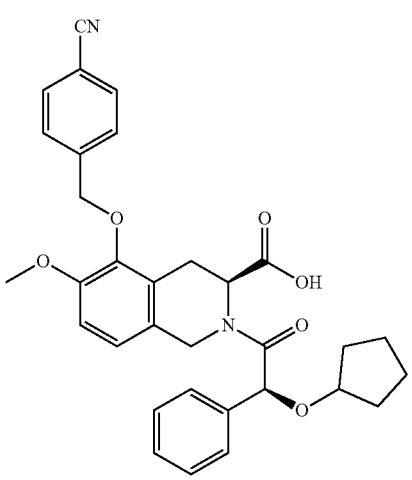
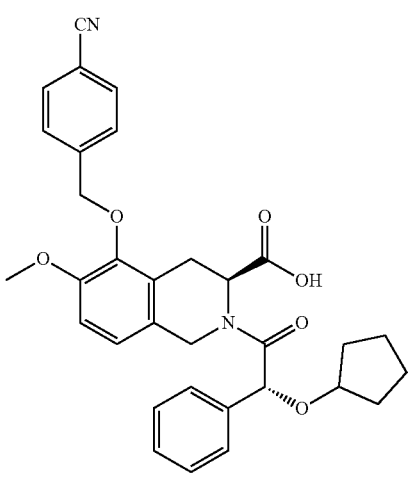

249
-continued
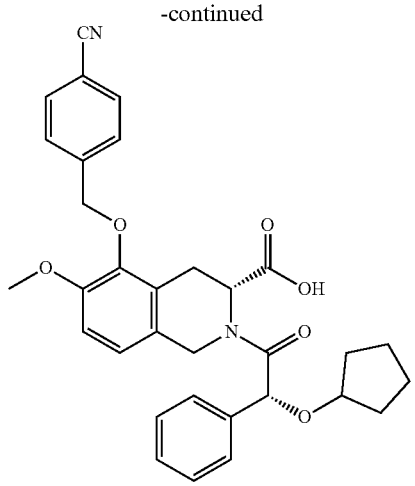
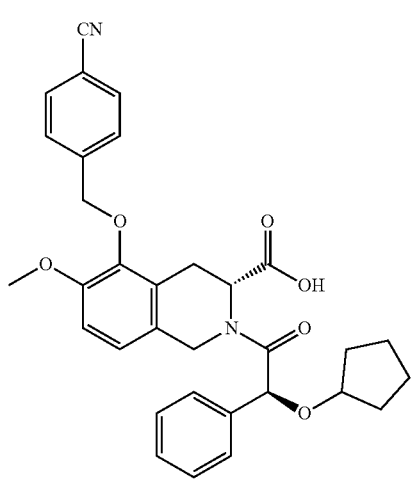
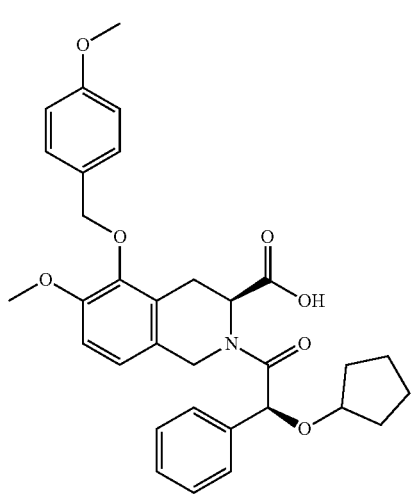
250
-continued
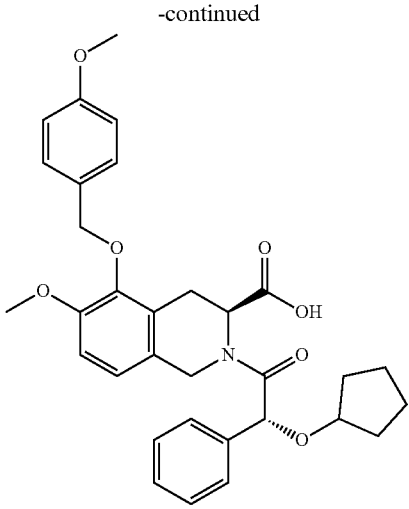
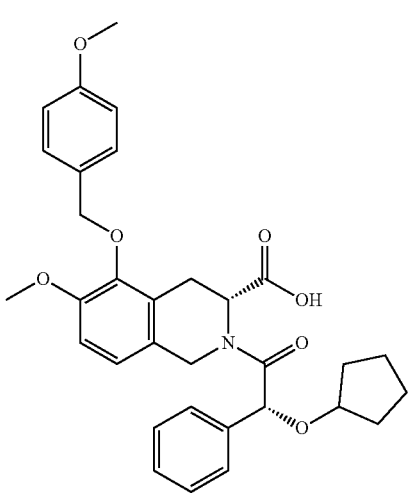
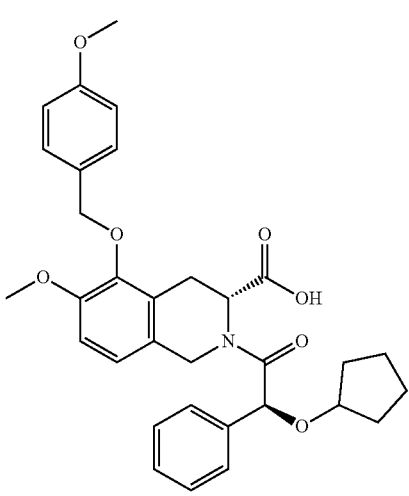

251
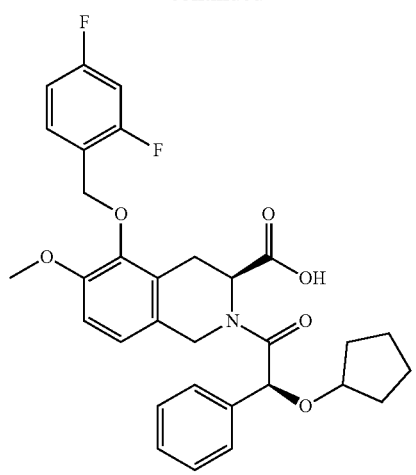
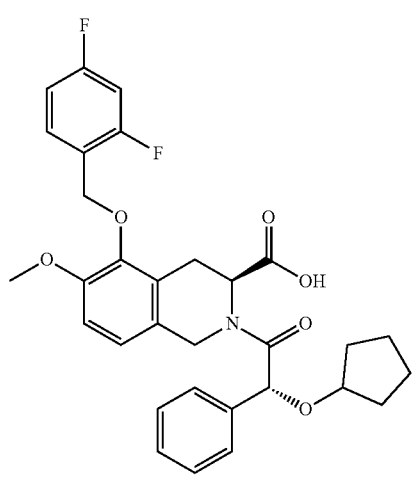
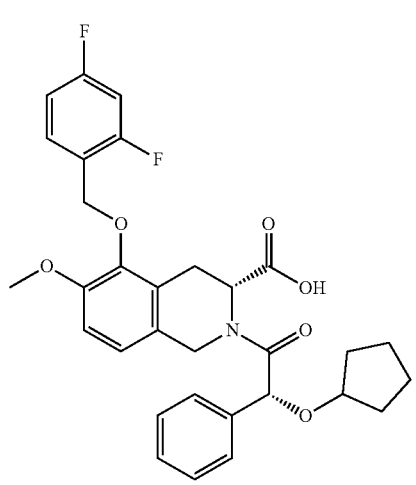
252
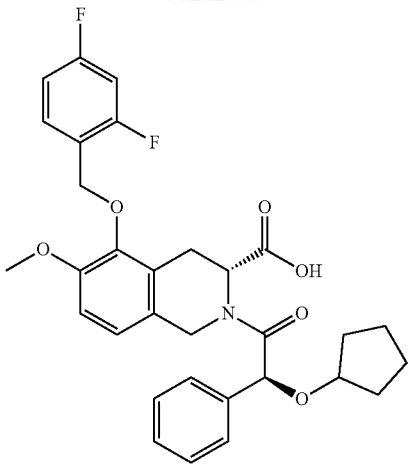
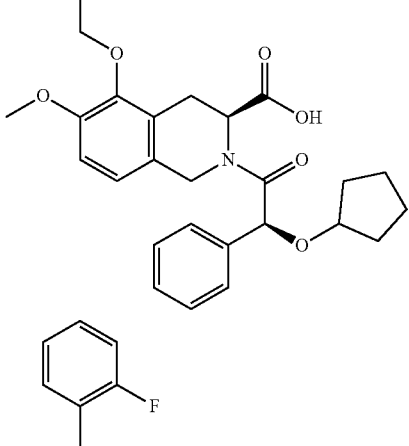
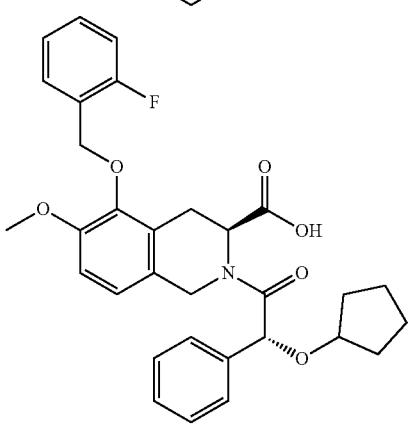
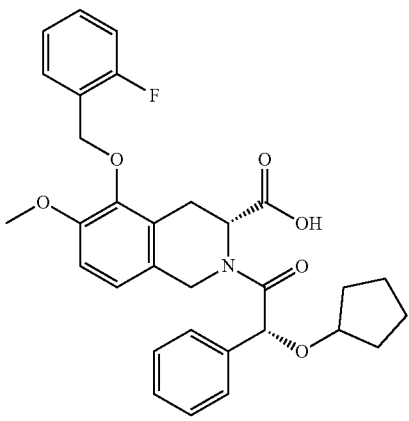

253
-continued
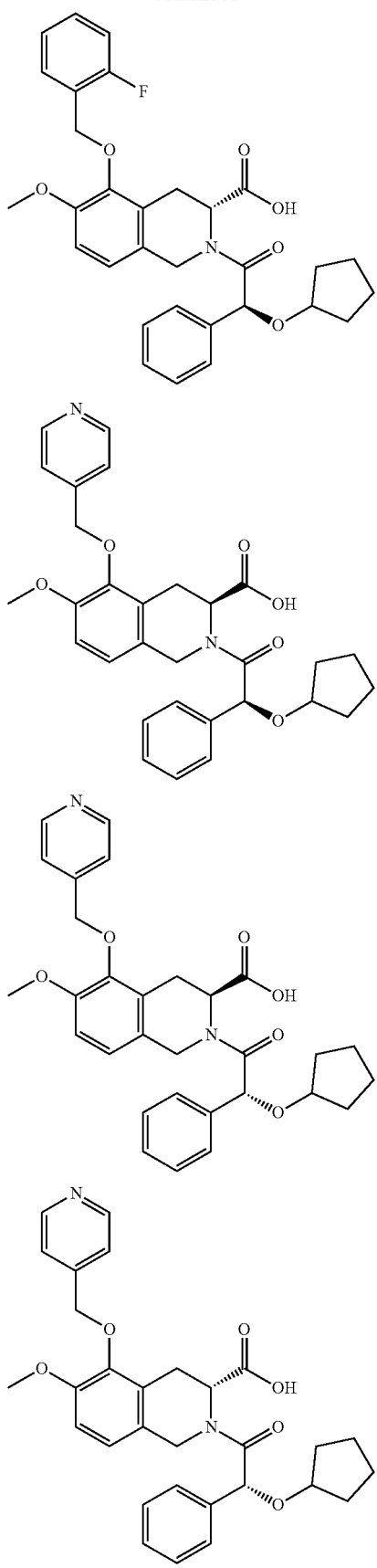
254
-continued
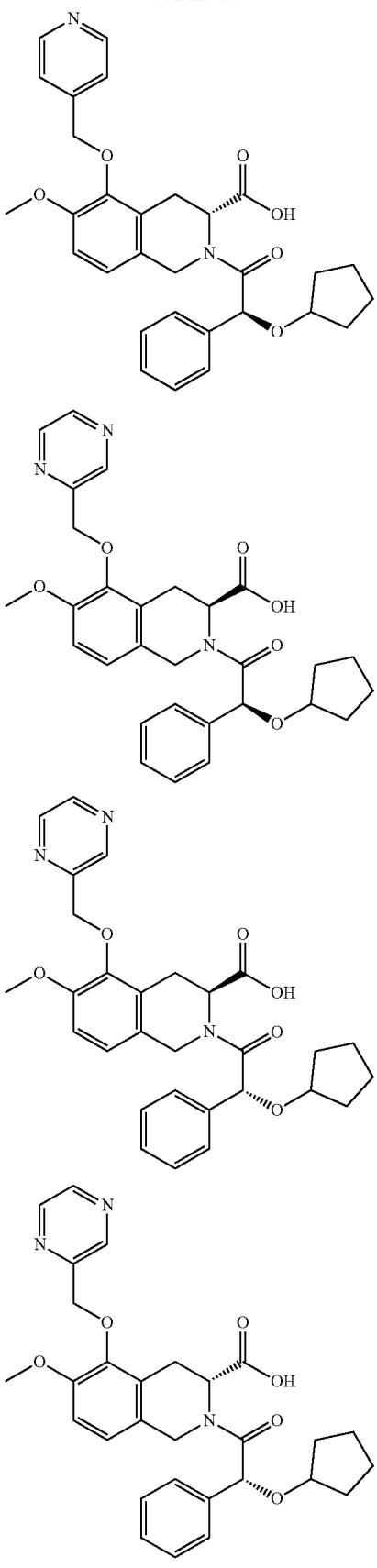

255
-continued
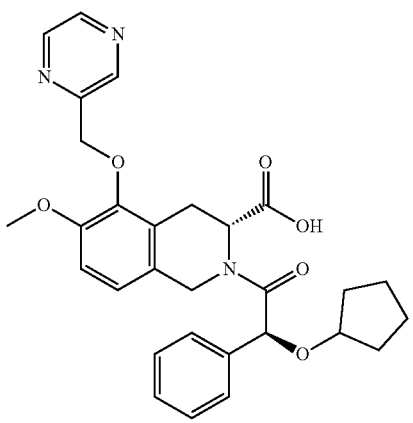
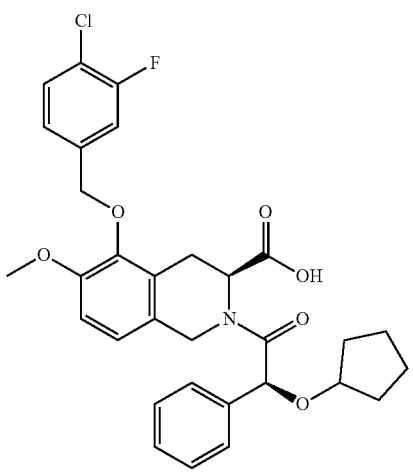
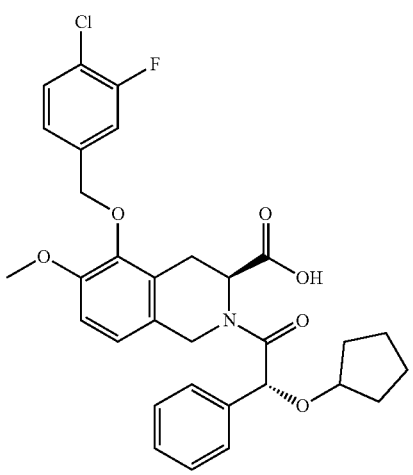
256
-continued
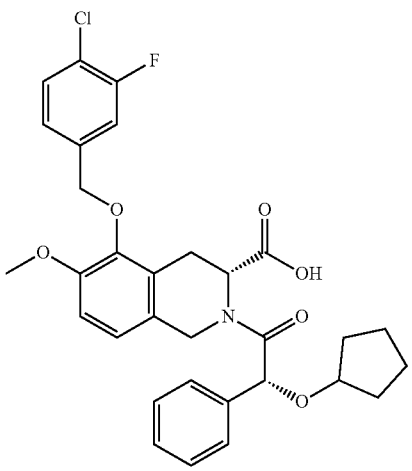
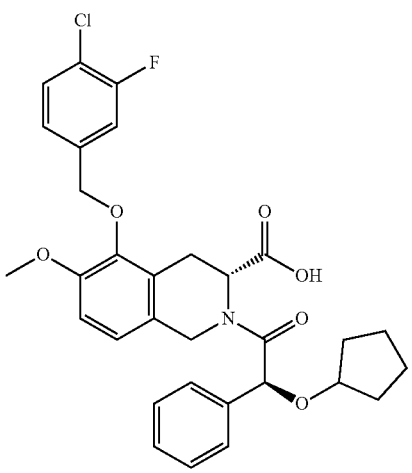
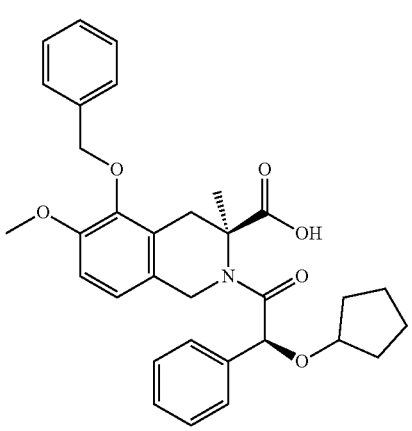

257
-continued
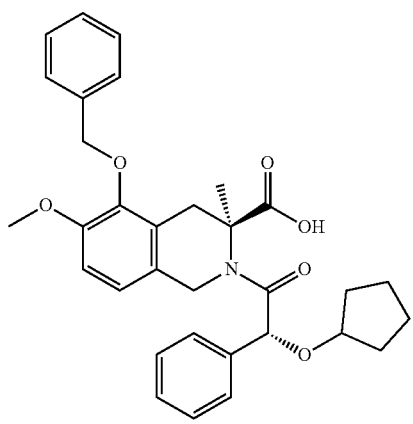
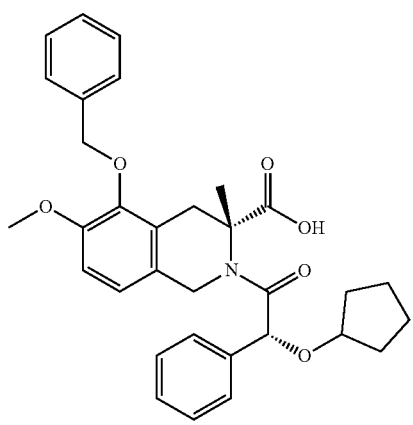
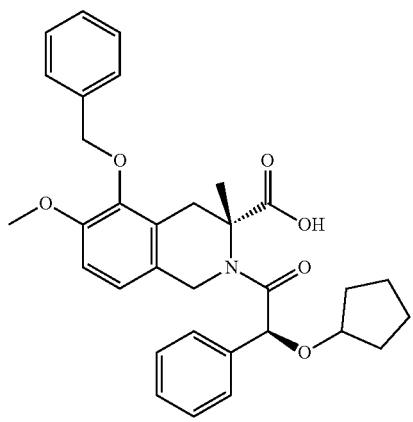
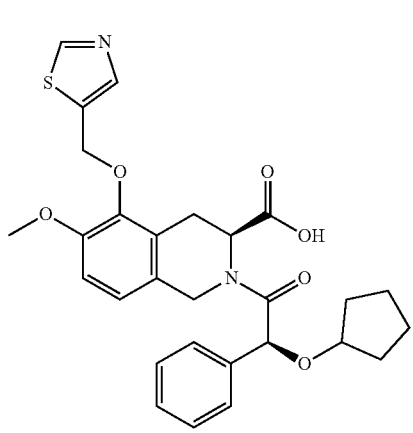
258
-continued
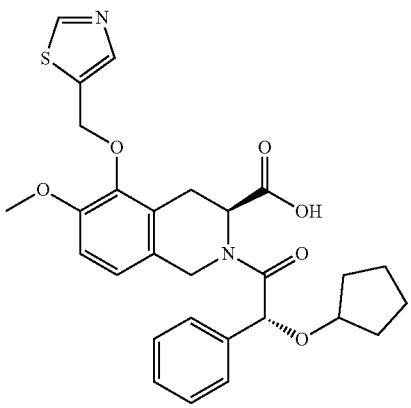
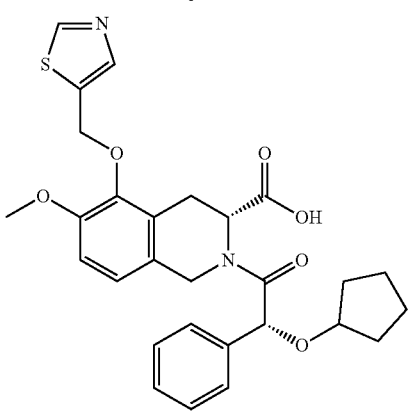
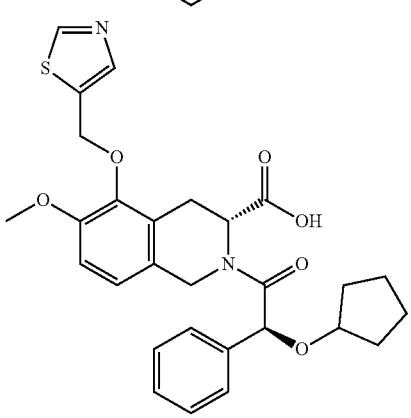
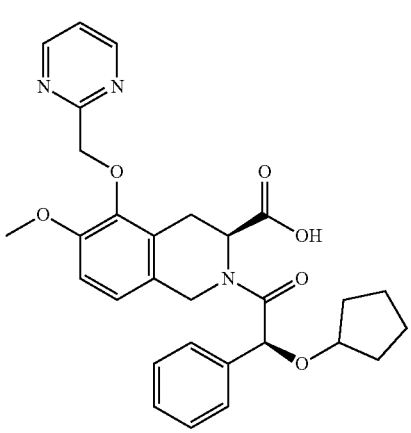

259
-continued
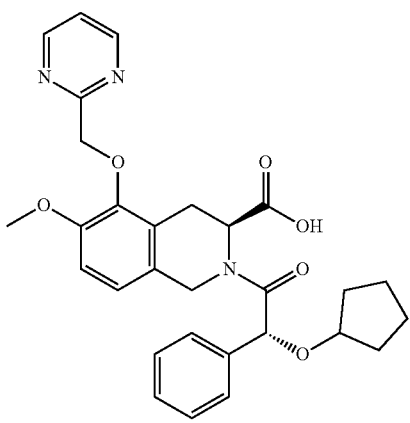
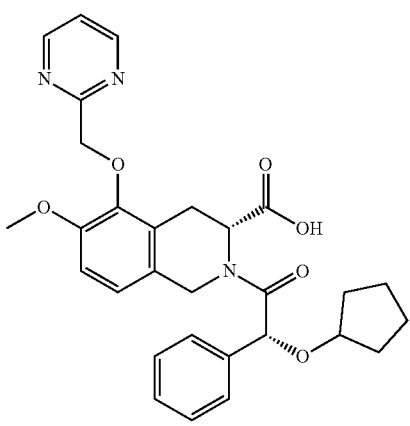
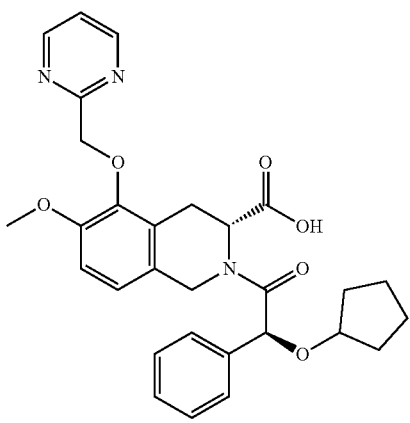
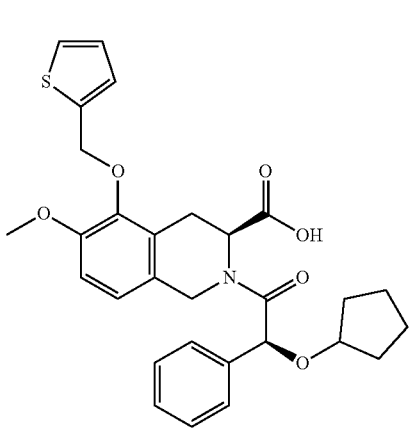
260
-continued
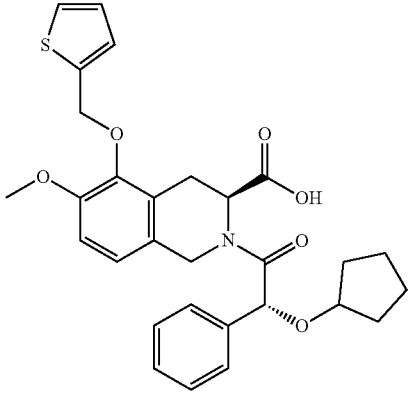
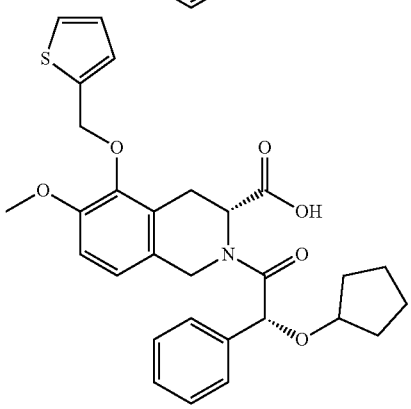
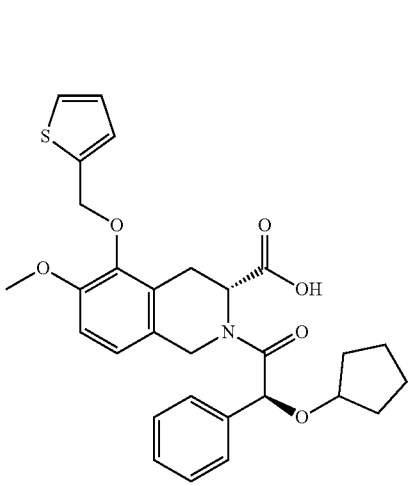
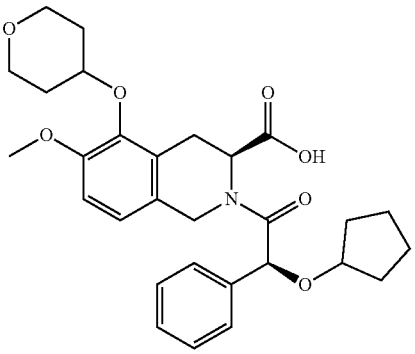

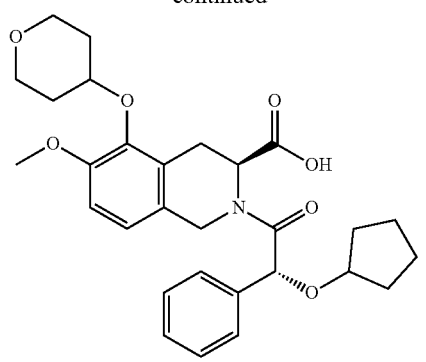
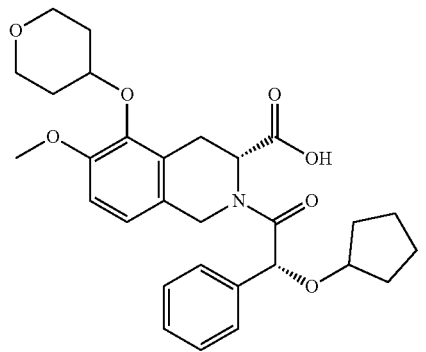
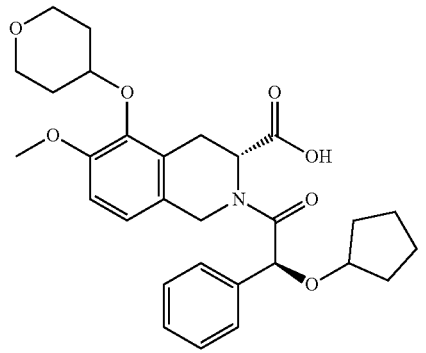
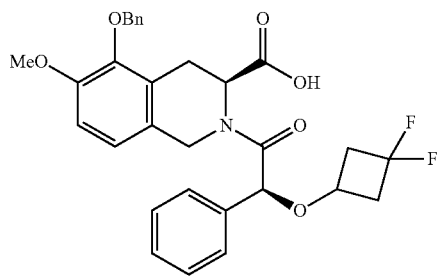
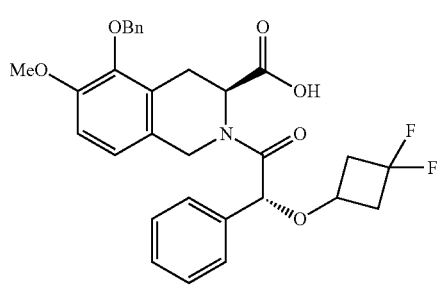
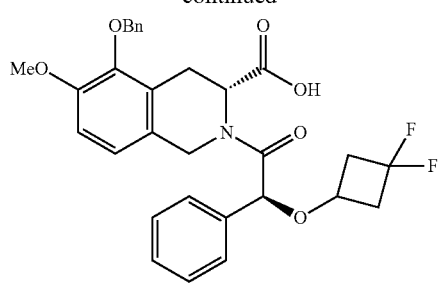
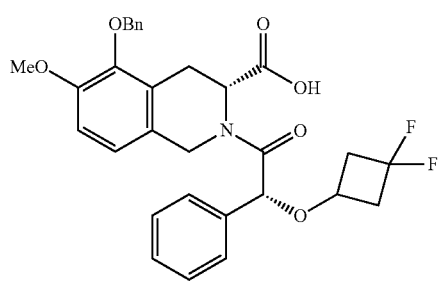
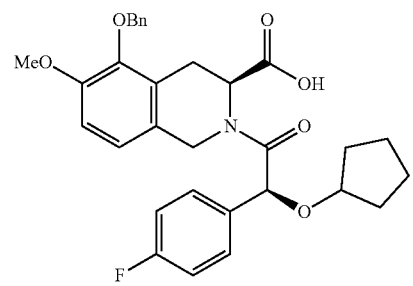
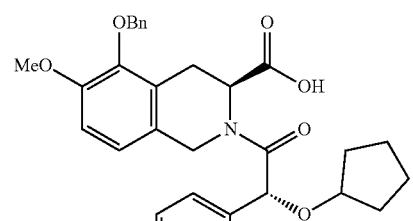 [SMILES: COc1ccc2c(c1OCc1ccccc1)C[C@@H](C(=O)O)N(C(=O)C(OC1CCCC1)c1ccccc1)C2]
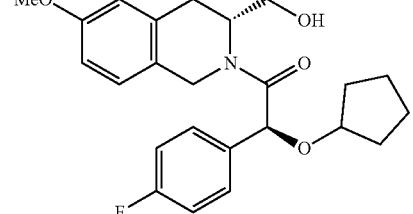
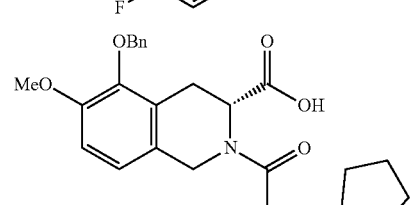
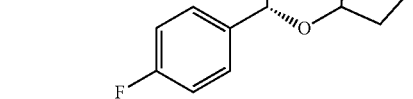

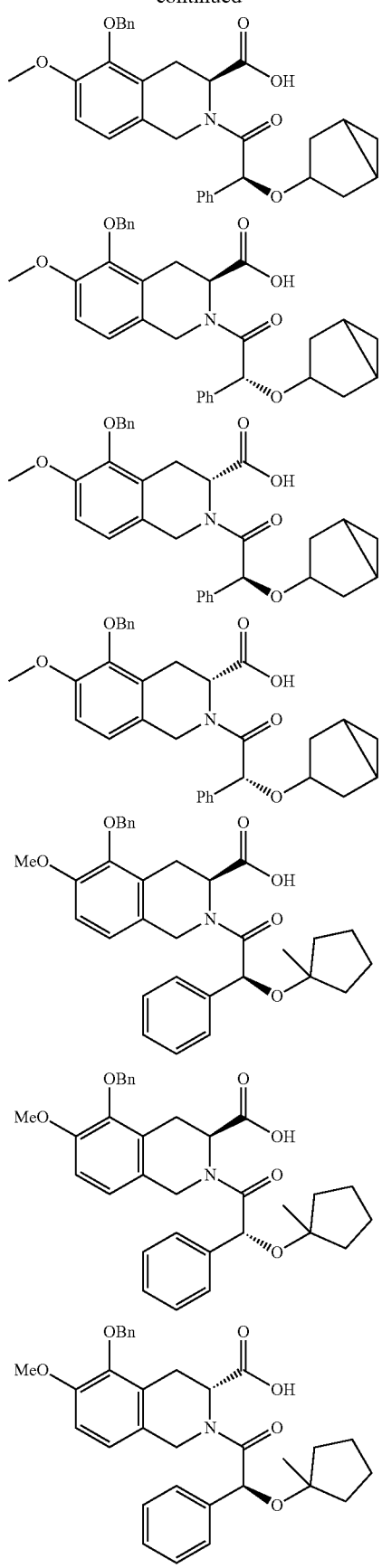
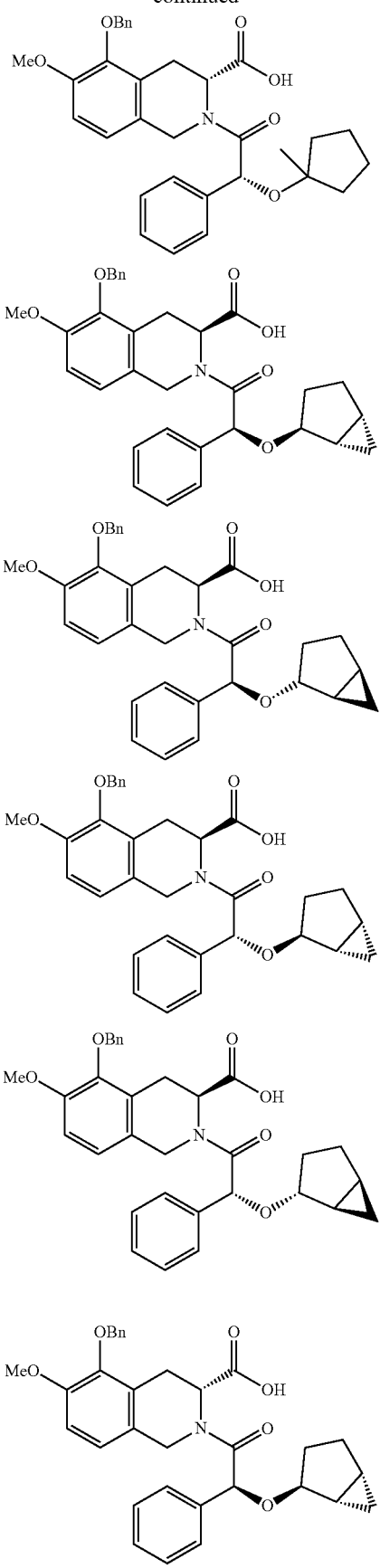

265
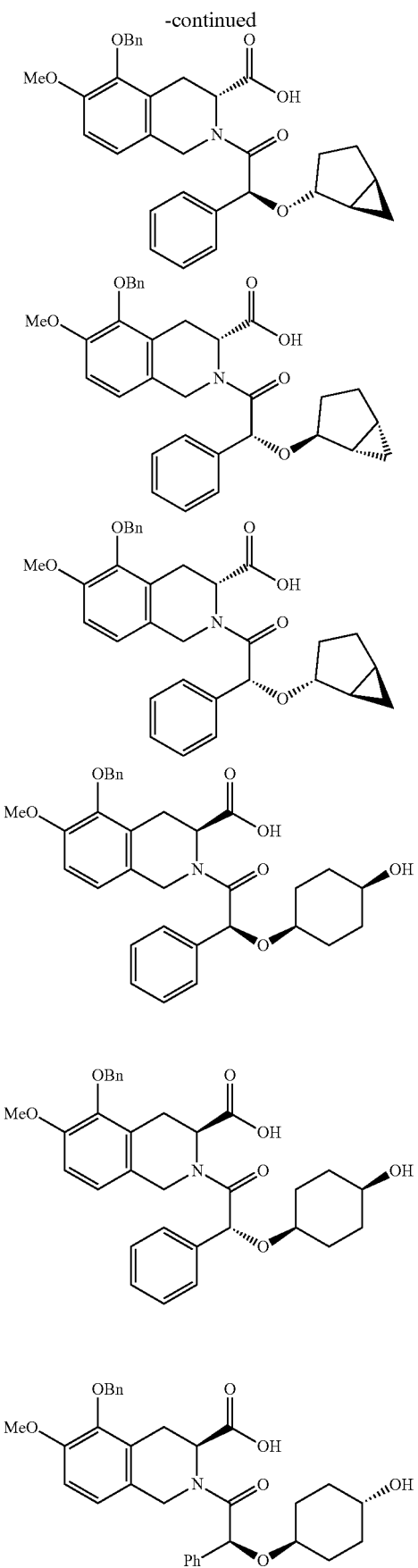
266
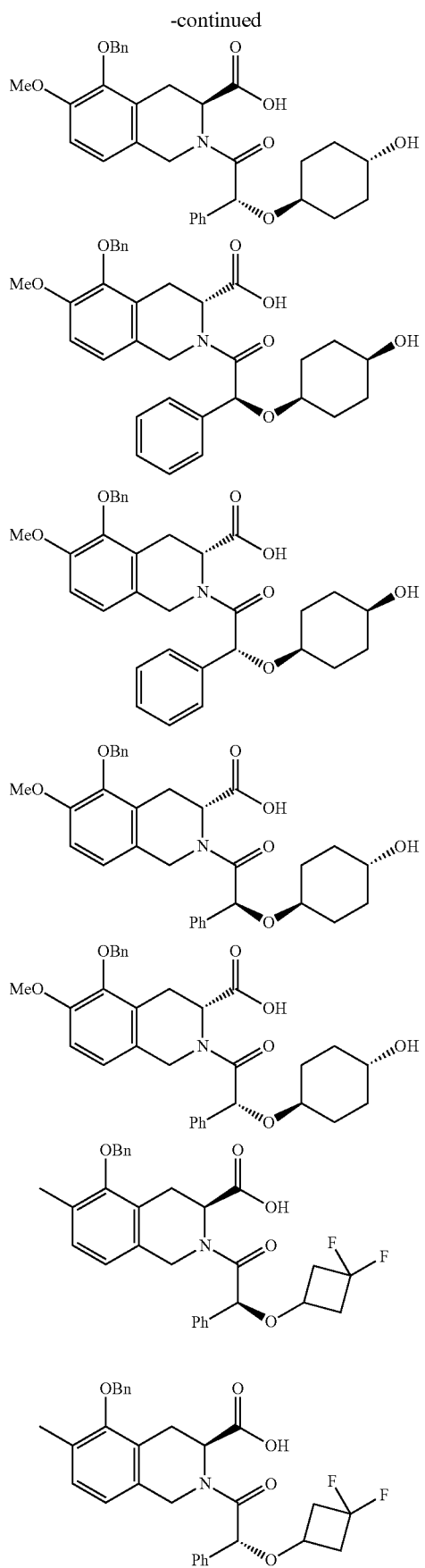

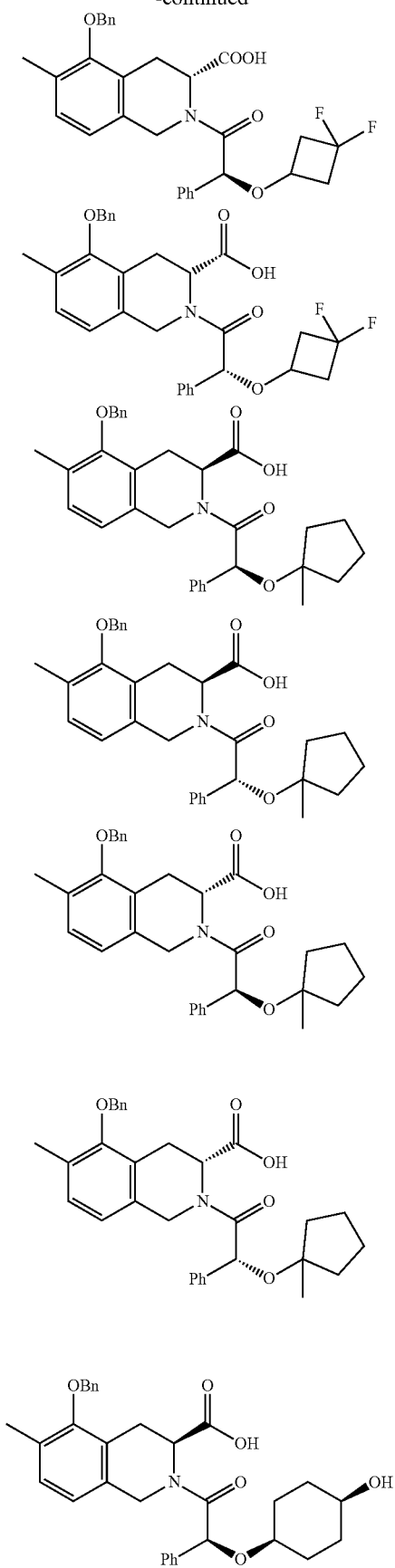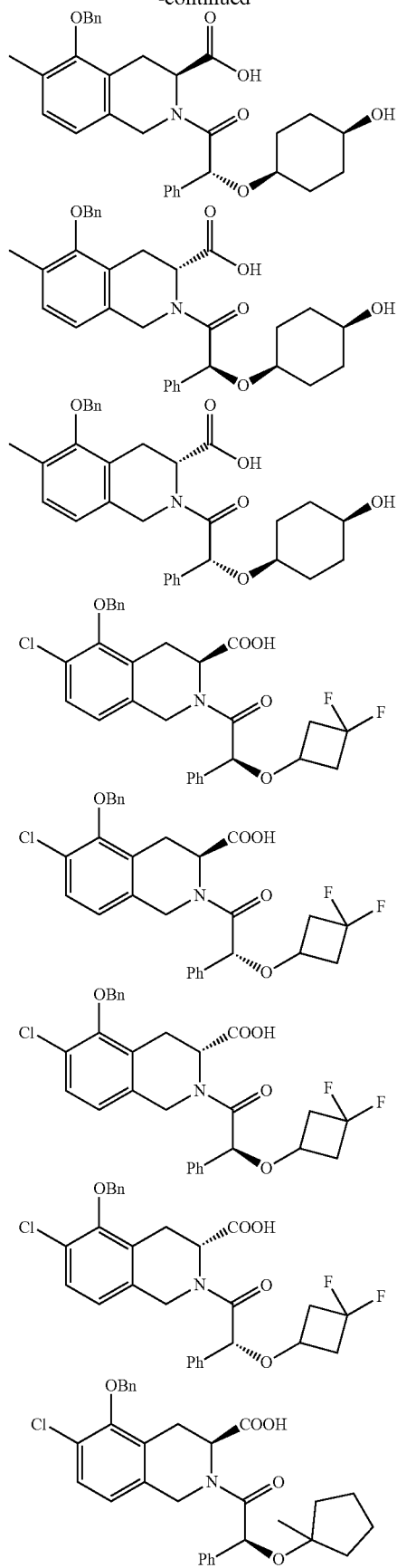

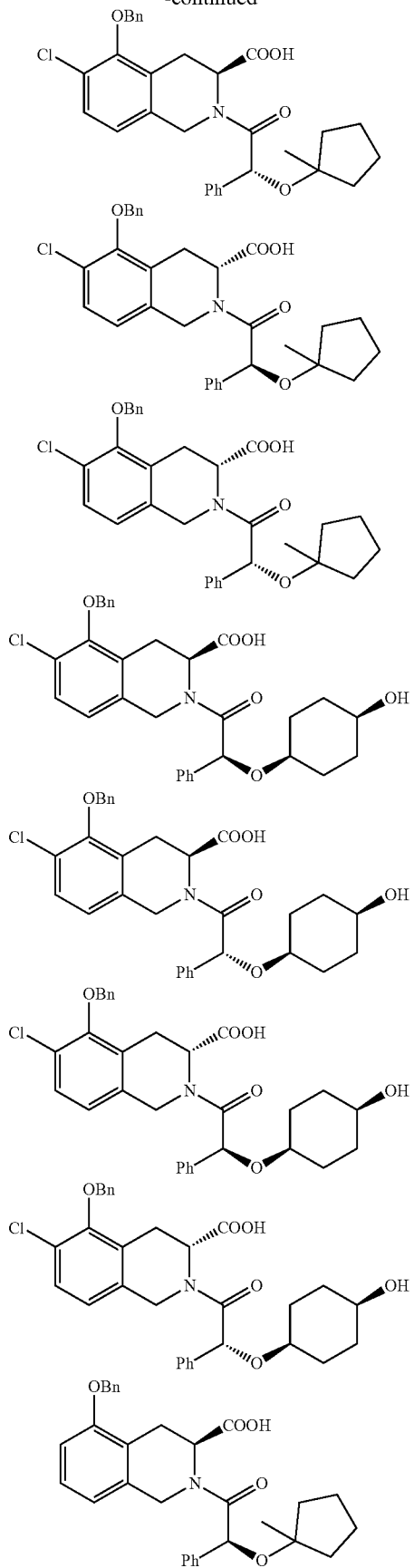
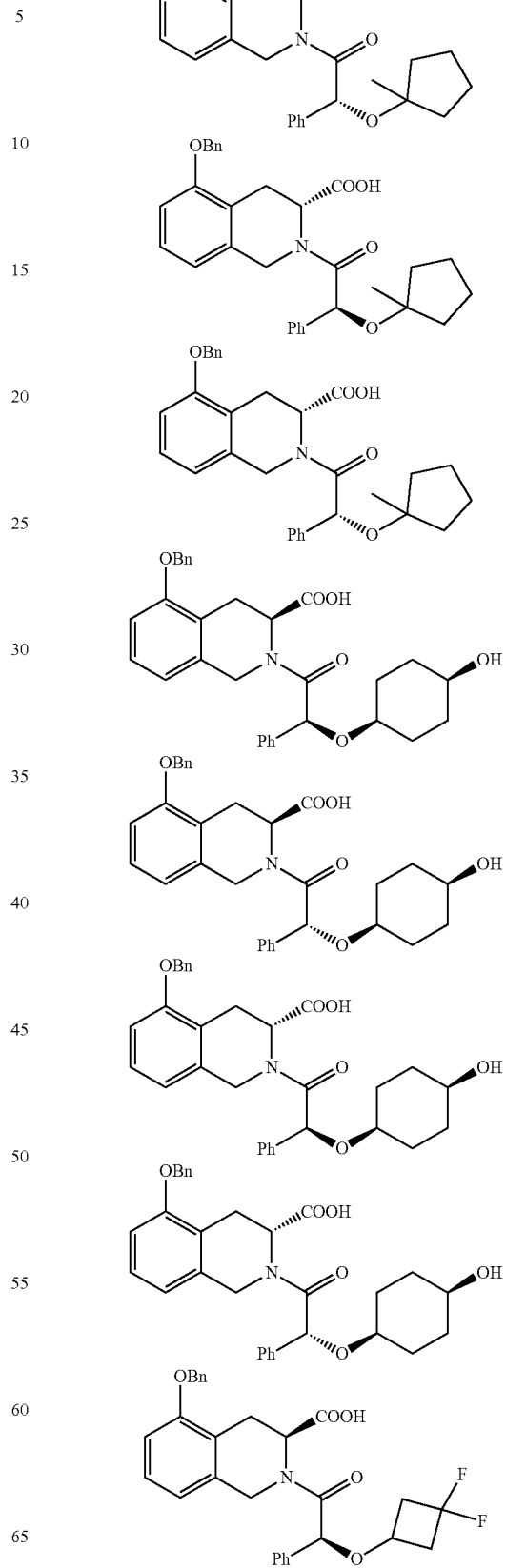

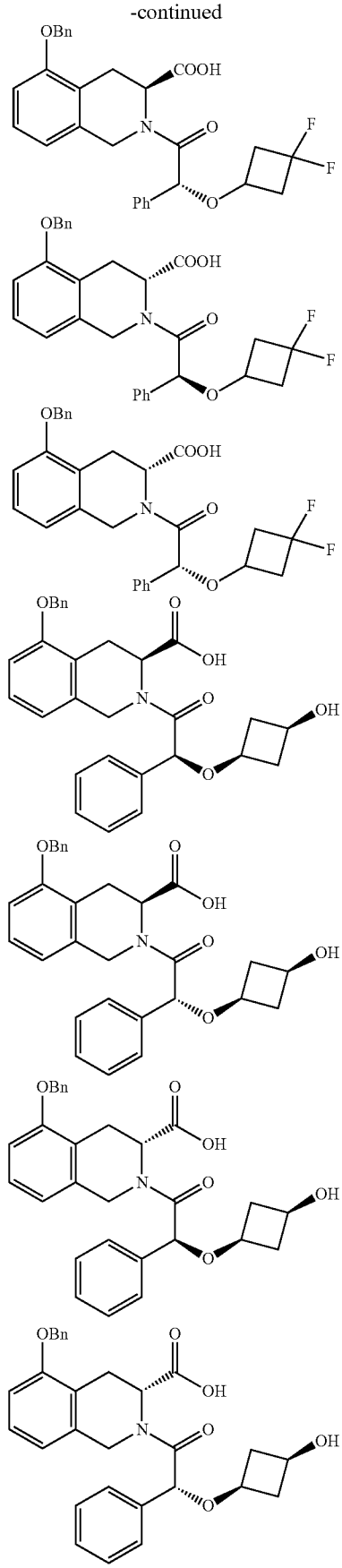
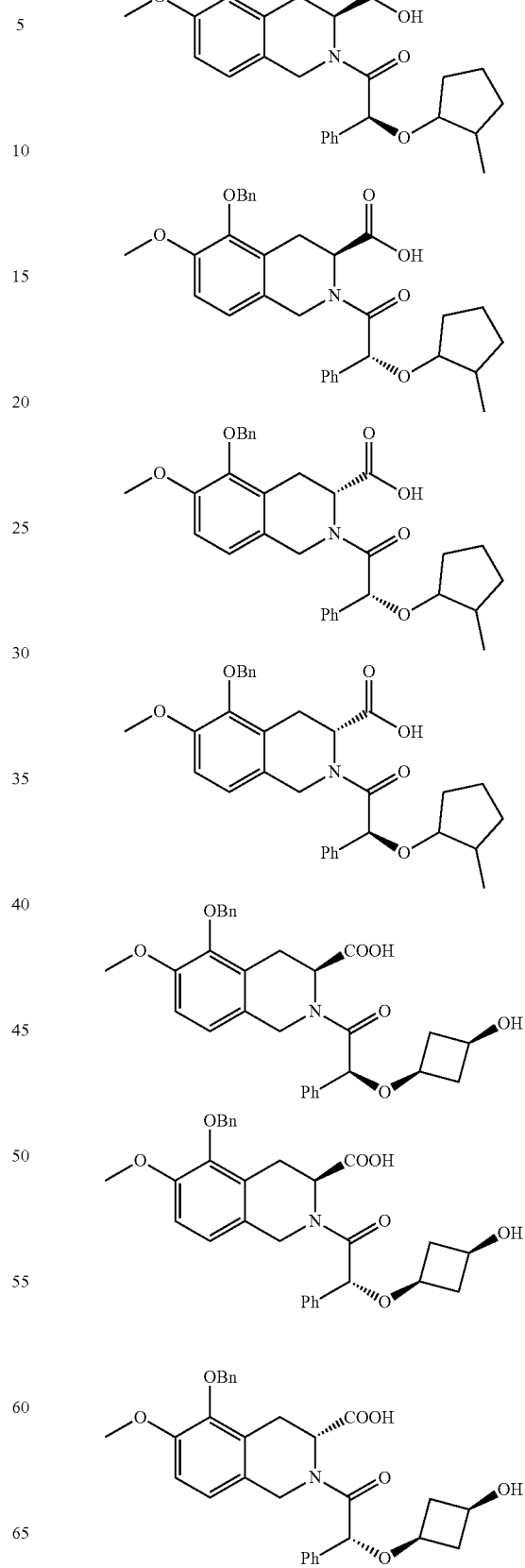

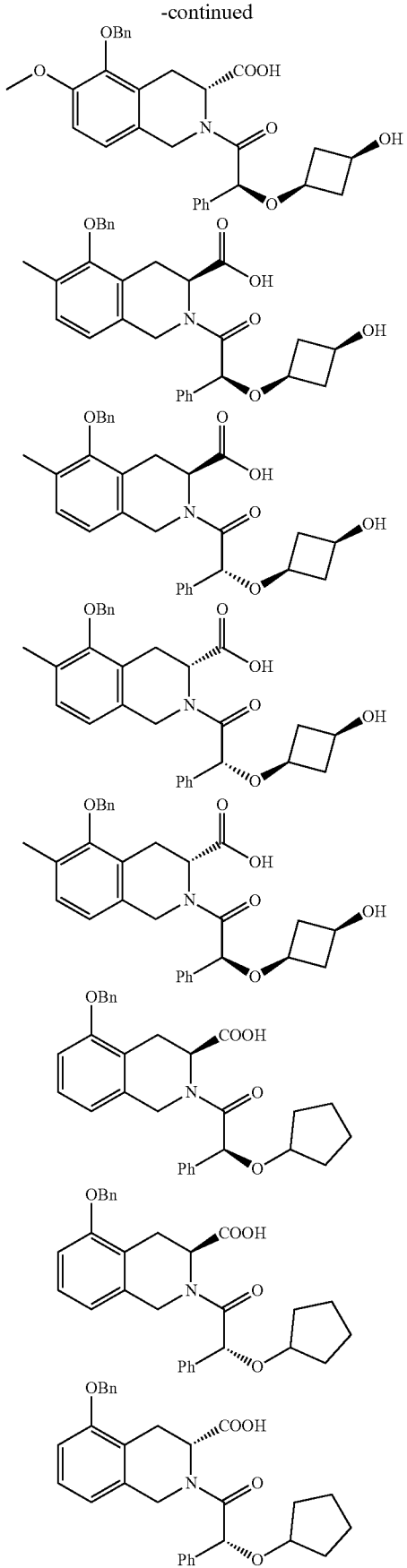
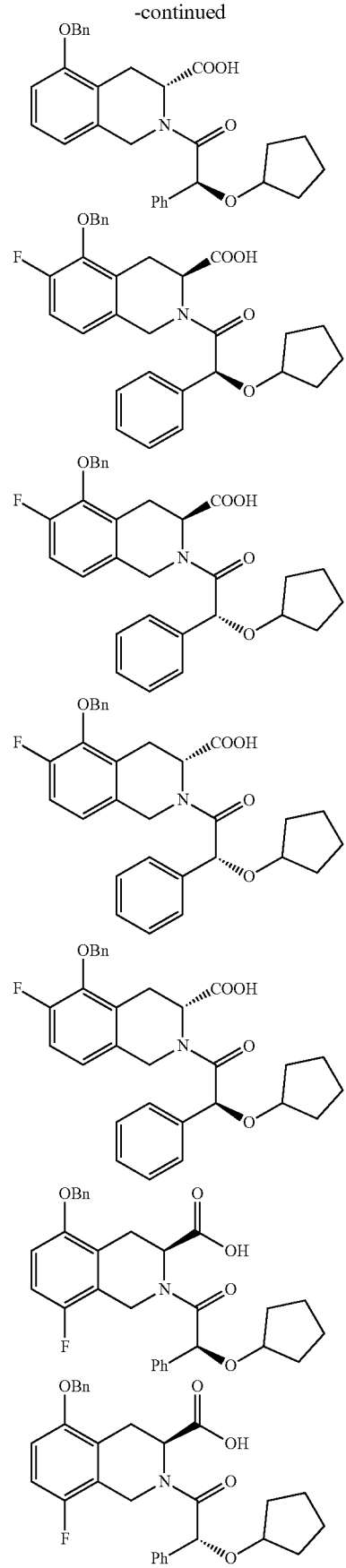

-continued
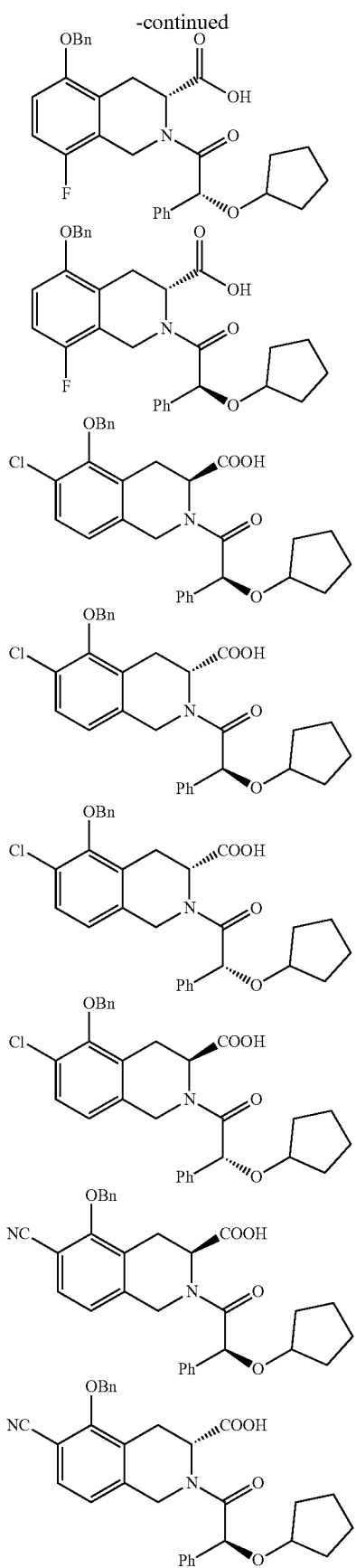
-continued
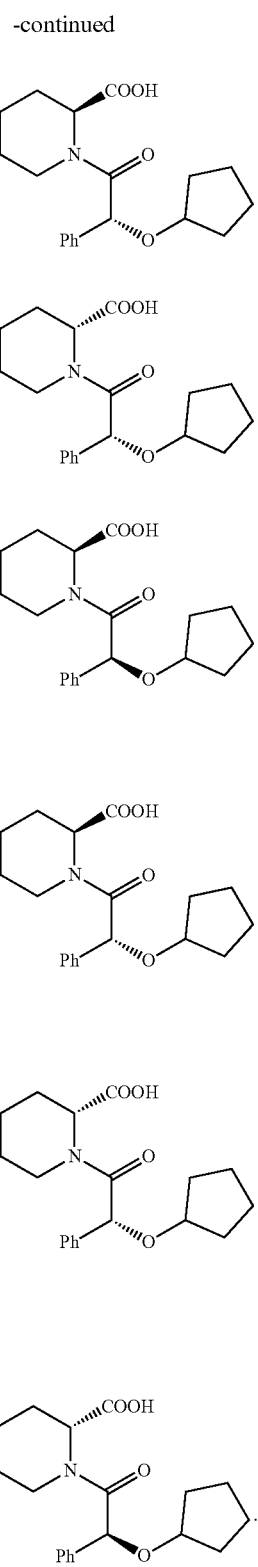
20. A method for the treatment of chronic pain associated with an AT$_2$R receptor, comprising a step of administering the compound or the pharmaceutically acceptable salt thereof according to claim 1 to a subject in need.
* * * * *